(12) United States Patent
Palladino et al.

(10) Patent No.: US 8,133,915 B2
(45) Date of Patent: Mar. 13, 2012

(54) INTERLEUKIN-1 AND TUMOR NECROSIS FACTOR-α MODULATORS; SYNTHESES OF SUCH MODULATORS AND METHODS OF USING SUCH MODULATORS

(75) Inventors: Michael A. Palladino, Olivenhain, CA (US); Emmanuel A. Theodorakis, San Diego, CA (US); Venkat Rami Reddy Macherla, San Diego, CA (US); Ta-Hsiang Chao, San Diego, CA (US); Young-Ger Suh, Kyungki-do (KR)

(73) Assignees: Nereus Pharmaceuticals, Inc., San Diego, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/007,573

(22) Filed: Jan. 14, 2011

(65) Prior Publication Data

US 2011/0160309 A1 Jun. 30, 2011

Related U.S. Application Data

(62) Division of application No. 11/487,018, filed on Jul. 14, 2006, now Pat. No. 7,893,299.

(60) Provisional application No. 60/701,932, filed on Jul. 21, 2005, provisional application No. 60/734,590, filed on Nov. 7, 2005, provisional application No. 60/734,679, filed on Nov. 7, 2005, provisional application No. 60/749,542, filed on Dec. 12, 2005, provisional application No. 60/785,223, filed on Mar. 22, 2006.

(51) Int. Cl.
*A61K 31/165* (2006.01)
(52) U.S. Cl. ....................................... 514/623
(58) Field of Classification Search ................... 514/623
See application file for complete search history.

(56) References Cited

U.S. PATENT DOCUMENTS

| | | | |
|---|---|---|---|
| 4,009,206 A | 2/1977 | Murai et al. |
| 4,024,280 A | 5/1977 | Murai et al. |
| 4,874,891 A | 10/1989 | Covey et al. |
| 5,192,817 A | 3/1993 | Takaishi et al. |
| 5,900,434 A | 5/1999 | Pyun et al. |
| 6,051,590 A | 4/2000 | Bao et al. |
| 6,365,768 B1 | 4/2002 | Palladino et al. |
| 6,593,363 B1 | 7/2003 | Suh et al. |

FOREIGN PATENT DOCUMENTS

| DE | 2519943 A1 | 12/1975 |
|---|---|---|
| WO | WO 02/079137 A1 | 10/2002 |

OTHER PUBLICATIONS

The Journal of Organic Chemistry, Journal, Jun. 13, 1975, 1784-1792, vol. 40, American Chemical Society.

Cai et al. (2003) Inhibitory effect of kaurane type diterpenoids from acanthopanax koreanum on TNF-Alpha. Secretion from trysin-stimulated HMC-1 cells. Archives of Pharmacal Research, Natl. Fisheries University, Pusan, KR. 26(9):731-734.
Chao et al. (2006) The novel acanthoic acid analog, NPI-1387 inhibts tumor cell proliferation, reduces NF-KB DNA binding activity and functions upstream in the NF-KB signaling pathway. Proceedings of the Annual Meeting of the American Association for Cancer Research, New York, NY, US. 47:896-Abstract 3812, XP001248777.
Chauhan et al. (2005) Targeting therapy for resistant multiple myeloma with a novel inhibitor of NF-KB, NPI-1387. Blood, W.B. Saunders Company, Orlando, FL, US. vol. 106, No. 11 Part 1, p. 190A-Abstract 640, XP009076268.
Fujita et al. (1991) New hypocholesterolemic abietamide derivaties. II. Synthesis and hypochlesterolemic activity of P-phenyl-1-dihydroabietamides. Chemical and Pharmaceutical Bulletin, Pharmaceutical Society of Japan, Tokyo, JP. 39(5):1193-1198.
Khanbolooki et al. (2006) Novel NFKB inhibitors NPI-1342/NPI-1387 and proteasome inhibitior NPI-0052 overcome resistance of pancreatic carcinoma to RH trail. Proceedings of the Annual Meeting of the American Association for Cancer Research, New York, NY, US. 47:184-Abstract 780, XP001248776.
Suh et al. (2004) Synthesis and anti-inflammatory effects of novel pimarane diterpenoid analogs. Bioorganic and Medicinal Chemistry Letters. 14:3487-3490.
Vieira et al. (2002) Novel derivatives of kaurenoic acid: preparation and evaluation of their trypanocidal activity. J. Brax. Chem. Soc. 13(2):151-157.
Chao et al. (2005) A new family of synthetic diterpenes that regulates cytokine synthesis by inhibiting 1κBα phosphorylation. ChemBioChem 6:133-144.
Fujita et al. (1980) New Hypocholesterolemic abietamide derivatives. I. Structure-activity relationship. Chem. Pharm. Bull. 28(2):453-458.
Chemical abstracts vol. 127, No. 1 Jul. 7, 1997 (Columbus Ohio) pp. 594, abstract No. 5280z F.G. Cruz et al. Relative stereochemistry determination of primaradienes through oxidation productions.
Chemical abstracts vol. 116, No. 11 Mar. 16, 1992 (Columbus Ohio) p. 411, abstract No. 102659c, C.M. Chamy et al. Diterpenoids from calceolaria species, part 10. Diterpenes from calceolaria polifolia. Phytochemistry 1991 30(10):3365-3368.
Chemical abstracts vol. 114, No. 3 Jan. 21, 1991 (Columbus Ohio) p. 408, abstract No. 20960p, C.M. Chamy et al. Diterpenoids from calceolaria species part 5. Diterpenes from calceolaria lepida. Phytochemistry 1990 29(9):2943-2946.

(Continued)

*Primary Examiner* — Shailendra Kumar
(74) *Attorney, Agent, or Firm* — Knobbe Martens Olson & Bear LLP

(57) ABSTRACT

Described herein are chemical compounds and pharmaceutical compositions, including novel chemical compounds and pharmaceutical compositions thereof, useful in the treatment of various diseases and disease states. Also described are methods of synthesizing natural products and novel, structurally-related chemical compounds. More particularly, disclosed are new analogs of and processes for the preparation of compounds and pharmaceutical compositions thereof useful in the treatment of, for example, inflammation, cancer, multiple myeloma, cachexia, cardiovascular disease, anti-infectious, diabetes, otitis media, sinusitis and transplant rejection.

2 Claims, 69 Drawing Sheets

OTHER PUBLICATIONS

Chemical abstracts vol. 77, No. 15 Oct. 9, 1972 (Columbus Ohio) p. 193, abstract No. 98751h, V.K. Morozkov et al. Neutral fraction of the oleoresim of pinus sylvestri 3. Norditerpene compounds. Izv. Sib. Otd. Akad Nauk SSSR, Ser. Khim. Nauk 1972 (1):128-134.

Chapman et al. (1963) Journal of the Chemical Society. Abstract Aug. 1963 4010-4017.

Cruz et al. (1992) Diterpene Acids from Mikania Triangularis: Phytochemistry. 31(8):2793-2796.

Jaki, B. (1999) A novel extracellular diterpenoid with antibacterial activity from the cyanobacterium N. commune. J Natural Products. 62(3)502-503.

Kaufman et al. (1987) Synthesis and 13C nuclear magetic resonance spectral analysis of some diterpenoids related to the cleisanthane type hydrocarbon isolated from *Amphilbolis Antarctica*. Canadian Journal of Chemistry. 65(9):2024-2026.

Kaufman et al. (1995) Synthesis and mass spectral data of four potential biomarkers related to the C19 tricyclanes found in Australian oils and Puget Sound sediments. Synth. Commun. 25(8):1205-1221.

Kim et al. (1998) Pimaradiene diterpenes from acanthopanax koreanum. Journal of Natural Products. 51(6):1080-1083; p. 1080, paragraphs 1-3, compound No. 2, p. 1082, paragraph Extraction and isolation.

Knudsen et al. (1986) Pimaradiene Diterpenes from Mikania Triangularis: Phytochemistry. 25(5):1240-1242.

Ling et al. (2000) Stereoselective synthesis of (−)—acanthoic acid. Organic Letters. 2:2073-2076.

Ohtsuka et al. (1973) Diterpenoids. Chemical and Pharmaceutical Bulletin. 21(3):643-652.

Suh et al. (2001) Pimarane cyclooxygenase 2 (COX-2) inhibitor and its structure-activity relationship. Bioorganic & Medicinal Chemistry Letters. 11:559-562.

Taticchi et al. (1969) Tetrahedron vol. 25:5341-5348.

| | | | |
|---|---|---|---|
| NPI 1302 | (structure) | | |
| TTL1 | (structure) | $C_{20}H_{30}O_2$<br>Mol. Wt.: 302.45 | 2.9 mg |
| TTL2 | (structure) | $C_{19}H_{30}O_3$<br>Mol. Wt.: 306.44 | 2.5 mg |
| TTL3 | (structure) | $C_{21}H_{32}O_2$<br>Mol. Wt.: 316.48 | 1.8 mg |
| TTL4 | (structure) | $C_{20}H_{32}O_3$<br>Mol. Wt.: 320.47 | 2.1 mg |
| TTL5 | (structure) | $C_{20}H_{30}O_2$<br>Mol. Wt.: 302.45<br>1:1 mixture of diastereomers at C° | 1.2 mg |

FIG. 17

TTL3

α-peak in HPLC
(+) enantiomer

Stereochemistry
of Wieland-
Miescher Ketone
intermediate

TTL3

β-peak in HPLC
(-) enantiomer

Formula (IIBB-1) decreases the phosphorylation level of IkBα induced by LPS in Human Peripheral Blood Mononuclear Cells.

Formula (IIBB-1) decreases the phosphorylation level of IκBα induced by LPS in RPMI 8226 cells.

Formula (IIBB-1) specifically inhibits LPS-induced phosphorylation of IκBα and p38 MAP kinase in RPMI 8226 cells.

Formula (IIBB-1) inhibits the phosphorylation of IκBα induced by Toll-like receptor ligands in RPMI 8226 cells. TLR 2= Toll-like receptor 2, TLR 4= Toll-like receptor 4, TLR 9= Toll-like receptor 9.

Formula (IIBB-1) reduces LPS-induced IL-8 and IL-10 production in a dose-dependent manner in RPMI 8226 cells.

Effect of TTL3 and its analogs on NOS-2, COX-2 and NO in RAW264.7 cells stimulated with LPS/IFNγ. Compound 1, 2, 3, 4 and 5 represent TTL3, TTL1, LT-1-45, LT-1-85 and formula (IIBB-1), respectively. Results show the mean ± SD. *P<0.05, **P<0.01 vs the LPS/IFNγ condition.

Effect of TTL3, TTL1, LT-1-45, LT-1-85 and formula (IIBB-1) on the NIK/ NF-κB pathway. Compound 1, 2, 3, 4 and 5 represent TTL3, TTL1, LT-1-45, LT-1-85 and formula (IIBB-1), respectively. Results show the mean ± SD. *P<0.05, **P<0.01 vs the LPS/IFNγ condition.

Effect of TTL3 and formula (IIBB-1) on NIK activity. Compound 1 and 5 represent TTL3 and formula (IIBB-1).

TTL3 and formula (IIBB-1) inhibit TPA-induced ear edema. Results show the mean ± SD. *P<0.05, **P<0.01 vs the corresponding control.

Formula (IIBB-1): $^1$H NMR spectrum in $CDCl_3$

NPI-1387 inhibits NF-κB p65 subunit nuclear translocation in a dose-dependent manner upon LPS stimulation in RAW264.7 cells NPI-1387 inhibits the TNF-α synthesis in LPS-stimulated RAW264.7 cells.

NPI-1387 inhibits the phosphorylation of IRAK1 and kinase activity of IKKα in a dose-dependent manner upon LPS stimulation in RAW264.7 cells NPI-1387 inhibits TNF-α or LPS-induced NF-κB DNA binding activity in cancer cells.

INTERLEUKIN-1 AND TUMOR NECROSIS FACTOR-α MODULATORS; SYNTHESES OF SUCH MODULATORS AND METHODS OF USING SUCH MODULATORS

CROSS-REFERENCE TO RELATED APPLICATIONS

This application is a divisional of U.S. patent application Ser. No. 11/487,018 now U.S. Pat. No. 7,893,299, filed on Jul. 14, 2006 which claims priority under 35 U.S.C. §119(e) to U.S. Provisional Application Nos. 60/701,932 filed Jul. 21, 2005, 60/734,590 filed Nov. 7, 2005, 60/734,679 filed Nov. 7, 2005, 60/749,542 filed Dec. 12, 2005, 60/785,223 filed Mar. 22, 2006 each of which is hereby incorporated by reference in its entirety.

FIELD OF THE INVENTION

The invention relates to chemical compounds and pharmaceutical compositions, including novel chemical compounds and pharmaceutical compositions thereof, useful in the treatment of various diseases and disease states. The invention also relates to methods of synthesizing natural products and novel, structurally-related chemical compounds. More particularly, the present invention relates to novel analogs of and processes for the preparation of compounds and pharmaceutical compositions thereof useful in the treatment of, for example, inflammation, cancer, cachexia, cardiovascular disease, anti-infectious, diabetes, otitis media, sinusitis and transplant rejection.

BACKGROUND OF THE INVENTION

Pancreatic adenocarcinoma is the fifth leading cause of cancer deaths in the United States, with a five-year survival rate of less than five percent. Nuclear Factor kappa B (NFκB) is a dimeric transcription factor that has been implicated in suppression of apoptosis, angiogenesis, and metastasis.

Acanthoic acid is a pimaradiene diterpene isolated from the Korean medicinal plant, *Acanthopanax koreanum* Nakai (Araliaceae). The root and stem barks of *Acanthopanax koreanum* have been used in traditional medicine as a tonic and sedative as well as in the treatment of rheumatism and diabetes in Korea. *Acanthopanax koreanum* Nakai (Araliaceae), which is found indigenously in Cheju Island, The Republic of Korea, has also been used traditionally as a remedy for, for example, neuralgia, paralysis, and lumbago. Various useful components, including acanthoic acid, a compound having the chemical structure of Formula (I), have been isolated from the root bark of this tree. Furthermore, certain analogs of the compound of Formula (I), for example, wherein the COOH group is replaced by a methanolic group, by a methyl-acetyl ether, by a methyl group, and by a methyl-ester have each also been isolated from the root bark of *Acanthopanax koreanum* Nakai (Araliaceae). See Kim, Y. H. and Chung, B. S., J. Nat. Pro., 51, 1080-83 (1988). (The proper chemical names of these analogs are provided in this reference.) This reference and all the other patents and printed publication cited herein are, in their entirety, incorporated by reference herein.

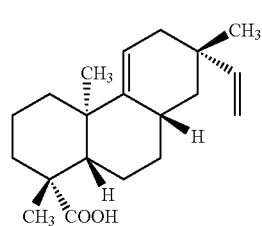

(I)

The compound of Formula (I), also known as acanthoic acid, has been reported to have certain pharmacological effects, including, for example, analgesic and anti-inflammatory activity. The compound of Formula (I) also exhibits very low toxicity; 1000 mg/kg is the minimum lethal dose (MLD) when administered orally or I.V. to a rat (See Lee, Y. S., "Pharmacological Study for (−)-Pimara-9(11), 15-Diene-19-oic Acid, A Component of *Acanthopanax koreanum* Nakai," Doctorate Thesis, Dept. of Pharmacy, Seoul National University, Korea (1990)). The compound of Formula (I) and/or its naturally-occurring analogs, may exhibit these known pharmacological effects by inhibiting leukocyte migration and prostaglandin $E_2(PGE_2)$ synthesis, and is a suspected effector of both Interleukin-1 (IL-1) and Tumor Necrosis Factor-α (TNF-α) production. Additionally, a process for the preparation of acanthoic acid, and use of the acanthoic acid for treatment of immune disease is described in International Patent Publication WO 95/34300 (Dec. 21, 1995).

Also, the compound of Formula (IA), kauranoic acid, and the corresponding methyl-ester analog of the compound of Formula (IA), as well as methanolic reduction analogs of the compound of Formula (IA) have been isolated from the root bark of *Acanthopanax koreanum* Nakai (Araliaceae). See Kim, Y. H. and Chung, B. S., J. Nat. Pro., 51, 1080 (1988). (The proper chemical name of kauranoic acid, (−)-kaur-16-en-19-oic acid, and of the known analogs of kauranoic acid are provided in this reference.)

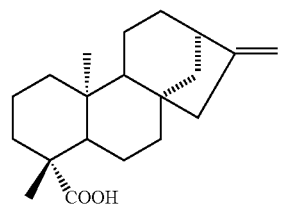

(IA)

Tumor Necrosis Factor-α (herein "TNF-α" or "TNF") and/or Interleukin-1 (herein "IL-1") are involved in various biochemical pathways and, thus modulators of TNF-α and/or IL-1 activity or production and other molecules regulated by TNF-α or Il-1, especially novel modulators of TNF-α and/or IL-1 activity or novel compounds that influence the production of either IL-1 or TNF-α, or both, are highly desired. Such compounds and classes of compounds would be valuable in maintaining the human immune system and in treating diseases such as for example, tuberculous pleurisy, rheumatoid pleurisy, and diseases not conventionally considered to be immune disorders, such as cancer, cardiovascular disease, skin redness, viral infection, diabetes, and transplant rejection.

Although numerous approaches to regulate the production of TNF-α and the interleukins are known, novel approaches, compounds, and pharmaceutical formulations to regulate the production of TNF-α and interleukins are highly desirable and have been long sought by those of skill in the art.

SUMMARY OF THE INVENTION

Also described are the synthetic and semi-synthetic preparation of the compounds of Formulae (I) and (IA) and their structural analogs, including novel analogs, of the compounds of Formulae (I) and (IA), including cyclic amide-containing compounds.

Dislcosed compounds also include, for example, compounds having the chemical structure of Formula (II) and compounds having the chemical structure of Formula (IIA). Regarding compounds having the chemical structure of Formula (II), disclosed compounds include:

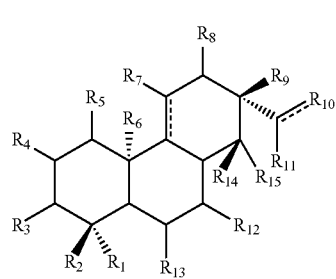

(II)

and their stereo-isomers wherein if any $R_3$-$R_5$, $R_7$, $R_8$, $R_{11}$-$R_{13}$ is not hydrogen, $R_2$ or $R_6$ or $R_9$ is not methyl, or $R_{10}$ is not $CH_2$, then $R_1$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, primary amide, $C_1$-$C_{12}$ secondary amides, $(C_1$-$C_{12})(C_1$-$C_{12})$ tertiary amides, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls, and $C_5$-$C_{12}$ aryls; however, if all $R_3$-$R_5$, $R_7$, $R_8$, $R_{11}$-$R_{13}$ are hydrogen, $R_2$, $R_6$, and $R_9$ are each methyl, and $R_{10}$ is $CH_2$, then $R_1$ is selected from hydrogen, a halogen, $C_1$-$C_{12}$ carboxylic acids, $C_1$-$C_{12}$ acyl halides, $C_1$-$C_{12}$ acyl residues, $C_2$-$C_{12}$ esters, $C_2$-$C_{12}$ secondary amides, $(C_1$-$C_{12})(C_1$-$C_{12})$ tertiary amides, $C_2$-$C_{12}$ alcohols, $(C_1$-$C_{12})(C_1$-$C_{12})$ ethers other than methyl-acetyl ether, $C_2$-$C_{12}$ alkyls, $C_1$-$C_{12}$ substituted alkyls, $C_2$-$C_{12}$ alkenyls, $C_2$-$C_{12}$ substituted alkenyls, $C_2$-$C_{12}$ aryls and the like;

$R_2$ and $R_9$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ acyl, $C_1$-$C_{12}$ alcohol, $C_5$-$C_{12}$ aryl and the like; and $R_3$-$R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl, and the like;

in particularly preferred embodiments, $R_{11}$ can be a $C_1$-$C_6$ alkyl, or $C_1$-$C_6$ substituted alkyl, and all other R groups can be hydrogen;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like, and preferably, both $R_1$ and $R_2$ are not simultaneously methyl.

Regarding compounds having the chemical structure of Formula (IIA), disclosed compounds include:

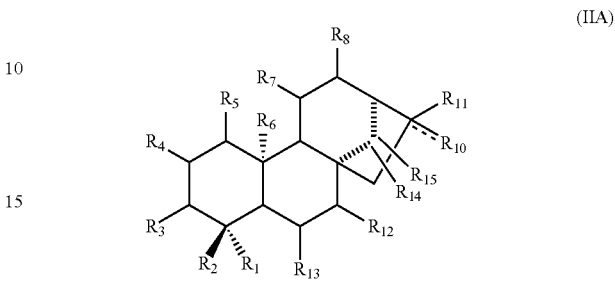

(IIA)

and their stereoisomers wherein, if any $R_3$-$R_5$, $R_7$, $R_8$, $R_{11}$-$R_{13}$ is not hydrogen, $R_2$ or $R_6$ is not methyl, $R_{10}$ is not $CH_2$, or if it is not true that $R_{10}$ is $CH_2OH$ and $R_{11}$ is OH, then can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})(C_1$-$C_{12})$ tertiary amides, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls and the like; but if all $R_3$-$R_5$, $R_7$, $R_8$, $R_{11}$-$R_{13}$ are hydrogen, $R_2$ and $R_6$ are each methyl, and $R_{10}$ is $CH_2$ or $CH_2OH$, then $R_1$ can be, for example, hydrogen, a halogen, $C_1$-$C_{12}$ carboxylic acids, $C_1$-$C_{12}$ acyl halides, $C_1$-$C_{12}$ acyl residues, $C_2$-$C_{12}$ esters, $C_1$-$C_{12}$ secondary amides, $(C_1$-$C_{12})(C_1$-$C_{12})$ tertiary amides, $C_2$-$C_{12}$ alcohols, $(C_1$-$C_{12})(C_1$-$C_{12})$ ethers, $C_2$-$C_{12}$ alkyls, $C_2$-$C_{12}$ substituted alkyls, $C_2$-$C_{12}$ alkenyl, $C_2$-$C_{12}$ substituted alkenyl and the like;

$R_2$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ acyl, $C_1$-$C_{12}$ alcohol, $C_5$-$C_{12}$ aryl and the like;

$R_3$, $R_4$, $R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, and $C_5$-$C_{12}$ aryl. In particularly preferred embodiments, $R_{11}$ can be a $C_1$-$C_6$ alkyl, or $C_1$-$C_6$ substituted alkyl, and all other R groups can be hydrogen;

$R_6$ can be, for example hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ may be stereo-specific, and can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, and $C_5$-$C_6$ aryl, and preferably, both $R_1$ and $R_2$ are not simultaneously methyl.

It is a further object to provide compounds having the chemical structure of Formula (IIB), and to provide processes for the synthetic and semi-synthetic preparation of compounds having the chemical structure of Formula (IIB). Regarding said compounds having the chemical structure of Formula (IIB), for example, the compounds herein designated TTL1, TTL2, TTL3, TTL4, and their analogs and derivatives, the invention includes:

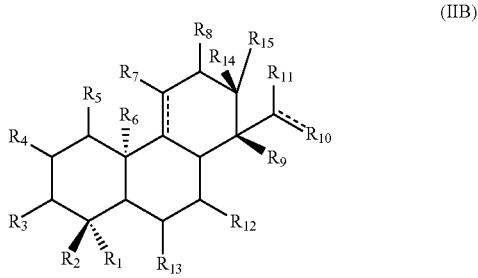

(IIB)

and their stereoisomers wherein $R_1$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})(C_1$-$C_{12})$ tertiary amides, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls, and $C_5$-$C_{12}$ aryls. Under these conditions, $R_1$ is preferably selected from COOH, $C_1$-$C_{12}$ carboxylic acids, $C_1$-$C_{12}$ acyl halides, $C_1$-$C_{12}$ acyl residues, $C_1$-$C_{12}$ secondary amides and $C_1$-$C_{12}$ esters, and is most preferably selected from COOH, cyclic secondary amides and the $C_1$-$C_6$ esters.

$R_2$ and $R_9$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ acyl, $C_1$-$C_{12}$ alcohol, $C_5$-$C_{12}$ aryl and the like;

$R_3$-$R_5$, $R_7$, $R_9$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like. In particularly preferred embodiments, $R_{11}$ is a $C_1$-$C_6$ alkyl, or $C_1$-$C_6$ substituted alkyl, and all other R groups are hydrogen;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ is can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{14}$ and $R_{15}$ are stereo-specific and can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like, and preferably, both $R_1$ and $R_2$ are not simultaneously methyl.

It also will be appreciated that the various R groups, most particularly $R_3$, $R_4$, $R_5$, $R_7$, $R_8$, and $R_{11}$-$R_{13}$, may be chosen such that cyclic system are formed. For example, both $R_{13}$ and $R_{12}$ may be ethylene moieties and may include a covalent C—C linkage between their respective terminal carbons, generating an additional six-membered ring in the compound of Formula (IIB). As a further example, bis-cyclic rings may be formed by choosing appropriate chemical species for the various R groups, most particularly $R_3$, $R_4$, $R_5$, $R_7$, $R_8$, and $R_{11}$-$R_{13}$ of Formula (IIB).

The disclosed compounds include the prodrug esters of the any of the disclosed compounds, including, for example, compounds of Formulae (II), (IIA), and (IIB), and the acid-addition salts of the compounds of Formulae (II), (IIA), and (IIB), including cyclice amide containing compounds, and pharmaceutical compositions comprising a therapeutically effective amount of the described compounds, including their prodrug esters and their acid-addition salts, optionally in conjunction with a pharmaceutically acceptable carrier. Such compositions are useful as, for example, anti-inflammatory analgesics, in the treatment of immune and auto-immune disorders, as anti-cancer or anti-tumor agents, and are useful in the treatment of cardiovascular disease, skin redness, viral infection, diabetes, otitis media, sinusitis and/or transplant rejection. Particularly, a pharmaceutical composition comprising a therapeutically effective amount of a compound of Formulae (II), (IIA), or (IIB), or a pro-drug ester and acid addition salt of a compound of Formulae (II), (IIA), or (IIB), may be used as an anti-cancer, anti-tumor agent, anti-viral agent, and may be useful in the treatment of cardiovascular disease, skin redness, viral infection, diabetes, otitis media, sinusitis and/or transplant rejection.

Methods of synthesizing the above described compounds and their analogs are also disclosed, comprising the step of performing a Diels-Alder reaction reacting a diene having two or more rings with a dienophile compound to yield a resultant compound have three of more rings; and yielding a desired synthetic compound. The Diels-Alder reaction, along with the selection of the diene and the dienophile affords flexibility in synthesizing a variety of compounds, and allows for the use of combinatorial chemistry libraries of compounds, for use biological assays, including clinical trials.

Some embodiments relate to compounds having the following chemical structure:

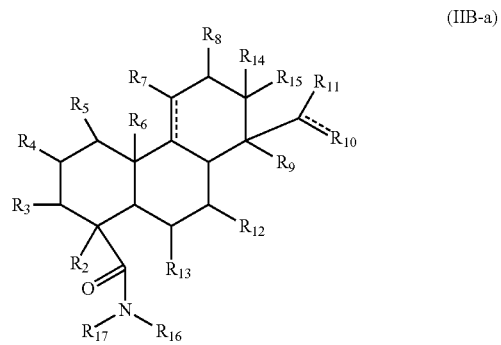

(IIB-a)

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})$ $(C_1$-$C_{12})$ tertiary amides, $(C_1$-$C_{12})$ cyclic amides, $(C_1$-$C_{12})$ amines, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls, and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl, $C_5$-$C_{12}$ aryls, and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl, and the like;

$R_3$-$R_5$, $R_7$, $R_8$, and $R_{11}$-$R_{13}$ each can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl, and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{14}$ and $R_{15}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like; and $R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})$ $(C_1$-$C_{12})$ tertiary amides, $(C_1$-$C_{12})$ cyclic amides, $(C_1$-$C_{12})$ amines, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like; and wherein the compound also includes the prodrug esters of the above compounds, and the acid-addition salts thereof.

In some aspects, $R_{16}$ can be, for example, hydrogen. In other aspects, $R_{17}$ can be for example, cyclohexane. In still other aspects, $R_3$-$R_5$, $R_7$, $R_8$, $R_{11}$-$R_{15}$ can each be, for example hydrogen.

Another embodiment includes the compound:

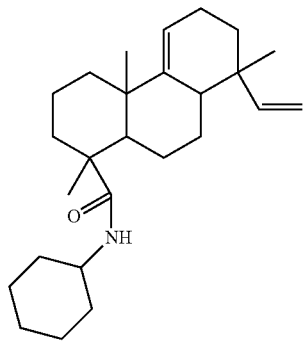

(IIB-a1)

and prodrug esters and acid-addition salts thereof.

Yet other embodiments relate to methods of treating a disease condition. The disease condition can be, for example, inflammation, tuberculous pleurisy, rheumatoid pleurisy, cancer, the reduction of fatigue associated with cancer or its treatment, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, chemotherapy related mucosal injury, and the like. The methods can include, for example, contacting a compound to living tissue of said animal, wherein the compound has the following chemical structure:

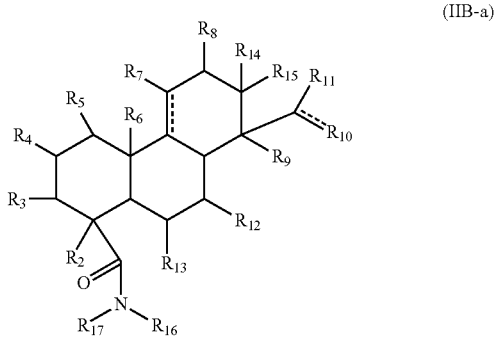

(IIB-a)

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl and $C_5$-$C_{12}$ aryls and the like;

and $R_9$ can be, for example hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_8$, and $R_{11}$-$R_{13}$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, and $C_2$-$C_{12}$ alkynyl;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

wherein the compound can include the prodrug esters of the above compounds, and the acid-addition salts thereof.

In another aspect, the method of treatment can include contacting a compound to living tissue of said animal, wherein the compound has the following chemical structure

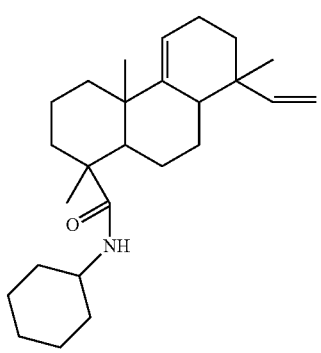

(IIB-a1)

and prodrug esters and acid-addition salts thereof.

Still further embodiments relate to methods of treating an inflammatory condition in an animal. The methods can include contacting a compound to living tissue of said animal, wherein the compound has the following chemical structure:

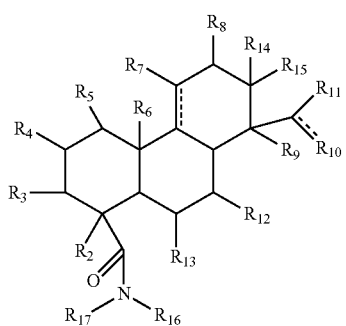

(IIB-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl and $C_5$-$C_{12}$ aryls; and $R_9$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_8$, and $R_{11}$-$R_{13}$ can each be, for example, from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

wherein the compound can include the prodrug esters and the acid-addition salts thereof.

In one aspect, the inflammatory condition can be, for example, tuberculous pleurisy, rheumatoid pleurisy, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, chemotherapy related mucosal injury, and the like.

In another aspect, the compound can have the following structure:

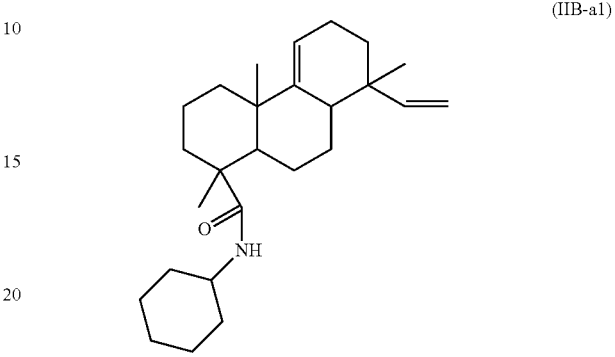

(IIB-a1)

and prodrug esters and the acid-addition salts thereof.

Some embodiments relate to methods of treating a cancer in an animal. The methods can include contacting a compound to living tissue of said animal, wherein the compound has the following chemical structure:

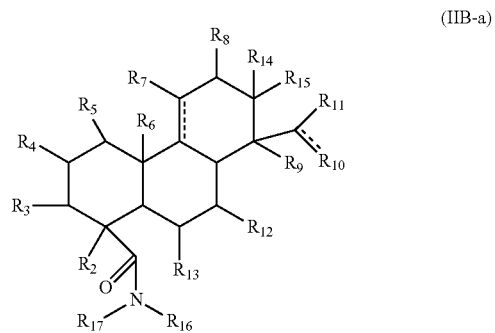

(IIB-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl and $C_5$-$C_{12}$ aryls; and $R_9$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, and $C_5$-$C_{12}$ aryl;

and $R_9$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_9$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ ary and the like;

wherein the compound can include the prodrug esters of the above compounds, and the acid-addition salts.

In one aspect, the cancer can be, for example, multiple myeloma human prostate adenocarcinoma and the like.

In another aspect, the compound can have the following structure:

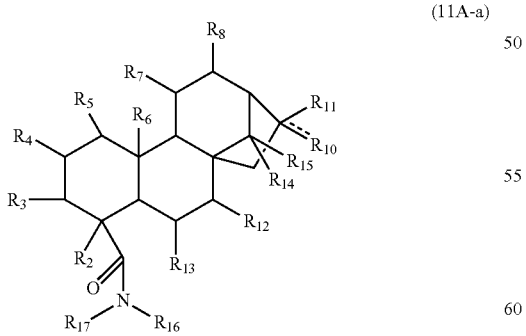

(IIB-a1)

including the prodrug esters and the acid-addition salts thereof.

Some embodiments related to compounds having the following chemical structure:

(11A-a)

wherein:

If any $R_3$-$R_5$, $R_7$, $R_8$, $R_{11}$-$R_{13}$ is not hydrogen, $R_6$ is not methyl, $R_{10}$ is not $CH_2$, or if $R_{10}$ is $CH_2OH$ and $R_{11}$ is OH, $R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})(C_1$-$C_{12})$ tertiary amides, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls and the like;

if all $R_3$-$R_5$, $R_7$, $R_8$, $R_{11}$-$R_{13}$ are hydrogen, $R_6$ is methyl, and $R_{10}$ is $CH_2$ or $CH_2OH$, then $R_2$ can be, for example, hydrogen, a halogen, $C_1$-$C_{12}$ carboxylic acids, $C_1$-$C_{12}$ acyl halides, $C_1$-$C_{12}$ acyl residues, $C_2$-$C_{12}$ esters, $C_1$-$C_{12}$ secondary amides, $(C_1$-$C_{12})(C_1$-$C_{12})$ tertiary amides, $C_2$-$C_{12}$ alcohol, $(C_1$-$C_{12})(C_1$-$C_{12})$ ethers, $C_2$-$C_{12}$ alkyls, $C_2$-$C_{12}$ substituted alkyls, $C_2$-$C_{12}$ alkenyl, $C_2$-$C_{12}$ substituted alkenyl and the like;

$R_3$, $R_4$, $R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})(C_1$-$C_{12})$ tertiary amides, $(C_1$-$C_{12})$ cyclic amides, $(C_1$-$C_{12})$ amines, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl $C_5$-$C_{12}$ aryls and the like;

wherein the compound can include the prodrug esters of the above compounds, and the acid-addition salts thereof.

In one aspect, $R_{16}$ can be, for example, hydrogen and the like. In another aspect, $R_{17}$ can be, for example, cyclohexane and the like. In yet another aspect, $R_3$-$R_5$, $R_7$, $R_8$, $R_{11}$-$R_{15}$ can each be, for example hydrogen and the like.

In another embodiment the compound can have the following structure:

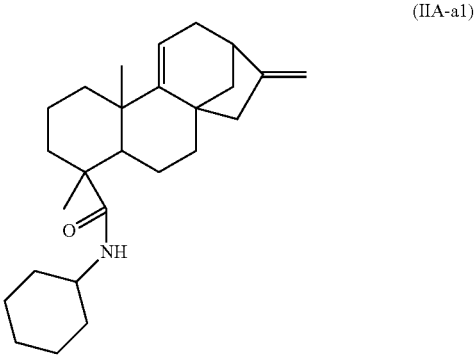

(IIA-a1)

and prodrug esters and acid-addition salts thereof.

Some embodiments relate to a method of treating a disease condition. Examples of the disease condition can be inflammation, tuberculous pleurisy, rheumatoid pleurisy, cancer, the reduction of fatigue associated with cancer or its treatment, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, and chemotherapy related mucosal injury and the like.

The methods can include, for example, contacting a compound to living tissue of said animal, wherein the compound has the following chemical structure:

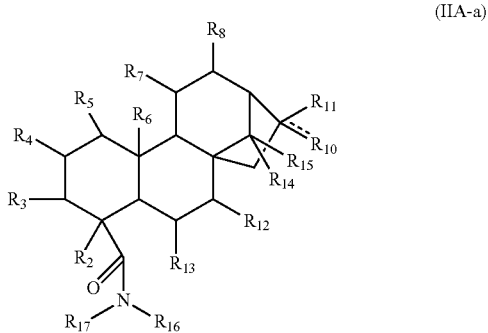

(IIA-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_3$-$R_5$, $R_7$, $R_9$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; C5-$C_{12}$ substituted cyclic alkyls; $C_5$-$C_{12}$ substituted cyclic alkenyls; phenyl $C_5$-$C_{12}$ aryls and the like;

wherein the compound can include the prodrug esters of the above compounds, and the acid-addition salts thereof.

In one aspect, the compound can have the following structure:

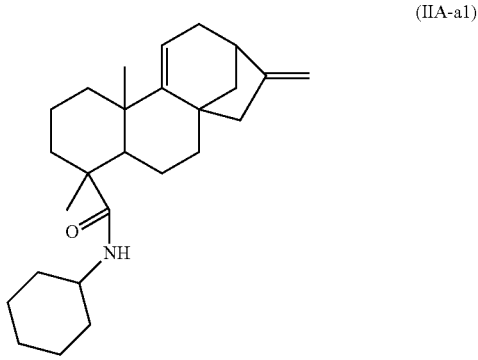

(IIA-a1)

and prodrug esters and acid-addition salts thereof.

Other embodiments relate to methods of treating an inflammatory condition in an animal. Examples of such methods include contacting a compound to living tissue of said animal, wherein the compound has the following chemical structure:

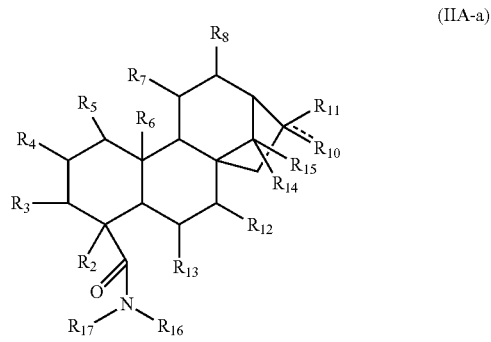

(IIA-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_3$-$R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)

($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl $C_5$-$C_{12}$ aryls and the like;

wherein the compound can include the prodrug esters and the acid-addition salts thereof.

In some aspects, the inflammatory condition can be, for example, tuberculous pleurisy, rheumatoid pleurisy, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, chemotherapy related mucosal injury and the like.

In another aspect, the compound can have the following structure:

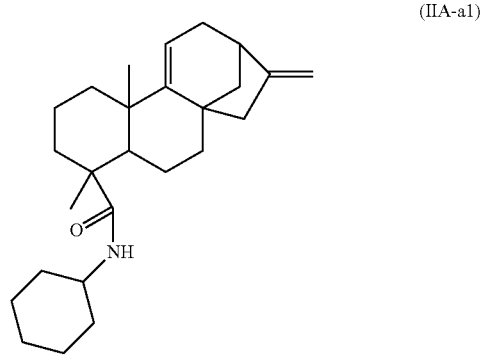

(IIA-a1)

and prodrug esters and the acid-addition salts thereof.

Still another embodiment relates to methods of treating a cancer in an animal. Examples of such methods include contacting a compound to living tissue of said animal, wherein the compound has the following chemical structure:

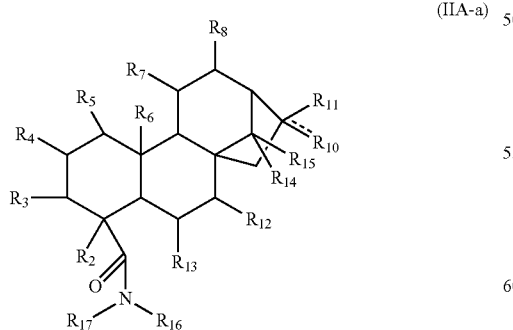

(IIA-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$) ($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_3$-$R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$) ($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl $C_5$-$C_{12}$ aryls and the like;

wherein the compound includes the prodrug esters of the above compounds, and the acid-addition salts.

In one aspect, the cancer can be, for example, multiple myeloma and human prostate adenocarcinoma.

In another aspect, the compound can have the following structure:

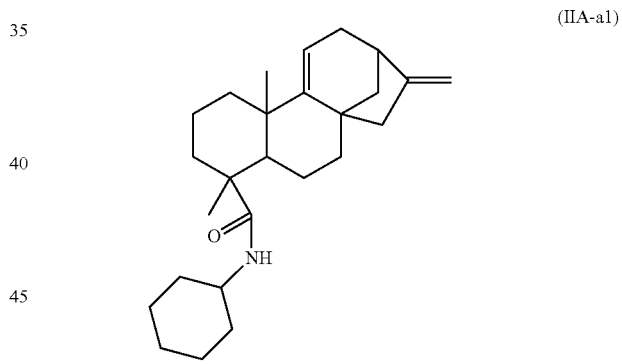

(IIA-a1)

including the prodrug esters and the acid-addition salts thereof.

Some other embodiments relate to compounds having the following chemical structure:

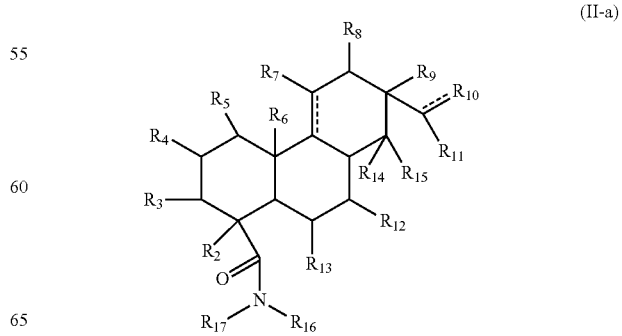

(II-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_8$, and $R_{11}$-$R_{13}$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{14}$ and $R_{15}$ are can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like; and $R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl $C_5$-$C_{12}$ aryls and the like;

wherein the compound includes the prodrug esters of the above compounds, and the acid-addition salts thereof.

In one aspect, $R_{16}$ can be, for example hydrogen and the like. In another aspect, $R_{17}$ can be, for example, cyclohexane and the like. In yet another aspect, $R_3$-$R_5$, $R_7$, $R_8$, $R_{11}$-$R_{15}$ can each be, for example, hydrogen and the like.

Other embodiments relate to compounds with the following structure:

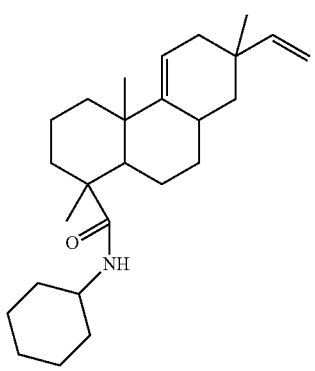

(II-a1)

and prodrug esters and acid-addition salts thereof.

Some embodiments relate to methods of treating a disease condition. The disease condition can be, for example, inflammation, tuberculous pleurisy, rheumatoid pleurisy, cancer, the reduction of fatigue associated with cancer or its treatment, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, chemotherapy related mucosal injury including and the like:

Examples of such methods can include contacting a compound to living tissue of said animal, wherein the compound has the following chemical structure:

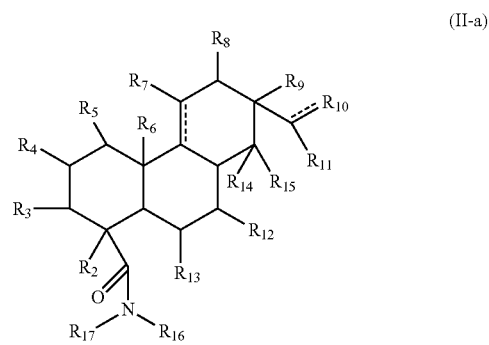

(II-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl and $C_5$-$C_{12}$ aryls;

and $R_9$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

wherein the compound includes the prodrug esters of the above compounds, and the acid-addition salts thereof.

In one aspect, the compound can have the following structure:

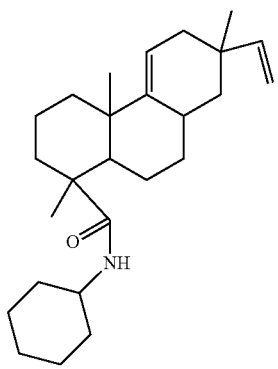

(II-a1)

and prodrug esters and acid-addition salts thereof.

Some other embodiments relate to methods of treating an inflammatory condition in an animal. For example, such methods can include contacting a compound to living tissue of said animal, wherein the compound has the following chemical structure:

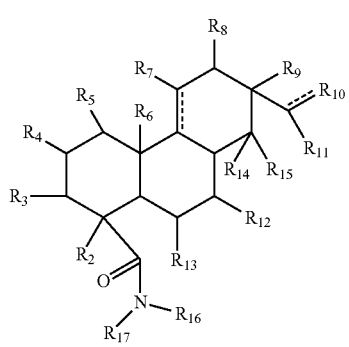

(II-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl, $C_5$-$C_{12}$ aryls and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

wherein the compound includes the prodrug esters and the acid-addition salts thereof.

In one aspect, the inflammatory condition can be, for example, tuberculous pleurisy, rheumatoid pleurisy, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, chemotherapy related mucosal injury and the like.

In another aspect, the compound can have the following structure:

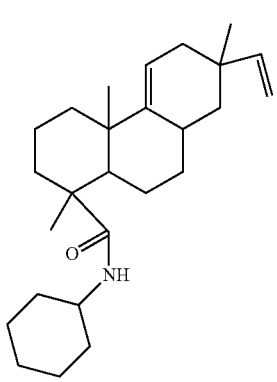

(II-a1)

and prodrug esters and the acid-addition salts thereof.

Another embodiment relates to methods of treating a cancer in an animal. Examples of the methods include contacting a compound to living tissue of said animal, wherein the compound has the following chemical structure:

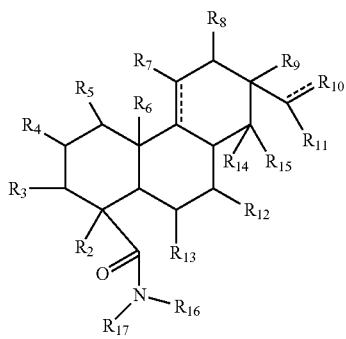

(II-a)

wherein:

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{16}$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_{17}$ can be, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl $C_5$-$C_{12}$ aryls and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_9$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ is selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

wherein the compound includes the prodrug esters of the above compounds, and the acid-addition salts.

In one aspect, the cancer can be, for example, multiple myeloma human prostate adenocarcinoma and the like.

In another aspect, the compound can have the following structure:

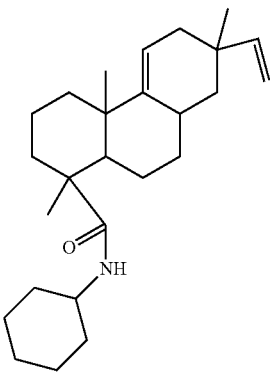

(II-a1)

including the prodrug esters and the acid-addition salts thereof.

Some embodiments relate to compounds having the following chemical structure:

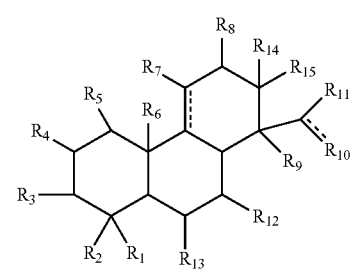

(IIB-b)

$R_1$ can be, for example:

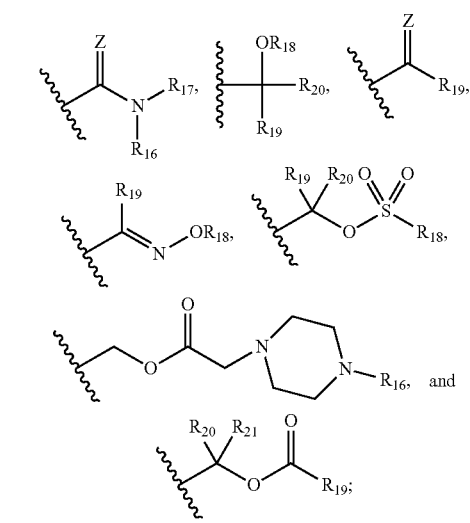

Z is O or S;

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$)

amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls, and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl, and the like;

$R_3$-$R_5$, $R_7$, $R_8$, and $R_{11}$-$R_{13}$ each can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl, and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{14}$ and $R_{15}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like; and $R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

wherein the compound also includes the prodrug esters of the above compounds, and the acid-addition salts thereof.

In some aspects, $R_{16}$ can be, for example, hydrogen. In some aspects, $R_3$-$R_5$, $R_7$, $R_8$, $R_{11}$-$R_{15}$ can each be, for example hydrogen.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

Some embodiments relate to compounds having the following structure:

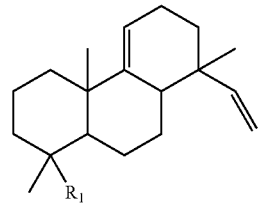

(IIB-b1)

$R_1$ can be, for example:

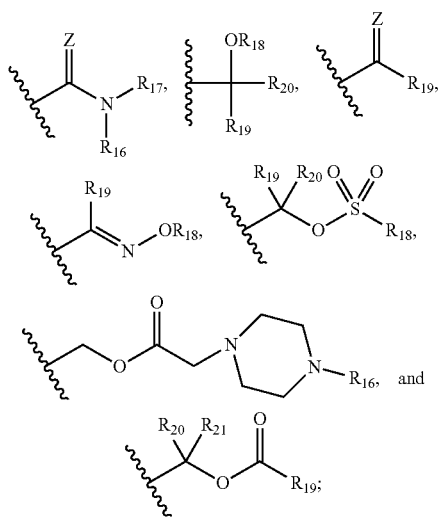

wherein Z is O or S;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

And prodrug esters and acid-addition salts thereof.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

Some embodiments relate to compounds having the structure:

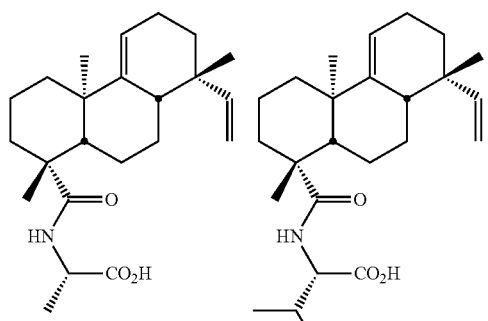

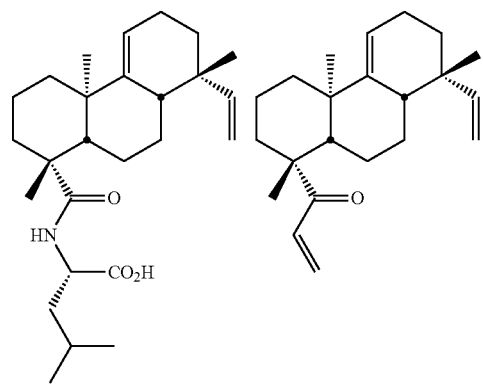

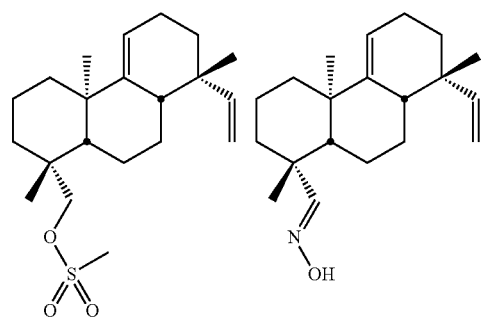

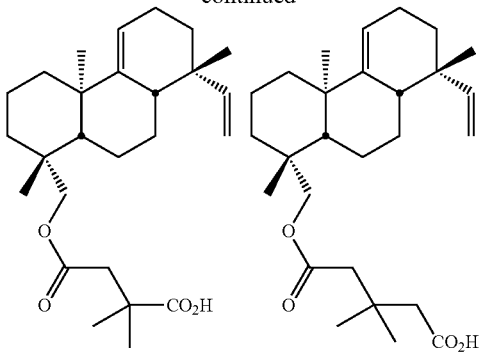

and prodrug esters and acid-addition salts thereof.

Some embodiments related to compounds having the following chemical structure:

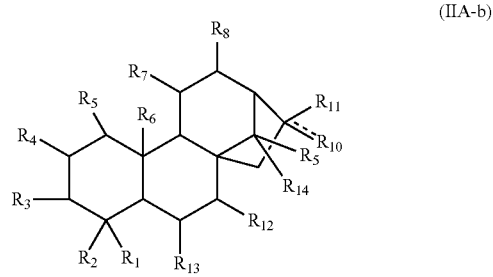

(IIA-b)

wherein $R_1$ is selected from the group consisting of:

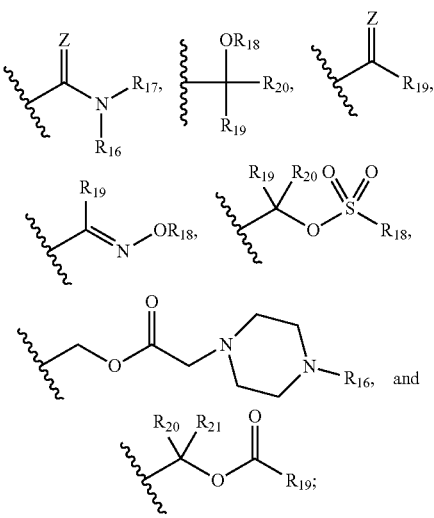

wherein Z is O or S;

If any $R_3$-$R_5$, $R_7$, $R_8$, $R_{11}$-$R_{13}$ is not hydrogen, $R_6$ is not methyl, $R_{10}$ is not $CH_2$, or if $R_{10}$ is $CH_2OH$ and $R_{11}$ is OH, $R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls and the like;

if all $R_3$-$R_5$, $R_7$, $R_8$, $R_{11}$-$R_{13}$ are hydrogen, $R_6$ is methyl, and $R_{10}$ is $CH_2$ or $CH_2OH$, then $R_2$ can be, for example, hydrogen, a halogen, $C_1$-$C_{12}$ carboxylic acids, $C_1$-$C_{12}$ acyl halides, $C_1$-$C_{12}$ acyl residues, $C_2$-$C_{12}$ esters, $C_1$-$C_{12}$ secondary amides, ($C_1$-$C_{12}$)($C_1$-$C_{12}$) tertiary amides, $C_2$-$C_{12}$ alcohol, ($C_1$-$C_{12}$)($C_1$-$C_{12}$) ethers, $C_2$-$C_{12}$ alkyls, $C_2$-$C_{12}$ substituted alkyls, $C_2$-$C_{12}$ alkenyl, $C_2$-$C_{12}$ substituted alkenyl and the like;

$R_3$, $R_4$, $R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

wherein the compound can include the prodrug esters of the above compounds, and the acid-addition salts thereof.

In one aspect, $R_{16}$ can be, for example, hydrogen and the like. In another aspect, $R_3$-$R_5$, $R_7$, $R_8$, $R_{11}$-$R_{15}$ can each be, for example hydrogen and the like.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

In another embodiment the compound can have the following structure:

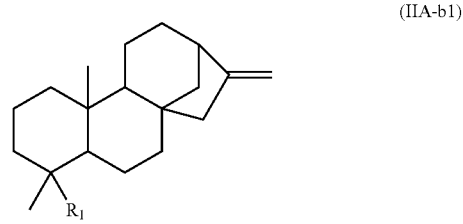

(IIA-b1)

wherein $R_1$ is selected from the group consisting of:

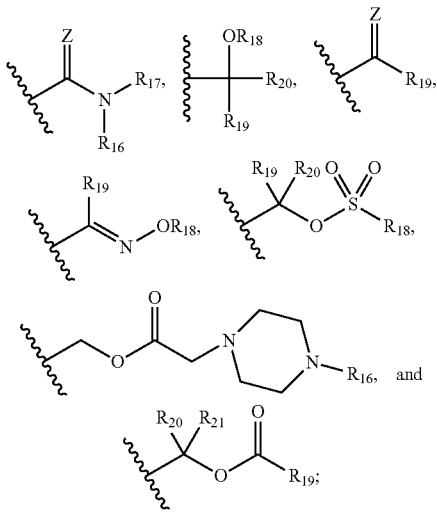

Wherein Z is O or S;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

and prodrug esters and acid-addition salts thereof.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

In some aspects the compound can be, for example:

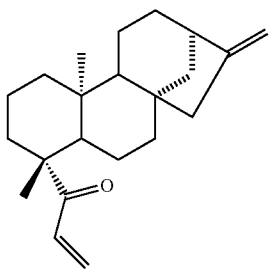

and prodrug esters and acid-addition salts thereof.

Some embodiments related to compounds having the following chemical structure:

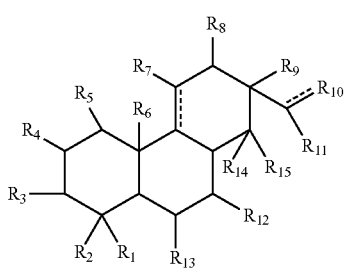
(II-b)

wherein $R_1$ is selected from the group consisting of:

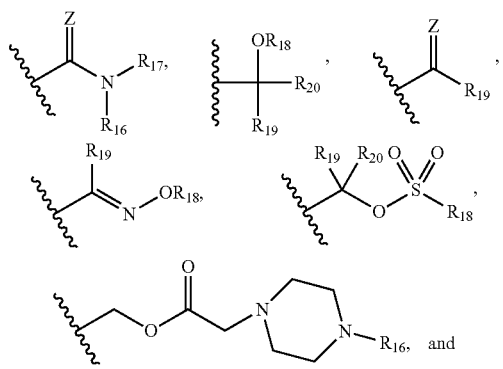

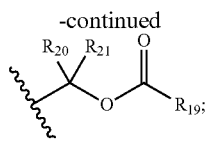

wherein Z is O or S;

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ is selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

wherein the compound includes the prodrug esters of the above compounds, and the acid-addition salts.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

Some embodiments relate to compounds having the structure:

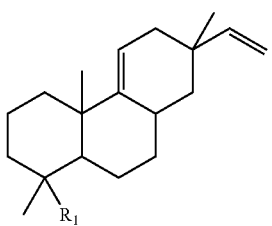

(II-b1)

wherein $R_1$ can be, for example:

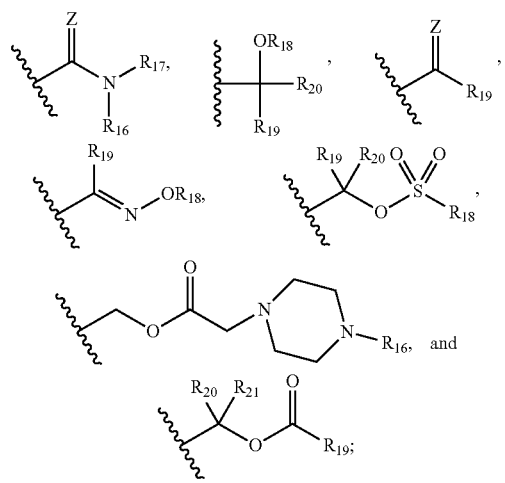

Wherein Z is O or S;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

and prodrug esters and acid-addition salts thereof.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

In some aspects the compound can be, for example:

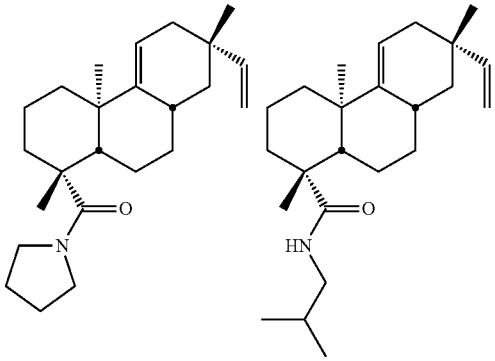

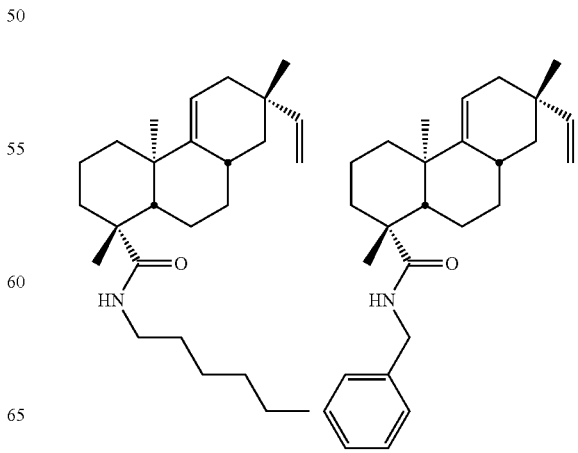

33
-continued
34
-continued
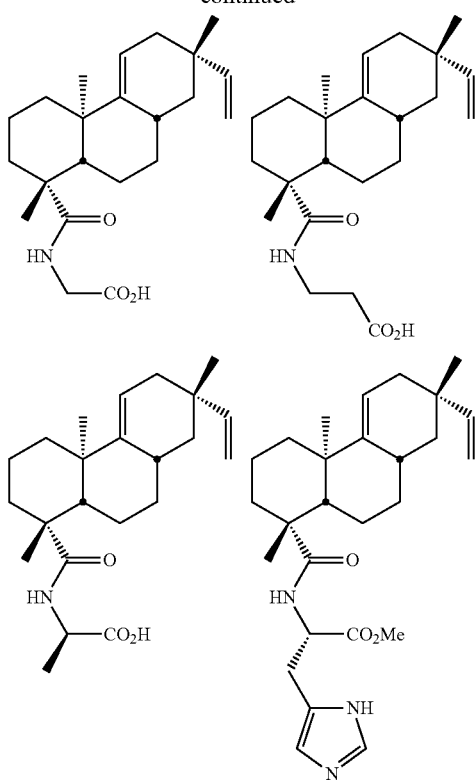
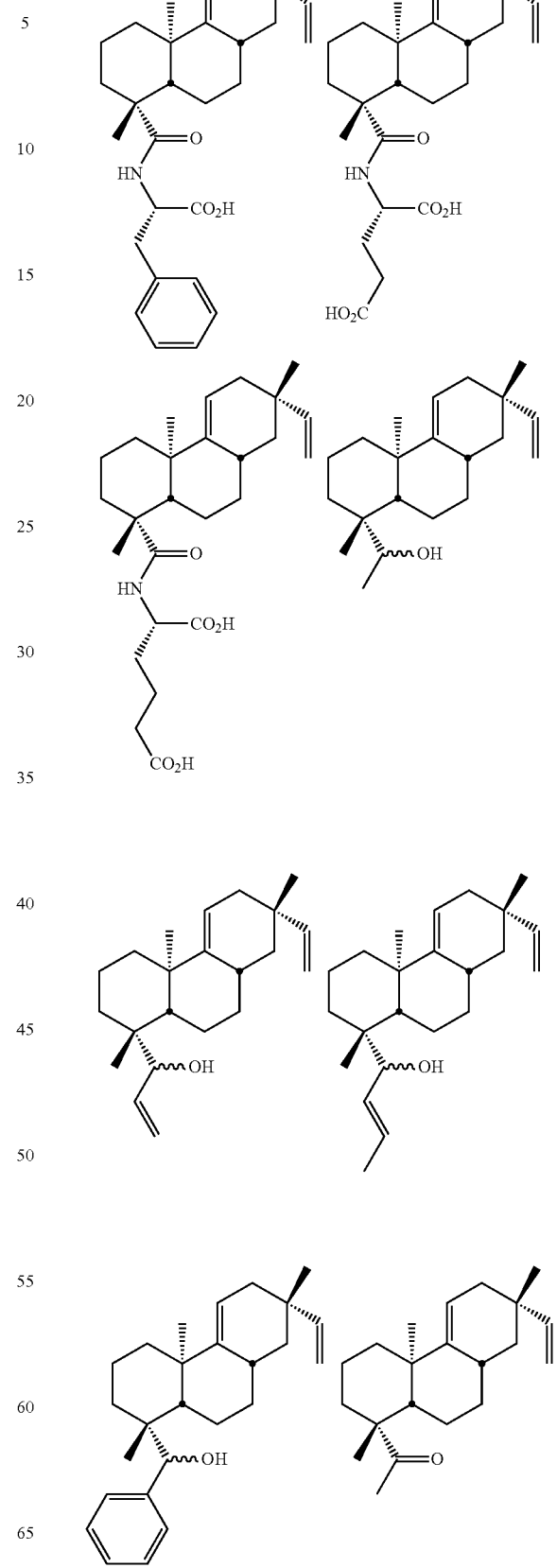

| 35 | 36 |
|---|---|
| -continued | -continued |
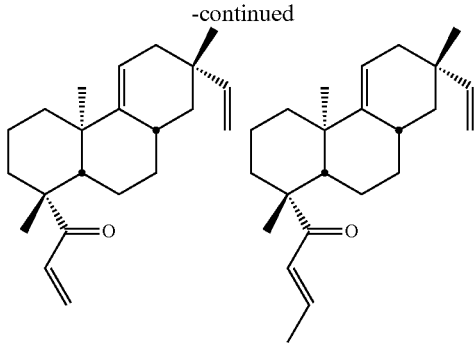 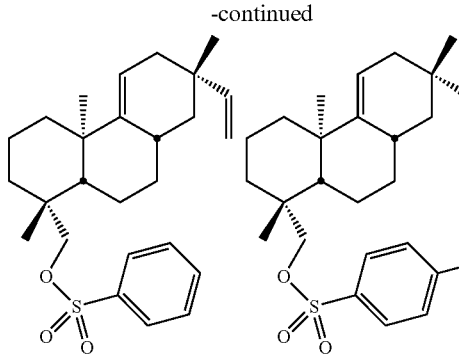
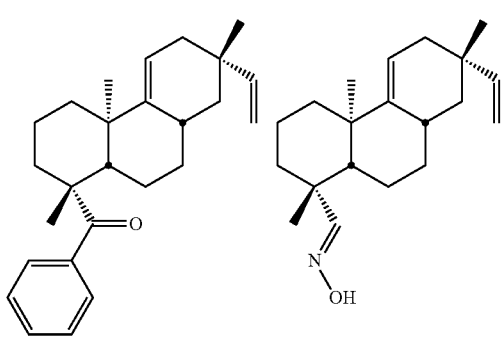 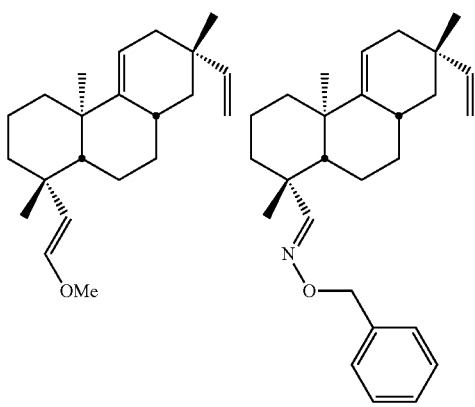
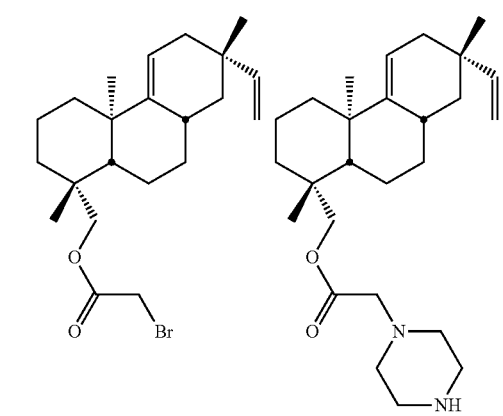 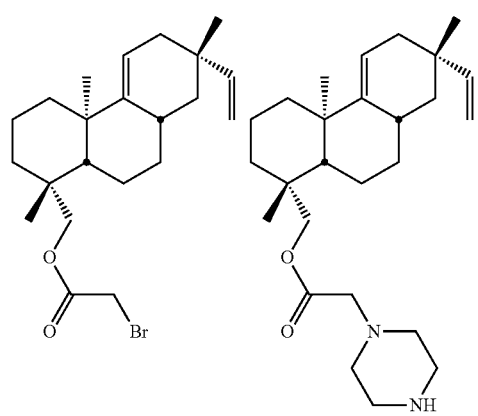
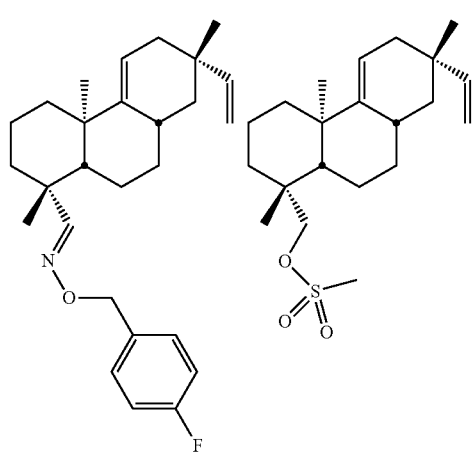 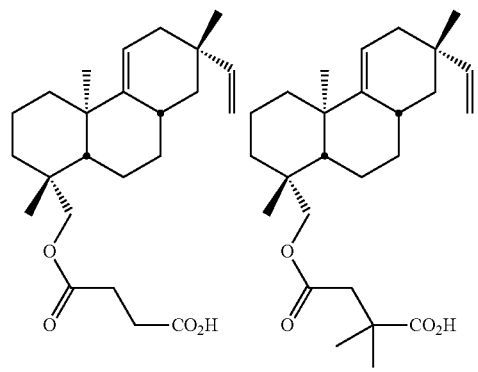

-continued

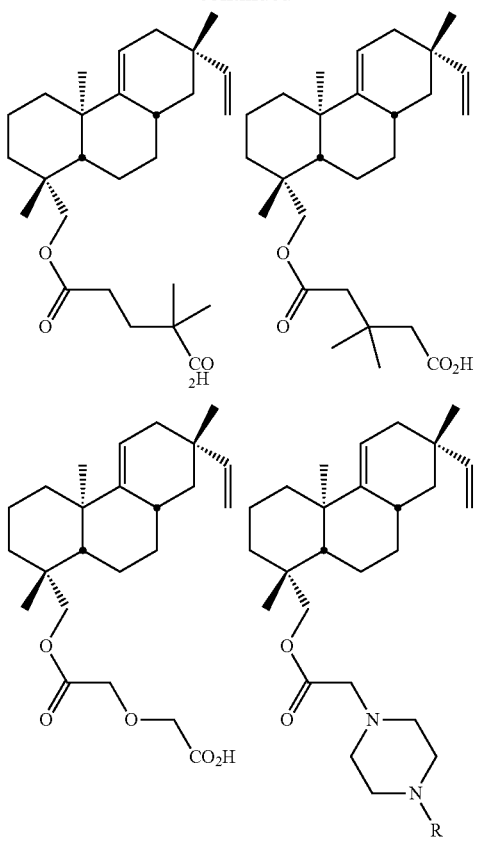

and prodrug esters and acid-addition salts thereof.

In some aspects the compound can be, for example, one or more of the following:

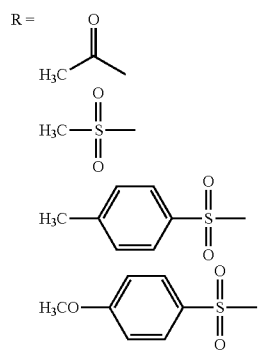

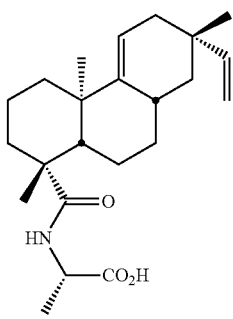
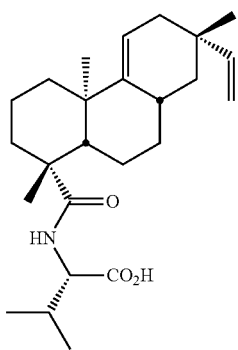

-continued

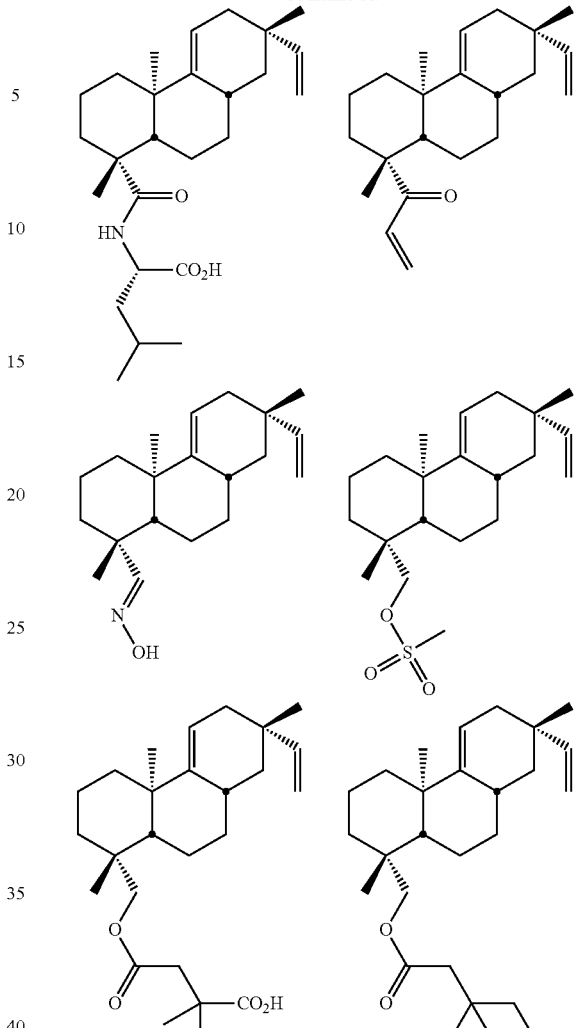

and prodrug esters and acid-addition salts thereof.

In some aspects the compound can be, for example:

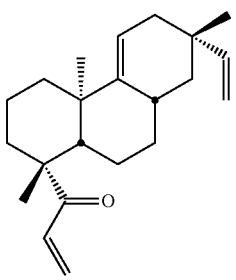

and prodrug esters and acid-addition salts thereof.

Still other embodiments relate to methods of treating a disease condition. The disease condition can be, for example, inflammation, tuberculous pleurisy, rheumatoid pleurisy, cancer, the reduction of fatigue associated with cancer or its treatment, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, chemotherapy related mucosal injury, and the like. The methods can include, for example, contacting a compound as described above and elsewhere herein, including for example, the compounds of formula II-b, IIA-b, and IIB-b to living tissue of said animal.

Still further embodiments relate to methods of treating an inflammatory condition in an animal. The methods can include contacting a compound to living tissue of said animal. The compound can be, for example, any one or more of the compounds of formula II-b, IIA-b, and IIB-b.

Some embodiments relate to methods of treating or inhibiting a neoplastic disease in an animal. The methods can include the step of administering to the animal, a therapeutically effective amount of any one or more of the compounds described above or elsewhere herein and pharmaceutically acceptable salts and pro-drug esters. For example, the neoplastic disease can be cancer, including for example any of the following: breast cancer, sarcoma, leukemia, ovarian cancer, uretal cancer, bladder cancer, prostate cancer, colon cancer, rectal cancer, stomach cancer, lung cancer, lymphoma, multiple myeloma, pancreatic cancer, bone cancer, liver cancer, kidney cancer, endocrine cancer, skin cancer, melanoma, angioma, and brain (including glioma) or central nervous system (CNS) cancer. The cancer can be a multiple myeloma, a colorectal carcinoma, a prostate carcinoma, a breast adenocarcinoma, a non-small cell lung carcinoma, other lung carcinomas, an ovarian carcinoma, a melanoma, and the like.

In some aspects, the cancer can be a drug resistant cancer. The drug-resistant cancer can display, for example, at least one of the following: Bcl-2-overexpression, elevated levels of the P-glycoprotein efflux pump, increased expression of the multidrug-resistance associated protein 1 encoded by MRP1, reduced drug uptake, alteration of the drug's target or increasing repair of drug-induced DNA damage, alteration of the apoptotic pathway or the activation of cytochrome P450 enzymes. The drug resistant cancer can be, for example, a multiple myeloma, a sarcoma, a lymphoma (including non-Hodgkin's), a leukemia, or any other resistant cancer. The cancer can be one that is innately resistant or that is resistant to a chemotherapeutic, a biologic, radiation or an immunotherapeutic, for example. The cancer can be resistant to rituximab, Gleevac, velcade, Gleveec, Revlimid, Avastin, Tarceva, Erbitux, bortezomib, thalidomide, and the like. Some additional specific examples of resistant lines include MES-SA cell line, its multidrug-resistant derivative MES-SA/Dx5, HL-60 and HL-60/MX2.

Some embodiments relate to use of the compounds as described herein to treat or inhibit neoplastic diseases, for example, to inhibit the growth of tumors, cancers and other neoplastic tissues. The methods of treatment disclosed herein can be employed with any patient suspected of carrying tumorous growths, cancers, or other neoplastic growths, either benign or malignant ("tumor" or "tumors" as used herein encompasses tumors, solid tumors, cancers, disseminated neoplastic cells and localized neoplastic growths). Examples of such growths include but are not limited to breast cancers; osteosarcomas, angiosarcomas, fibrosarcomas and other sarcomas; leukemias; sinus tumors; ovarian, uretal, bladder, prostate and other genitourinary cancers; colon, esophageal and stomach cancers and other gastrointestinal cancers; lung cancers; lymphomas; myelomas; pancreatic cancers; liver cancers; kidney cancers; endocrine cancers; skin cancers; melanomas; angiomas; and brain or central nervous system (CNS; glioma) cancers. In general, the tumor or growth to be treated can be any tumor or cancer, primary or secondary. Certain embodiments relate to methods of treating neoplastic diseases in animals. The method can include, for example, administering an effective amount of a compound to a patient in need thereof. Other embodiments relate to the use of compounds in the manufacture of a pharmaceutical or medicament for the treatment of a neoplastic disease.

The compounds or compositions can be administered or used in combination with treatments such as chemotherapy, radiation, and biologic therapies. Some embodiments relate to methods of treating disease by administering a compound or composition as disclosed herein in combination with a chemotherapeutic, radiation, an immunotherapeutic or a biologic therapy. In some embodiments the compounds can be administered or used with a chemotherapeutic agent. Examples of such chemotherapeutics include Alkaloids, alkylating agents, antibiotics, antimetabolites, enzymes, hormones, platinum compounds, immunotherapeutics (antibodies, T-cells, epitopes), BRMs, and the like. Examples include, Vincristine, Vinblastine, Vindesine, Paclitaxel (Taxol), Docetaxel, topoisomerase inhibitors epipodophyllotoxins (Etoposide (VP-16), Teniposide (VM-26)), Camptothecin, nitrogen mustards (cyclophosphamide), Nitrosoureas, Carmustine, lomustine, dacarbazine, hydroxymethylmelamine, thiotepa and mitocycin C, Dactinomycin (Actinomycin D), anthracycline antibiotics (Daunorubicin, Daunomycin, Cerubidine), Doxorubicin (Adriamycin), Idarubicin (Idamycin), Anthracenediones (Mitoxantrone), Bleomycin (Blenoxane), Plicamycin (Mithramycin, Antifolates (Methotrexate (Folex, Mexate)), purine antimetabolites (6-mercaptopurine (6-MP, Purinethol) and 6-thioguanine (6-TG). The two major anticancer drugs in this category are 6-mercaptopurine and 6-thioguanine, Chlorodeoxyadenosine and Pentostatin, Pentostatin (2'-deoxycoformycin), pyrimidine antagonists, fluoropyrimidines (5-fluorouracil(Adrucil), 5-fluorodeoxyuridine (FdUrd) (Floxuridine)), Cytosine Arabinoside (Cytosar, ara-C), Fludarabine, L-ASPARAGI-NASE, Hydroxyurea, glucocorticoids, antiestrogens, tamoxifen, nonsteroidal antiandrogens, flutamide, aromatase inhibitors Anastrozole(Arimidex), Cisplatin, 6-Mercaptopurine and Thioguanine, Methotrexate, Cytoxan, Cytarabine, L-Asparaginase, Steroids: Prednisone and Dexamethasone. Also, proteasome inhibitors such as bortezomib can be used in combination with the instant compounds, for example. Examples of biologics can include agents such as TRAIL antibodies to TRAIL, integrins such as alpha-V-beta-3 ($\alpha V\beta 3$) and/or other cytokine/growth factors that are involved in angiogenesis, VEGF, EGF, FGF and PDGF. In some aspects, the compounds can be conjugated to or delivered with an antibody. The above-described combination methods can be used to treat a variety of conditions, including cancer and neoplastic diseases, inflammation, and microbial infections.

Some embodiments relate to pharmaceutical compositions that include a compound as described above and elsewhere here, and pharmaceutically acceptable salts and pro-drug esters thereof. In some aspects the pharmaceutical composition can further include an anti-microbial agent. The compositions can be used in any of the methods described above and elsewhere herein.

Some embodiments relate to a compound of having the following chemical structure:

(SP-100)

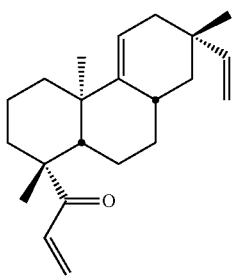

wherein the compound includes the prodrug esters of the above compound, and the acid-addition salts thereof.

Some other embodiments relate to a method of preparing a synthetic compound having the following chemical structure:

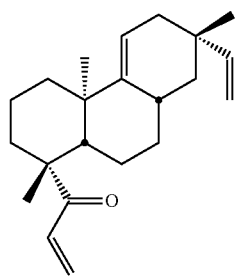

wherein the compound includes the prodrug esters of the above compound, and the acid-addition salts thereof, comprising the steps of:

performing a Diels-Alder reaction reacting a diene having two or more rings with a dienophile compound to yield a resultant compound having three or more rings; and yielding the synthetic compound.

Other embodiments relate to a method of purifying a compound having the following chemical structure:

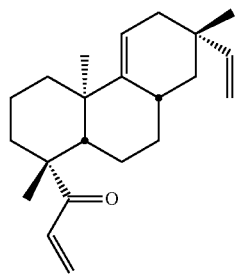

comprising a chromatography process.

Still other embodiments relate to a method of treating an inflammatory condition or a neoplatic condition in an animal comprising:

contacting a compound to living tissue of said animal, wherein the compound has the following chemical structure:

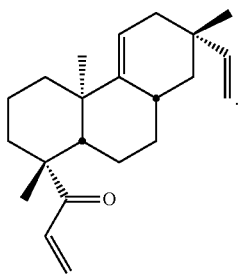

In some aspects, the inflammatory disease can be, for example, tuberculous pleurisy, rheumatoid pleurisy, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, or chemotherapy related mucosal injury.

In other aspects, the neoplastic disease is cancer.

In some embodiments, the cancer can be, for example, breast cancer, sarcoma, leukemia, ovarian cancer, uretal cancer, bladder cancer, prostate cancer, colon cancer, rectal cancer, stomach cancer, lung cancer, lymphoma, multiple myeloma, pancreatic cancer, liver cancer, kidney cancer, endocrine cancer, skin cancer, melanoma, angioma, and brain or central nervous system (CNS) cancer.

Some embodiments relate to a compound of having the following chemical structure:

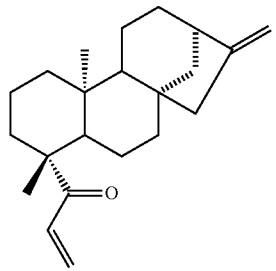

wherein the compound includes the prodrug esters of the above compound, and the acid-addition salts thereof.

Other embodiments relate to a method of preparing a synthetic compound having the following chemical structure:

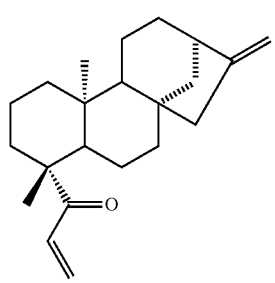

wherein the compound includes the prodrug esters of the above compound, and the acid-addition salts thereof, comprising the steps of:

performing a Diels-Alder reaction reacting a diene having two or more rings with a dienophile compound to yield a resultant compound having three or more rings; and yielding the synthetic compound.

Other embodiments relate to a method of purifying a compound having the following chemical structure:

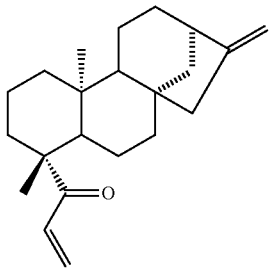

comprising a chromatography process.

Some embodiments relate to a method of treating an inflammatory condition or a neoplastic condition in an animal comprising:

contacting a compound to living tissue of said animal, wherein the compound has the following chemical structure:

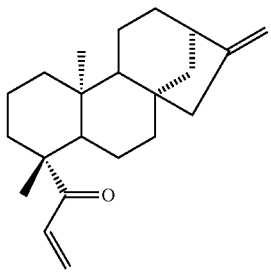

In some aspects, the inflammatory disease can be, for example, tuberculous pleurisy, rheumatoid pleurisy, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, and chemotherapy related mucosal injury.

In some embodiments, the neoplastic disease is cancer.

In some aspects, the cancer can be, for example, breast cancer, sarcoma, leukemia, ovarian cancer, uretal cancer, bladder cancer, prostate cancer, colon cancer, rectal cancer, stomach cancer, lung cancer, lymphoma, multiple myeloma, pancreatic cancer, liver cancer, kidney cancer, endocrine cancer, skin cancer, melanoma, angioma, and brain or central nervous system (CNS) cancer.

Some embodiments relate to the use of a compound with the following chemical structure:

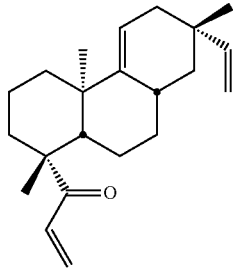

in the manufacture of a medicament for treating a disease selected from the group consisting of: tuberculous pleurisy, rheumatoid pleurisy, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, and chemotherapy related mucosal injury, breast cancer, sarcoma, leukemia, ovarian cancer, uretal cancer, bladder cancer, prostate cancer, colon cancer, rectal cancer, stomach cancer, lung cancer, lymphoma, multiple myeloma, pancreatic cancer, liver cancer, kidney cancer, endocrine cancer, skin cancer, melanoma, angioma, and brain or central nervous system (CNS) cancer.

Other embodiments relate to the use of a compound with the following chemical structure:

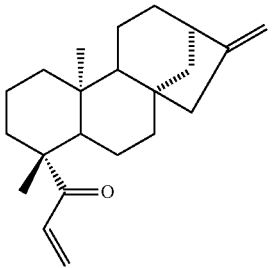

in the manufacture of a medicament for treating a disease selected from the group consisting of: tuberculous pleurisy, rheumatoid pleurisy, cardiovascular disease, skin redness, diabetes, transplant rejection, otitis media (inner ear infection), sinusitis and viral infection, septic shock, transplantation, graft-vs-host disease, ischemia/reperfusion injury, Graves' ophthalmopathy, Hashimoto's thyroiditis, thryoid-associated ophthalmopathy, nodular goiter, herpetic stromal keratitis, microbial keratitis, peripheral ulcerative keratitis, Behcet's disease, uveitis, vitreoretinal proliferative disease, rabies virus ocular disease, Vogt-Koyanagi-Harada's disease, retinopathy, retinal laser photocoagulation, acute retinal necrosis syndrome, systemic vasculitis, recurrent aphthous stomatitis, neovascular glaucoma, eye infections, ocular allergic diseases, retinal detachment, optic neuritis, multiple sclerosis, systemic sclerosis, hereditary retinal degeneration, trachoma, autoimmune diseases, and chemotherapy related mucosal injury, breast cancer, sarcoma, leukemia, ovarian cancer, uretal cancer, bladder cancer, prostate cancer, colon cancer, rectal cancer, stomach cancer, lung cancer, lymphoma, multiple myeloma, pancreatic cancer, liver cancer, kidney cancer, endocrine cancer, skin cancer, melanoma, angioma, and brain or central nervous system (CNS) cancer.

Still other embodiments relate to a pharmaceutical composition comprising a pharmaceutically acceptable carrier and at least one compound selected from:

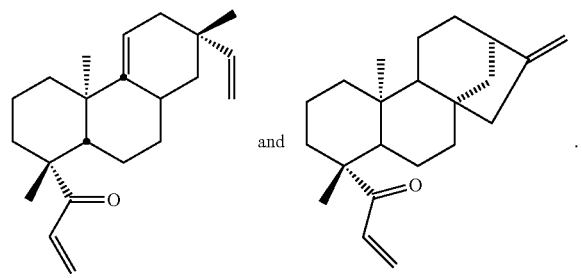

and

BRIEF DESCRIPTION OF THE FIGURE

Certain preferred embodiments are illustrated in the Figures. The Figures merely illustrate certain preferred embodiments of the invention and/or certain preferred methods of making and/or of using the invention. The Figures are not intended to limit the scope of the invention described and claimed herein.

FIG. 17 depicts a summary of the syntheses of certain compounds, and the physical properties of these compounds. Compounds TTL1, TT12, TTL3, and TTL4 are defined as depicted in this Figure.

DETAILED DESCRIPTION OF THE PREFERRED EMBODIMENTS

Figure 1:
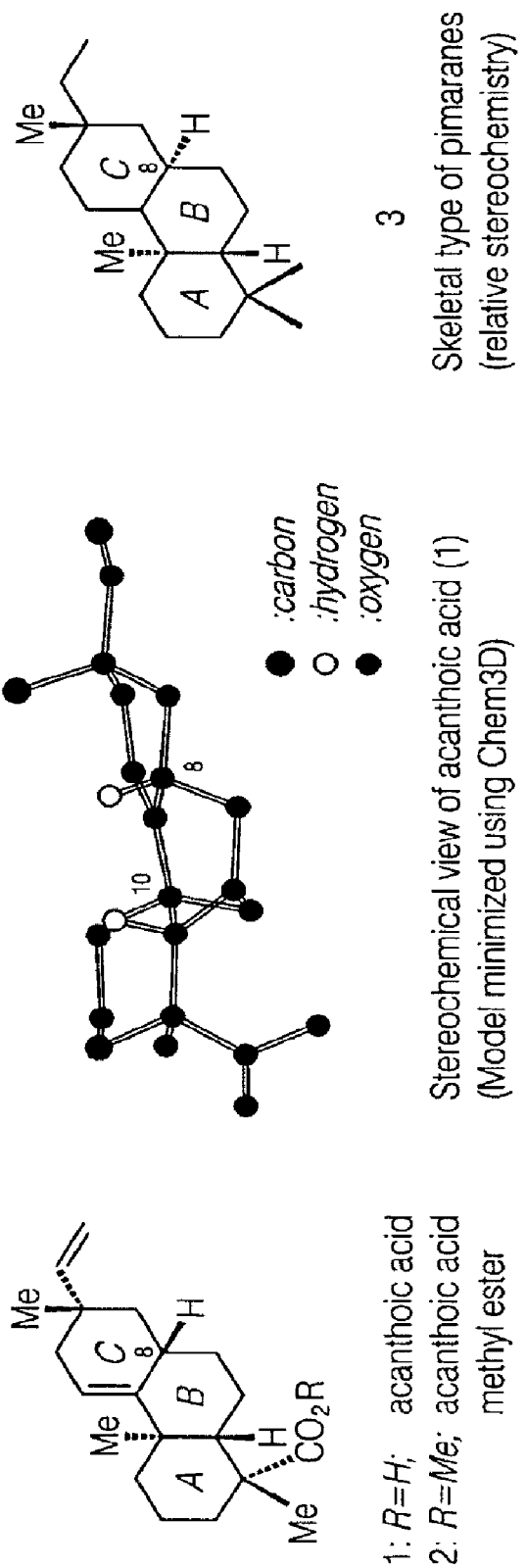
FIG. 1 depicts the structure of acanthoic acid and acanthoic acid methyl ester, a stereo chemical view of acanthoic acid, and a skeletal-type view of certain compounds of the invention.

Certain disclosed compounds have the chemical structure shown in Formula (II).

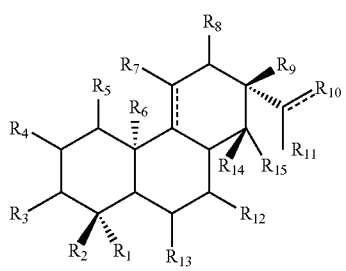

(II)

The R-groups of the compound of Formula (II) may be selected in the following manner. In the event that (1) any $R_3$-$R_5$, $R_7$, $R_8$, $R_{11}$-$R_{13}$ is not hydrogen, (2) $R_2$, $R_6$ or $R_9$ is not methyl, or (3) $R_{10}$ is not $CH_2$, $R_1$ is selected from the group consisting of hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, primary amide, $C_1$-$C_{12}$ secondary amides, ($C_1$-$C_{12}$)($C_1$-$C_{12}$) tertiary amides, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, and $C_5$-$C_{12}$ aryls. Under these conditions, $R_1$ is preferably selected from COOH, $C_1$-$C_{12}$ carboxylic acids, $C_1$-$C_{12}$ acyl halides, $C_1$-$C_{12}$ acyl residues, and $C_1$-$C_{12}$ esters, and is most preferably selected from $C_1$-$C_{12}$ secondary amides, COOH and the $C_1$-$C_6$ esters.

However, in the event that (1) all $R_3$-$R_5$, $R_7$, $R_8$, $R_{11}$-$R_{13}$ are hydrogen, (2) $R_2$, $R_6$, and $R_9$ are each methyl, and (3) $R_{10}$ is $CH_2$, $R_1$ is selected from $R_1$ is selected from hydrogen, a halogen, $C_1$-$C_{12}$ carboxylic acids, $C_1$-$C_{12}$ acyl halides, $C_1$-$C_{12}$ acyl residues, $C_2$-$C_{12}$ esters, primary amide, $C_2$-$C_{12}$ secondary amides, ($C_1$-$C_{12}$)($C_1$-$C_{12}$) tertiary amides, $C_2$-$C_{12}$ alcohols, ($C_1$-$C_{12}$)($C_1$-$C_{12}$) ethers other than methyl-acetyl ether, $C_2$-$C_{12}$ alkyls, $C_1$-$C_{12}$ substituted alkyls, $C_2$-$C_{12}$ alkenyls, $C_2$-$C_{12}$ substituted alkenyls, and $C_2$-$C_{12}$ aryls. Under these conditions, $R_1$ is preferably selected from $C_1$-$C_{12}$ carboxylic acids, $C_1$-$C_{12}$ acyl halides, $C_1$-$C_{12}$ acyl residues, and $C_2$-$C_{12}$ esters, and is most preferably a $C_4$-$C_8$ ester.

$R_2$ and $R_9$ are each separately selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ acyl, $C_1$-$C_{12}$ alcohol, and $C_5$-$C_{12}$ aryl. Preferably, $R_2$ and $R_9$ are each separately selected from the alkyl and alkenyl residues. Most preferably, $R_2$ and $R_9$ are each methyl residues, although one of $R_2$ and $R_9$ may be methyl and the other not methyl in preferred embodiments of the compound of Formula (II).

$R_3$, $R_4$, $R_5$, $R_7$, $R_8$, and $R_{11}$-$R_{13}$ are each separately selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, and $C_5$-$C_{12}$ aryl. Preferably, $R_3$, $R_4$, $R_5$, $R_7$, $R_8$, and $R_{11}$-$R_{13}$ are each hydrogen or a $C_1$-$C_6$ alkyl, and most preferably $R_3$, $R_4$, $R_5$, $R_7$, $R_8$, and $R_{11}$-$R_{13}$ are each hydrogen. Nevertheless, any one or several of $R_3$, $R_4$, $R_5$, $R_7$, $R_8$, and $R_{11}$-$R_{13}$ may be hydrogen, while the others may be not hydrogen, in preferred embodiments of the compound of Formula (II).

$R_6$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, and $C_2$-$C_{12}$ alkynyl. Preferably, $R_6$ is selected from hydrogen, a halogen, $C_1$-$C_6$ alkyl. More preferably, $R_6$ is a $C_1$-$C_6$ alkyl, and most preferably, $R_6$ is methyl.

$R_{10}$ is selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, and $C_5$-$C_{12}$ aryl. The bond linking $R_{10}$ to the remainder of the compound of Formula (II) is preferably a C—C double bond, but may be a C—C single bond, a C—H single bond, or a heteroatomic single bond. Preferably, $R_{10}$ is $CH_2$ or $CH_2R'$ wherein R' is a $C_1$-$C_6$ alkyl, or a $C_1$-$C_6$ substituted alkyl. Most preferably, $R_{10}$ is $CH_2$.

$R_{14}$ and $R_{10}$ are separately selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, and $C_5$-$C_6$ aryl, with hydrogen and $C_1$-$C_6$ alkyl, $C_1$-$C_6$ substituted alkyl most preferred, and preferably, both $R_1$ and $R_2$ are not simultaneously methyl.

It also will be appreciated that the various R groups, most particularly $R_3$, $R_4$, $R_5$, $R_7$, $R_8$, and $R_{11}$-$R_{13}$, may be chosen such that cyclic system are formed. For example, both $R_{13}$ and $R_{12}$ may be ethylene moieties and may include a covalent C—C linkage between their respective terminal carbons, generating an additional six-membered ring in the compound of Formula (II). As a further example, bis-cyclic rings may be formed by choosing appropriate chemical species for the various R groups, most particularly $R_3$, $R_4$, $R_5$, $R_7$, $R_8$, and $R_{11}$-$R_{13}$, of Formula (II).

Some embodiments related to compounds having the following chemical structure:

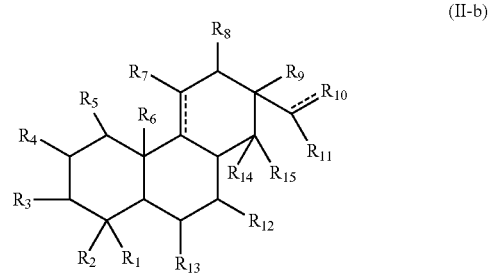

(II-b)

wherein $R_1$ is selected from the group consisting of:

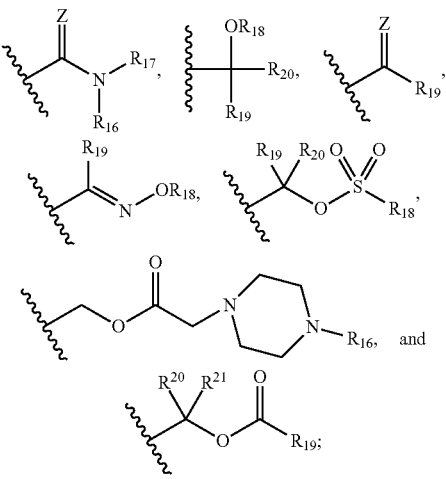

wherein Z is O or S;

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl and the like;

$R_3$-$R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ is selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like; and $R_{14}$ and $R_{15}$ can each be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

wherein the compound includes the prodrug esters of the above compounds, and the acid-addition salts.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

Some embodiments relate to compounds having the structure:

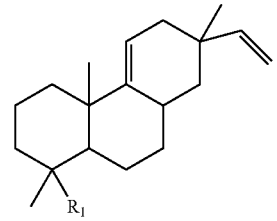

(II-b1)

wherein $R_1$ can be, for example:

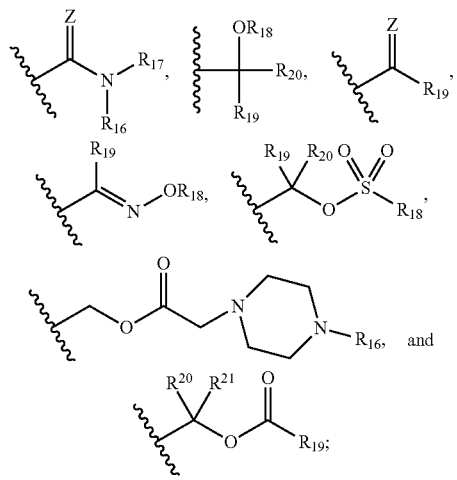

Wherein Z is O or S;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

and prodrug esters and acid-addition salts thereof.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

Certain disclosed compounds have the structure shown in Formula (IIA).

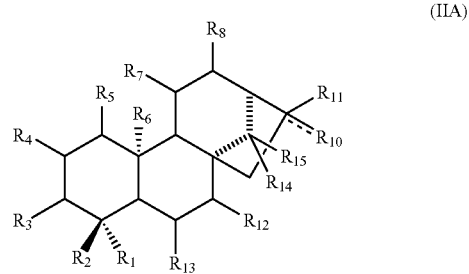

(IIA)

The R-groups of the compound of Formula (IIA) may be selected in the following manner. In the event that if any $R_3$-$R_5$, $R_7$, $R_8$, $R_{11}$-$R_{13}$ is not hydrogen, $R_2$ or $R_6$ is not methyl, $R_{10}$ is not $CH_2$, or if it is not true that $R_{10}$ is $CH_2OH$ and $R_{11}$ is OH, $R_1$ is selected from the group consisting of hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, primary amide, $C_1$-$C_{12}$ secondary amides, ($C_1$-$C_{12}$)($C_1$-$C_{12}$) tertiary amides, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls. Under these conditions, $R_1$ is preferably selected from COOH, $C_1$-$C_{12}$ carboxylic acids, $C_1$-$C_{12}$ acyl halides, $C_1$-$C_{12}$ acyl residues, and $C_1$-$C_{12}$ esters, and is most preferably selected from COOH and the $C_1$-$C_6$ esters.

In the event that all $R_3$-$R_5$, $R_7$, $R_8$, $R_{11}$-$R_{13}$ are hydrogen, $R_2$ and $R_6$ are each methyl, and $R_{10}$ is $CH_2$ or $CH_2OH$, $R_1$ is selected from hydrogen, a halogen, $C_1$-$C_{12}$ carboxylic acids, $C_1$-$C_{12}$ acyl halides, $C_1$-$C_{12}$ acyl residues, $C_2$-$C_{12}$ esters, $C_1$-$C_{12}$ secondary amides, ($C_1$-$C_{12}$)($C_1$-$C_{12}$) tertiary amides, $C_2$-$C_{12}$ alcohol, ($C_1$-$C_{12}$)($C_1$-$C_{12}$) ethers, $C_2$-$C_{12}$ alkyls, $C_2$-$C_{12}$ substituted alkyls, $C_2$-$C_{12}$ alkenyl, and $C_2$-$C_{12}$ substituted alkenyl. Under these conditions, $R_1$ is preferably selected from $C_1$-$C_{12}$ carboxylic acids, $C_1$-$C_{12}$ acyl halides, $C_1$-$C_{12}$ acyl residues, and $C_2$-$C_{12}$ esters, and is most preferably a $C_4$-$C_8$ ester.

$R_2$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ acyl, $C_1$-$C_{12}$ alcohol, and $C_5$-$C_{12}$ aryl. Preferably, $R_2$ and $R_9$ are each separately selected from the alkyl and alkenyl residues. Most preferably, $R_2$ and $R_9$ are each methyl residues, although one of $R_2$ and $R_9$ may be methyl and the other not methyl in preferred embodiments of the compound of Formula (IIA).

$R_3$, $R_4$, $R_5$, $R_7$, $R_8$, and $R_{11}$-$R_{13}$ are each separately selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, and $C_5$-$C_{12}$ aryl. Preferably, $R_3$, $R_4$, $R_5$, $R_7$, $R_8$, and $R_{11}$-$R_{13}$ are each hydrogen or a $C_1$-$C_6$ alkyl, and most preferably $R_3$, $R_4$, $R_5$, $R_7$, $R_8$, and $R_{11}$-$R_{13}$ are each hydrogen. Nevertheless, any one or several of $R_3$, $R_4$, $R_5$, $R_7$, $R_8$, and $R_{11}$-$R_{13}$ may be hydrogen, while the others may be not hydrogen, in preferred embodiments of the compound of Formula (IIA).

$R_6$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, and $C_2$-$C_{12}$ alkynyl. Preferably, $R_6$ is selected from hydrogen, a halogen, $C_1$-$C_6$ alkyl. More preferably, $R_6$ is a $C_1$-$C_6$ alkyl, and most preferably, $R_6$ is methyl.

$R_{10}$ is selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, and $C_5$-$C_{12}$ aryl. The bond linking $R_{10}$ to the remainder of the compound of Formula (IIA) is preferably a C—C double bond, but may be a C—C single bond, a C—H single bond, or a heteroatomic single bond. Preferably, $R_{10}$ is $CH_2$ or $CH_2R'$ wherein R' is a $C_1$-$C_6$ alkyl, or a $C_1$-$C_6$ substituted alkyl. Most preferably, $R_{10}$ is $CH_2$, and preferably, both $R_1$ and $R_2$ are not simultaneously methyl.

It also will be appreciated that the various R groups, most particularly $R_3$, $R_4$, $R_5$, $R_7$, $R_8$, and $R_{11}$-$R_{13}$, may be chosen such that cyclic system are formed. For example, both $R_{13}$ and $R_{12}$ may be ethylene moieties and may include a covalent C—C linkage between their respective terminal carbons, generating an additional six-membered ring in the compound of Formula (IIA). As a further example, bis-cyclic rings may be formed by choosing appropriate chemical species for the various R groups, most particularly $R_3$, $R_4$, $R_5$, $R_7$, $R_8$, and $R_{11}$-$R_{13}$ of Formula (IIA).

Some embodiments related to compounds having the following chemical structure:

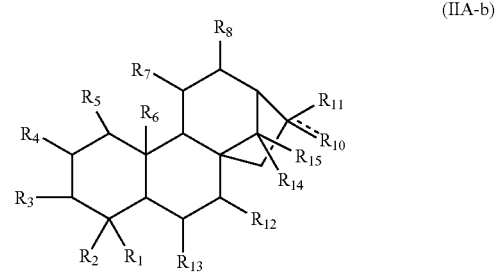

(IIA-b)

wherein $R_1$ is selected from the group consisting of:

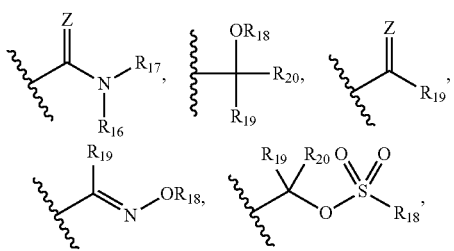

-continued

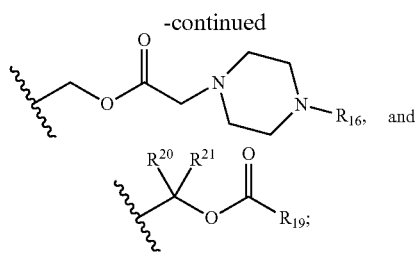

wherein Z is O or S;

If any $R_3$-$R_5$, $R_7$, $R_8$, $R_{11}$-$R_{13}$ is not hydrogen, $R_6$ is not methyl, $R_{10}$ is not $CH_2$, or if $R_{10}$ is $CH_2OH$ and $R_{11}$ is OH, $R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})(C_1$-$C_{12})$ tertiary amides, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls and the like;

if all $R_3$-$R_5$, $R_7$, $R_8$, $R_{11}$-$R_{13}$ are hydrogen, $R_6$ is methyl, and $R_{10}$ is $CH_2$ or $CH_2OH$, then $R_2$ can be, for example, hydrogen, a halogen, $C_1$-$C_{12}$ carboxylic acids, $C_1$-$C_{12}$ acyl halides, $C_1$-$C_{12}$ acyl residues, $C_2$-$C_{12}$ esters, $C_1$-$C_{12}$ secondary amides, $(C_1$-$C_{12})(C_1$-$C_{12})$ tertiary amides, $C_2$-$C_{12}$ alcohol, $(C_1$-$C_{12})(C_1$-$C_{12})$ ethers, $C_2$-$C_{12}$ alkyls, $C_2$-$C_{12}$ substituted alkyls, $C_2$-$C_{12}$ alkenyl, $C_2$-$C_{12}$ substituted alkenyl and the like;

$R_3$, $R_4$, $R_5$, $R_7$, $R_8$, and $R_{11}$-$R_{13}$ can each be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

wherein the compound can include the prodrug esters of the above compounds, and the acid-addition salts thereof.

In one aspect, $R_{16}$ can be, for example, hydrogen and the like. In another aspect, $R_3$-$R_5$, $R_7$, $R_8$, $R_{11}$-$R_{15}$ can each be, for example hydrogen and the like.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

In another embodiment the compound can have the following structure:

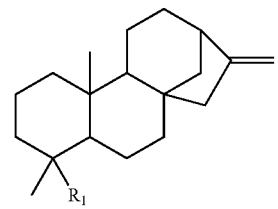

(IIA-b1)

wherein $R_1$ is selected from the group consisting of:

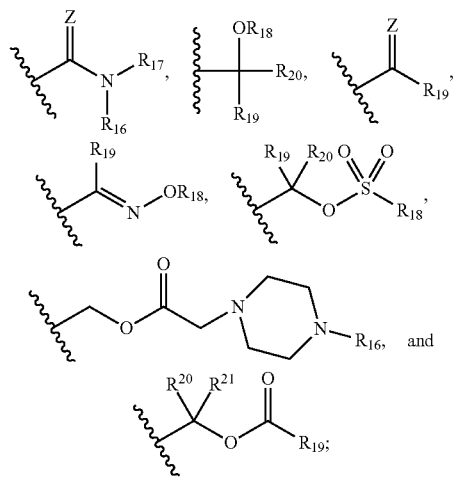

Wherein Z is O or S;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

and prodrug esters and acid-addition salts thereof.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

Certain disclosed compounds, including compounds herein designated TTL1, TTL2, TTL3, and TTL4 have the chemical structure described in Formula (IIB).

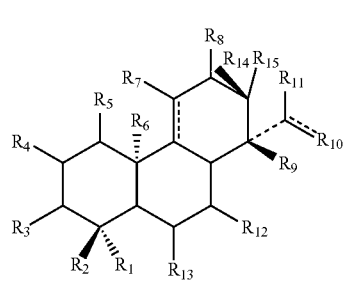

(IIB)

The R-groups of the compound of Formula (IIB) may be selected in the following manner: $R_1$ is selected from the group consisting of hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, primary amide, $C_1$-$C_{12}$ secondary amides, ($C_1$-$C_{12}$)($C_1$-$C_{12}$) tertiary amides, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, and $C_5$-$C_{12}$ aryls. Under these conditions, $R_1$ is preferably selected from COOH, $C_1$-$C_{12}$ carboxylic acids, $C_1$-$C_{12}$ acyl halides, $C_1$-$C_{12}$ acyl residues, and $C_1$-$C_{12}$ esters, and is most preferably selected from COOH and the $C_1$-$C_6$ esters.

$R_2$ and $R_9$ are each separately selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ acyl, $C_1$-$C_{12}$ alcohol, and $C_5$-$C_{12}$ aryl. Preferably, $R_2$ and $R_9$ are each separately selected from the alkyl and alkenyl residues. Most preferably, $R_2$ and $R_9$ are each methyl residues, although one of $R_2$ and $R_9$ may be methyl and the other not methyl in preferred embodiments of the compound of Formula (IIB).

$R_3$, $R_4$, $R_5$, $R_7$, $R_8$, and $R_{11}$-$R_{13}$ are each separately selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, and $C_5$-$C_{12}$ aryl. Preferably, $R_3$, $R_4$, $R_5$, $R_7$, $R_8$, and $R_{11}$-$R_{13}$ are each hydrogen or a $C_1$-$C_6$ alkyl, and most preferably $R_3$, $R_4$, $R_5$, $R_7$, $R_8$, and $R_{11}$-$R_{13}$ are each hydrogen. Nevertheless, any one or several of $R_3$, $R_4$, $R_5$, $R_7$, $R_8$, and $R_{11}$-$R_{13}$ may be hydrogen, while the others may be not hydrogen, in preferred embodiments of the compound of Formula (IIB).

$R_6$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, and $C_2$-$C_{12}$ alkynyl. Preferably, $R_6$ is selected from hydrogen, a halogen, $C_1$-$C_6$ alkyl. More preferably, $R_6$ is a $C_1$-$C_6$ alkyl, and most preferably, $R_6$ is methyl.

$R_{10}$ is selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, and $C_5$-$C_{12}$ aryl. The bond linking $R_{10}$ to the remainder of the compound of Formula (II) is preferably a C—C double bond, but may be a C—C single bond, a C—H single bond, or a heteroatomic single bond. Preferably, $R_{10}$ is $CH_2$ or $CH_2R'$ wherein R' is a $C_1$-$C_6$ alkyl, or a $C_1$-$C_6$ substituted alkyl. Most preferably, $R_{10}$ is $CH_2$, and preferably, both $R_1$ and $R_2$ are not simultaneously methyl.

It also will be appreciated that the various R groups, most particularly $R_3$, $R_4$, $R_5$, $R_7$, $R_8$, and $R_{11}$-$R_{13}$, may be chosen such that cyclic system are formed. For example, both $R_{13}$ and $R_{12}$ may be ethylene moieties and may include a covalent C—C linkage between their respective terminal carbons, generating an additional six-membered ring in the compound of Formula (IIB). As a further example, bis-cyclic rings may be formed by choosing appropriate chemical species for the various R groups, most particularly $R_3$, $R_4$, $R_5$, $R_7$, $R_8$, and $R_{11}$-$R_{13}$ of Formula (IIB).

Certain disclosed compounds, including preferred formula (IIB-A1), have the chemical structure shown in the following structure:

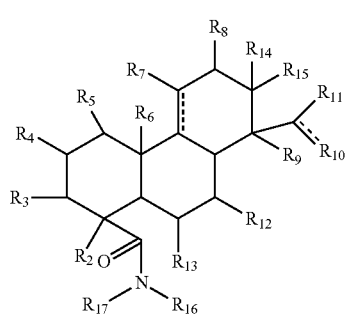

(IIB-a1)

wherein:

$R_2$ is selected from the group consisting of hydrogen, a halogen, —COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$) ($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, and $C_5$-$C_{12}$ aryls;

$R_{16}$ is selected from the group consisting of hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})(C_1$-$C_{12})$ tertiary amides, $(C_1$-$C_{12})$ cyclic amides, $(C_1$-$C_{12})$ amines, $C_1$-$C_{12}$ alcohols, $(C_1$-$C_{12})$ $(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls, and $C_5$-$C_{12}$ aryls;

$R_{17}$ is a cyclic moiety including, for example, $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl and $C_5$-$C_{12}$ aryls; wherein $R_{16}$ and $R_{17}$ can form a 3-12 membered ring structure;

$R_9$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, and $C_5$-$C_{12}$ aryl;

$R_3$-$R_5$, $R_7$, $R_8$, and $R_{11}$-$R_{13}$ are each separately selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, and $C_5$-$C_{12}$ aryl;

$R_6$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, and $C_2$-$C_{12}$ alkynyl;

$R_{10}$ is selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, and $C_5$-$C_{12}$ aryl;

$R_{14}$ and $R_{15}$ are separately selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, and $C_5$-$C_6$ aryl; and wherein the compound includes prodrug esters and the acid-addition salts, and may be in any of the various possible stereoforms, including racemates and optically active enantiomers or diasteriomers.

Some embodiments relate to compounds of Formula IIB-b, prodrugs and salts thereof, wherein formula II-b has the following structure:

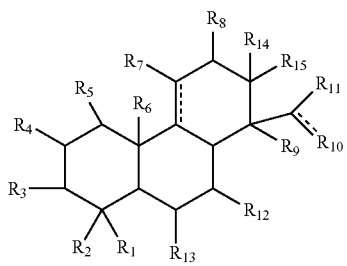

(IIB-b)

$R_1$ can be, for example:

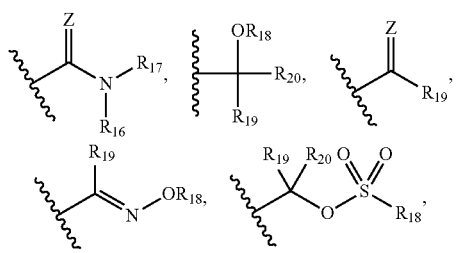

-continued

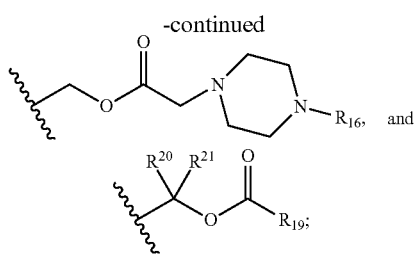

Z is O or S;

$R_2$ can be, for example, hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, $(C_1$-$C_{12})$ $(C_1$-$C_{12})$ tertiary amides, $(C_1$-$C_{12})$ cyclic amides, $(C_1$-$C_{12})$ amines, $C_1$-$C_{12}$ alcohols, $(C_1$-$C_{12})(C_1$-$C_{12})$ ethers, $C_1$-$C_{12}$ alkyls, $C_1$-$C_{12}$ substituted alkyls, $C_2$-$C_{12}$ alkenyls, $C_2$-$C_{12}$ substituted alkenyls, $C_5$-$C_{12}$ aryls, and the like;

$R_9$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, $C_5$-$C_{12}$ aryl, and the like;

$R_3$-$R_5$, $R_7$, $R_8$, and $R_{11}$-$R_{13}$ each can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_5$-$C_{12}$ aryl, and the like;

$R_6$ can be, for example, hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl and the like;

$R_{10}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, $C_5$-$C_{12}$ aryl and the like;

$R_{14}$ and $R_{15}$ can be, for example, hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, $C_5$-$C_6$ aryl and the like; and $R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro;

cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

wherein the compound also includes the prodrug esters of the above compounds, and the acid-addition salts thereof.

In some aspects, $R_{16}$ can be, for example, hydrogen. In some aspects, $R_3$-$R_5$, $R_7$, $R_8$, $R_{11}$-$R_{15}$ can each be, for example hydrogen.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

Some embodiments relate to compounds having the following structure:

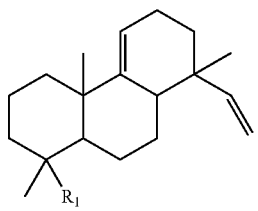

(IIB-b1)

$R_1$ can be, for example:

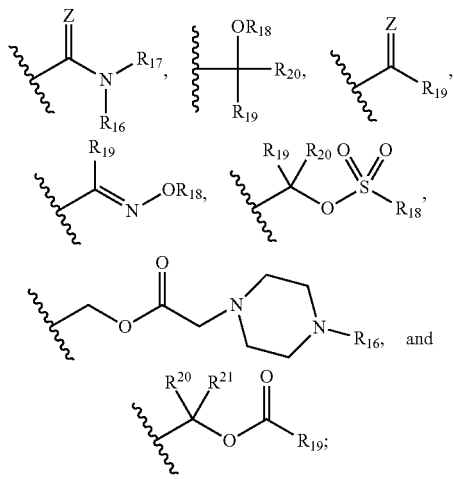

wherein Z is O or S;

$R_{16}$ and $R_{17}$ can be, for example, independently selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, $C_1$-$C_{12}$ alkylsulfonyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, $C_6$-$C_{12}$ arylsulfonyl, $C_4$-$C_{12}$ heteroarylsulfonyl, and the like;

$R_{16}$ and $R_{17}$ can optionally be bound together to form an optionally substituted $C_2$-$C_{12}$ heterocycloalkyl, optionally substituted $C_4$-$C_{12}$ heterocycloalkenyl, optionally substituted $C_4$-$C_{12}$ heterocycloalkynyl, or optionally substituted $C_4$-$C_{12}$ heteroaryl;

$R_{18}$ can be selected from hydrogen; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like;

$R_{19}$, $R_{20}$, and $R_{21}$ can be independently selected from hydrogen; halogen; hydroxyl; carboxyl; amino; thio; nitro; cyano; mono-substituted, poly-substituted or unsubstituted, straight or branched chain variants of the following residues: $C_1$-$C_{12}$ alkyl, $C_2$-$C_{12}$ alkenyl, $C_2$-$C_{12}$ alkynyl, $C_2$-$C_{12}$ alkoxy, $C_1$-$C_{12}$ ether, $C_2$-$C_{12}$ acylalkyl, $C_7$-$C_{24}$ arylalkyl, and $C_5$-$C_{24}$ heteroarylalkyl; and mono-substituted, poly-substituted or unsubstituted variants of the following residues: $C_3$-$C_{12}$ cycloalkyl, $C_3$-$C_{12}$ cycloalkenyl, $C_3$-$C_{12}$ cycloalkoxy, $C_6$-$C_{12}$ aryl, $C_4$-$C_{12}$ heteroaryl, $C_2$-$C_{12}$ heterocycloalkyl, $C_4$-$C_{12}$ heterocycloalkenyl, $C_4$-$C_{12}$ heterocycloalkynyl, and the like.

And prodrug esters and acid-addition salts thereof.

Any group that is optionally substituted can be optionally substituted with one or more of $C_1$-$C_6$ alkyl, $C_2$-$C_6$ alkenyl, $C_2$-$C_6$ alkynyl, $C_2$-$C_6$ alkoxy, halogen, hydroxyl, carboxyl, amino, thio, nitro, or cyano.

Definitions

As used herein, the term "purify" or "purified" or "purifying" or "purification" refers to any species wherein at least some of the components with which is normally associated are removed.

As used herein, the term "alkyl" means any unbranched or branched, saturated hydrocarbon, with $C_1$-$C_6$ unbranched, saturated, unsubstituted hydrocarbons being preferred, and with methyl, ethyl, iosbutyl, and tert-butyl being most preferred. Among the substituted, saturated hydrocarbons, $C_1$-$C_6$ mono- and di- and pre-halogen substituted saturated hydrocarbons and amino-substituted hydrocarbons are preferred, with perfluoromethyl, perchloromethyl, perfluoro-tert-butyl, and perchloro-tert-butyl being the most preferred. The term "substituted alkyl" means any unbranched or branched, substituted saturated hydrocarbon, with unbranched $C_1$-$C_6$ alkyl secondary amines, substituted C1-C6 secondary alkyl amines, and unbranched $C_1$-$C_6$ alkyl tertiary amines being within the definition of "substituted alkyl," but not preferred. The term "substituted alkyl" means any unbranched or branched, substituted saturated hydrocarbon. Cyclic compounds, both cyclic hydrocarbons and cyclic compounds having heteroatoms, are within the meaning of "alkyl."

As used herein, the term "substituted" means any substitution of a hydrogen atom with a functional group.

As used herein, the term "functional group" has its common definition, and refers to chemical moieties preferably selected from the group consisting of a halogen atom, $C_1$-$C_{20}$ alkyl, substituted $C_1$-$C_{20}$ alkyl, perhalogenated alkyl, cyloalkyl, substituted cycloalkyl, aryl, substituted aryl, benzyl, heteroaryl, substituted heteroaryl, cyano, and nitro. Functional groups may also be selected from the group consisting of —$SR_S$, —$OR_O$, —$NR_{n1}R_{n2}$, —$N^+R_{n1}R_{n2}R_{n3}$, —N=N—$R_{n1}$, —$P^+R_{n1}R_{n2}R_{n3}$, —$COR_C$, —C(=$NOR_O$)$R_C$, —$CSR_C$, —$OCOR_C$, —$OCONR_{n1}R_{n2}$, —$OCO_2R_C$, —$CONR_{n1}R_{n2}$, —C(=N)NR$_{n1}$R$_{n2}$, —CO$_2$R$_O$, —SO$_2$NR$_{n1}$R$_{n2}$, SO$_3$R$_O$, —SO$_2$R$_O$, —PO(OR$_O$)$_2$, —NR$_{n1}$CSNR$_{n2}$R$_{n3}$. Substituents of these functional groups R$_{n1}$, R$_{n2}$, R$_{n3}$, R$_O$ and R$_S$ are preferably each separately selected from the group consisting of a hydrogen atom, C$_1$-C$_{20}$ alkyl, substituted C$_1$-C$_{20}$ alkyl, cyloalkyl, substituted cycloalkyl, aryl, substituted aryl, benzyl, heteroaryl, substituted heteroaryl and may constitute parts of an aliphatic or aromatic heterocycle. R$_C$ are preferably selected from the group consisting of a hydrogen atom, C$_1$-C$_{20}$ alkyl, substituted C$_1$-C$_{20}$ alkyl, perhalogenated alkyl, cyloalkyl, substituted cycloalkyl, aryl, substituted aryl, benzyl, heteroaryl, substituted heteroaryl and cyano.

As used herein, the terms "halogen" and "halogen atom" refer to any one of the radio-stable atoms of column 17 of the Periodic Table of the Elements, preferably fluorine, chlorine, bromine, or iodine, with fluorine and chlorine being particularly preferred.

As used herein, the term "alkenyl" means any unbranched or branched, substituted or unsubstituted, unsaturated hydrocarbon, with C$_1$-C$_6$ unbranched, mono-unsaturated and di-unsaturated, unsubstituted hydrocarbons being preferred, and mono-unsaturated, di-halogen substituted hydrocarbons being most preferred. The term "substituted alkenyl" means any unbranched or branched, substituted unsaturated hydrocarbon, substituted with one or more functional groups, with unbranched C$_2$-C$_6$ alkenyl secondary amines, substituted C$_2$-C$_6$ secondary alkenyl amines, and unbranched C$_2$-C$_6$ alkenyl tertiary amines being within the definition of "substituted alkyl." The term "substituted alkenyl" means any unbranched or branched, substituted unsaturated hydrocarbon. Cyclic compounds, both unsaturated cyclic hydrocarbons and cyclic compounds having heteroatoms, are within the meaning of "alkenyl."

As used herein, the term "alcohol" means any unbranched or branched saturated or unsaturated alcohol, with C$_1$-C$_6$ unbranched, saturated, unsubstituted alcohols being preferred, and with methyl, ethyl, isobutyl, and tert-butyl alcohol being most preferred. Among the substituted, saturated alcohols, C$_1$-C$_6$ mono- and di-substituted saturated alcohols are preferred. The term "alcohol" includes substituted alkyl alcohols, and substituted alkenyl alcohols.

As used herein, the term "aryl" encompasses the terms "substituted aryl," "heteroaryl," and "substituted heteroaryl" which refer to aromatic hydrocarbon rings, preferably having five or six atoms comprising the ring. The terms "heteroaryl" and "substituted heteroaryl" refer to aromatic hydrocarbon rings in which at least one heteroatom, for example, oxygen, sulfur, or nitrogen atom, is in the ring along with at least one carbon atom. "Aryl," most generally, and "substituted aryl," "heteroaryl," and "substituted heteroaryl" more particularly, refer to aromatic hydrocarbon rings, preferably having five or six atoms, and most preferably having six atoms comprising the ring. The term "substituted aryl" includes mono and poly-substituted aryls, substituted with, for example, alkyl, aryl, alkoxy, azide, amine, and amino groups. "Heteroaryl" and "substituted heteroaryl," if used separately, specifically refer to aromatic hydrocarbon rings in which at least one heteroatom, for example, oxygen, sulfur, or nitrogen atom, is in the ring along with at least one carbon atom.

The terms "ether" and "alkoxy" refer to any unbranched, or branched, substituted or unsubstituted, saturated or unsaturated ether, with C$_1$-C$_6$ unbranched, saturated, unsubstituted ethers being preferred, with dimethyl, diethyl, methyl-isobutyl, and methyl-tert-butyl ethers being most preferred. The terms "ether" and "alkoxy," most generally, and "cycloalkoxy" and cyclic ether" more particularly, refer to any non-aromatic hydrocarbon ring, preferably having five to twelve atoms comprising the ring.

The term "ester" refer to any unbranched, or branched, substituted or unsubstituted, saturated or unsaturated ester, with C$_1$-C$_6$ unbranched, saturated, unsubstituted esters being preferred, with methyl ester, and isobutyl ester being most preferred.

The term "pro-drug ester," especially when referring to a pro-drug ester of the compound of Formula (I), refers to a chemical derivative of the compound that is rapidly transformed in vivo to yield the compound, for example, by hydrolysis in blood. The term "pro-drug ester" refers to derivatives of the compound of the present invention formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as pro-drugs for compounds containing carboxyl groups).

The term "pharmaceutically acceptable salt," especially when referring to a pharmaceutically acceptable salt of the compound of Formula (I), refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example C$_1$-C$_7$ alkylamine, cyclohexylamine, triethanolamine, ethylenediamine or tris-(hydroxymethyl)-aminomethane. With respect to disclosed compounds that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid. Preferred pharmaceutical compositions of the present invention include pharmaceutically acceptable salts and pro-drug esters of the compound of Formulae (II), (IIA), and (IIB).

The terms "purified," "substantially purified," and "isolated" as used herein refer to a disclosed compound being free of other, dissimilar compounds with which the compound is normally associated in its natural state, so that the compound comprises at least 0.5%, 1%, 5%, 10%, or 20%, and most preferably at least 50% or 75% of the mass, by weight, of a given sample. In one preferred embodiment, these terms refer to the compound comprising at least 95% of the mass, by weight, of a given sample.

The terms "anti-cancer," "anti-tumor" and "tumor-growth-inhibiting," when modifying the term "compound," and the terms "inhibiting" and "reducing", when modifying the terms "compound" and/or the term "tumor," mean that the presence of the subject compound is correlated with at least the slowing of the rate of growth of the tumor or cancerous mass. More preferably, the terms "anti-cancer," "anti-tumor," "tumor-growth-inhibiting," "inhibiting," and "reducing" refer to a correlation between the presence of the subject compound and the temporary cessation of tumor growth or growth of the cancerous mass. The terms "anti-cancer," "anti-tumor," "tumor-growth-inhibiting," "inhibiting," and "reducing" also refer to, particularly in the most preferred embodiment, a correlation between the presence of the subject compound and at least the temporary reduction in the mass of the tumor. These terms refer to cancer and various malignancies in animals, specifically in mammals, and most specifically in humans.

The term "skin redness" means any skin redness, especially a chronic skin redness having a neurogenic origin, consistent with, but not limited by, its meaning in EP 7744250, which is hereby incorporated by reference herein in its entirety.

The term "viral infection" means any infection of a viral origin including rhinovirus, and preferably, but not exclusively, refers to human immunodeficiency virus (HIV), human cytomegalovirus, hepatitis A, hepatitis B, and hepatitis C viruses.

The term "cardiovascular disease" refers to the various diseases of the heart and vascular systems, including but not limited to congestive heart failure, cardiac dysfunction, reperfusion injury, and various known peripheral circulatory abnormalities. "Cardiovascular disease" refers to such diseases in animals, specifically in mammals, and most specifically in humans.

As used herein, the term "diabetes" refers to the various diseases related to elevated insulin levels, Insulin Resistance, or Diabetes, including Type 1 Diabetes, Type 2 Diabetes, and various related condition, including, but not limited to Stein-Leventhal Syndrome or Polycystic Ovary Syndrome (PCOS).

As used herein, the term "transplant rejection" refers to the conditions, and related symptoms known as allograft rejection, xenograft rejection, and autograft rejection, and in preferred embodiments, refers to human-human allograft rejection.

As used herein, the terms "modulator" or "modulation" refer to the capacity of a compound or course of treatment to alter the presence or production of a modulated compound, especially TNF-α or IL-1, in an individual. Most preferably, "modulator" or "modulation" refer to the capacity of a compound or course of treatment to reduce the presence or production of a modulated compound.

As used herein, the terms TTL1, TTL2, TTL3, TTL4 and TTL5 refer to the specific chemical entities identified in, among other figures, FIG. 17.

All other chemical, medical, pharmacological, or otherwise technical terms used herein are to be understood as they would be understood by persons of ordinary skill in the art.
Interleukin-1 (IL-1)

IL-1 is a regulatory factor which participates in a wide range of mammalian immune and inflammatory mechanisms and other defensive mechanisms, especially in the human body (See, e.g., Dinarello, D. A., *FASEB J.*, 2, 108 (1988)). IL-1, first discovered as produced by activated macrophages, is secreted by various cells, for example, fibroblasts, keratinocytes, T cells, B cells, and astrocytes of the brain, and has various functions including: stimulating the proliferation of CD4+T cells, see Mizel, S. B., *Immunol. Rev.*, 63, 51 (1982); stimulating the cell-killing effect of thymic $T_C$ cells through its binding to a T cell receptor, TCR, see McConkey, D. J., et al., *J. Biol. Chem.*, 265, 3009 (1990); inducing the production of various materials participating in the inflammatory mechanisms, for example, $PGE_2$, phospholipase $A_2$ ($PLA_2$) and collagenase, see Dejana, E., et al., *Bolid*, 69, 695-699 (1987)); inducing the production of acute-phase proteins in liver, see Andus, T., et al., *Eur. J. Immunol.*, 123, 2928 (1988)); raising blood pressure in the vascular system, see Okusawa, S., et al., *J. Clin. Invest.*, 81, 1162 (1988)); and inducing the production of other cytokines, for example, IL-6 and TNF-α, see Dinarello, C. A., et al., *J. Immunol.*, 139, 1902 (1987). IL-1 modulation is also known to effect rheumatoid arthritis, see Nouri, A. M., et al., *Clin. Exp. Immunol.*, 58, 402(1984); transplant rejection, see Mauri and Teppo, *Transplantation*, 45, 143 (1988); and septicemia, see Cannon, J. G., et al., *Lymphokine Res.*, 7, 457 (1988), and IL-1 may induce fever and pain when administered in large doses. See Smith, J., et al., *Am. Soc. Clin. Oncol.*, 9, 710 (1990)).

The occurrence of septicemia, arthritis, inflammations, and related conditions in animal models can be decreased by inhibiting IL-1 binding to its receptors by employing naturally occurring IL-1 receptor inhibitors (IL-1 Ra), see Dinarello, C. A. and Thompson, R. C., *Immunol. Today*, 12, 404 (1991), and certain methods for inhibiting the activity of IL-1 by employing particular antibodies have been proposed, see Giovine, D. F. S, and Duff, G. W., *Immunol. Today.* 11, 13 (1990). In case of IL-6, proliferation of myelocytes in a patient suffering from myeloma has been suppressed by employing antibodies against IL-6 or IL-6 receptor, see Suzuki, H., *Eur. J. Immuno.*, 22, 1989 (1992)). The disease condition treatable according to the invention, via TNF-α and IL-1 modulation induced by the compounds, include but are not necessarily limited to the disease conditions herein described.

Tumor Necrosis Factor-α (TNF-α)

Human TNF-α was first purified in 1985 (Aggarwal, B. B.; Kohr, W. J. "Human tumor necrosis factor. Production, purification and characterization". *J. Biol. Chem.* 1985, 260, 2345-2354). Soon after, the molecular cloning of the TNF cDNA and the cloning of the human TNF locus were accomplished (See Pennica, D.; Nedwin, G. E.; Hayflick, J. S. et al "Human necrosis factor: precursor structure, expression and homology to lymphotoxin". *Nature* 1984, 312, 724-729. Wang, A. M.; Creasy, A. A.; Ladner, M. B. "Molecular cloning of the complementary DNA for human Tumor Necrosis Factor". *Nature* 1985, 313, 803-806). TNF-α is a trimeric 17-KDa polypeptide mainly produced by macrophages and many other cell types. This peptide is initially expressed as a 26-KDa transmembrane protein from which the 17-KDa subunit is cleaved and released following proteolytic cleavage by an enzyme known as TACE. This work clarified the immense and multifaceted biological implications of TNF-α and spurred the development of therapeutic approaches targeting its overproduction.

TNF-α is typically produced by various cells, for example, activated macrophages and fibroblasts. TNF-α induces IL-1 production, see Dinarello, D. A., *FASEB J.*, 2, 108 (1988), is cytotoxic for the fibrosarcoma L929 cells, see Espevik and Nissen-Meyer, *J. Immunol. Methods*, 95, 99 (1986); to stimulate the proliferation of fibroblasts, see Sugarman, B. J., et al., *Science*, 230, 943 (1985); to induce the production of $PGE_2$ and arachidonic acid, both of which may be involved in inflammatory responses, see Suttys, et al., *Eur. J. Biochem.*, 195, 465 (1991); and to induce the production of IL-6 or other growth factors, see Van Hinsbergh, et al., *Blood*, 72, 1467 (1988)). TNF-α also participates, either directly or indirectly, in various diseases such as infectious diseases carried by *trypanosoma* strains of the genus *Plasmodium*., see Cerami, A., et al., *Immunol. Today*, 9, 28 (1988)); autoimmune diseases such as systemic lupus erythematosus (SLE) and arthritis, see Fiers, W., *FEBS*, 285, 199 (1991); Acquired Immune Deficiency Syndrome (AIDS), see Mintz, M., et al., *Am. J. Dis. Child.*, 143, 771 (1989); septicemia, see Tracey, K. J., et al., *Curr. Opin. Immunol.*, 1, 454 (1989); and certain types of infections, see Balkwill, F. R., *Cytokines in Cancer Therapy*, Oxford University Press (1989).

TNF-α and Inflammatory Response

Infection and tissue injury induce a cascade of biochemical changes that trigger reactions of the immune system, collectively referred to as inflammatory response. The evolution of this response is based, at least in part, on local vasodilation or enhancing vascular permeability and activation of the vascular endothelium, which allows white blood cells to efficiently circulate and migrate to the damaged site, thereby increasing their chances to bind to and destroy any antigens. The vascular endothelium is thought to then be activated or inflamed. Generally, inflammation is a welcomed immune response to a variety of unexpected stimuli, and as such it exhibits rapid onset and short duration (acute inflammation). Its persistent or uncontrolled activity (chronic inflammation) has, however, detrimental effects to the body and results in the pathogenesis of several immune diseases, such as: septic shock, rheumatoid arthritis, inflammatory bowel diseases and congestive heart failure. See "Tumor Necrosis Factors. The molecules and their emerging role in medicine" B. Beutler, Ed., Raven Press, N.Y. 1992, pages 1-590.

The unfolding of an effective immune response typically requires the recruitment of a variety of cells and the orchestration of a series of biological events. This complex intercellular coordination and interaction is mediated by locally secreted low molecular weight proteins that are collectively called cytokines. These proteins bind to specific receptors on the cell surface and trigger signal-transduction pathways that ultimately alter gene expression in the target cells, thereby regulating an efficient inflammatory response.

Cytokines may exhibit properties of pleiotropism (a given protein exerts different effects on different cells), redundancy (two or more cytokines mediate similar functions), synergism (the combined effect of two cytokines is greater than the additive effect of each individual protein) and antagonism (the effect of one cytokine inhibiting the effect of others). To this end, some of the cytokines are pro-inflammatory (induce inflammation), while some others are anti-inflammatory (inhibit inflammation). The class of pro-inflammatory cytokines includes: interleukin-1 (IL-1), interleukin-6 (IL-6) and tumor necrosis factor-alpha (TNF-α). See "Tumor Necrosis Factors. The molecules and their emerging role in medicine" B. Beutler, Ed., Raven Press, N.Y. 1992, pages 1-590. These cytokines are secreted by macrophages shortly after the initiation of the inflammatory response and induce coagulation, increase the vascular permeability and activate the expression of adhesion molecules on vascular endothelial cells (for example, TNF-α stimulates expression of E-selection, that binds to and recruits neutrophils to the site of damage). Subsequently, and during a more systemic immune response, these cytokines act on several organs of the body, including bone marrow and liver to ensure the increased production of white blood cells and the synthesis of appropriate hormones and acute-phase proteins. In addition, they act on the hypothalamus and induce fever, which helps to inhibit the growth of pathogens and enhances the overall immune reaction.

TNF-α and the Pathogenesis of Various Diseases and Conditions

As with any cytokine, TNF-α is neither completely beneficial nor completely destructive to the host. Rather, balance of its production and regulation is maintained to ensure that the host can effectively react to invading microorganisms without compromising host well-being in the process. Being a mediator of inflammation, TNF-α helps the body in its fight against bacterial infections and tissue injuries. However, its overproduction of TNF-α leads to chronic inflammation, has detrimental effects to the body and plays a major role in the pathogenesis of several diseases some of which are summarized below.

Bacterial septic shock. This disease typically develops following infection by certain gram-negative bacteria, such as *E. coli, Enterobacter aerogenes* and *Neisseria meningitidis*. These bacteria bear on their cell walls certain lipopolysaccharides (endotoxins) that stimulate macrophages to overproduce IL-1 and TNF-α, which in turn cause the septic shock. The symptoms of this condition, which are often fatal, include a drop in blood pressure, fever, diarrhea and widespread blood clotting. In the United States alone, this condition afflicts about 500,000 persons per year and causes more than 70,000 deaths. The annual cost for treating this disease is an estimated $ 5-10 billion.

Rheumatoid Arthritis. This is the most common human autoimmune disease, affecting about 1% of the Western population and is a major source of disability, which in its severe form leads to death. See Szekanecz, Z.; Kosh, A. E.; Kunkel, S. L.; Strieter, R. M. "Cytokines in rheumatoid arthritis. Potential targets for pharmacological applications". *Clinical Pharmacol.* 1998, 12, 377-390. Camussi, G.; Lupin, E. "The future role of anti-tumor necrosis factor products in the treatment of rheumatoid arthritis". *Drugs* 1998, 55, 613-620. This condition is characterized by inflammation and cellular proliferation of the synovium, which results in the invasion of the adjacent cartilage matrix, its subsequent erosion and ultimately bone destruction. Although the origins of this inflammatory response are poorly understood, an increased expression of TNF-α and IL-1 have been found around the area of cartilage erosion. More recently, the pathogenic role of TNF-α in this disorder has been extensively studied and experimentally verified. Furthermore, clinical data suggest that neutralization of TNF-α may be a therapeutic approach to reduce the erosive process. To date, however, current therapy, while providing temporary relief does not alter the fundamental mechanisms of progress or process of the disease.

Inflammatory bowel diseases and related conditions. This class of diseases which include Crohn's disease and ulcerative colitis are debilitating disorders, characterized by chronic inflammation of intestinal mucosa and lamina propria. Although the events that trigger their onset are unknown, they are associated with significant leukocyte infiltrate and local production of soluble mediators. TNF-α is therefore considered to be a key mediator in the pathogenesis of these conditions, either by a direct cytotoxic action or as an orchestrator of the inflammatory cascade. See, for example, Armstrong, A. M.; Gardiner, K. R.; Kirk, S. J.; Halliday, M. J.; Rowlands, B. J. "Tumour necrosis factor and inflammatory bowel disease". Brit. J. Surgery 1997, 84, 1051-1058. Data based on accepted animal models also supports the rationale for a therapeutic study in human IBD, aimed at reducing the effect of TNF. See Van Deventer, S. J. H. "Tumour necrosis factor and Crohn's disease" Gut, 1997, 40, 443.

Congestive heart failure. Activation of cytokines, and especially TNF-α, occurs in patients with chronic heart failure and acute myocardial infarction. See Ferrari, R. "Tumor necrosis factor in CHF: a double facet cytokine". Cardiovascular Res. 1998, 37, 554-559. Moreover, TNF-α has been demonstrated to trigger the apoptotic process in cardiac myocytes both directly (by binding to and genetically reprogramming these cells) and indirectly (through local NO production, which also leads to cell death).

HIV replication. Replication of HIV is activated by the inducible transcription factor NF-κB, which in turn is induced by TNF-α. HIV expression can be induced by TNF in macrophage lines and T-cell clones chronically infected with the virus. Infusion of recombinant TNF in a small number of patients with AIDS-related Kaposi's sarcoma appeared to cause an increase in the HIV p24 antigen level, a marker of viral replicative activity. See "Therapeutic modulation of cytokines" CRC Press, Inc., N.Y. 1996, pages 221-236. These results provide a mechanistic basis for considering the use of a TNF blocker to reduce infectious HIV burden.

Other TNF mediated pathologies. There is an ever-increasing list of conditions in which there is some evidence that TNF is involved. "Therapeutic modulation of cytokines" CRC Press, Inc., N.Y. 1996, pages 221-236. In some cases, such as transplantation, graft-vs-host disease, and ischemia/reperfusion injury the potential mechanism of pathogenesis implicates the pro-inflammatory activity of TNF-α to a variety of tissue cells. Others, such as the suppression of insulin responsiveness in non-insulin-dependent diabetes, relate to more selective actions of TNF-α that appear to fall outside the standard pro-inflammatory model. TNF-α has been detected locally in patients afflicted with otitis media (inner ear infection, with or without effusion), see for example, Willett, D. N., Rezaee, R. P., Billy, J. M., Tighe, M. A., and DeMaria, T. F., *Ann. Rhinol Laryngol,* 107 (1998); Maxwell, K., Leonard, G., and Kreutzer, D. L., *Arch Otolarygol Head Neck Surg,* vol. 123, p. 984 (September 1997), and with sinusitis, see for example Nonoyana, T., Harada, T., Shinogi, J., Yoshimura, E., Sakakura, Y., *Auris Nasus Larynx,* 27(1), 51-58 (January 2000); Buehring I., Friedrich B., Schaff, J., Schmidt H., Ahrens P., Zielen S., *CLin Exp Immul,* 109(3), 468-472, September 1997).

Methods of Use

Further embodiments relate to the use of the disclosed compounds and pharmaceutical compositions including the disclosed compounds, in the treatment of diseases, detailed above, that include inflammation, cancer, cachexia, otitis media, sinusitis and transplant rejection, and the reduction or cessation of fatigue associated with cancer and/or its treatment.

Specific examples of or other such treatable diseases, which may be specifically associated with the eye, nose, and/or ear include thyroid-related diseases (Hunt et al., *Clin Endocrinol,* 55(4):491-9 (2001)), such as Graves' ophthalmopathy (Villanueva et al., *Thyroid,* 10(9):791-8 (2000); Jones et al., *Thyroid,* 10(8):701-7 (2000); Wakelkamp et al., *Clin. Exp. Immunol.,* 121(3) 453-7 (2000); Song et al., *Horm. Metabl. Res.,* 32(7): 277-82 (2000)), Hashimoto's thyroiditis (Paolieri et al., *Ann. NY Acad. Sci.,* 876:221-8 (1999)), thryoid-associated ophthalmopathy (TAO) (Pappa et al., *Clin. Exp. Immunol.,* 109(2):362-9 (1997)) and nodular goiter (Nygaard et al., *Horm. Metabl. Res.* 32(7):283-7 (2000)); herpetic stromal keratitis (Keadle et al., *Invest. Ophthalmol. Vis. Sci.,* 41(1):96-102 (2000)) and microbial keratitis and peripheral ulcerative keratitis (Dana et al., *Cornea,* 19(5): 625-43 (2000); Behcet's disease (Sfikakis et al., *Lancet.,* 358(9278):295-6 (2001)); Goossens et al., *Ann. Rheum. Dis,* 60(6):637 (2001)); Robertson et al., *Rheumatology,* 40(4): 473-4 (2001)); Hassard et al., *Gastroenterology,* 120(4):995-9 (2001); Sakane et al., *Expert Opin. Investig. Drugs,* 9(9):1993-2005 (2000)); uveitis (Lemaitre et al., *Invest. Ophthalmol. Vis. Sci.,* 42(9):2022-30 (2001)); Shao et al., *Invest. Ophthalmol. Vis. Sci.,* 42(9): 2016-21 (2001); Baatz et al., *Exp. Eye Res.,* 73(1): 101-9 (2001)); Sjogren's syndrome (Magnusson et al., *Scand. J. Immunol.,* 54(1-2):55-61 (2001); Koski et al., *Clin. Exp. Rheumatol.,* 19(2):131-7 (2001); Fox, R., *Expert Opin. Investig. Drugs,* 9(9):2007-16 (2000); Nakamura et al., *Lab Invest,* 80(9):1421-7 (2000); Guggenbuhl et al., *Joint Bone Spine,* 67(4):290-5 (2000)); tuberculosis (Saita et al., 68(10):5991-7 (2000)); inflammatory diseases, such as cochlear inflammation (Ichimiya et al., *Int. J. Pediatr. Otorhinolaryngol.,* 56(1):45-51 (2000)) and inflammatory eye disease (Smith et al., *Arthritis Rheum.,* 45(3):252-7 (2001)); vitreoretinal proliferative disease (Limb et al., *Invest. Ophthalmol. Vis. Sci.,* 42(7): 1586-91 (2001); El-Ghrably et al., *Br. J. Ophthalmol.,* 85(4): 461-70 (2001); rabies virus ocular disease (Camelo et al., *J. Virol.* 75(7): 3427-34 (2001)); Vogt-Koyanagi-Harada's disease (Kitaichi et al., *Microbiol. Immunol.,* 44(12):107507 (2000)); retinopathy (Yossuck et al., *Mol. Genet. Metab.,* 72(2):164-7 (2001)); vernal keratoconjunctivitis (Leonardi et al., *Invest. Ophthalmol. Vis. Sci.,* 41(13):4175-81 (2000)); retinal laser photocoagulation (Er et al., *Ophthalmic Surg Lasers,* 31(6):479-83 (2000)); acute retinal necrosis syndrome (Sato et al., *Nippon Ganka Gakkai Zasshi,* 104(5):354-62 (2000)); systemic vasculitis (McKibbin et al., *Br. J. Ophthalmol.,* 84(4):395-8 (2000)); sarcoid myopathy (Penis et al, *Clin. Rheumatol.,* 18(6):488-91 (1999)); recurrent aphthous stomatitis (RAS) (Freysdottir et al., *Clin. Exp. Immunol.,* 118(3):451-7 (1999)); neovascular glaucoma (Chen et al., *Invest. Ophthalmol. Vis. Sci.,* 40(11):2627-32 (1999)); bacterial eye infections, such as *Staphylococcus aureus* endophthalmitis (Giese et al., *Invest. Ophthalmol. Vis. Sci.,* 39(13):2785-90 (1998)) and *Pseudomonas aeruginosa* corneal infection (Kernacki et al., *Infect. Immun.,* 66(1):376-9 (1998)); ocular allergic diseases (Hingorani et al., *J. Allergy Clin. Immunol.,* 102(5):821-30 (1998)), such as allergic conjunctiva (Macleod et al., *Clin. Exp. Allergy,* 27(11):1328-34 (1997)); sarcoidosis (Maniwa et al., *Intern. Med.,* 37(9):757-61 (1998)); retinal detachment (Bakunowicz-Lazarczk et al., *Klin. Oczna,* 99(2):87-9 (1997)); optic neuritis (Boiko et al., *J. Neurovirol.,* 6 (Suppl 2):5152-5 (2000); Kivisakk et al., *Neurology,* 50(1):217-23 (1998)); ocular rosacea (Barton et al., *Ophthalmology,* 104 (11):1868-74 (1997)), multiple sclerosis (Cooper et al., *Med. Hypotheses,* 49(4):307-11 (1997)) and systemic sclerosis (Hebbar et al., *Arthritis Rheum.,* 38(3):406-12 (1995)); hereditary retinal degeneration (de Kozak et al., *Ocul. Immunol. Inflamm.,* 5(2):85-94 (1997)); retinal dystrophy (Cotinet et al., *Glia.,* 20(1):59-69 (1997)); trachoma (Conway et al., *Infect. Immun.,* 65(3):1003-6 (1997)); autoimmune diseases, including autoimmune dacryoadenitis (Takahashi et al., *Clin. Exp. Immunol.,* 109(3):555-61 (1997)), autoimmune uveoretinitis (Thillaye-Goldenberg et al., *J. Neuroimmunol,* 110(1-2):31-44 (2000)) and AIDS (Lin et al., *Curr. Eye Res.,* 16(10): 1064-8 (1997)) and autoimmune sialoadenitis (Mustafa et al., *Clin. Exp. Immunol.,* 112(3):389-96 (1998)); scleritis (Di Girolamo et al., *Am. J. Pathol.,* 150(2):653-66 (1997)); rheumatic diseases, such as systemic lupus erythematosus, rheumatoid arthritis (al-Janadi et al., *J. Clin. Immunol.,* 13(1):58-67 (1993), as mentioned above, rheumatic heart disease (Miller et al., *J. Rheumatol.,* 1989) and rheumatoid vasculitis (Flipo et al., *Ann. Rheum. Dis.,* 56(1):41-4 (1997)); optic neuropathy (Madigan et al., *Neurol. Res.,* 18(3):233-6 (1996)); ocular toxoplasmosis (Davidson et al., *Antimicrob. Agents Chemother.,* 40(6):1352-9 (1996)); vitroretinal disorders (Esser et al., *Ger. J. Ophthalmol.,* 4(5): 269-74 (1995)); neovascular eye diseases (Spranger et al., *Med. Klin.,* 90(3): 134-7 (1995); endocrine orbitopathy (Heufelder et al., *Med. Klin.,* 88(4):181-4 (1993)); granulocyte-macrophage colony stimulating factor GM-CSF disease (Lang et al., *Growth Factors,* 6(2):131-8 (1992)); non-neoplastic diseases (Billington, *Drug Des. Discov.,* 8(1):3-35 (1991)); Wegener's granulomatosis (Mayet et al., *J. Immunol. Methods,* 143(1):57-68 (1991)); keratoconus (Fabre et al., *Curr. Eye Res.,* 10(7):585-92 (1991)); intraocular tumors (Wong et al., *Cornea,* 10(2): 131-5 (1991)) such as intraocular melanomas (Ma et al.,

*Invest. Ophthalmol. Vis. Sci.,* 39(7):1067-75 (1998)), retinoblastoma (Detrick et al., *Invest. Ophthalmol. Vis. Sci.,* 32(6): 1714-22 (1991)) and colorectal carcinoma (Kemeny et al., *Cancer,* 66(4):659-63 (1990)); nasal polyp disease (Saji et al., *Auris Nasus Larynx,* 27(3):247-52 (2000)); cholesteatoma (Amar et al., *J. Laryngol Otol.,* 110(6):534-9 (1996); thrombotic thrombocytopenic purpura and hemolytic-uremic syndrome (Mauro et al., *Am. J. Hematol.,* 66(1):12-22 (2001)); Still's disease (Cavagna et al., *Clin. Exp. Rheumatol.,* 19(3): 329-32 (2001)); tonsillar hypertrophy and recurrent tonsillitis (Agren et al., *ORL J. Otorhinolaryngol Relat. Spec.,* 60(1): 35-41 (1998)), psoriasis (Mizutani et al., *J. Dermatol. Sci.,* 14(2):145-53 (1997)); mononucleosis (Andersson et al., *Clin. Exp. Immunol.,* 92(1):7-13 (1993)); autoimmune encephalomyelitis (Weissert, *J. Immunol.,* 166(12):7588-99 (2001)), chronic proliferative dermatitis (HogenEsch et al., *J. Immunol.,* 162(7):3890-6 (1999)); retinal vein occlusion (Conway et al., *Int. Ophthalm.,* 19(4):249-52 (1995)); Irvine-Gass Syndrome; and age-related macular degeneration (Abe et al., *Tohoku J. Exp. Med.,* 189(3):179-89 (1999)). Other specific examples of inflammation-associated diseases that may be treated according to the invention include autoimmune diseases that affect the eyes, nose, throat or ear, such as the autoimmune disease that affects upper and lower respiratory tracts, Wegener's granulomatosis (Hewins et al., *Curr. Opin. Rheumatol.,* 12(1):3-10 (2000); Yi et al., *Semin. Diagn. Pathol.,* 18(1):34-46 (2001)), and the autoimmune disease that affects sight, smell and taste, Sjogrens syndrome (Carsons, S., *Am J. Manag. Care,* 7(14): S433-43 (2001); Lash et al., *Nurse Pract.,* 26(8):50 (2001)). More specifically, inflammatory diseases that affect joints such as the systemic inflammatory rheumatic disease involving spinal and sacroiliac joints, ankylosing spondylitis (Toussirto et al., *Expert Opin. Investig. Drugs,* 10(1):21-9 (2001)), the inflammatory joint diseases, spondyloarthropathies (Braun et al., *Curr. Opin. Rheumatol,* 8(4):275-87 (1996); Gladman, D D, *Am. J. Med. Sci.,* 316(4):234-8 (1998))), the joint and spine-affected arthritis, psoriatic arthritis (Gladman et al., *Expert Opin. Investig. Drugs,* 9(7):1511-22 (2000); Scarpa et al., *Curr. Opin. Rheumatol.,* 12(4):274-80 (2000)) and joint disorders such as temporomandibular joint disorder (Stack et al., *Am. Fam. Physician,* 46(1):143-50 (1992)) are included.

Further examples of diseases that may be treated according to the invention include diseases associated with the oral airway such as molar extractions, chemotherapy related mucosal injury (Spijkervet et al., *Curr. Opin. Oncol.,* 10 (Suppl. 1):523-7 (1998); Khan et al., *J. Natl. Cancer Inst. Monogr.,* 29:31-6 (2001)), non-infectious lung injury following bone marrow transplant, such as respiratory distress syndrome (Hite et al., *Drugs,* 61(7):897-907 (2001)) and bronchiolitis obliterans pneumonia (Nagai et al., *Curr. Opin. Pulm. Med.,* 2(5):419-23 (1996); Epler, G R, *Semin. Respir. Infect.,* 10(2):65-77 (1995)).

TNF-α and IL-1 Modulation as Therapeutic Approaches

Prior to the isolation of TNF-α, the employed therapeutic approaches to the above diseases were targeting the reduction of chronic inflammation and were based on steroidal and non-steroidal anti-inflammatory treatment. However, recent understanding of TNF-α has led to the development of alternative strategies based on its selective inhibition. These general strategies are summarized below.

Steroidal treatment This treatment, which includes the use of corticosteroids, causes the reduction in the number and the activity of the immune-system cells. The mechanism of action of the corticosteroids involves crossing of the plasma membrane and binding on receptors in the cytosol. The resulting complexes are then transported to the cell nucleus where they bind to specific regulatory DNA sequences, thereby down-regulating the cytokine production. Although currently employed, this strategy has several disadvantages since it is not specific for TNF-α but also down-regulates several other cytokines that may play important roles in an effective immune reaction. Moreover, use of steroids is also implicated with the development of cancer (for example prostate cancer).

Non-steroidal anti-inflammatory treatment. This strategy includes use of compounds such as aspirin that indirectly reduce inflammation. This is usually accomplished by inhibiting the cyclooxygenase pathway by which prostaglandins and thromboxanes are produced. This action reduces the vascular permeability and provides temporary relief. To this end, this strategy does not regulate the production of cytokines and has little or no effect in diseases associated with chronic inflammation.

Engineered monoclonal anti-TNF antibodies. This strategy involves a selection of monoclonal antibodies that are capable of binding to and neutralizing TNF-α. Although the preliminary clinical studies have shown some positive results, this approach is still in its infancy and not generally accepted. One of the problems to be addressed is that the monoclonal antibodies are of murine origin and in humans they elicit anti-immunoglobulin immune responses which limit their clinical use. Recombinant engineering techniques are being pursued to create "humanized" versions of the rodent antibodies that will maintain activity against TNF-a and will be accepted more easily by the human immune system.

Use of soluble TNF-α receptors. The use of soluble receptors against TNF-α is a new therapeutic approach. Although these receptors are created to bind and neutralize TNF-α, they also enhance its activity by prolonging its lifespan in blood circulation. Furthermore, the long term immunological response to this type of treatment is being evaluated.

Gene therapy. The goal of this approach is to decrease inflammation not by decreasing the expression of TNF-α but by increasing the local production of anti-inflammatory cytokines. The treatment consists of direct injection of cDNA expression vectors encoding for anti-inflammatory cytokines to the inflamed area, which could antagonize the effect of TNF. The efficacy of this method is currently under investigation in preclinical studies and its long term effects on the immune response remain unknown.

Other disease states and conditions. Additionally, TNF-α and/or IL-1 have been more recently identified as participating in modulating angiogenic vascular endothelial growth factor (VEGF), see E. M. Paleolog et al., *Arthritis & Rheumatism,* 41, 1258 (1998), and may participate in tuberculous pleurisy, rheumatoid pleurisy, and other immune disorders, see T. Söderblom, *Eur. Respir.* 1, 9, 1652 (1996). TNF-α has also been reported to effect expression of certain cancer cell genes for multidrug resistance-associated protein (MRP) and lung resistance protein (LRP), see V. Stein, *J. Nat. Canc. Inst.,* 89, 807 (1997), and to participate in chronic and congestive heart failure, and related cardiovascular disease, see for example R. Ferrari, *Cardiovascular Res.,* 37, 554 (1998); C. Ceconi et al., *Prog. Cardiovascular Dis.,* 41, 25 (1998), and to either directly or indirectly mediate viral infection, see D. K. Biswas, et al., *J. Acquired Immune Defic Syndr. Hum Retrovirol.,* 18, 426-34 (1998) (HIV-1 replication); R. LeNauor, et al., *Res. Virol.,* 145, 199-207 (1994) (same); T. Harrer, et al., *J. Acquir. Immune Defic. Syndr.,* 6, 865-71 (1993) (same); E. Fietz, et al., *Transplantation,* 58 (6), 675-80 (1994) (human cytomegalovirus (CMV) regulation); D. F. Zhang, et al., *Chin. Med.* 1, 106, 335-38 (1993) (HCV and HBV infection). Furthermore, antagonists of TNF-α have also been shown useful in the treatment of skin redness of a neurogenic origin. See European Patent EPO-774250-B1 (to De Lacharriere et al.).

TNF-α has also been identified as expressed at heightened levels in humans diagnosed as obese or exhibiting insulin resistance, and is thus, a modulator of diabetes. See Hotamisligil, G., Arner, P., Atkuinson, R., Speigelman, B. (1995), "Increased adipose tissue expression of tumor necrosis factor-α (TNF-α) in human obesity and insulin resistance. *J. Clin. Invest.* 95:2409-2415. TNF-α has also been identified as an important modulator of transplant rejection. See Imagawa, D., Millis, J., Olthoff, K., Derus, L., Chia, D., Sugich, L., Ozawa, M., Dempsey, R., Iwaki, Y., Levy, P., Terasaki, P., Busuttil, R. (1990) "The role of tumor necrosis factor in allograft rejection" *Transplantation*, vol. 50, No. 2, 219-225.

Pharmaceutical Compositions

Other embodiments relate to pharmaceutical compositions useful in the treatment of various diseases and disease states. Such disclosed pharmaceutical compositions may comprise a pharmaceutically acceptable carrier or diluent, well known in the pharmaceutical art and described, for example, in Remington's Pharmaceutical Sciences, Mack Publishing Co. (A. R. Gennaro edit. 1985) and a pharmaceutically effective amount of a chemical compound. Such compositions may further comprise preservatives, stabilizers, dyes, flavoring agents, antioxidants and suspending agents. Further disclosed herein are various pharmaceutical compositions well known in the pharmaceutical art for uses that include intraocular, intranasal, and intraauricular delivery. Pharmaceutical formulations for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Ophthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1):101-6 (1999)); and ocular inserts. Suitable pharmaceutical formulations for intraocular delivery are most often and preferably formulated to be sterile, isotonic and buffered for stability and comfort. Pharmaceutical compositions for intranasal delivery include drops and sprays often prepared to simulate in many respects nasal secretions to ensure maintenance of normal ciliary action. As disclosed in Remington's Pharmaceutical Sciences (Mack Publishing, 18$^{th}$ Edition), and well-known to those skilled in the art, suitable nasal formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

Methods of Administration

Still further embodiments relate to methods for administering the disclosed chemical compounds and the disclosed pharmaceutical compositions. Such disclosed methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

These observations highlight the importance and desirability of identifying novel strategies and/or novel compounds and classes of compounds that selectively influence the production of TNF-α and/or IL-1. Small molecules that selectively inhibit these cytokines are therefore particularly medicinally and biologically important in, for example, maintaining an active immune system and in treating inflammation based diseases.

Preferred Methods of Synthesis of the Present Invention

Certain embodiments relate to novel methods of making the disclosed compounds, including for example, compounds having the chemical structure of Formulae (II), (IIA), or (IIB), as well as novel methods of making known analogs of the known the compounds having the chemical structure of Formulae (II), (IIA), or (IIB), for example, the compounds of Formulae (I) and (IA).

The compounds of the present invention, and specifically, the compounds having the chemical structure of Formula (II), (IIA), or (IIB), may be prepared either synthetically or semi-synthetically. If prepared synthetically, commonly available starting materials may be used, including, but not limited to bicyclic compounds having reactive halide moieties. The at-least-three-ringed compounds of the present invention may be synthesized according to various ring closure reactions. Such reactions include, but are not limited to the Diels-Alder reaction, and the Dieckmann Condensation reaction. The Diels-Alder reaction preferably involves the reaction of a diene and an α substituted alkenyl moiety, such that the third ring of the desired compound is formed. The Dieckmann Condensation reaction may be preferably followed by the reduction of the resulting cycloketone moiety. Compounds of the present invention may be purified and isolated, following such synthetic methods and other well-known synthetic methods, by use of procedures, such a chromatography or HPLC, as well known to those skilled in the art.

Alternatively, according to the present invention, the compounds having the chemical structure of Formulae (I) and (IA), and certain specific analogs and derivatives thereof, may be extracted and isolated, at least in the form of a crude extract comprising acanthoic acid, from the root bark of *Acanthopanax koreanum* Nakai. Such an extract may preferably be produced according to the following method:

Approximately one kilogram of dried root bark of *A. koreanum* Nakai is obtained, chipped, and covered with between 1 L to 3 L, and preferably 2 L, of a suitable solvent, most preferably methanol. This mixture is maintained at a temperature ranging from 20° to 60°, and may be maintained at room temperature, for at least 10 hours, and preferably for 12 hours. The mixture is then filtered to remove and retain the filtrate. This procedure is repeated, preferably at least two additional times, and the combined filtrates are concentrated under a reduced pressure to obtain an extract.

Approximately 100 grams of the extract is partitioned with 200 mL to 400 mL, preferably 300 mL, of an aqueous solution, preferably water and 200 mL to 400 mL, preferably 300 mL, of an organic solution, preferably diethyl ether. The organic fraction is separated therefrom and then concentrated under a reduced pressure to obtain a further extract. Said further extract is purified, preferably by column chromatography and even more preferably by use of a silica gel column, using a mixture of suitable organic solvents, preferably hexane and ethyl acetate as an eluent to obtain isolated acanthoic acid.

This isolated compound of Formulae (I) and (IA) may then by synthetically modified to yield certain compounds of the present invention, specifically the compounds having the chemical structure of Formula (II) or (IIA). For example, ester $R_1$ analogs of acanthoic acid may be formed according to acid-catalyzed nucleophilic addition of an alkyl alcohol to the carboxylic acid moiety of acanthoic acid. Ether $R_1$ analogs of acanthoic acid may be formed from either primary alkyl halides or alcohols according to the Williamson Ether synthesis, or via the reduction of a primary alcohol moiety. Alkyl, alkenyl, and alcoholic $R_{10}$ analogs of acanthoic acid may be formed via catalytic hydrogenation of the alkenyl group, or via electrophilic addition of, preferably, HCl or HBr or other suitable alkyl halides. Substitution analogs at the other R positions of acanthoic acid may be formed by displacement reactions involving alkyl halides, provided suitable reactive groups and related protecting groups are employed to encourage the desired reaction. According to these reaction and other well-known synthetic reactions, the production of the full range of the compounds of the present invention, given the description of those compounds provided herein, is within the skill of those of the art.

Fully-synthetic approaches for the preparation of the compounds of the invention, including compounds of general Formulae (I), (IA), (II), (IIA), and (IIB) are described herein. The approaches are applicable to any of the compounds described herein, including subgenra of the compounds of Formulae (I), (IA), (II), (IIA), and (IIB), such as for example, compounds of Formulae IIAA, IIA-A1, IIBB, IIB-A1, II2, II2-1, and the like. This synthesis includes one or more retrosynthetic analyses of acanthoic acid and its analogs, syntheses of radioactively labeled acanthoic acid and its analogs, syntheses of dimers and conjugates of the compounds of general Formulae (I), (IA), (II), (IIA), and (IIB). Those of skill in the art will also appreciate that these approaches are also fully applicable to the preparation of kauranoic acid and its analogs.

The Compound of Formula (I) and its Naturally-Occurring Analogs

The root bark of *Acanthopanax koreanum* Nakai (Araliaceae), which is found indigenously in Cheju Island, The Republic of Korea, has been used traditionally as a tonic and sedative, as well as a remedy for the treatment of rheumatism and diabetes. During their investigation of this folk medicine, Chung and coworkers identified from its pharmacologically active extracts two novel tricyclic diterpenes: acanthoic acid (Compound 1) and its methyl ester (Compound 2), as depicted in FIG. 1. See Kim, Y. H.; Chung, B. S.; Sankawa, U. "Pimaradiene diterpenes from *Acanthopax Koreanum*". *J. Nat. Prod.* 1988, 51, 1080-1083. Acanthoic acid is a pimarane (3). However, in sharp contrast to the other members of the pimaranes family, 1 is distinguished by an unusual stereochemical relationship between the C8 and C10 centers that provides a unique mode of connectivity of the BC ring system. Acanthoic acid also can be obtained by the procedure described below in the synthesis of compounds of Formula II2-1 and IIA-A1.

Extraction and Isolation of Acanthoic Acid from Roots of *Coleonema pulchrum*

Prior to this invention, no complete chemical synthesis existed for production of the chemical having the structure of Formula (I) or its analogs. Importantly, the chemical structure of Formula (I), 1, (FIG. 1) possesses a biological profile as an anti-inflammatory agent. More specifically, in vitro studies with activated (inflammed) monocytes/macrophages revealed that treatment with 1 (approximately 0.1 to approximately 1.0 microgram/ml for 48 hours) leads to an approximately 90% inhibition of the TNF-α and IL-1 production. This inhibition was concentration dependent and cytokine-specific, since under the same conditions the production of IL-6 or IFN-γ (interferon-gamma) were not affected. The in vivo effects of acanthoic acid were evaluated in mice suffering from silicosis (chronic lung inflammation) and cirrhosis (liver inflammation and hepatic fibrosis). Histologic analysis revealed that treatment with compound 1 led to a substantial reduction of fibrotic granulomas and a remarkable recovery of the cirrotic liver cells. These dramatic results can be attributed, at least partially, to inhibition of pro-inflammatory cytokines, such as TNF-α and IL-1, mediated by 1. Compound 1 also shows very little toxicity in mice and only upon orally administering a high concentration (LD>300 mg/100 g of body weight). See Kang, H.-S.; Kim, Y.-H.; Lee, C.-S.; Lee, J.-J.; Choi, I.; Pyun, K.-H., *Cellular Immunol.* 1996, 170, 212-221. Kang, H.-S.; Song, H. K.; Lee, J.-J.; Pyun, K.-H.; Choi, I., *Mediators Inflamm.* 1998, 7, 257-259.

The chemical structure of Formula (I) thus has potent anti-inflammatory and anti-fibrotic effects and reduces the expression of TNF-α and IL-1. Acanthoic acid is thus used as a chemical prototype for the development of the novel compounds.

Retrosynthetic Analyses of the Compounds of Formulae (I), (II) and (IIB)

Figure 2:
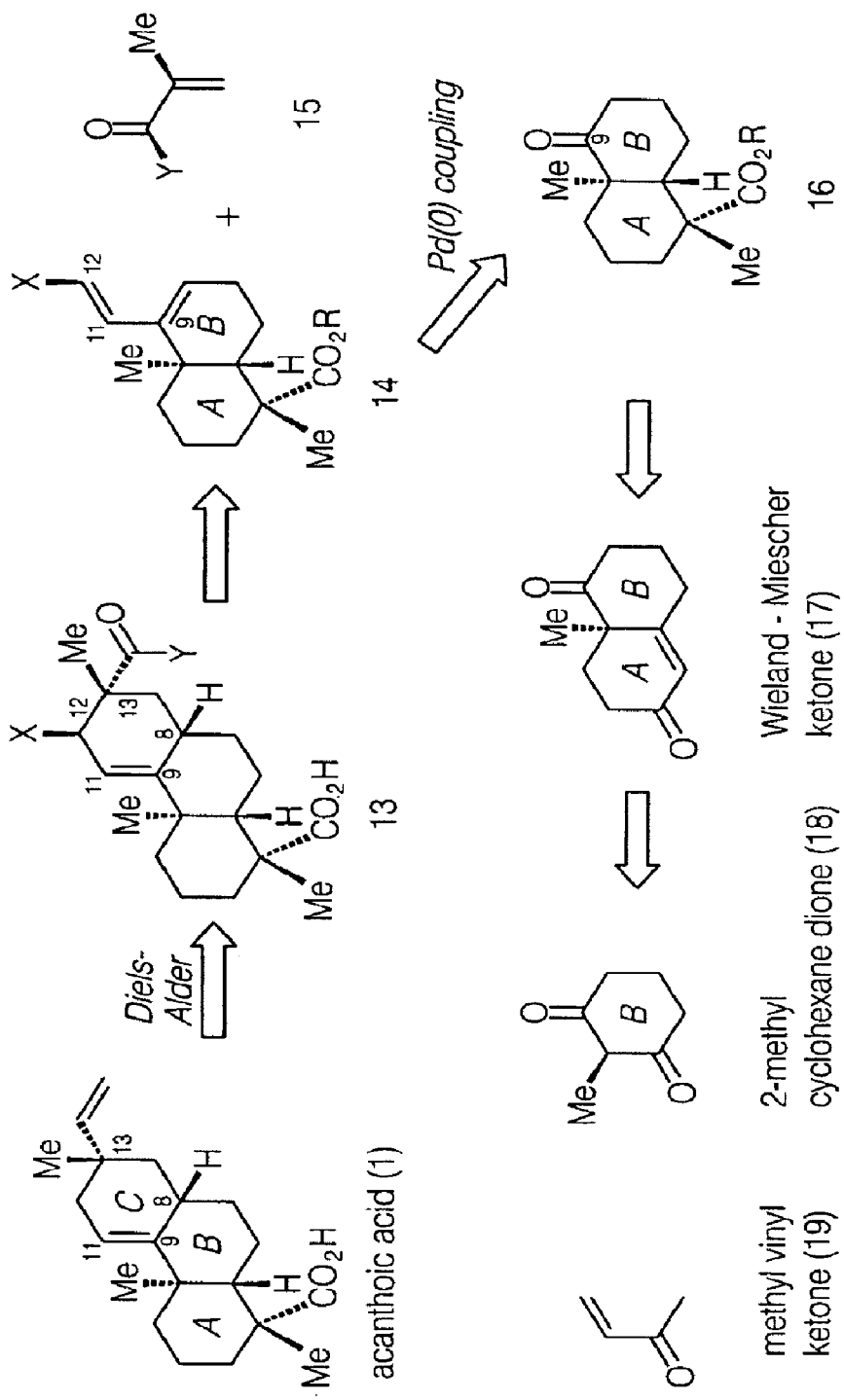
FIG. 2 depicts the retrosynthetic analysis and strategic bond associations of certain compounds.

The compounds of Formulae (I), (II) and (IIB), and preferably the compound of Formula (I) and compounds of Formulae (IIB) designated TTL1, TTL2, TTL3, and TTL4 herein, the may be synthesized according to an aspect of the invention. The bond disconnections of the compounds of Formulae (I) are shown in FIG. 2. The novel structural arrangement of the BC rings and the presence of the quaternary C13 center constitute an unusual motif and lead to a novel strategy that is one aspect of the invention. This motif is fixed, in one step, into the desired stereochemistry by employing a Diels-Alder methodology. A diene, for example, 14, and a dienophile, such as 15 (Y: oxazolidinone-based auxiliary), were identified as the appropriate starting materials for an endo selective Diels-Alder reaction. To further ensure the desired regiochemical outcome of this cycloaddition, diene 14 was functionalized transiently with a heteroatom (for example, X=OTBS or SPh), which will be subsequently removed from the product 13. The generally observed endo preference of this reaction was used to predict the stereochemical relationship between the C12 and C13 centers as shown in product 13, while the diastereofacial seletivity of the process will be controlled either by a chiral auxiliary at the carbonyl center of the dienophile or by using a chiral catalyst. See Xiang, A. X.; Watson, D. A.; Ling. T.; Theodorakis, E. A. "Total Synthesis of Clerocidin via a Novel, Enantioselective Homoallenylboration Methodology". *J. Org. Chem.* 1998, 63, 6774-6775.

Diene 14 may be formed by a palladium (0) catalyzed construction of the C8-C11 bond, revealing ketone 16 as its synthetic progenitor. This ketone was formed from the known Wieland-Miescher ketone (17), which in turn was readily available by condensation of methyl vinyl ketone (19) with 2-methyl 1,3-cyclohexane dione (18) (FIG. 2).

Figure 5:
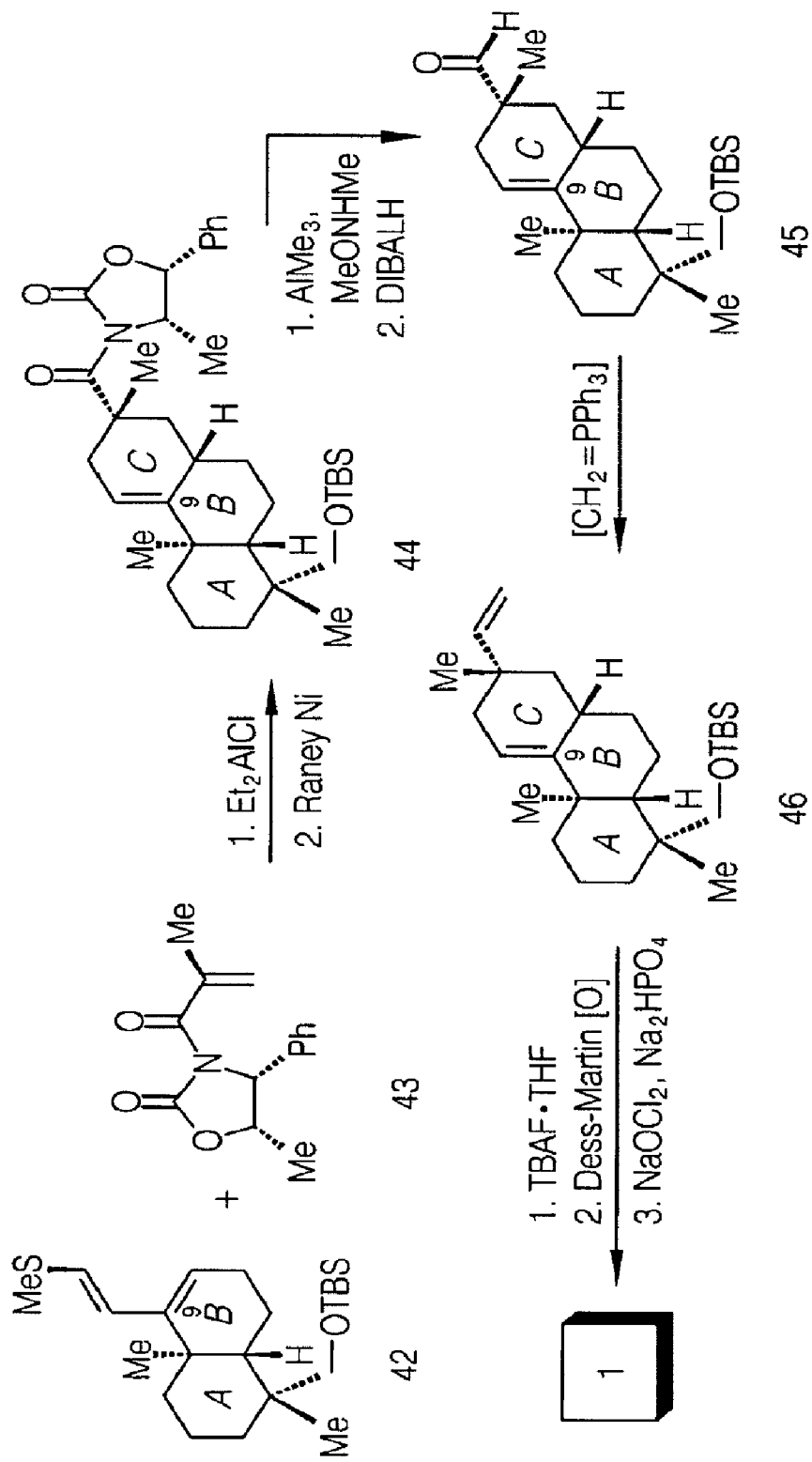
FIG. 5 depicts a synthetic scheme (Scheme 2) by which the synthesis of acanthoic acid and certain compounds may be completed.
Figure 6:
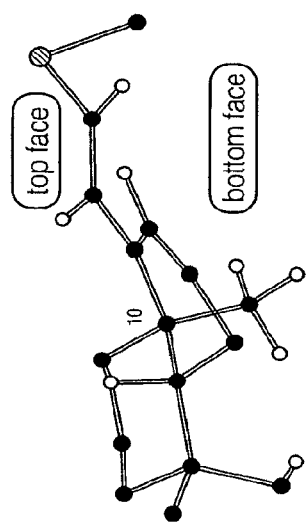
FIG. 6 depicts the minimized, three-dimensional model of diene 42, as described in the detailed description.
Figure 7:
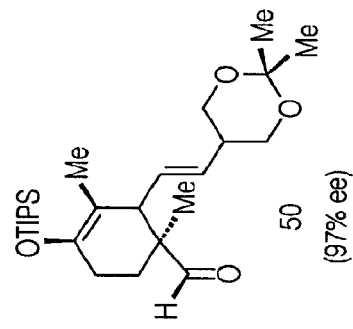
FIG. 7 depicts a synthetic scheme (Scheme 3) for the development and application of catalyst 49, as described in the detailed description of the preferred embodiment, an asymmetric Diels-Alder reaction.
Figure 7:
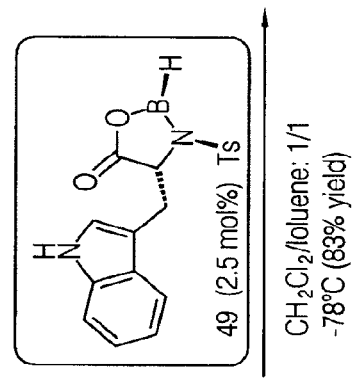
Figure 7:
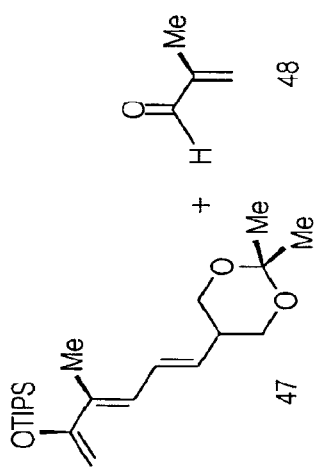

In one aspect of the invention, it is recognized that the functionalities and relative stereochemistry of the AB ring system of acanthoic acid (1) are akin to those in the structure of podocapric acid (20). See "The total synthesis of natural products." ApSimon, Ed.; John Wiley & Sons, Inc., 1973, Volume 8, pages 1-243. Among the several synthetic strategies toward 20, highlights of the ones may be are relevant to the proposed synthesis of 1 are shown in FIG. 5. According to the invention, these approaches allowed the prediction of the stereochemical outcome of the synthesis of The compounds of Formulae (I), (II) and the contrary stereochemical of the compounds of Formulae (IIB), and the compounds of Formulae (IIB) that are designated TTL1, TTL2, TTL3, and TTL4 herein.

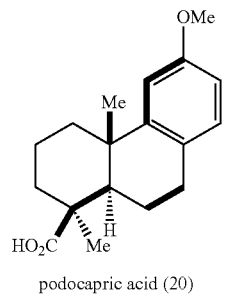

podocapric acid (20)

Complete Syntheses of the Compounds of Formulae (I), (II) and (IIB)

Figure 3:
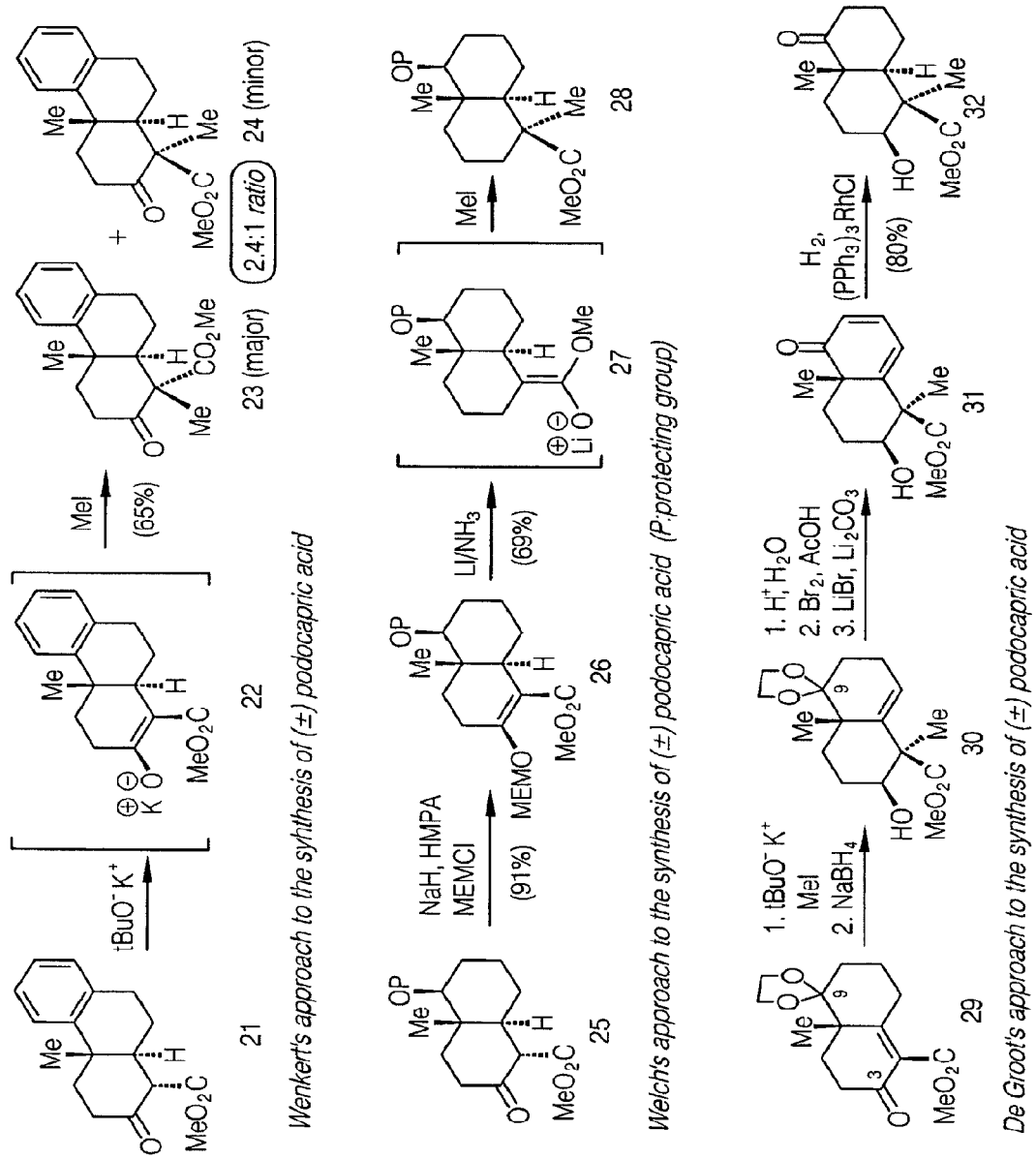
FIG. 3 depicts selected approaches to the construction of the AB ring of certain compounds including: Wenkert's approach to the synthesis of (±) podocapric acid; Welch's approach to the synthesis of (±) podocapric acid; and DeGrot's approach to the synthesis of (±) podocapric acid.

The initial step of the synthesis of acanthoic acid (1), and of all compounds of Formulae (I), (II) and (IIB), involves the reaction of a Wieland-Miesher ketone (17). This compound was readily available from compounds 18 and 19 as a single enantiomer by a Michael addition/Robinson annulation sequence using catalytic amounts of (R)-proline. Selective protection of the more basic C9 carbonyl group of 17, followed by a reductive alkylation of enone 34 with methyl cyanoformate gave rise to ketoseter 36. Transformation of 36 to 39 was based on previous studies, see Welch, S. C.; Hagan, C. P. "A new stereoselective method for developing ring A of podocapric acid compounds" *Synthetic Commun.* 1972, 2, 221-225, as depicted in FIG. 3. Reduction of the ester functionality of 39, followed by silylation of the resulting alcohol and acid-catalyzed deprotection of the ketal unit then afforded ketone 40. Conversion of 40 to the desired diene 42 was accomplished by a two step sequence involving transformation of 40 to its corresponding enol triflate derivative, followed by palladium catalyzed coupling with vinyl stannane 41. See Farine, V.; Hauck, S. I.; Firestone, R. A. "Synthesis of cephems bearing olefinic sulfoxide side chains as potential b-lactamase inhibitors" *Bioorg. & Medicinal Chem. Lett.* 1996, 6, 1613-1618.

The steps that were used in the completion of the synthesis of acanthoic acid (1), and are used in the completion of the syntheses of compounds of Formulae (I), (II) and (IIB) are depicted in FIG. 5, as Scheme 2. A Diels-Alder cycloaddition between diene 42 and dienophile 43, followed by reductive desulfurization with Raney Ni produces the tricyclic system 44 with the desired stereochemistry. Transformation of 44 to the Weinreb amide, followed by reduction with DIBALH generated aldehyde 45, which upon Wittig reaction gave rise to olefin 46. Fluoride-induced desilylation of 46, followed by a two steps oxidation of the resulting alcohol to the carboxylic acid produced acanthoic acid (1), and may be used to produce the compounds of Formulae (I), (II) and (IIB) by appropriate substitution of the intermediates.

One important step to the synthesis of compounds of Formulae (I) and (IA), and the compounds of Formulae (II), (IIA) and (IIB), is the Diels-Alder reaction. This reaction, and the use and selection of one or more appropriately substituted dienes and/or dienophiles permits the selective synthesis of compounds of Formula (II) or the selective synthesis of compounds of Formula (IIB). For example, the following preferred dienophiles may be used in place of the dienophiles, for example, compound 43 and pimarane (103), as depicted herein in, for example, FIGS. 5, 7, 8, 21, and 23, as Reaction Schemes 2, 3, 4, 5, and 6, to selectively yield compounds of Formulae (II) and (IIB). Exemplary dienophiles include those of Formulae (III):

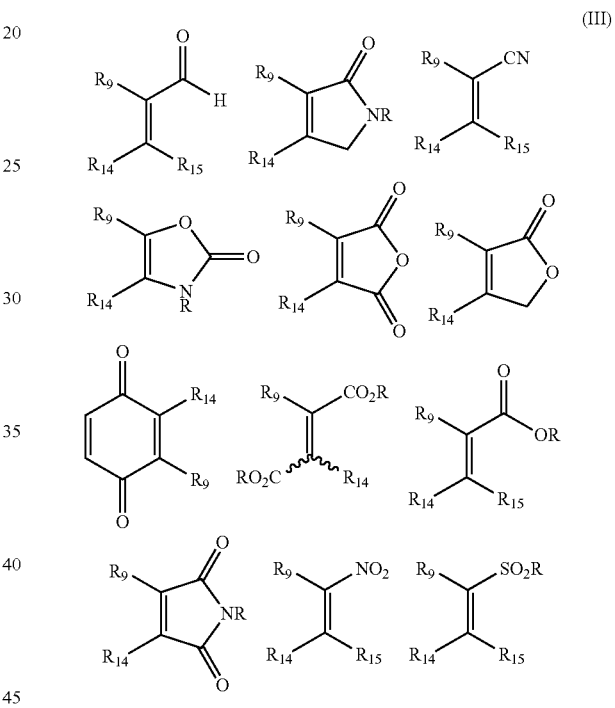

wherein the numbered R-groups ($R_9$, $R_{14}$, and $R_{15}$) are as designated above for the compounds of Formula (IIB), and the unnumbered R groups may be any of $R_1$ through $R_{15}$ as designated above for the compounds of Formula (IIB).

Furthermore, the electronic conformation of the diene, for example compound (42) and compound (112), as depicted herein in, for example, FIGS. 5, 7, 8, 21, and 23, as Reaction Schemes 2, 3, 4, 5, and 6, respectively, may be altered by the covalent linkage of electron-donating or electron-withdrawing group, for example, pH5, to the diene. As exemplified herein, such a covalently linked electron-donating or electron-withdrawing group effects the orientation of the incoming dieneophile.

Thus, according to one aspect of the invention, the chiral nature of diene 42 allows it to be used to induce asymmetry during the cycloaddition. Examination of a minimized model of 42 indicates that the angular methyl at C10 influences the facial selectivity of the reaction and allow more efficient approach of the dienophile from the top face of the diene. This approach produced the adduct that leads to compounds of Formulae (IIB). This approach also allowed for the development of a catalytic asymmetric variant of the Diels Alder reaction. The benefits of using chiral catalysts, as opposed to chiral auxiliaries, are obvious and well documented in the recent literature.

One preferred embodiment is the use of catalyst 49, that was developed and applied by Corey toward an improved asymmetric synthesis of cassiol (Scheme 3). See Corey, E. J.; Imai, N.; Zhang, H.-Y. *J. Am. Chem. Soc.* 1994, 116, 3611. Compound 49 was shown to allow Diels-Alder cycloaddition of an electronically rich diene 47 with methacrolein (48) and produce exclusively the endo adduct in excellent yield and enantiomeric excess (83% yield, 97% ee).

Figure 8:
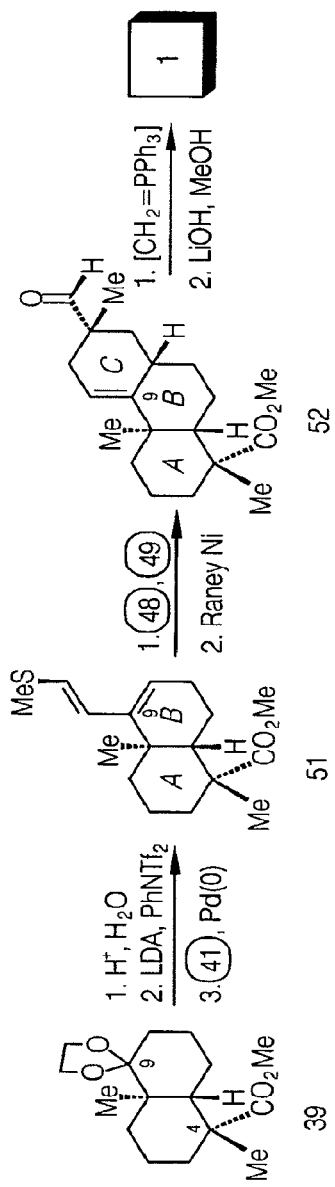
FIG. 8 depicts a synthetic scheme (Scheme 4) for the synthesis of the compound of Formula (I) and certain compounds based on an asymmetric Diels-Alder methodology.

Application of the above methodology to one preferred synthesis is depicted in FIG. 8, as Scheme 4. Use of catalyst 49 provided additional versatility and significantly shorten the total amount of steps required for completion of the total synthesis of 1.

Synthesis of Radiolabeled Compounds of Formula (I)

Figure 4:
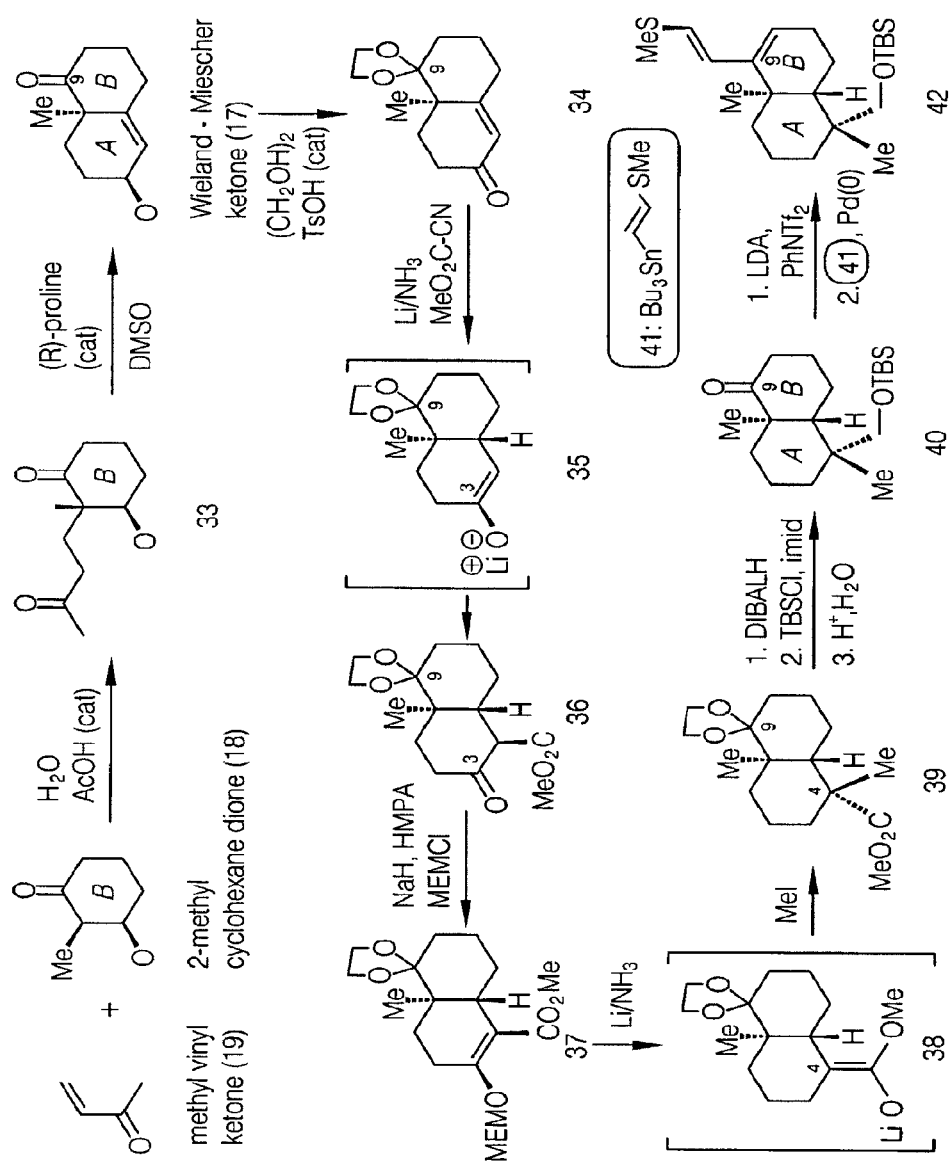
FIG. 4 depicts a schematic synthetic scheme (Scheme 1) of the synthesis of the AB ring system of acanthoic acid and certain compounds.

A radiolabeled sample of a compound of Formulae (I), (II), (IIA) or (IIB) may be synthesized and is useful in pharmacological and pharmacokinetic studies, For example, a C14-labeled methylene carbon is incorporated on the compound of Formulae (I) using aldehyde 52 as a starting material (as depicted in FIG. 4, Scheme 4). The C14-labeled yield, required for the Wittig chemistry, is prepared in two steps from C14-labeled iodomethane and triphenyl-phosphine, followed by treatment with a base, such as NaHMDS. Base-induced deprotection of the methylester produces radiolabeled a compound of Formulae (I), (II), (IIA) or (IIB).

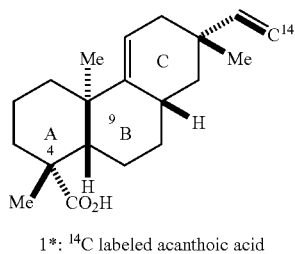

1*: $^{14}$C labeled acanthoic acid

Objectives of the Syntheses of the Compounds of Formula (II). (IIA) and (IIB)

One aspect of the invention is the identification of novel anti-inflammatory drugs having the structure of the compounds of Formula (II), (IIA) and (IIB). Biological screening of synthetic intermediates and rationally designed compounds of Formula (II) provide information and guide the design requirements.

The design and synthesis of analogs of the compounds of Formula (II) is based on the following objectives: (a) defining the minimum structural and functional requirements the compounds of Formula (II) that are responsible for the TNF-α and IL-1 modulating activity (minimum pharmacophore); (b) improving the TNF-α and IL-1 modulating activity of the compounds of Formula (II) by altering the structure, particularly the R-groups of the minimum pharmacophore (for example, SAR studies and molecular recognition experiments); (c) examining the mode of action of the compounds of Formula (II) by photoaffinity labeling studies; (d) modifying and improving the solubility and membrane permeability of the compounds of Formula (II); (e) synthesizing and study dimers or conjugates of the compounds of Formula (II); selective delivery units and (f) redesigning and refining the target structure by evaluating the obtained biological data.

Figure 9:
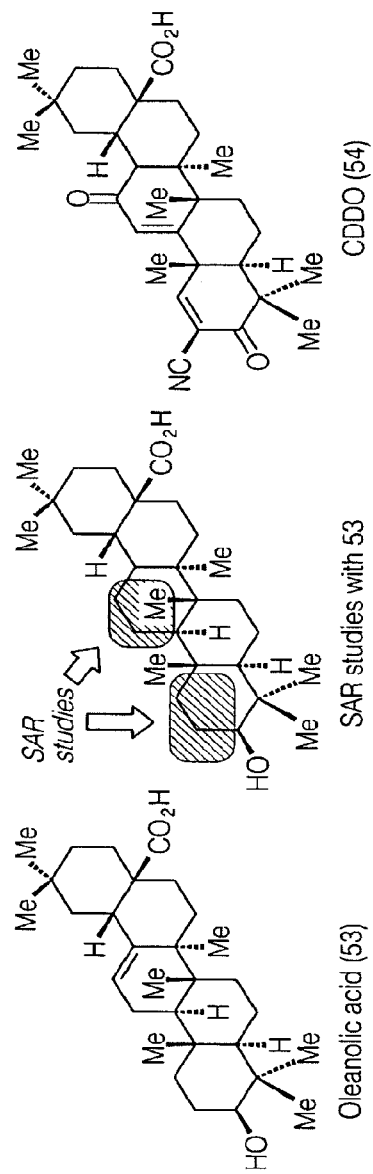
FIG. 9 depicts the structure activity relationship and the focus of structure activity relationship studies of oleanolic acid and its derivatives and certain compounds.

Of particular significance to the rational design of novel the compounds of Formulae (II), (IIA) and (IIB) are the recent reports that modification of the A and C rings of oleanolic acid (53), as depicted in FIG. 9, lead to enhanced antiproliferative and antiinflammatory activity. See Honda, T.; Rounds, B. V.; Gribble, G. W.; Suh, N.; Wang, Y.; Sporn, M. B. "Design and synthesis of 2-cyano-3,12-dioxoolean-1,9-dien-28-oic acid, a novel and highly active inhibitor of nitric oxide production in mouse macrophages" *Biorg. & Medic. Chem. Lett.* 1998, 8, 2711-2714. Suh, N. et al "A novel synthetic oleanane triterpenoid, 2-cyano-3,12-dioxoolean-1,9-dien-28-oic acid, with potent differentiating, antiproliferative and anti-inflammatory activity" *Cancer Res.* 1999, 59, 336-341. More specifically, SAR studies with commercially available 53 and semi-synthetic derivatives thereof have led to the recognition that that: (a) attachment of electron-withdrawing groups, such as nitrile, at the C2 position increases the biological potency of 53 (FIG. 9); (b) an α,β unsaturated ketone functionality at the C ring is a strong enhancer of potency. The combination of these observations lead to the semisynthesis of a designed triterpenoid 54 (FIG. 9), shown to be 500-fold more active than any other known triterpenoid in suppressing the inflammatory enzymes iNOS (inducible nitric oxide synthase) and COX-2 (cyclooxygenase-2) (FIG. 9).

Synthesis of the Compounds of Formulae (II), (IIA) and (IIB)

Figure 10:
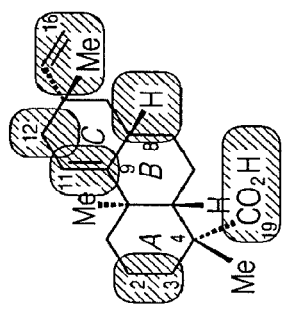
FIG. 10 depicts sites identified for the structural alteration and structure activity relationship studies of Compound 1.
Figure 11:
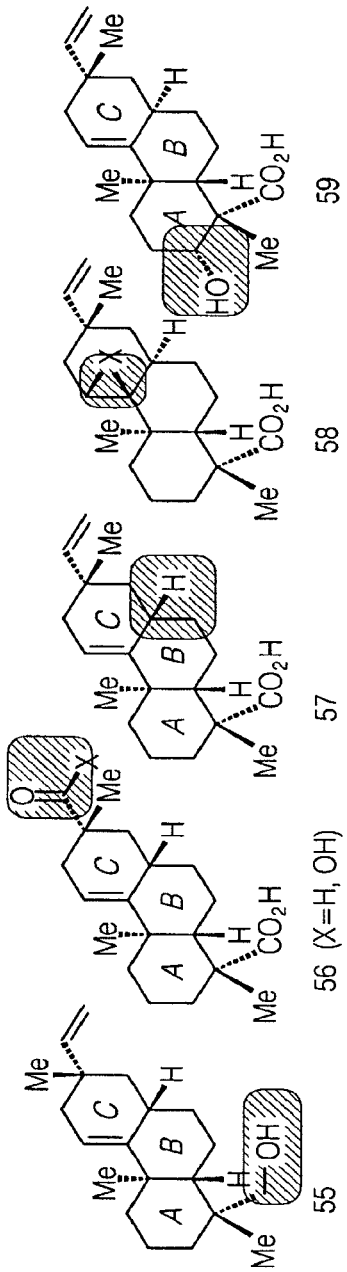
FIG. 11 depicts preferred, representative examples of analogs of Compound 1 for use in structure activity relationship studies and chemical biological studies.

The thirteen-step synthesis of the compounds of Formulae (II), (IIA) and (IIB) (as shown in FIGS. 4 and 8, Schemes 1 and 4, respectively) is efficient and as such, it allows the preparation of a variety of analogs useful in SAR studies. The biological significance of the unusual tricyclic scaffold of the compounds of Formulae (II), (IIA) and (IIB) (the C8 epimer is constructed using the appropriate Diels-Alder catalyst). The sites that are easily altered via the synthetic approach of the invention, or by standard modifications of our synthetic intermediates are shown in the FIG. 10, and representative examples of the compounds of Formula (II) are shown in FIG. 11.

The desired chemical scaffold of the compounds of Formula (II), (IIA) and (IIB) may also be incorporated into solid support such as, for example, a Wang resin. This permits the facile construction of combinatorial libraries of the compounds of Formula (II), (IIA) and (IIB). Furthermore, according to the invention, preferred TNF-α and IL-1 modulators may be more rapidly identified and screen that currently possible.

Figure 12:
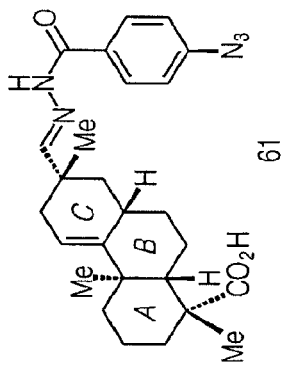
FIG. 12 depicts certain preferred, representative derivatives of Compound 1 for photo affinity labeling studies.
Figure 13:
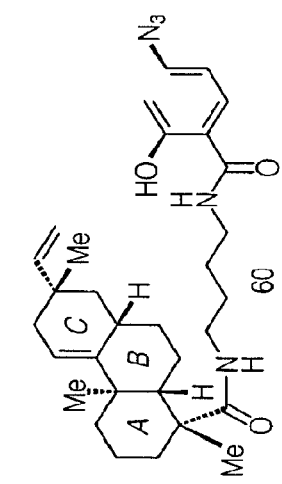
FIG. 13 depicts certain preferred, representative examples of dimers and/or conjugates of Compound 1.
Figure 13:
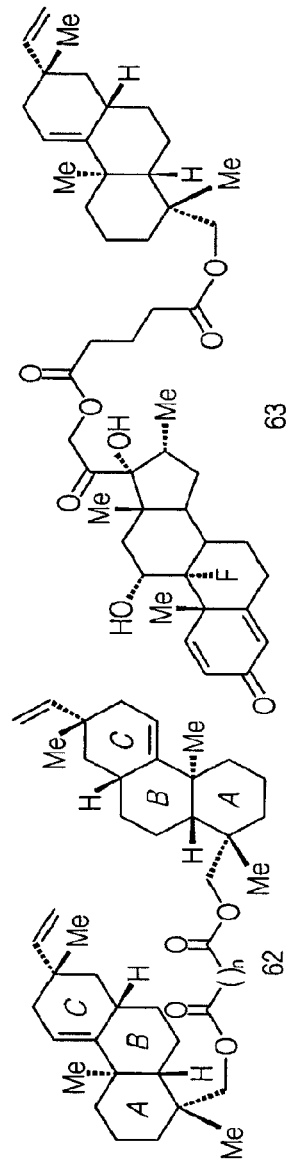

Photoaffinity labeling studies. The backbone of the compounds of Formula (II), (IIA) and (IIB) is also preferably labeled with a reactive cross-linker, that is useful in photoaffinity labeling studies. These studies assist in the identification of the in vivo target of the compounds of Formula (II), (IIA) and (IIB) and provide fundamental insights into the mode of action of acanthoic acid and on the activation of TNF-α. The C19 carboxylic acid or the C15 aldehyde (precursor of 1) are useful in cross-linking experiments with the appropriate photosensitive reagents (see 60 and 61, FIG. 12).

Synthesis of Dimers and Conjugates of the Compounds of Formula (II), (IIA) and (IIB)

Dimeric forms the compounds of Formula (II), (IIA) and (IIB), such as for example 62 (n=1), have been isolated from natural sources and, furthermore, the dexamethasone-acanthoic acid conjugate 63 provides biologically interesting results toward a drug targeting a steroid receptor with potential implications in cancer research. See Chamy, M. C.; Piovano, M.; Garbarino, J. A.; Miranda, C.; Vicente, G. *Phytochemistry* 1990, 9, 2943-2946. While no biological studies of this class of compounds has been performed, according to the invention, dimeric analogs of Formula (II), (IIA) and (IIB)

are evaluated. Synthetic acanthoic acid or bioactive analogs of 1 are used as monomeric partners and their coupling is performed using standard techniques, included those described herein.

Experimental Techniques

All reactions were carried out under an argon atmosphere in dry, freshly distilled solvents under anhydrous conditions, unless otherwise noted. Tetrahydrofuran (THF) and diethyl ether ($Et_2O$) were distilled from sodium/benzophenone; dichloromethane ($CH_2Cl_2$), hexamethyl phosphoramide (HMPA), and toluene from calcium hydride; and dimethyl formamide (DMF) from calcium chloride. Yields refer to chromatographically and spectroscopically ($^1H$ NMR) homogeneous materials, unless otherwise stated. Reagents were purchased at highest commercial quality and used without further purification, unless otherwise stated. Reactions were monitored by thin-layer chromatography carried out on 0.25 mm E. Merck silica gel plates (60F-254) using UV light as visualizing agent and 7% ethanolic phosphomolybdic acid, or p-anisaldehyde solution and heat as developing agents. E. Merck silica gel (60, particle size 0.040-0.063 mm) was used for flash chromatography. Preparative thin-layer chromatography separations were carried out on 0.25 or 0.50 mm E. Merck silica plates (60F-254). NMR spectra were recorded on a Varian 400 and/or 500 Mhz instruments and calibrated using a residual undeuterated solvent as an internal reference. The following abbreviations were used to explain the multiplicities: s=singlet; d=doublet, t=triplet; q=quartet, m=multiplet, b=broad. IR spectra were recorded on a Nicolet Avatar 320 FT-IR spectrometer. Optical rotations were recorded on a Perkin Elmer 241 polarimeter. High resolution mass spectra (HRMS) were recorded on a VG 7070 HS mass spectrometer under chemical ionization (CI) conditions or on a VG ZAB-ZSE mass spectrometer under fast atom bombardment (FAB) conditions.

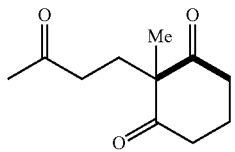

2

Triketone 2. A solution of diketone 1 (50 g, 0.40 mol) in ethyl acetate (500 ml) was treated with triethylamine (72 ml, 0.52 mol) and methyl vinyl ketone (36 ml, 0.44 mol). The reaction mixture was refluxed at 70° C. for 10 h and then cooled to 25° C. The solvent was removed under pressure and the resulting crude material was chromatographed directly (10-40% ether in hexanes) to yield triketone 2 (61 g, 0.31 mol, 78%). 2: colorless oil; $R_f$=0.25 (silica, 50% ether in hexanes); $^1$H NMR (400 MHz, $CDCl_3$) δ 2.75-2.59 (m, 4H), 2.34 (t, 2H, J=7.2 Hz), 2.10 (s, 3H), 2.07-2.05 (m, 3H), 1.98-1.94 (m, 1H), 1.24 (s, 3H).

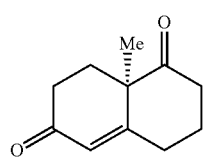

3

Wieland-Miescher ketone (3) A solution of triketone 2 (61 g, 0.31 mol) in dimethyl sulfoxide (400 ml) was treated with finely grounded D-proline (1.7 g, 0.01 mol). (As noted below, see Examples 18 through 21, triketone 2 in dimethyl sulfoxide (400 ml) may also be treated with finely grounded L-proline to yield the enantiomer of the Wieland-Miescher ketone (3)). The solution was stirred at 25° C. for 4 days and then stirred at 40° C. for 1 more day. The resulting purple colored solution was cooled to 25 C, diluted with water (300 ml) and brine (100 ml), and poured into a separatory funnel. The mixture was extracted with ethyl ether (3×800 ml). The organic layers were concentrated (without drying) and subjected to chromatography (10-40% ether in hexanes) to give 59 g of a crude reddish-violet oil. The material was again subjected to chromatography (10-40% ether in hexanes) and concentrated to yield 57 g of a yellow oil. The oil was dissolved in ethyl ether (400 ml) and kept at 4° C. for 30 min, after which time a layer of hexanes (100 ml) was added on top of the ether. The two-layered solution was seeded with a few crystals and placed into a freezer (−28° C.) overnight. The resulting crystals were collected by filtration, rinsed with ice-cold hexanes (2×100 ml), and dried under pressure. Concentration of the mother liquor afforded another crop, and combining the crystals afforded the Wieland-Miescher ketone (3) (43 g, 0.24 mol, 78%). 3: tan crystals; $R_f$=0.25 (silica, 50% ether in hexanes); $[\alpha]^{25}_D$: −80.0 (c=1, $C_6H_6$); $^1$H NMR (400 MHz, $CDCl_3$) δ 5.85 (s, 1H), 2.72-2.66 (m, 2H), 2.51-2.42 (m, 4H), 2.14-2.10 (m, 3H), 1.71-1.68 (m, 1H), 1.44 (s, 3H); $^{13}$C NMR (100 MHz, $CDCl_3$) δ 210.7, 198.0, 165.6, 125.7, 50.6, 37.7, 33.7, 31.8, 29.7, 23.4, 23.0.

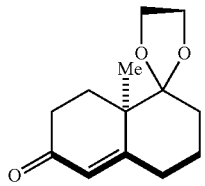

4

Acetal 4. A solution of ketone 3 (43 g, 0.24 mol) in benzene (700 ml) was treated with p-toluenesulfonic acid (4.6 g, 0.024 mol) and ethylene glycol (15 ml, 0.27 mol). The reaction was refluxed with a Dean-Stark apparatus and condenser at 120 C. Once water stopped collecting in the Dean-Stark apparatus, the reaction was complete (approx. 4 h). Leaving the reaction for longer periods of time tended to darken the reaction mixture and lower the overall yield. The reaction was cooled to 25° C., quenched with triethylamine (5 ml, 0.036 mol), and poured into a separatory funnel containing water (300 ml) and saturated sodium bicarbonate (200 ml). The resulting mixture was then extracted with ether (3×800 ml). The organic layers were combined, dried over $MgSO_4$, concentrated, and subjected to chromatography (10-40% ether in hexanes) to afford acetal 4 (48 g, 0.22 mol, 90%). 4: yellow oil; $R_f$=0.30 (silica, 50% ether in hexanes); $[\alpha]^{25}_D$: −77 (c=1, $C_6H_6$); IR (film) $\nu_{max}$ 2943, 2790, 1667, 1450, 1325, 1250; $^1$H NMR (400 MHz, $CDCl_3$) d 5.80 (s, 1H), 3.98-3.93 (m, 4H), 2.43-2.35 (m, 3H), 2.34-2.20 (m, 3H), 1.94-1.82 (m, 1H), 1.78-1.60 (m, 3H), 1.34 (s, 3H); $^{13}$C NMR (100 MHz, $CDCl_3$) δ 198.9, 167.5, 125.5, 112.2, 65.4, 65.1, 45.1, 34.0, 31.5, 30.1, 26.9, 21.8, 20.6.

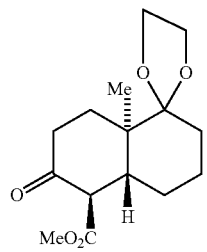

Ketoester 5. A solution of lithium (0.72 g, 0.10 mol) in liquid ammonia (400 ml) at −78 C was treated dropwise with a solution of acetal 4 (10 g, 0.045 mol) and tert-butyl alcohol (3.7 ml, 0.045 mol) in ether (40 ml). The resulting blue mixture was allowed to warm and stir at reflux (−33° C.) for 15 min and then cooled to −78° C. again. Sufficient isoprene (approx. 8 ml) was added dropwise to discharge the residual blue color of the reaction mixture. The reaction was then warmed in a water bath (50° C.). and the ammonia quickly evaporated under a stream of dry nitrogen. The remaining ether was removed under pressure to leave a white foam. After a further 5 min under high vacuum, the nitrogen atmosphere was restored, and the lithium enolate was suspended in dry ether (150 ml) and cooled to −78° C. Methyl cyanoformate (4.0 ml, 0.050 mol) was then added and the reaction stirred for 40 min at −78 C. The reaction was warmed to 0° C. and stirred for 1 h more. Water (300 ml) and ether (200 ml) were added and the mixture poured into a separatory funnel containing saturated sodium chloride (100 ml). After separating the organic layer, the aqueous phase was extracted with ether (2×400 ml). The combined organic layers were dried over MgSO$_4$, concentrated, and subjected to chromatography (10-40% ether in hexanes) to afford ketoester 5 (7.0 g, 0.025 mol, 55%). 5: white powdery precipitate; R$_f$=0.40 (silica, 50% ether in hexanes; [α]$^{25}$$_D$: −2.9 (c=1, C$_6$H$_6$); IR (film) ν$_{max}$ 2943, 1746, 1700; $^1$H NMR (400 MHz, CDCl$_3$) δ 4.00-3.96 (m, 2H), 3.95-3.86 (m, 2H), 3.74 (s, 3H), 3.23 (d, 1H, J=13.2 Hz), 2.50-2.42 (m, 3H), 2.05-1.92 (m, 1H), 1.79-1.50 (m, 5H), 1.32-1.28 (m, 2H), 1.21 (s, 3H); $^{13}$C NMR (100 MHz, CDCl$_3$) δ 205.4, 170.0, 111.9, 65.2, 65.1, 59.9, 52.0, 43.7, 41.6, 37.5, 30.3, 29.8, 26.2, 22.5, 14.0; HRMS, calcd for C$_{15}$H$_{22}$O$_5$ (M+Na$^+$) 305.1359, found 305.1354.

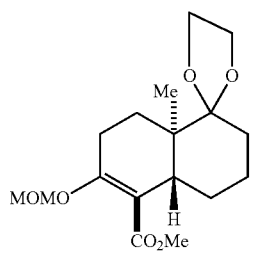

Ester 6. A solution of ketoester 5 (7.0 g, 0.025 mol) in HMPA (50 ml) was treated with sodium hydride (0.71 g, 0.030 mol). After stirring for 3 h at 25° C., the resulting yellow-brown reaction mixture was quenched with chloromethyl methyl ether (2.3 ml, 0.030 mol) and the reaction allowed to stir an additional 2 h at 25° C. The resulting white-yellow mixture was then poured into a separatory funnel containing ice-water (100 ml), saturated sodium bicarbonate (50 ml), and ether (200 ml). After the layers were separated, the aqueous layer was extracted with ether (3×200 ml). The combined ethereal extracts were dried over MgSO$_4$, concentrated, and subjected to chromatography (silica, 10-40% ether in hexanes) to yield ester 6 (7.7 g, 0.024 mol, 95%). 6: yellow oil; R$_f$ 0.45 (silica, 50% ether in hexanes); [α]$^{25}$$_D$: +26.3 (c=1, C6H6); IR (film) ν$_{max}$ 2951, 1728, 1690, 1430, 1170; $^1$H NMR (400 MHz, CDCl$_3$) δ 4.89 (dd, 2H, J=22.8, 6.4 Hz), 3.93-3.91 (m, 2H), 3.90-3.84 (m, 2H), 3.69 (s, 3H), 3.40 (s, 3H), 2.72-2.68 (m, 1H), 2.24 (bs, 2H), 1.80-1.42 (m, 4H), 1.37-1.15 (m, 2H), 0.960 (s, 3H), 0.95-0.80 (m, 2H); $^{13}$C NMR (100 MHz, CDCl$_3$) δ 167.8, 150.5, 115.8, 112.1, 93.0, 65.2, 65.1, 56.3, 51.3, 40.7, 40.3, 30.3, 26.4, 23.6, 22.9, 22.3, 13.9; HRMS, calcd for C$_{17}$H$_{26}$O$_6$ (M+Na$^+$) 349.1622, found 349.1621.

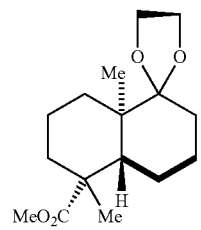

Acetal 7. A solution of lithium (1.1 g, 0.17 mol) in liquid ammonia (400 ml) at −78 C was treated dropwise with a solution of ester 6 (7.7 g, 0.024 mol) in 1,2-DME (30 ml). The blue reaction mixture was allowed to warm and stir at reflux (−33° C.) for 20 min. The reaction mixture was then cooled to −78° C. again and rapidly quenched with excess iodomethane (15 ml, 0.24 mol). The resulting white slurry was allowed to stir at reflux (−33° C.) for 1 h, after which time the reaction was warmed in a water bath (50° C.) with stirring for 1 h, allowing the ammonia to evaporate. The reaction mixture was quenched with water (100 ml), sodium bicarbonate (100 ml), and ether (200 ml) and poured into a separatory funnel. After the layers were separated, the aqueous layer was extracted with ether (3×200 ml). The combined ethereal extracts were dried over MgSO$_4$, concentrated, and subjected to chromatography (silica, 10-30% ether in hexanes) to yield acetal 7 (4.1 g, 0.014 mol, 61%). 7: semi-crystalline yellow oil; R$_f$=0.80 (silica, 50% ether in hexanes); [α]$^{25}$$_D$: +16.9 (c=10, C$_6$H$_6$); IR (film) ν$_{max}$ 2934, 1728, 1466, 1379, 1283, 1125, 942; $^1$H NMR (400 MHz, CDCl$_3$) δ 3.95-3.80 (m, 4H), 3.64 (s, 3H), 2.17-2.15 (m, 1H), 1.84-1.37 (m, 11H), 1.16 (s, 3H), 1.05-1.00 (m, 1H), 0.87 (s, 3H); $^{13}$C NMR (100 MHz, CDCl$_3$) δ 177.7, 112.9, 65.2, 64.9, 51.2, 44.0, 43.7, 38.1, 30.7, 30.3, 28.8, 23.4, 19.1, 14.7; HRMS, calcd for C$_{16}$H$_{26}$O$_4$ (M+H$^+$) 283.1904, found 283.1904.

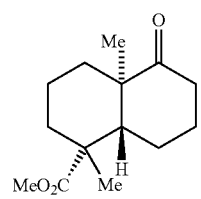

Ketone 8. A solution of acetal 7 (4.1 g, 0.014 mol) in THF (50 ml) was treated with 1M HCl dropwise (approx. 15 ml) at 25° C. with stirring. The reaction was monitored by thin layer chromatography and neutralized with sodium bicarbonate (30 ml) once the starting material disappeared. The resulting mixture was poured into a separatory funnel containing water (100 ml) and ether (100 ml). After the layers were separated, the aqueous layer was extracted with ether (3×100 ml). The combined ethereal extracts were dried over MgSO$_4$, concentrated, and subjected to chromatography (silica, 10-20% ether in hexanes) to yield ketone 8 (3.3 g, 0.014 mol, 95%). 8: white crystals; R$_f$=0.70 (silica, 50% ether in hexanes); [α]$^{25}_D$: +3.5 (c=1.0, C$_6$H$_6$); IR (film) ν$_{max}$ 2943, 1728, 1449, 1239, 1143, 1095, 985; $^1$H NMR (400 MHz, CDCl$_3$) δ 3.62 (s, 3H), 2.55-2.45 (m, 1H), 2.92-1.95 (m, 5H), 1.8-1.6 (m, 2H), 1.50-1.30 (m, 4H), 1.14 (s, 3H), 0.98-0.96 (m, 1H), 0.90 (s, 3H); $^{13}$C NMR (100 MHz, CDCl$_3$) δ 214.8, 177.0, 54.4, 51.3, 49.3, 44.2, 37.9, 37.7, 33.1, 28.6, 26.4, 22.8, 18.8, 17.0; HRMS, calcd for C$_{14}$H$_{22}$O$_3$ (M+Na$^+$) 261.1461, found 261.1482.

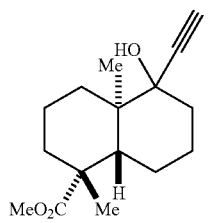

9

Alkyne 9. A solution of ketone 8 (2.0 g, 8.3 mmol) in ether (50 ml) was treated with lithium acetylide (0.40 g, 13 mmol). The reaction was stirred at 25 C for 1 h and then quenched with sodium bicarbonate (20 ml) and water (30 ml). The mixture was poured into a separatory funnel and the layers were separated. The aqueous layer was extracted with ether (3×50 ml). The organic layers were combined, dried with MgSO$_4$, concentrated, and subjected to chromatography (silica, 10-30% ether in hexanes) to afford alkyne 9 (2.0 g, 7.6 mmol, 90%). 9: white solid; R$_f$=0.65 (silica, 50% ether in hexanes); $^1$H NMR (400 MHz, CDCl$_3$) δ 3.64 (s, 3H), 2.56 (s, 1H), 2.18-2.10 (m, 1H), 1.92-1.40 (m, 12H), 1.18 (s, 3H), 1.17-1.01 (m, 1H), 0.81 (s, 3H); $^{13}$C NMR (100 MHz, CDCl$_3$) 177.6, 86.8, 76.5, 75.0, 51.2, 50.5, 43.9, 52.5, 37.9, 35.3, 33.4, 28.8, 23.5, 22.5, 19.1, 11.5; HRMS, calcd for C$_{16}$H$_{24}$O$_3$ (M+H$^+$—H$_2$O) 247.1693, found 247.1697.

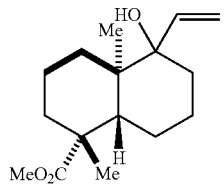

10

Alkene 10. A solution of alkyne 9 (0.50 g, 1.9 mmol) in 1,4-dioxane (20 ml) and pyridine (2 ml) was treated with Lindlar's catalyst (100 mg). The mixture was hydrogenated under pressure (30 lbs/in$^2$) for 7 min. The reaction mixture was then diluted with ether (10 ml), filtered through a pad of celite, and washed with ether (2×50 ml). The solvent was evaporated under reduced pressure to afford alkene 10 (0.48 g, 1.8 mmol, 95%). 10: colorless oil; $^1$H NMR (400 MHz, CDCl$_3$) δ 6.58 (dd, 1H), 5.39 (d, 1H), 5.14 (d, 1H), 3.64 (s, 3H), 2.20-2.11 (m, 2H), 1.93-1.65 (m, 4H), 1.61 (s, 2H), 1.52-1.25 (m, 4H), 1.19 (s, 3H), 1.17-0.90 (m, 2H), 0.89 (s, 3H).

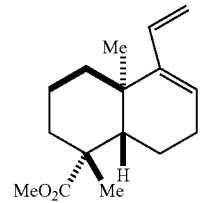

11

Diene 11. A solution of alkene 10 (0.48 g, 1.8 mmol) in benzene (80 ml) and THF (20 ml) was treated with boron trifluoride etherate (1 ml, 7.9 mmol), and the reaction mixture was refluxed at 100 C for 5 h. After cooling, the reaction was quenched with 1N NaOH (1 ml, 26 mmol) and the mixture was poured into a separatory funnel containing water (100 ml) and ether (100 ml). After separating the layers, the aqueous layer was extracted with ether (3×100 ml). The organic layers were combined, dried with MgSO$_4$, concentrated, and subjected to chromatography (silica, 5% ether in hexanes) to afford diene 11 (0.42 g, 1.7 mmol, 95%). 11: colorless oil; R$_f$ 0.95 (silica, 50% ether in hexanes); $^1$H NMR (400 MHz, CDCl$_3$) δ 6.26-6.23 (dd, 1H), 5.70 (s, 1H), 5.253 (d, 1H, J=19.2 Hz), 4.91 (d, 1H, J=12.8 Hz), 3.64 (s, 3H), 2.22-2.12 (m, 2H), 2.10-1.94 (m, 2H) 1.92-1.67 (m, 3H), 1.60-1.44 (m, 3H), 1.378 (d, 1H, J=13.6), 1.21 (s, 1H), 1.19-1.00 (m, 2H), 0.86 (s, 3H); $^{13}$C NMR (100 MHz, CDCl$_3$) δ 177.7, 146.7, 136.1, 121.9, 113.3, 53.0, 51.2, 43.9, 38.0, 37.9, 37.4, 28.5, 27.8, 20.5, 19.5, 18.3.

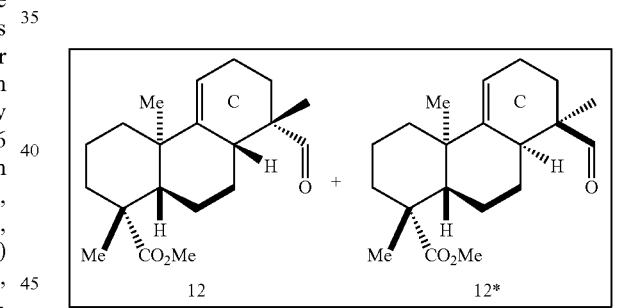

Aldehyde 12. A solution of methacrolein (0.5 ml, 5.2 mmol) and diene 11 (0.1 g, 0.40 mmol) was stirred for 8 h at 25° C. under neat conditions. The excess methacrolein was then removed under reduced pressure. The crude product was subjected to chromatography (silica, 10-20% ether in hexanes) to afford aldehydes 12 and 12* (0.13 g, 0.40 mmol, 100%) as a mixture of diastereomers (3:1-4:1 ratio at C13). 12 and 12*: colorless oil; R$_f$=0.55 (silica, 25% ether in hexanes); 12: IR (film) ν$_{max}$ 3441, 2936, 1726, 1451, 1233, 1152; $^1$H NMR (400 MHz, CDCl$_3$) δ9.70 (s, 1H), 5.58 (m, 1H), 3.62 (s, 3H), 2.38-2.25 (m, 1H), 2.21-2.18 (m, 1H), 2.17-1.98 (m, 4H), 1.96-1.62 (m, 6H), 1.61-1.58 (m, 1H), 1.57-1.43 (m, 2H), 1.40-1.23 (m, 1H), 1.17 (s, 3H), 1.04 (s, 3H), 0.92 (s, 3H); $^{13}$C (100 MHz, CDCl$_3$) δ 207.6, 177.7, 148.3, 188.6, 51.3, 47.8, 47.0, 44.2, 41.2, 39.3, 38.8, 38.1, 29.5, 28.4, 22.9, 22.5, 21.8, 20.6, 20.5, 19.7; 12*: [α]$^D_{25}$: +36.8 (c=0.7, C$_6$H$_6$); IR (film) ν$_{max}$ 3441, 2936, 1726, 1451, 1233, 1152; $^1$H NMR (400 MHz, CDCl$_3$) δ9.64 (s, 1H), 5.42 (m, 1H), 3.66 (s, 3H), 2.29-2.10 (m, 4H), 2.09-1.84 (m, 4H), 1.81-1.77 (m, 2H), 1.75-1.63 (m, 2H), 1.62-1.58 (m, 2H), 1.57-1.45 (m, 1H), 1.43 (s, 1H), 1.13 (s, 3H), 1.03 (s, 3H), 0.87 (s, 3H); $^{13}$C NMR (100 MHz, CDCl$_3$) δ 207.3, 177.5, 147.4, 114.6, 55.8, 51.3, 47.3, 44.5, 40.7, 40.4, 38.4, 37.5, 31.5, 28.6, 25.0, 24.2, 21.9, 19.9, 19.6, 18.7.

The preferred way to purify the diastereomeric aldehydes is to reduce them with sodium borohydride in MeOH and separate the alcohols. The major compound (top diastereomer) can then be oxidized to the desired aldehyde 12 upon treatment with Dess-Martin periodinane.

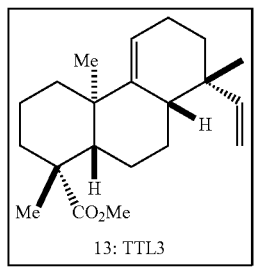

13: TTL3

Alkene 13 (TTL3). A solution of (methyl)-triphenyl-phosphonium bromide (357 mg, 1.0 mmol) in THF (40 ml) was treated with 1M NaHMDS in THF (0.86 ml, 0.86 mmol). The resulting yellow mixture was allowed to stir at 25° C. for 30 min. After this time, a solution of aldehyde 12 (91 mg, 0.29 mmol) in THF (10 ml) was added to the reaction via cannula. The reaction mixture was stirred at 25° C. for 8 hours and then quenched with sodium bicarbonate (30 ml) and water (20 ml). The mixture was poured into a separatory funnel containing ether (50 ml). After separating the layers, the aqueous layer was extracted with ether (3×50 ml). The organic layers were combined, dried with MgSO$_4$, condensed, and subjected to chromatography (silica, 10% ether in hexanes) to afford alkene 13 (84 mg, 0.28 mmol, 97%). 13: colorless oil; $R_f$=0.75 (silica, 25% ether in hexanes); 13: $^1$H NMR (400 MHz, CDCl$_3$) δ 5.96 dd, 1H, J=16.8, 11.6 Hz), 5.50 (m, 1H), 4.98 (m, 2H), 3.62 (s, 3H), 2.20-2.11 (m, 1H), 2.10-1.91 (m, 4H), 1.90-1.70 (m, 4H), 1.69-1.51 (m, 3H), 1.50-1.38 (m, 3H), 1.36-1.24 (m, 1H), 1.17 (s, 3H), 1.04 (s, 3H), 0.90 (s, 3H); $^{13}$C NMR (100 MHz, CDCl$_3$) δ 177.9, 149.1, 143.8, 117.9, 111.7, 51.2, 47.7, 44.4, 41.4, 41.2, 38.9, 38.3, 37.7, 34.8, 30.4, 28.4, 24.8, 23.1, 22.3, 22.2, 20.6, 19.8.

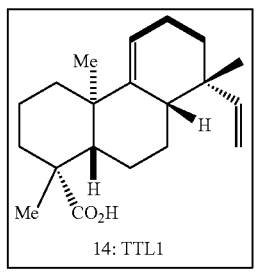

14: TTL1

Acid 14 (TTL1). A solution of alkene 13 (84 mg, 0.28 mmol) in dimethyl sulfoxide (20 ml) was treated with LiBr (121 mg, 1.4 mmol). The reaction mixture was refluxed at 180 C for 2 days. After cooling down, the reaction was diluted with water (30 ml) and extracted with ether (3×50 ml). The organic layers were combined, dried with MgSO$_4$, concentrated, and subjected to chromatography (silica, 30% ether in hexanes) to afford carboxylic acid 14 (TTL1) (78 mg, 0.26 mmol,). 14: white solid; $R_f$=0.30 (silica, 30% ether in hexanes); $^1$H NMR (400 MHz, CDCl$_3$) δ 5.96 (dd, 1H, J=14.4, 9.6 Hz), 5.52 (m, 1H), 4.98-4.95 (m, 2H), 2.20-1.72 (m, 10H), 1.64-1.58 (m, 3H), 1.57-1.37 (m, 4H), 1.22 (s, 3H), 1.04 (s, 3H), 0.99 (s, 3H); $^{13}$C NMR (100 MHz, CDCl$_3$) δ 182.9, 149.3, 143.9, 118.1, 111.9, 47.5, 44.2, 41.3, 41.2, 38.9, 38.0, 37.6, 34.8, 28.4, 24.7, 23.0, 22.4, 21.9, 20.3, 19.5.

Preparation of Ph$_3$P=$^{14}$CH$_2$.

Triphenylphosphine (0.16 g, 0.61 mmol) was added in a 15 ml reaction flask and dried overnight under vacuum at 25° C. To this flask was added 2 ml of THF (dried and degassed under vacuum), followed by $^{14}$CH$_3$I (50 mCi, 53 mCi/mmol, 0.9 mmol) dissolved in 1 ml of THF and the mixture was stirred for 24 hours under argon. Potassium hexamethyldisilylamide (2.5 ml, 1.25 mmol, 0.5 M in toluene) was then added and the reddish-yellow mixture was allowed to stirr for 3 h at 25° C.

Wittig Reaction with Ph$_3$P=$^{14}$CH$_2$.

The above mixture was cooled at −78° C. and treated with aldehyde 12 (63 mg, 0.2 mmol) in dry THF (1.5 ml). The mixture was allowed to warm slowly to 25° C., stirred for 8 h and quenched with sodium bicarbonate (10 ml) and water (10 ml). The mixture was extracted with ether (3×50 ml) and the organic layers were combined, dried with MgSO$_4$, condensed, and subjected to chromatography over silica gel (silica, 10% ether in hexanes) to afford alkene 13.

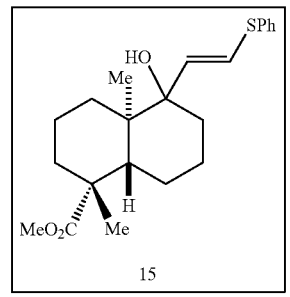

15

Alcohol 15. A solution of alkyne 9 (1.10 g, 4.2 mmol), thiophenol (1.37 g, 12.4 mmol) and 2,2'-azobisisobutyronitrile (AIBN, 34.5 mg, 0.21 mmol) in xylene (25 ml) was stirred at 110° C. (under argon) for 18 h. The reaction mixture was cooled to 25° C. and quenched with aqueous saturated sodium bicarbonate (50 ml). The organic layer was extracted with ethyl ether (3×50 ml), collected, dried (MgSO$_4$), concentrated and residue was chromatographed (silica, 2-5% ethyl ether in hexane) to afford alcohol 15 (1.35 g, 3.6 mmol, 85.7%); 15: colorless liquid; $R_f$=0.51 (silica, 5% ethyl ether in hexanes); $[\alpha]^{25}_D$: +24.20 (c=1.0, benzene); IR (film) $v_{max}$ 2946.8, 1724.5, 1472.6, 1438.4, 1153.5, 740.0, 690.9; $^1$H NMR (500 MHz, CDCl$_3$) δ 7.20-7.60 (m, 5H), 5.23 (d, 1H, J=10.5 Hz), 5.12 (d, 1H, J=10.0 Hz), 3.62 (s, 3H), 2.08-2.24 (m, 2H), 1.16-1.92 (m, 9H), 1.09 (s, 3H), 0.86-1.02 (m, 2H), 0.68 (s, 3H); $^{13}$C NMR (100 MHz, CDCl$_3$) δ 177.8, 151.7, 133.9, 133.7, 128.8, 127.9, 118.2, 54.9, 53.5, 51.1, 44.3, 40.4, 38.1, 37.3, 28.7, 27.7, 25.5, 23.5, 19.5, 18.5.

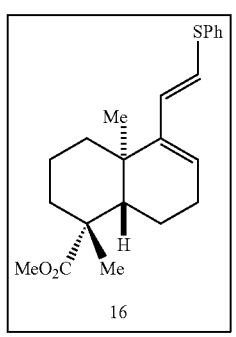

16

Diene 16. To a solution of alcohol 15 (1.10 g, 2.94 mmol) in hexamethyl phosphoramide (HMPA, 10 ml) was added dropwise phosphorus oxychloride (0.50 g, 3.3 mmol) and the mixture was stirred at 25° C. until clear. Pyridine (0.26 ml, 3.23 mmol) was then added and the mixture was stirred at 150° C. (under argon) for 18 hrs. The reaction mixture was cooled to 25° C. and quenched with aqueous saturated sodium bicarbonate (50 ml). The organic layer was extracted with ethyl ether (3×60 ml), collected, dried (MgSO$_4$) and concentrated and residue was chromatographed (silica, 2-5% ethyl ether in hexane) to afford diene 16 (0.85 g, 2.38 mmol, 81%); 16: colorless liquid; R$_f$=0.60 (silica, 5% ethyl ether in hexanes); [α]$^{25}_D$: −17.30 (c=1.08, benzene); IR (film) ν$_{max}$ 2957.0, 1726.6, 1581.6, 1478.3, 1439.0, 1234.7, 1190.8, 1094.8, 1024.4, 739.1; $^1$H NMR (500 MHz, CDCl$_3$) δ 7.20-7.60 (m, 5H), 6.43 (d, 1H, J=15.0 Hz), 6.36 (d, 1H, J=14.5 Hz), 5.72 (m, 1H), 3.64 (s, 3H), 1.48-2.32 (m, 10H), 1.43 (s, 3H), 1.21 (s, 3H), 1.05 (m, 1H), 0.88 (s, 3H); $^{13}$C NMR (125 MHz, CDCl$_3$) δ177.9, 133.7, 129.1, 128.9, 128.6, 127.5, 126.2, 123.4, 120.9, 52.8, 51.1, 43.7, 37.7, 37.3, 30.2, 28.3, 27.7, 20.1, 19.3, 18.3.

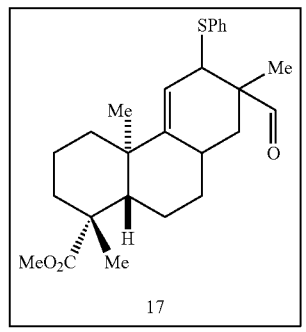

17

Aldehyde 17. To a solution of diene 16 (0.51 g, 1.43 mmol) and methacrolein (0.30 g, 4.30 mmol) in dichloromethane (5 ml) at −20° C. was added under argon dropwise tin (IV) chloride (0.29 ml of 1M solution in dichloromethane, 0.29 mmol). The resulting mixture was warmed to 0° C. within 1 hr and stirred at 0° C. for 18 h. The reaction was quenched with aqueous saturated sodium bicarbonate (15 ml) and the organic layer was extracted with ethyl ether (3×20 ml). The combined organic layers were dried (MgSO$_4$) and concentrated and residue was chromatographed (silica, 10-15% ethyl ether in hexane) to afford aldehyde 17 (0.51 g, 1.19 mmol, 83.7%); 4: colorless liquid; R$_f$=0.48 (silica, 10% ethyl ether in hexanes); [α]$^{25}_D$: +30.0 (c=1.13, benzene); IR (film) ν$_{max}$ 2930.8, 2871.4, 1724.9, 1458.4, 1226.4, 1149.8; $^1$H NMR (500 MHz, CDCl$_3$) δ 9.51 (s, 1H), 7.20-7.60 (m, 5H), 5.57 (m, 1H), 3.65 (s, 3H), 1.20-2.32 (m, 15H), 1.17 (s, 3H), 1.05 (s, 3H), 0.91 (s, 3H); $^{13}$C NMR (125 MHz, CDCl$_3$) δ203.6, 177.9, 153.7, 133.6, 133.5, 128.9, 127.8, 117.1, 51.3, 49.1, 47.7, 44.2, 41.6, 38.7, 38.1, 31.2, 28.3, 27.8, 26.9, 21.7, 20.2, 19.3, 18.6.

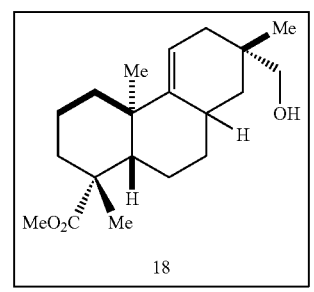

18

Alcohol 18. To a solution of aldehyde 17 (0.50 g, 1.17 mmol) in anhydrous ethanol (5 ml) was added portionwise sodium borohydride (50 mg, 1.32 mmol) and the mixture was stirred for 30 min. Aqueous saturated sodium bicarbonate (10 ml) was then added and the mixture was extracted with ethyl ether (3×20 ml). The organic layer was collected, dried (MgSO$_4$) and concentrated. The residue was redissolved in tetrahydrofuran (5 ml) and treated with excess of Raney Nickel under argon at 65° C. for 10 min. The reaction mixture was filtered, and the filtrate was dried (MgSO$_4$) and concentrated, and the residue was chromatographed (silica, 2-5% ethyl ether in hexane) to afford alcohol 18 as a major compound (0.21 g, 0.65 mmol, overall yield 56.1%). Note: the overall yield for the above two reactions is 91%); 18: colorless liquid; R$_f$=0.39 (silica, 30% ethyl ether in hexanes); [α]$^{25}_D$: −6.70 (c=1.0, benzene); IR (film) ν$_{max}$ 3436.8, 2929.0, 2872.2, 1728.1, 1433.9, 1260.6, 1029.7, 801.6; $^1$H NMR (500 MHz, CDCl$_3$) δ 5.37 (m, 1H), 3.62 (s, 3H), 2.28 (bs, 1H), 2.06-2.20 (m, 2H), 1.20-2.00 (m, 12H), 1.16 (s, 3H), 0.99 (m, 1H), 0.86 (s, 3H), 0.84 (s, 3H); $^{13}$C NMR (125 MHz, CDCl$_3$) δ178.2, 150.4, 116.4, 73.6, 51.2, 47.9, 44.2, 41.9, 38.8, 38.2, 34.3, 33.9, 28.3, 28.2, 27.8, 22.1, 20.3, 20.1, 18.9.

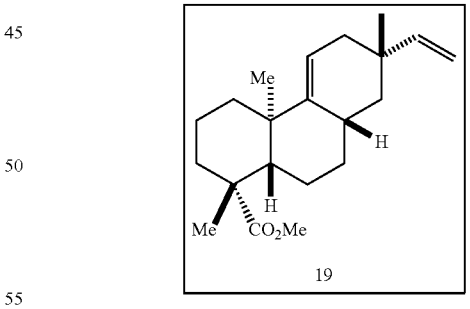

19

Alkene 19. To a solution of alcohol 18 (20.0 mg, 0.062 mmol) in dichloromethane (2 ml) was added Dess-Martin periodinane (35 mg, 0.08 mmol) in portions, and the mixture was stirred at 25° C. for 30 min. The reaction was quenched with aqueous saturated sodium bicarbonate (5 ml) and extracted with ethyl ether (3×10 ml). The organic layer was collected, dried (MgSO$_4$) and concentrated. The residue was redissolved in tetrahydrofuran (0.5 ml) and added under argon to a yellow suspension of (methyl) triphenyl-phosphonium bromide (60 mg, 0.17 mmol) and sodium bis(trimethylsilyl) amide (0.14 ml of 1.0 M in THF) in THF (1.5 ml).

After stirring at 25° C. for 18 h the mixture was diluted with aqueous saturated sodium bicarbonate (5 ml) and extracted with ethyl ether (3×10 ml). The organic layer was collected, dried (MgSO$_4$), concentrated and residue was chromatographed (silica, 2-5% ethyl ether in hexane) to afford alkene 19 (16.8 mg, 0.05 mmol, the overall yield for the two-step reactions is 86%); 19: colorless liquid; R$_f$=0.74 (silica, 5% ethyl ether in hexanes); [α]$^{25}_D$: −14.40 (c=0.50, benzene); IR (film) ν$_{max}$ 2929.5, 2873.4, 1726.8, 1637.7, 1460.7, 1376.8, 1225.1, 1150.4, 997.8, 908.7; $^1$H NMR (500 MHz, CDCl$_3$) δ 5.82 (dd, 1H), 5.39 (m, 1H), 4.85-4.94 (dd, 2H), 3.64 (s, 3H), 2.30 (bs, 1H), 2.14 (m, 1H), 2.02 (m, 1H), 1.80-1.98 (m, 2H), 1.68-1.80 (m, 2H), 1.20-1.68 (m, 7H), 1.18 (s, 3H), 0.96-1.08 (m, 2H), 0.95 (s, 3H), 0.88 (s, 3H); $^{13}$C NMR (125 MHz, CDCl$_3$) δ 178.3, 150.4, 125.6, 116.6, 109.2, 51.2, 47.9, 44.3, 41.9, 41.8, 38.3, 38.2, 37.4, 34.8, 30.2, 29.6, 28.6, 28.4, 27.8, 22.1, 20.4, 19.0.

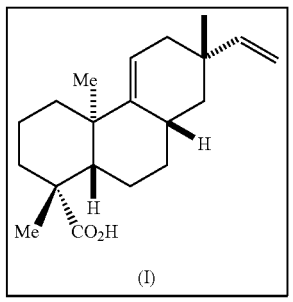

(I)

Compound of Formula (I). To a solution of alkene 19 (16.8 mg, 0.05 mmol) in N,N-dimethylformamide (2 ml) added lithium bromide (5.0 mg, 0.06 mmol) and the mixture was refluxed at 190° C. for 1 hr. The reaction mixture was then cooled to 25° C., diluted with H$_2$O (5 ml) and extracted with ethyl acetate (3×10 ml). The organic layer was collected, dried (MgSO$_4$) and concentrated and residue was chromatographed (silica, 15-20% ethyl ether in hexane) to afford Formula (I) (14.9 mg, 0.05 mmol, 92.6%);

Compound of Formula (I) is a colorless liquid; R$_f$=0.20 (silica, 30% ethyl ether in hexanes); [α]$^{25}_D$: −6.0 (c=0.33, benzene); IR (film) ν$_{max}$ 3080.6, 2928.9, 2857.6, 1693.6, 1638.2, 1464.7, 1413.8, 1376.4, 1263.1, 1179.3, 1095.9, 1027.5, 999.2, 909.2, 801.7; $^1$H NMR (500 MHz, CDCl$_3$) δ 5.82 (dd, 1H), 5.40 (m, 1H), 4.85-4.95 (dd, 2H), 2.30 (bs, 1H), 2.16 (m, 1H), 2.02 (m, 1H), 1.80-1.98 (m, 2H), 1.70-1.84 (m, 2H), 1.10-1.70 (m, 7H), 1.00-1.10 (m, 2H), 0.99 (s, 3H), 0.95 (s, 3H); $^{13}$C NMR (125 MHz, CDCl$_3$) δ 150.3, 149.9, 116.7, 109.2, 47.9, 41.8, 41.7, 38.3, 38.2, 37.4, 34.8, 31.8, 28.6, 28.5, 27.7, 22.6, 22.4, 22.1, 20.3, 18.9.

(Formula (IIB-A1)): Amide with Cyclic Substituent

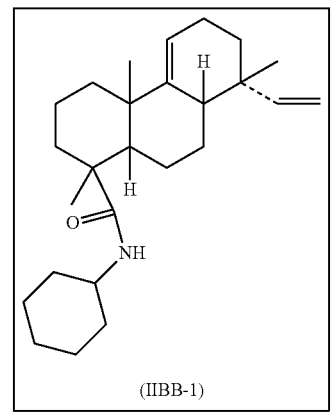

(IIBB-1)

Preparation of N-Cyclohexylamide Derivative of TTL (Formula IIB-A1)

To a solution of TTL-3 (1.0 g, 3.8 mmol) in dry N-methylpyrrolidone (6 mL) under N$_2$ was added in one portion sodium propane thiolate (0.37 g, 3.8 mmol), and the mixture heated gently till most of the solid had dissolved. After stirring at room temperature for 1 hour, water was added and the mixture washed with 10% ether in hexane (3×). The aqueous mixture was acidified to pH 2 with dilute HCl, and then extracted (2×) with ether. The organic phases were combined, washed with brine, dried (anhydrous sodium sulfate) and concentrated. The white solid was washed with hexane to remove any propane thiol, affording clean acid TTL-1.

To a 4 mL vial was added the carboxylic acid (320 mg, 1.06 mmol), 1,3-dicyclohexylcarbodiimide (DCC) (218 mg, 1.06 mmol) and catalytic 4-dimethylaminopyridine (DMAP). The mixture was immediately inserted into a hot sand bath and heated at 160° C. for 5-10 minutes. The mixture was chromatographed (2% ethyl acetate in hexane) to afford the title compound, Formula (IIB-A1) as a viscous oil.

(Formula (IIB-A1)): Amide with Cyclic Substituent

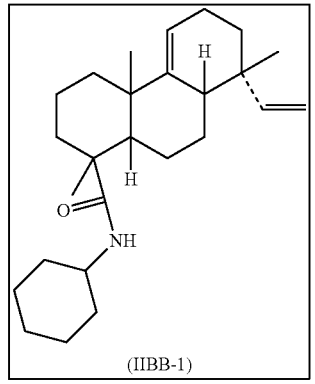

(IIBB-1)

-continued

Synthesis of Amide with Cyclic Substituent (Formula (IIB-A1))

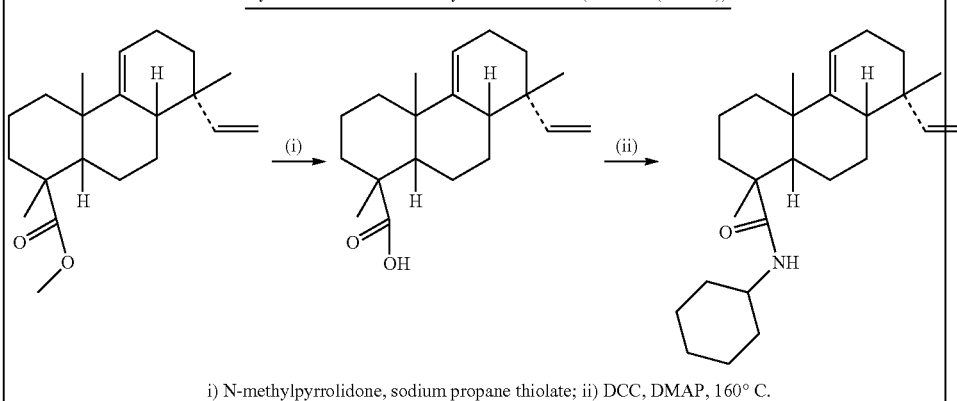

i) N-methylpyrrolidone, sodium propane thiolate; ii) DCC, DMAP, 160° C.

Synthesis of Compounds of Formulae II2-1 and IIA-A1

Acanthoic acid and kaurenoic acid can be used in the synthesis of compounds of Formulae II2-1 and IIA-A1 respectively. Acanthoic acid and kaurenoic acid can be obtained from any available source. A method for acanthoic acid extraction from *Coleonema pulchrum*, and its isolation is described below.

Extraction and Isolation of Acanthoic Acid from Roots of *Coleonema pulchrum*

Dry root of *Coleonema pulchrum* (440 g) was extracted with methanol (3×3 L) by soaking for 48 hrs per extraction step. The combined methanol extracts were concentrated to 500 ml by rotary evaporation and water was added to make up a 9:1 methanol/water solution, which was extracted with hexanes (3×500 mL). The combined hexane extracts were concentrated and dried by high vacuum to yield 5.1 g of crude extract containing acanthoic acid.

Isolation of Acanthoic Acid

The above hexane crude extract (4.5 g) was separated into various fractions by normal phase Vacuum Liquid Chromatography (VLC) using a hexanes/ethyl acetate step gradient as follows:

Column Dimensions: 15×3.4 cm
Solvent Gradients: Fractions
1) 300 mL of 100% hexanes
2) 200 mL of 95% hexanes/5% ethyl acetate
3) 200 mL of 90% hexanes/10% ethyl acetate
4) 200 mL of 85% hexanes/15% ethyl acetate
5) 200 mL of 80% hexanes/20% ethyl acetate
6) 200 mL of 75% hexanes/25% ethyl acetate
7) 200 mL of 50% hexanes/50% ethyl acetate
8) 200 mL of 0% hexanes/100% ethyl acetate All above fractions were analyzed by TLC and mass spectrometry to identify the acanthoic acid containing fractions. Fraction 3 (963 mg) and 4 (327 mg) contained acanthoic acid. Fraction 3 and 4 were purified by preparative HPLC using the following conditions:

Column: Ace 5 μC18
Dimensions: 15 cm×20 mm ID
Flow rate: 14.5 ml/min
Detection: UV Dual Wavelength (set at 210 & 250 nm)
Solvent: 80% acetonitrile/water to 100% acetonitrile in 8 min and 7 min in 100% acetonitrile Seven fractions were collected based on UV peak height at 210 and 250 nm. Fractions 6 contained acanthoic acid, which was concentrated to yield about 90% pure compound.

The above fraction 6 was further purified using a semi-preparative HPLC method described below to yield greater than 97% pure acanthoic acid:

Column: ACE 5 C18-HL
Dimensions: 25 cm×9.4 mm ID
Flow rate: 3 ml/min
Detection: UV Dual Wavelength (set at 210 & 250 nm)
Solvent: 80% acetonitrile/water to 100% acetonitrile in 8 min, and 7 min in 100% acetonitrile Preparation of N-Cyclohexylamide Derivative of Acanthoic Acid (Formula II2-1)

Acanthoic acid, including compound obtained by the above described methodology, can be dissolved in dry $CH_2Cl_2$ and treated with 10 equivalents of $(COCl)_2$ followed by two drops of DMF. When the reaction stops bubbling, the $CH_2Cl_2$ solvent and $(COCl)_2$ can be evaporated under vacuum and the reaction residue can be redissolved in dry benzene and then treated with 5 equivalents of cyclohexylamine to yield N-cyclohexylamide derivative of acanthoic acid.

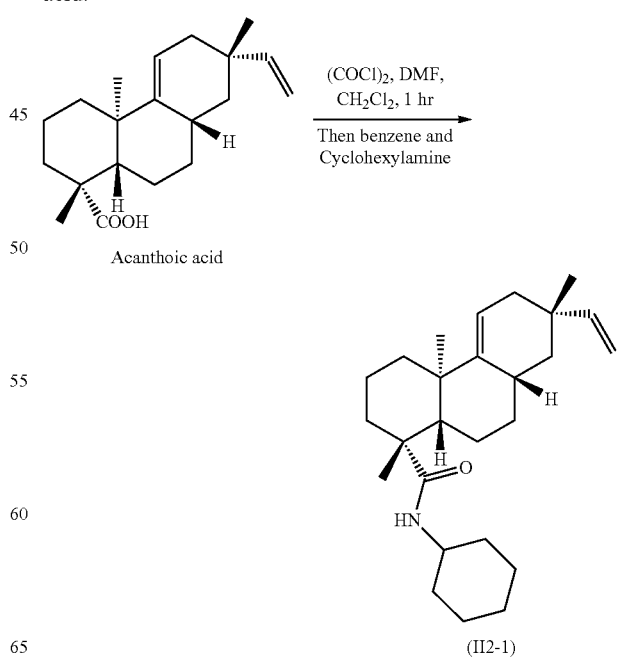

Preparation of N-Cyclohexylamide Derivative of Kaurenoic Acid (Formula IIA-A1)

Kaurenoic acid can be dissolved in dry $CH_2Cl_2$ and treated with 10 equivalents of $(COCl)_2$ followed by two drops of DMF. When the reaction stops bubbling, the $CH_2Cl_2$ solvent and $(COCl)_2$ can be evaporated under vacuum and the reaction residue can be redissolved in dry benzene and then treated with 5 equivalents of cyclohexylamine to yield N-cyclohexylamide derivative of kaurenoic acid.

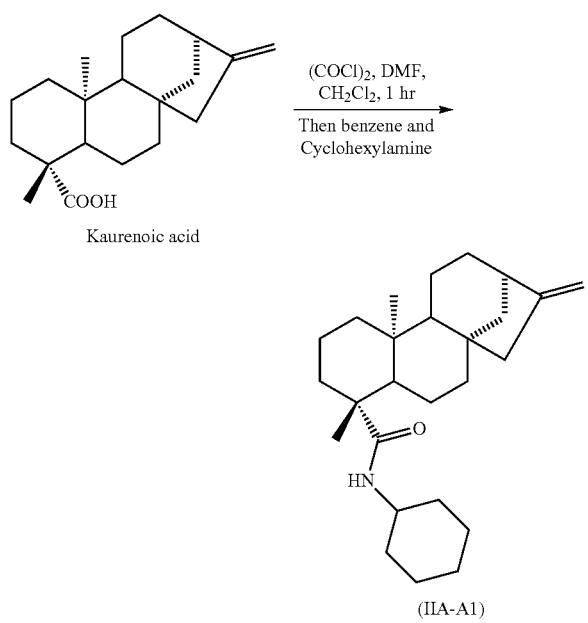

Methods of Making Compounds of Formula II-b

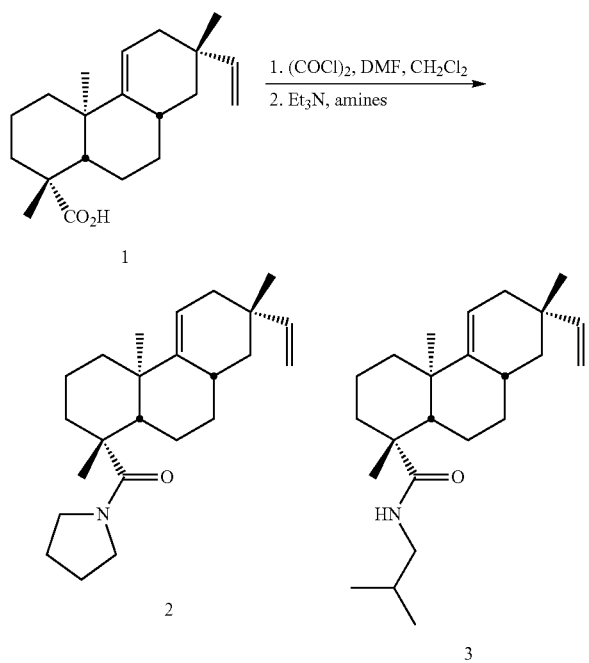

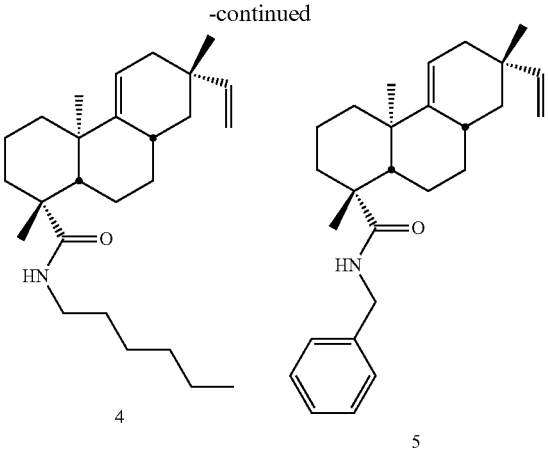

[(1S,4aS,7R)-1,4-a,7-Trimethyl-7-vinyl-1,2,3,4,4a,6, 7,8,8a,9,10,10a-dodecahydro-1-phenanthrenyl](1-pyrrolidinyl)methanone (2)

A solution of acanthoic acid 1 (30 mg, 0.10 mmol) in $CH_2Cl_2$ (3.0 ml) was treated with oxalyl chloride (0.013 ml, 0.15 mmol) in the presence of a catalytic amount of DMF at room temperature. The reaction mixture was stirred for 3 h at room temperature, distilled under reduced pressure, and then 3 ml of $CH_2Cl_2$ was added. Triethylamine (0.03 ml, 0.20 mmol) and pyrrolidine (0.02 ml, 0.20 mmol) were added to the reaction mixture. The reaction mixture was stirred for 30 min., quenched with water and extracted with 5 ml of $CH_2Cl_2$. The organic layer was washed with brine, dried over magnesium sulfate and concentrated under reduced pressure. The residue was purified by silica gel column chromatography (ethyl acetate:hexane=1:10) to afford 25 mg of the analog 2 (71%).

$^1$H-NMR ($CDCl_3$, 300 MHz) δ 5.75 (dd, 1H, J=17.6, 10.8 Hz), 5.35 (m, 1H), 4.87 (dd, 1H, J=10.8, 1.4 Hz), 4.82 (dd, 1H, J=5.5, 1.4 Hz), 3.40-3.53 (m, 4H), 2.38-2.43 (m, 3H), 0.95-2.1 (m, 17H), 1.18 (s, 3H), 1.05 (s, 3H), 0.95 (s, 3H); IR (neat) 2922, 1624, 1459, 1361 $cm^{-1}$; LRMS (EI) m/z 355 ($M^+$).

(1S,4aS,7R)—N-Isobutyl-1,4a,7-trimethyl-7-vinyl-1, 2,3,4,4a,6,7,8,8a,9,10,10a-dodecahydro-1-phenanthrenecarboxamide (3) (SP103)

The analog 3 was prepared (82% yield) according to the same procedure for the analog 2, using iso-butyl amine instead of pyrrolidine.

$^1$H-NMR ($CDCl_3$, 300MHz) δ 5.80 (dd, 1H, J=17.6, 10.8 Hz), 5.75 (m, 1H), 5.35 (m, 1H), 4.87 (dd, 1H, J=10.8, 1.4 Hz), 4.82 (dd, 1H, J=5.5, 1.4 Hz), 3.03 (m, 2H), 2.05-2.38 (m, 2H), 0.84-2.01 (m, 15H), 1.17 (s, 3H), 0.92 (s, 3H), 0.88 (s, 3H); IR (neat) 3390, 2924, 1640, 1518, 1462 $cm^{-1}$; LRMS (EI) m/z 357 ($M^+$).

(1S,4aS,7R)—N-Hexyl-1,4a,7-trimethyl-7-vinyl-1,2, 3,4,4a,6,7,8,8a,9,10,10a-dodecahydro-1-phenanthrenecarboxamide (4) (SP105)

The analog 4 was prepared (74% yield) according to the same procedure for the analog 2, using n-hexyl amine instead of pyrrolidine.

$^1$H-NMR (CDCl$_3$, 300MHz) δ 5.77 (dd, 1H, J=17.6, 10.8 Hz), 5.60 (m, 1H), 5.36 (m, 1H), 4.87 (dd, 1H, J=5.5, 1.4 Hz), 4.82 (dd, 1H, J=10.8, 1.4 Hz), 3.15-3.21 (m, 2H), 2.05-2.38 (m, 2H), 0.83-2.02 (m, 25H), 1.17 (s, 3H), 0.96 (s, 3H), 0.92 (s, 3H); IR (neat) 3387, 2926, 1636, 1522, 1459 cm$^{-1}$; LRMS (EI) m/z 385 (M$^+$).

(1S,4aS,7R)—N-Benzyl-1,4a,7-trimethyl-7-vinyl-1,2,3,4,4a,6,7,8,8a,9,10,10a-dodecahydro-1-phenanthrenecarboxamide (5) (SP104)

The analog 5 was prepared (75% yield) according to the same procedure for the analog 2, using benzyl amine instead of pyrrolidine.

$^1$H-NMR (CDCl$_3$, 300MHz) δ 7.19-7.28 (m, 5H), 5.83 (m, 1H), 5.73 (dd, 1H, J=17.6, 10.8 Hz), 5.32 (m, 1H), 4.87 (dd, 1H, J=10.8, 1.4 Hz), 4.82 (dd, 1H, J=5.5, 1.4 Hz), 4.34 (d, 2H, J=5.4 Hz), 2.05-2.38 (m, 2H), 0.85-2.02 (m, 14H), 1.18 (s, 3H), 0.91 (s, 3H), 0.88 (s, 3H); IR (neat) 3384, 2923, 1640, 1515, 1455 cm$^{-1}$; LRMS (EI) m/z 391 (M$^+$).

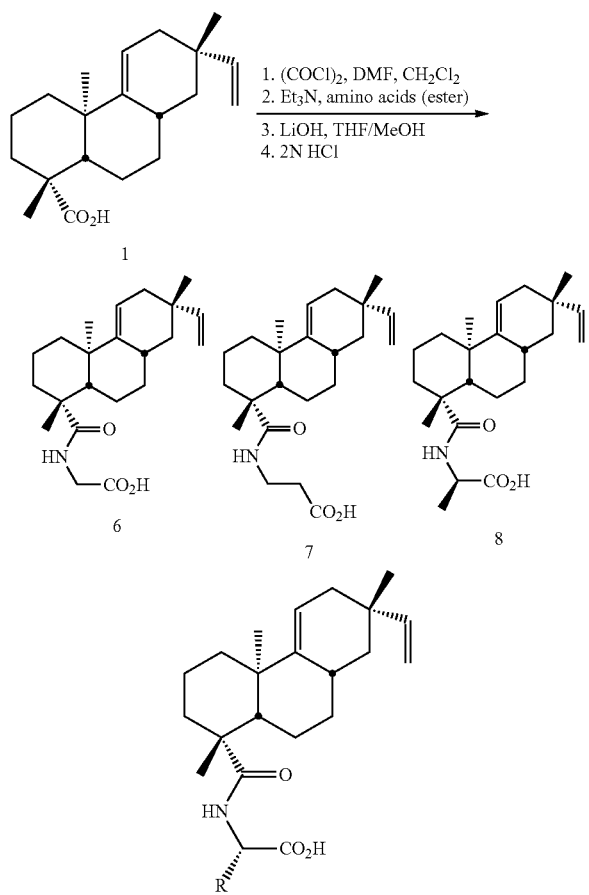

Scheme 2. Synthesis of the acanthoic acid analogs possessing peptide functionality R: Me 9
i-Propyl 10
i-Butyl 11
Phenyl 12
Benzyl 13
CH$_2$CO$_2$H 14
CH$_2$CH$_2$CO$_2$H 15

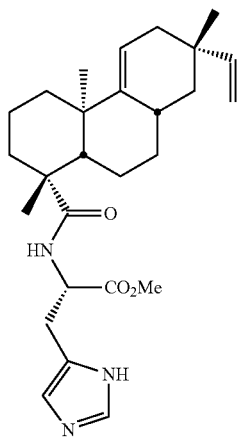

2-({[(1S,4aS,7R)-1,4a,7-Trimethyl-7-vinyl-1,2,3,4,4a,6,7,8,8a,9,10,10a-dodecahydro-1-phenanthrenyl]carbonyl}amino)acetic acid (6) (SP111)

A solution of acanthoic acid 1 (40 mg, 0.13 mmol) in CH$_2$Cl$_2$ (5.0 mL) was treated with oxalyl chloride (0.017 mL, 0.20 mmol) in the presence of a catalytic amount of DMF at room temperature. The reaction mixture was stirred for 3 h at room temperature, concentrated under reduced pressure, and then 5 ml of CH$_2$Cl$_2$ was added. Triethylamine (0.04 mL, 0.26 mmol) and aminoacetic acid methyl ester (14 mg, 0.16 mmol) were added to the reaction mixture. The reaction mixture was stirred for 30 min., quenched with water, and extracted with 5 ml of CH$_2$Cl$_2$. The organic layer was washed with brine, dried over magnesium sulfate, and concentrated under reduced pressure. The residue was purified by silica gel column chromatography (ethyl acetate:hexane=1:5) to afford 41 mg of the peptide intermediate (83%). To a solution of above peptide intermediate (41 mg, 0.11 mmol) in MeOH/THF (1:1, 6 ml), was added 2N LiOH (0.11 ml, 0.22 mmol). The reaction mixture was stirred for 3 h and then concentrated in vacuo. The residue was acidified with 2N aqueous HCl and extracted with 10 ml of ethyl acetate. The organic layer was washed with brine, dried over magnesium sulfate, and concentrated in vacuo to afford 37 mg of the analog 6 (96%)

$^1$H-NMR (CDCl$_3$, 300MHz) δ 6.22 (m, 1H), 5.72 (dd, 1H, J=17.6, 10.8 Hz), 5.31 (m, 1H), 4.87 (dd, 1H, J=10.8, 1.4 Hz), 4.82 (dd, 1H, J=5.5, 1.4 Hz), 4.40 (bs, 1H), 4.00 (m, 2H), 0.78-2.30 (m, 16H), 1.15 (s, 3H), 0.89 (s, 3H), 0.85 (s, 3H); IR (neat) 3396, 2925, 1734, 1643, 1519, 1457, 1217 cm$^{-1}$; LRMS (EI) m/z 359 (M$^+$).

3-({[(1S,4aS,7R)-1,4a,7-Trimethyl-7-vinyl-1,2,3,4,4a,6,7,8,8a,9,10,10a-dodecahydro-1-phenanthrenyl]carbonyl}amino)propanoic acid (7) (SP116)

The analog 7 was prepared (76% yield for 2 steps) according to the same procedure for the analog 6, using 3-amino propionic acid methyl ester instead of aminoacetic acid methyl ester.

$^1$H-NMR (CDCl$_3$, 300MHz) δ 6.26 (m, 1H), 5.75 (dd, 1H, J=17.6, 10.8 Hz), 5.31 (m, 1H), 4.87 (dd, 1H, J=10.8, 1.4 Hz), 4.82 (dd, 1H, J=5.5, 1.4 Hz), 4.50 (bs, 1H), 4.01 (m, 2H), 0.78-2.30 (m, 18H), 1.15 (s, 3H), 0.89 (s, 3H), 0.85 (s, 3H); IR (neat) 3434, 2925, 1714, 1607, 1530, 1455, 1192 cm$^{-1}$; LRMS (EI) m/z 373 (M$^+$).

(2R)-2-({[(1S,4aS,7R)-1,4a,7-Trimethyl-7-vinyl-1,2,3,4,4a,6,7,8,8a,9,10,10a-dodecahydro-1-phenanthrenyl]carbonyl}amino)propanoic acid (8) (SP113)

The analog 8 was prepared (73% yield for 2 steps) according to the same procedure for the analog 6, using D-alanine methyl ester instead of aminoacetic acid methyl ester.

$^1$H-NMR (CDCl$_3$, 300 MHz) δ 7.70 (bs, 1H), 6.19 (m, 1H), 5.78 (dd, 1H, J=17.6, 10.8 Hz), 5.37 (m, 1H), 4.87 (dd, 1H, J=10.8, 1.4 Hz), 4.82 (dd, 1H, J=5.5, 1.4 Hz), 4.51 (m, 1H), 2.29 (m, 1H), 0.66-2.11 (m, 15H), 1.43 (d, 3H, J=6.8 Hz), 1.15 (s, 3H), 0.97 (s, 3H), 0.93 (s, 3H); IR (neat) 3433, 2928, 1734, 1642, 1514, 1453, 1214 cm$^{-1}$; LRMS (EI) m/z 373 (M$^+$).

(2S)-2-({[(1S,4 aS,7R)-1,4a,7-Trimethyl-7-vinyl-1,2,3,4,4a,6,7,8,8a,9,10,10a-dodecahydro-1-phenanthrenyl]carbonyl}amino)propanoic acid (9) (SP114)

The analog 9 was prepared (75% yield for 2 steps) according to the same procedure for the analog 6, using L-alanine methyl ester instead of aminoacetic acid methyl ester.

$^1$H-NMR (CDCl$_3$, 300 MHz) δ 7.73 (bs, 1H), 6.19 (m, 1H), 5.78 (dd, 1H, J=17.6, 10.8 Hz), 5.37 (m, 1H), 4.87 (dd, 1H, J=10.8, 1.4 Hz), 4.82 (dd, 1H, J=5.5, 1.4 Hz), 4.51 (m, 1H), 2.29 (m, 1H), 0.66-2.11 (m, 15H), 1.43 (d, 3H, J=6.8 Hz), 1.15 (s, 3H), 0.97 (s, 3H), 0.93 (s, 3H); IR (neat) 3432, 2926, 1726, 1640, 1513, 1464, 1186 cm$^{-1}$; LRMS (EI) m/z 373 (M$^+$).

(2S)-2-({[(1S,4aS,7R)-1,4a,7-Trimethyl-7-vinyl-1,2,3,4,4a,6,7,8,8a,9,10,10a-dodecahydro-1-phenanthrenyl]carbonyl}amino)-3-methylbutanoic acid (10) (SP153)

The analog 10 was prepared (72% yield for 2 steps) according to the same procedure for the analog 6, using L-valine methyl ester instead of aminoacetic acid methyl ester.

$^1$H-NMR (CDCl$_3$, 300 MHz) δ 6.13 (m, 1H), 5.78 (dd, 1H, J=17.6, 10.8 Hz), 5.37 (m, 1H), 4.87 (dd, 1H, J=10.8, 1.4 Hz), 4.82 (dd, 1H, J=5.5, 1.4 Hz), 4.54 (m, 1H), 2.05-2.26 (m, 2H), 0.66-2.01 (m, 15H), 1.21 (s, 3H), 0.99 (m, 6H), 0.95 (s, 3H), 0.93 (s, 3H); IR (neat) 2925, 1724, 1638, 1511, 1469, 1180 cm$^{-1}$; LRMS (EI) m/z 401 (M$^+$).

(2S)-2-({[(1S,4aS,7R)-1,4a,7-Trimethyl-7-vinyl-1,2,3,4,4a,6,7,8,8a,9,10,10a-dodecahydro-1-phenanthrenyl]carbonyl}amino)-4-methylpentanoic acid (11) (SP115)

The analog 11 was prepared (75% yield for 2 steps) according to the same procedure for the analog 6, using L-leucine methyl ester instead of aminoacetic acid methyl ester.

$^1$H-NMR (CDCl$_3$, 300 MHz) δ 9.65 (bs, 1H), 5.98 (m, 1H), 5.78 (dd, 1H, J=17.6, 10.8 Hz), 5.38 (m, 1H), 4.87 (dd, 1H, J=10.8, 1.4 Hz), 4.82 (dd, 1H, J=5.5, 1.4 Hz), 4.57 (m, 1H), 1.10-2.31 (m, 19H), 0.88-1.05 (m, 12H), 1.19 (s, 3H); IR (neat) 2926, 1727, 1639, 1513, 1462, 1186 cm$^{-1}$; LRMS (EI) m/z 415 (M$^+$).

(2S)-2-({[(1S,4aS,7R)-1,4a,7-Trimethyl-7-vinyl-1,2,3,4,4a,6,7,8,8a,9,10,10a-dodecahydro-1-phenanthrenyl]carbonyl}amino)-2-phenylethanoic acid (12) (SP154)

The analog 12 was prepared (74% yield for 2 steps) according to the same procedure for the analog 6, using L-phenyl glycine methyl ester instead of aminoacetic acid methyl ester.

$^1$H-NMR (CDCl$_3$, 300 MHz) δ 8.21 (bs, 1H), 7.33 (m, 5H), 6.60 (m, 1H), 5.78 (dd, 1H, J=17.6, 10.8 Hz), 5.51 (m, 1H), 5.34 (m, 1H), 4.87 (dd, 1H, J=10.8, 1.4 Hz), 4.82 (dd, 1H, J=5.5, 1.4 Hz), 0.72-2.31 (m, 16H), 1.21 (s, 3H), 0.95 (s, 3H), 0.86 (s, 3H); IR (neat) 2923, 1730, 1643, 1517, 1471, 1182 cm$^{-1}$; LRMS (EI) m/z 435 (M$^+$).

(2S)-2-({[(S,4aS,7R)-1,4a,7-Trimethyl-7-vinyl-1,2,3,4,4a,6,7,8,8a, 9,10,10a-dodecahydro-1-phenanthrenyl]carbonyl}amino)-3-phenylpropanoic acid (13) (SP155)

The analog 13 was prepared (72% yield for 2 steps) according to the same procedure for the analog 6, using L-phenyl alanine methyl ester instead of aminoacetic acid methyl ester.

$^1$H-NMR (CDCl$_3$, 300 MHz) δ 7.16-7.32 (m, 5H), 5.96 (m, 1H), 5.78 (dd, 1H, J=17.6, 10.8 Hz), 5.33 (m, 1H), 4.87 (dd, 1H, J=10.8, 1.4 Hz), 4.82 (dd, 1H, J=5.5, 1.4 Hz), 4.77 (m, 1H), 3.02-3.29 (m, 2H), 0.79-2.31 (m, 16H), 1.07 (s, 3H), 0.93 (s, 3H), 0.79 (s, 3H); IR (neat) 2925, 1724, 1640, 1518, 1459 cm$^{-1}$; LRMS (EI) m/z 449 (M$^+$).

(2S)-2-({[(1S,4aS,7R)-1,4a,7-Trimethyl-7-vinyl-1,2,3,4,4a,6,7,8,8a,9,10,10a-dodecahydro-1-phenanthrenyl]carbonyl}amino)-butanedioic acid (14) (SP156)

The analog 14 was prepared (70% yield for 2 steps) according to the same procedure for the analog 6, using L-aspartic acid di-methyl ester instead of aminoacetic acid methyl ester.

$^1$H-NMR (CDCl$_3$, 300MHz) δ 6.85 (m, 1H), 5.75 (dd, 1H, J=17.6, 10.8 Hz), 5.31 (m, 1H), 4.87 (dd, 1H, J=10.8, 1.4 Hz), 4.82 (dd, 1H, J=5.5, 1.4 Hz), 4.64 (m, 1H), 2.71-2.96 (m, 2H), 0.79-2.31 (m, 16H), 1.12 (s, 3H), 0.92 (s, 3H), 0.86 (s, 3H); IR (neat) 3431, 1925, 1734, 1720, 1642 cm$^{-1}$; LRMS (EI) m/z 417 (M$^+$).

(2S)-2-({[(1S,4aS,7R)-1,4a,7-Trimethyl-7-vinyl-1,2,3,4,4a,6,7,8,8a,9,10,10a-dodecahydro-1-phenanthrenyl]carbonyl}amino)-pentanedioic acid (15) (SP157)

The analog 15 was prepared (73% yield for 2 steps) according to the same procedure for the analog 6, using L-glutamic acid di-methyl ester instead of aminoacetic acid methyl ester.

$^1$H-NMR (CDCl$_3$, 300MHz) δ 6.48 (m, 1H), 5.78 (dd, 1H, J=17.6, 10.8 Hz), 5.36 (m, 1H), 4.87 (dd, 1H, J=10.8, 1.4 Hz), 4.82 (dd, 1H, J=5.5, 1.4 Hz), 4.61 (m, 1H), 2.51 (m, 2H), 0.83-2.41 (m, 18H), 1.13 (s, 3H), 0.92 (s, 3H), 0.86 (s, 3H); IR (neat) 3429, 2927, 1736, 1721, 1644, 1513 cm$^{-1}$; LRMS (EI) m/z 431 (M$^+$).

Methyl (2S)-2-({[(1S,4aS,7R)-1,4a,7-trimethyl-7-vinyl-1,2,3,4,4a,6,7,8,8a,9,10,10a-dodecahydro-1-phenanthrenyl]carbonyl}amino)-3-(1H-imidazol-5-yl)propanoate acid (16) (SP158)

The analog 16 was prepared (82% yield) according to the same procedure for the analog 2, using L-histidine methyl ester instead of pyrrolidine.

$^1$H-NMR (CDCl$_3$, 300 MHz) δ 7.55 (s, 1H), 7.37 (m, 1H), 6.78 (s, 1H), 5.77 (dd, 1H, J=17.6, 10.8 Hz), 5.33 (m, 1H), 4.87 (dd, 1H, J=10.8, 1.4 Hz), 4.82 (dd, 1H, J=5.5, 1.4 Hz), 4.72 (m, 1H), 3.65 (s, 3H), 3.09 (m, 2H), 2.51 (m, 2H), 0.83-2.31 (m, 18H), 1.12 (s, 3H), 0.92 (s, 3H), 0.89 (s, 3H); IR (neat) 3420, 2924, 1730, 1644 cm$^{-1}$; LRMS (EI) m/z 453 (M$^+$).

Scheme 3. Synthesis of the acanthoic acid analogs possessing alcohol functionality

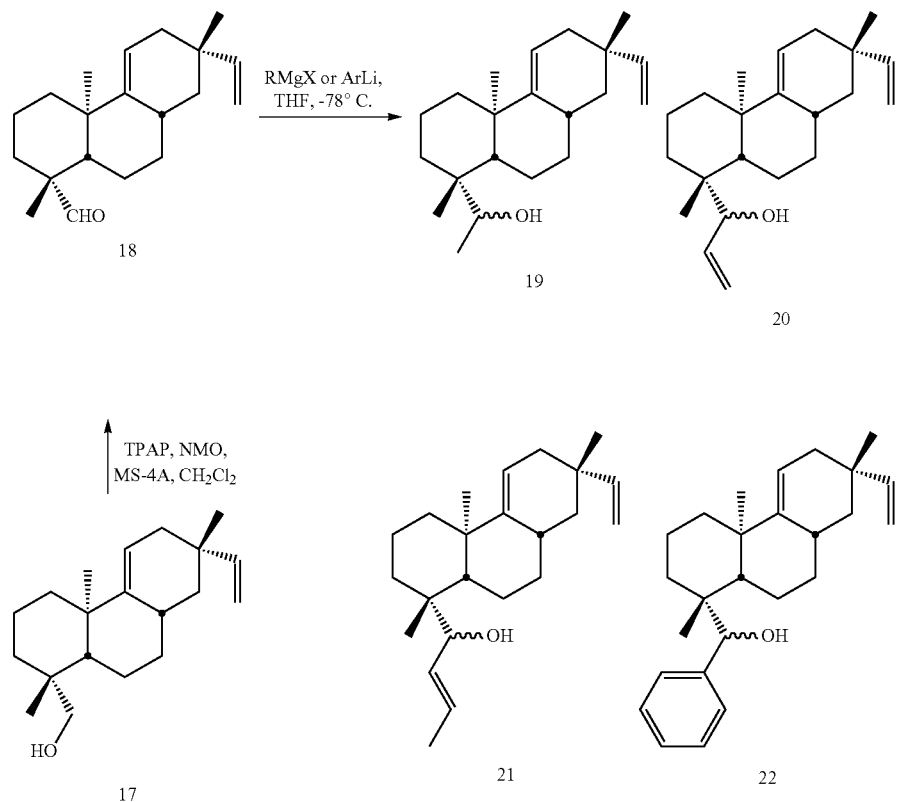

[(1S,4aS,7R)-1,4a,7-Trimethyl-7-vinyl-1,2,3,4,4a,6,7,8,8a,9,10,10a-dodecahydro-1-phenanthrenyl] methanol (17) (SP033)

To a solution of acanthoic acid 1 (830 mg, 2.7 mmol) in THF (30 ml) was added LAH (310 mg, 8.2 mmol). The reaction mixture was stirred for 12 h and quenched with water (1.55 ml) and 10% NaOH solution (0.31 ml) and filtered through celite. The filtrate was concentrated in vacuo and diluted with ethyl acetate (40 ml). The organic layer was washed with brine, dried over magnesium sulfate, and concentrated under reduced pressure. The residue was purified by silica gel column chromatography (ethyl acetate:hexane=1:5) to afford 670 mg of the analog 17 (85%).

$^1$H-NMR (CDCl$_3$, 300 MHz) δ 5.75 (dd, 1H, J=17.6, 10.8 Hz), 5.29 (m, 1H), 4.87 (dd, 1H, J=10.8, 1.4 Hz), 4.82 (dd, 1H, J=5.5, 1.4 Hz), 3.78 (d, 1H, J=10.9 Hz), 3.47 (d, 1H, J=10.9 Hz), 0.84-1.99 (m, 16H), 0.97 (s, 3H), 0.91 (s, 3H), 0.90 (s, 3H); IR (neat) 3368, 2926, 1328 cm$^{-1}$; LRMS (EI) m/z 288 (M$^+$).

(1S,4aS,7R)-1,4a,7-Trimethyl-7-vinyl-1,2,3,4,4a,6,7,8,8a,9,10,10a-dodecahydro-1-phenanthrenecarbaldehyde (18)

To a solution of the analog 17 (180 mg, 0.64 mmol) in CH$_2$Cl$_2$ (7 ml) were added NMO (116 mg, 0.96 mmol) and catalytic amount of TPAP in the presence of MS-4A powder. The reaction mixture was stirred for 2 h at room temperature and filtered through silica gel. The filtrate was concentrated under reduced pressure and the residue was purified by silica gel column chromatography (ethyl acetate:hexane=1:20) to afford 160 mg of the analog 18 (89%).

$^1$H-NMR (CDCl$_3$, 300 MHz) δ 9.86 (s, 1H), 5.75 (dd, 1H, J=17.6, 10.8 Hz), 5.33 (m, 1H), 4.87 (dd, 1H, J=10.8, 1.4 Hz), 4.82 (dd, 1H, J=5.5, 1.4 Hz), 0.86-1.99 (m, 16H), 0.96 (s, 3H), 0.90 (s, 3H), 0.86 (s, 3H); IR (neat) 1717 cm$^{-1}$; LRMS (EI) m/z 286 (M$^+$).

(1S)-1-[(1S,4aS,7R)-1,4a,7-Trimethyl-7-vinyl-1,2,3,4,4a,6,7,8,8a,9,10,10a-dodecahydro-1-phenanthrenyl]-1-ethanol (19) (SP108)

To a solution of the analog 18 (20 mg, 0.07 mmol) in THF (5 ml) was added MeLi (1.6M solution in THF, 0.087 mL, 0.14 mmol) dropwise. The reaction mixture was stirred for 10 min at room temperature and quenched with saturated NH$_4$Cl solution. The resulting mixture was concentrated in vacuo and extracted with ethyl acetate (10 ml). The organic layer was washed with brine, dried over magnesium sulfate, and concentrated under reduced pressure. The residue was purified by silica gel column chromatography (ethyl acetate:hexane=1:10) to afford 20 mg of the analog 19 (95%).

$^1$H-NMR (CDCl$_3$, 300 MHz) δ 5.76 (dd, 1H, J=17.6, 10.8 Hz), 5.34 (m, 1H), 4.87 (dd, 1H, J=10.8, 1.4 Hz), 4.82 (dd, 1H, J=5.5, 1.4 Hz), 4.33 (m, 1H), 0.85-2.03 (m, 19H), 0.97 (s, 3H), 0.88 (s, 3H), 0.85 (s, 3H); IR (neat) 3443, 2922, 1644, 1539, 1458, 1372 cm$^{-1}$; LRMS (EI) m/z 302 (M$^+$).

(1S)-1-[(1S,4aS,7R)-1,4a,7-Trimethyl-7-vinyl-1,2,3,4,4a,6,7,8,8a,9,10,10a-dodecahydro-1-phenanthrenyl]-2-propen-1-ol (20) (SP099)

The analog 20 was prepared (82% yield) according to the same procedure for the analog 19, using vinyl magnesium bromide solution instead of methyl lithium solution.

$^1$H-NMR (CDCl$_3$, 300MHz) δ 5.80 (m, 1H), 5.74 (dd, 1H, J=17.6, 10.8 Hz), 5.31 (m, 1H), 5.02-5.14 (m, 2H), 4.87 (dd, 1H, J=10.8, 1.4 Hz), 4.82 (dd, 1H, J=5.5, 1.4 Hz), 4.59 (m, 1H), 0.81-2.33 (m, 16H), 0.92 (s, 3H), 0.88 (s, 3H), 0.84 (s, 3H); IR (neat) 3307, 2928, 1641, 1453 cm$^{-1}$; LRMS (EI) m/z 314 (M$^+$).

(1S,2E)-1-[(1S,4aS,7R)-1,4a,7-Trimethyl-7-vinyl-1,2,3,4,4a,6,7,8,8a,9,10,10a-dodecahydro-1-phenanthrenyl]-2-butenen-1-ol (21) (SP137)

The analog 21 was prepared (85% yield) according to the same procedure for the analog 19, using 1-propenyl magnesium bromide solution instead of methyl lithium solution.

$^1$H-NMR (CDCl$_3$, 300MHz) δ 5.79 (dd, 1H, J=17.6, 10.8 Hz), 5.65 (m, 2H), 5.35 (m, 1H), 4.87 (dd, 1H, J=10.8, 1.4 Hz), 4.82 (dd, 1H, J=5.5, 1.4 Hz), 4.54 (m, 1H), 0.81-2.33 (m, 16H), 1.68 (d, 2H, J=6.1 Hz), 1.23 (s, 3H), 0.94 (s, 3H), 0.91 (s, 3H); IR (neat) 3358, 2925, 1645, 1302 cm$^{-1}$; LRMS (EI) m/z 328 (M$^+$).

(S)-[(1S,4aS,7R)-1,4a,7-Trimethyl-7-vinyl-1,2,3,4,4a,6,7,8,8a,9,10,10a-dodecahydro-1-phenanthrenyl](phenyl)methanol (22) (SP101)

The analog 22 was prepared (83% yield) according to the same procedure for the analog 19, using phenyl magnesium bromide solution instead of methyl lithium solution.

$^1$H-NMR (CDCl$_3$, 300MHz) δ 7.17-7.29 (m, 5H), 5.73 (dd, 1H, J=17.6, 10.8 Hz), 5.26 (m, 1H), 5.24 (s, 1H), 4.88 (dd, 1H, J=10.8, 1.4 Hz), 4.83 (dd, 1H, J=5.5, 1.4 Hz), 0.79-2.33 (m, 16H), 1.68 (d, 2H, J=6.1 Hz), 1.26 (s, 3H), 0.92 (s, 3H), 0.90 (s, 3H); IR (neat) 3382, 2934. 1642, 1431 cm$^{-1}$; LRMS (EI) m/z 364 (M$^+$).

Scheme 4. Synthesis of the acanthoic acid analogs possessing ketone functionality

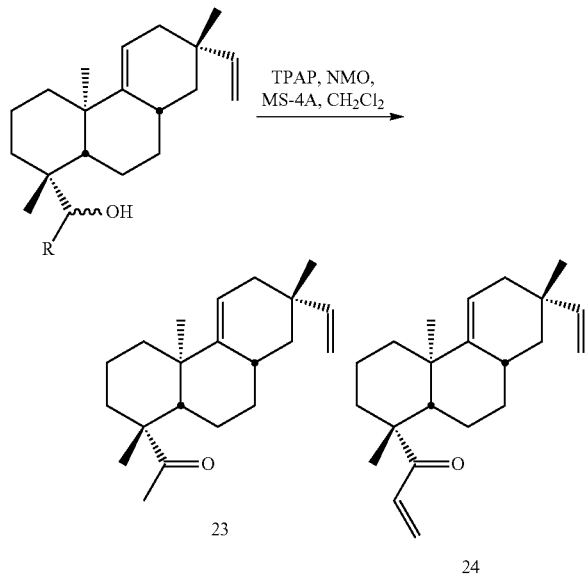

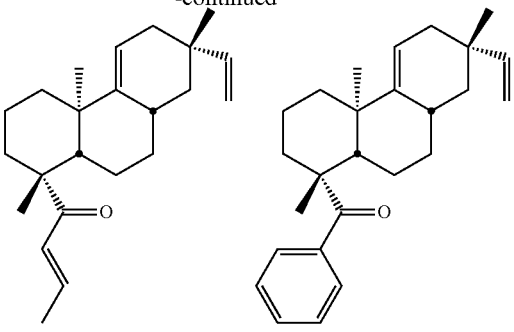

1-[(1S,4aS,7R)-1,4a,7-Trimethyl-7-vinyl-1,2,3,4,4a,6,7,8,8a,9,10,10a-dodecahydro-1-phenanthrenyl]-1-ethanone (23) (SP138)

To a solution of the analog 19 (10 mg, 0.03 mmol) in CH$_2$Cl$_2$ (3 ml) were added NMO (5.8 mg, 0.05 mmol) and catalytic amount of TPAP in the presence of MS-4A powder. The reaction mixture was stirred for 2 h at room temperature and filtered through silica gel. The filtrate was concentrated under reduced pressure and the residue was purified by silica gel column chromatography (ethyl acetate:hexane=1:20) to afford 9.4 mg of the analog 23 (95%).

$^1$H-NMR (CDCl$_3$, 300MHz) δ 5.78 (dd, 1H, J=17.6, 10.8 Hz), 5.26 (m, 1H), 4.88 (dd, 1H, J=10.8, 1.4 Hz), 4.83 (dd, 1H, J=5.5, 1.4 Hz), 0.79-2.33 (m, 16H), 2.13 (s, 3H), 1.23 (s, 3H), 0.94 (s, 3H), 0.89 (s, 3H); IR (neat) 2924, 1698, 1538, 1458 cm$^{-1}$; LRMS (EI) m/z 300 (M$^+$).

1[(1S,4aS,7R)-1,4a,7-Trimethyl-7-vinyl-1,2,3,4,4a,6,7,8,8a,9,10,10a-dodecahydro-1-phenanthrenyl]-2-propen-1-one (24) (SP100)

The analog 24 was prepared (93% yield) from the analog 20 by the procedure described for the analog 23.

$^1$H-NMR (CDCl$_3$, 300MHz) δ 6.79 (dd, 1H, J=20.4, 5.7 Hz), 6.22 (dd, 1H, J=20.4, 3.1 Hz), 5.76 (dd, 1H, J=17.6, 10.8 Hz), 5.57 (dd, 1H, J=5.7, 3.1 Hz), 5.34 (m, 1H), 4.93 (dd, 1H, J=10.8, 1.4 Hz), 4.86 (dd, 1H, J=5.5, 1.4 Hz), 0.74-2.33 (m, 16H), 1.15 (s, 3H), 0.93 (s, 3H), 0.84 (s, 3H); IR (neat) 3396, 2927, 1684, 1459 cm$^{-1}$; LRMS (EI) m/z 312 (M$^+$).

(E)-1-[(1S,4aS,7R)-1,4a,7-Trimethyl-7-vinyl-1,2,3,4,4a,6,7,8,8a,9,10,10a-dodecahydro-1-phenanthrenyl]-2-buten-1-one (25) (SP139)

The analog 25 was prepared (91% yield) from analog 21 by the procedure described for the analog 23.

$^1$H-NMR (CDCl$_3$, 300MHz) δ 6.77 (m, 1H), 5.49 (d, 1H, J=16.7 Hz), 5.76 (dd, 1H, J=17.6, 10.8 Hz), 5.28 (m, 1H), 4.93 (dd, 1H, J=10.8, 1.4 Hz), 4.86 (dd, 1H, J=5.5, 1.4 Hz), 0.74-2.33 (m, 19H), 1.15 (s, 3H), 0.93 (s, 3H), 0.84 (s, 3H); IR (neat) 2924, 1682, 1621, 1457 cm$^{-1}$; LRMS (EI) m/z 326 (M$^+$).

[(1S,4aS,7R)-1,4a,7-Trimethyl-7-vinyl-1,2,3,4,4a,6,7,8,8a,9,10,10a-dodecahydro-1-phenanthrenyl](phenyl)methanone (26) (SP102)

The analog 26 was prepared (90% yield) from the analog 22 by the procedure described for the analog 23.

$^1$H-NMR (CDCl$_3$, 300MHz) δ 7.29-7.41 (m, 5H), 5.72 (dd, 1H, J=17.6, 10.8 Hz), 5.23 (m, 1H), 4.88 (dd, 1H, J=10.8, 1.4

Hz), 4.83 (dd, 1H, J=5.5, 1.4 Hz), 0.74-2.33 (m, 16H), 1.15 (s, 3H), 0.98 (s, 3H), 0.87 (s, 3H); IR (neat) 2924, 1680, 1539, 1457 cm$^{-1}$; LRMS (EI) m/z 362 (M$^+$).

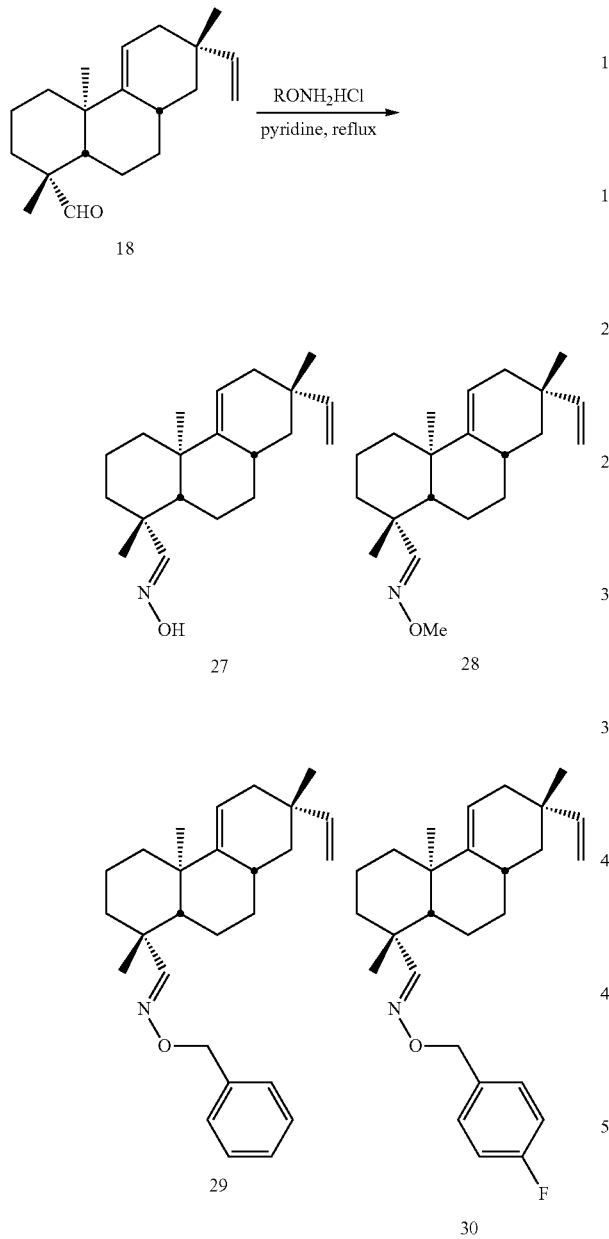

(1S,4 aS,7R)-1,4a,7-Trimethyl-7-vinyl-1,2,3,4,4a,6,7,8,8a,9,10,10a-dodecahydro-1-phenanthrenecarbaldehyde oxime (27) (SP109)

To a solution of the analog 18 (20 mg, 0.07 mmol) in pyridine (3 ml) was added hydroxylamine hydrochloride (5.8 mg, 0.08 mmol). The reaction mixture was stirred for 1 h at 80° C., cooled to room temperature, and concentrated in vacuo. The residue was purified by silica gel column chromatography (ethyl acetate:hexane=1:10) to afford 16 mg of analog 27 (77%).

$^1$H-NMR (CDCl$_3$, 300 MHz) δ 7.55 (s, 1H), 5.78 (dd, 1H, J=17.6, 10.8 Hz), 5.35 (m, 1H), 4.88 (dd, 1H, J=10.8, 1.4 Hz), 4.83 (dd, 1H, J=5.5, 1.4 Hz), 0.74-2.33 (m, 16H), 1.05 (s, 3H), 0.96 (s, 3H), 0.91 (s, 3H); IR (neat) 3307, 2928, 1641, 1453 cm$^{-1}$; LRMS (EI) m/z 301 (M$^+$).

(1S,4aS,7R)-1,4a,7-Trimethyl-7-vinyl-1,2,3,4,4a,6,7,8,8a,9,10,10a-dodecahydro-1-phenanthrenecarbaldehyde O-methyloxime (28) (SP140)

The analog 28 was prepared (72% yield) according to the same procedure for the analog 27, using O-methylamine hydrochloride instead of hydroxylamine hydrochloride.

$^1$H-NMR (CDCl$_3$, 300 MHz) δ 7.48 (s, 1H), 5.78 (dd, 1H, J=17.6, 10.8 Hz), 5.35 (m, 1H), 4.88 (dd, 1H, J=10.8, 1.4 Hz), 4.83 (dd, 1H, J=5.5, 1.4 Hz), 3.74 (s, 3H), 0.74-2.33 (m, 16H), 1.05 (s, 3H), 0.96 (s, 3H), 0.91 (s, 3H); IR (neat) 2927, 1716, 1647, 1458 cm$^{-1}$; LRMS (EI) m/z 315 (M$^+$).

(1S,4aS,7R)-1,4a,7-Trimethyl-7-vinyl-1,2,3,4,4a,6,7,8,8a,9,10,10a-dodecahydro-1-phenanthrenecarbaldehyde O-benzyloxime (29) (SP141)

The analog 29 was prepared (72% yield) according to the same procedure for the analog 27, using O-benzylamine hydrochloride instead of hydroxylamine hydrochloride.

$^1$H-NMR (CDCl$_3$, 300 MHz) δ 7.54 (s, 1H), 7.18-7.34 (m, 5H), 5.78 (dd, 1H, J=17.6, 10.8 Hz), 5.35 (m, 1H), 5.03 (s, 2H), 4.88 (dd, 1H, J=10.8, 1.4 Hz), 4.83 (dd, 1H, J=5.5, 1.4 Hz), 3.74 (s, 3H), 0.74-2.33 (m, 16H), 1.05 (s, 3H), 0.96 (s, 3H), 0.91 (s, 3H); IR (neat) 2927, 1646, 1456 cm$^{-1}$; LRMS (EI) m/z 391 (M$^+$).

(1S,4 aS, 7R)-1,4a,7-Trimethyl-7-vinyl-1, 2, 3, 4, 4a, 6,7,8,8a,9,10,10a-dodecahydro-1-phenanthrenecarbaldehyde O-(4-fluorobenzyl) oxime (30) (SP142)

The analog 30 was prepared (71% yield) according to the same procedure for the analog 27, using O-(4-fluorobenzyl) amine hydrochloride instead of hydroxylamine hydrochloride.

$^1$H-NMR (CDCl$_3$, 300MHz) δ 7.93 (s, 1H), 7.02-7.29 (m, 4H), 5.78 (dd, 1H, J=17.6, 10.8 Hz), 5.35 (m, 1H), 5.03 (s, 2H), 4.88 (dd, 1H, J=10.8, 1.4 Hz), 4.83 (dd, 1H, J=5.5, 1.4 Hz), 3.74 (s, 3H), 0.74-2.33 (m, 16H), 1.05 (s, 3H), 0.96 (s, 3H), 0.91 (s, 3H); IR (neat) 2925, 1654, 1473 cm$^{-1}$; LRMS (EI) m/z 409 (M$^+$).

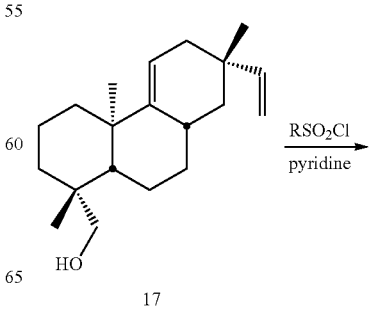

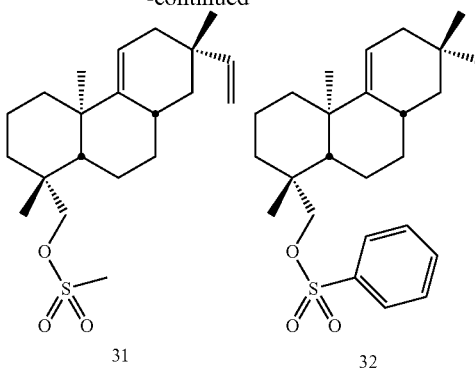

31

32

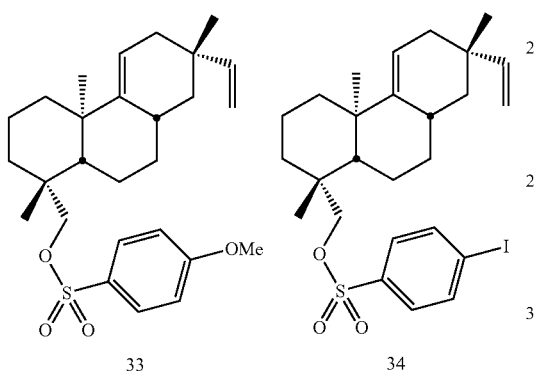

33

34

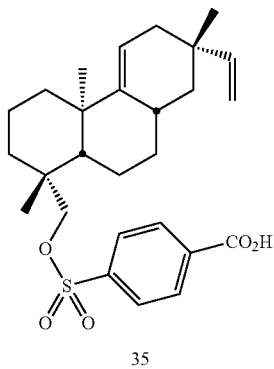

35

[(1S,4aS,7R)-1,4a,7-Trimethyl-7-vinyl-1,2,3,4,4a,6,
7,8,8a,9,10,10a-dodecahydro-1-phenanthrenyl]methyl methanesulfonate (31) (SP143)

To a solution of the analog 17 (20 mg, 0.070 mmol) in pyridine (3 ml) was added methanesulfonyl chloride (0.0064 ml, 0.083 mmol). The reaction mixture was stirred for 2 h at room temperature and concentrated in vacuo. The residue was purified by silica gel column chromatography (ethyl acetate: hexane=1:5) to afford 21 mg of the analog 31 (85%).

$^1$H-NMR (CDCl$_3$, 300MHz) δ 5.76 (dd, 1H, J=17.6, 10.8 Hz), 5.34 (m, 1H), 4.87 (dd, 1H, J=10.8, 1.4 Hz), 4.82 (dd, 1H, J=5.5, 1.4 Hz), 4.43 (d, 1H, J=10.9 Hz), 4.24 (d, 1H, J=10.9 Hz), 2.98 (s, 3H), 0.72-2.03 (m, 19H), 1.12 (s, 3H), 0.88 (s, 3H), 0.85 (s, 3H); IR (neat) 2927, 1647, 1539, 1355 cm$^{-1}$; LRMS (EI) m/z 366 (M$^+$).

[(1S,4aS,7R)-1,4a,7-Trimethyl-7-vinyl-1,2,3,4,4a,6,7,8,
8a,9,10,10a-dodecahydro-1-phenanthrenyl]methyl benzenesulfonate (32) (SP144)

The analog 32 was prepared (78% yield) according to the same procedure for the analog 31, using benzenesulfonyl chloride instead of methanesulfonyl chloride.

$^1$H-NMR (CDCl$_3$, 300MHz) δ 7.47-7.85 (m, 5H), 5.70 (dd, 1H, J=17.6, 10.8 Hz), 5.34 (m, 1H), 4.87 (dd, 1H, J=10.8, 1.4 Hz), 4.83 (dd, 1H, J=5.5, 1.4 Hz), 4.19 (d, 1H, J=10.9 Hz), 3.87 (d, 1H, J=10.9 Hz), 2.98 (s, 3H), 0.79-2.03 (m, 16H), 1.12 (s, 3H), 0.90 (s, 3H), 0.87 (s, 3H); IR (neat): 2926, 1646, 1365, 1185, 957 cm$^{-1}$; LRMS (EI) m/z 428 (M$^+$).

[(1S,4aS,7R)-1,4a,7-Trimethyl-7-vinyl-1,2,3,4,4a,6,
7,8,8a,9,10,10a-dodecahydro-1-phenanthrenyl]methyl 4-methoxybenzenesulfonate (33) (SP145)

The analog 33 was prepared (83% yield) according to the same procedure for the analog 31, using 4-methoxybenzenesulfonyl chloride instead of methanesulfonyl chloride.

$^1$H-NMR (CDCl$_3$, 300MHz) δ 7.78 (m, 2H), 6.95 (m, 2H), 5.70 (dd, 1H, J=17.6, 10.8 Hz), 5.28 (m, 1H), 4.87 (dd, 1H, J=10.8, 1.4 Hz), 4.83 (dd, 1H, J=5.5, 1.4 Hz), 4.13 (d, 1H, J=10.9 Hz), 3.82 (s, 3H), 3.80 (d, 1H, J=10.9 Hz), 0.79-2.03 (m, 16H), 0.96 (s, 3H), 0.91 (s, 3H), 0.86 (s, 3H); IR (neat) 2927, 1596, 1361, 1262, 1026 cm$^{-1}$; LRMS (EI) m/z 458 (M$^+$).

[(1S,4aS,7R)-1,4a,7-Trimethyl-7-vinyl-1,2,3,4,4a,6,
7,8,8a,9,10,10a-dodecahydro-1-phenanthrenyl]methyl 4-iodobenzenesulfonate (34) (SP146)

The analog 34 was prepared (81% yield) according to the same procedure for the analog 31, using 4-iodobenzenesulfonyl chloride instead of methanesulfonyl chloride.

$^1$H-NMR (CDCl$_3$, 300MHz) δ 7.91 (m, 2H), 7.61 (m, 2H), 5.76 (dd, 1H, J=17.6, 10.8 Hz), 5.33 (m, 1H), 4.87 (dd, 1H, J=10.8, 1.4 Hz), 4.83 (dd, 1H, J=5.5, 1.4 Hz), 4.25 (d, 1H, J=10.9 Hz), 3.88 (d, 1H, J=10.9 Hz), 0.79-2.03 (m, 16H), 0.92 (s, 3H), 0.91 (s, 3H), 0.86 (s, 3H); IR (neat) 2926, 1645, 1176 cm$^{-1}$; LRMS (EI) m/z 554 (M$^+$).

4-({[(1S,4aS,7R)-1,4a,7-Trimethyl-7-vinyl-1,2,3,4,
4a,6,7,8,8a,9,10,10a-dodecahydro-1-phenanthrenyl]methoxy}sulfonyl)benzene carboxylic acid (35) (SP147)

The analog 35 was prepared (78% yield) according to the same procedure for the analog 31, using 4-(chlorosulfonyl) benzoic acid instead of methanesulfonyl chloride.

$^1$H-NMR (CD$_3$OD, 300MHz) δ 8.05 (m, 2H), 7.91 (m, 2H), 5.79 (dd, 1H, J=17.6, 10.8 Hz), 5.43 (m, 1H), 4.87 (dd, 1H, J=10.8, 1.4 Hz), 4.83 (dd, 1H, J=5.5, 1.4 Hz), 4.65 (d, 1H, J=10.9 Hz), 4.18 (d, 1H, J=10.9 Hz), 0.79-2.03 (m, 16H), 1.23 (s, 3H), 1.17 (s, 3H), 0.87 (s, 3H); IR (neat) 3498, 2926, 1721, 1539, 1188 cm$^{-1}$; LRMS (EI) m/z 472 (M$^+$).

Scheme 7. Synthesis of the acanthoic acid analogs possessing ester functionality

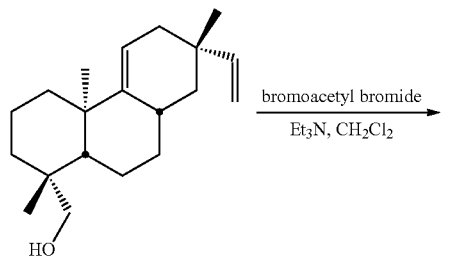

17 bromoacetyl bromide
―――――――――――→
Et₃N, CH₂Cl₂

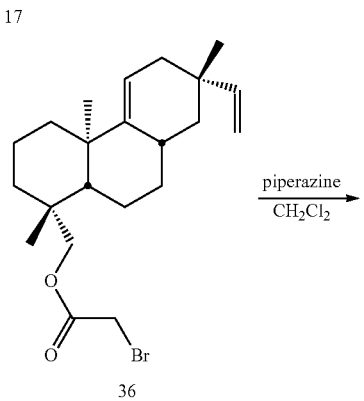

36 piperazine
―――――→
CH₂Cl₂

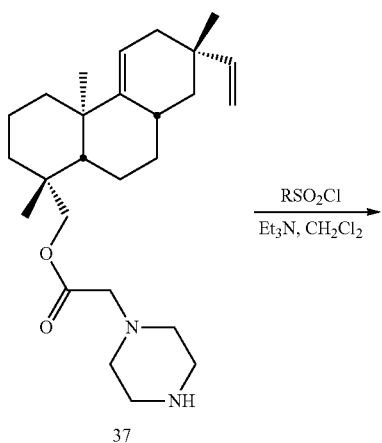

37

RSO₂Cl
―――――→
Et₃N, CH₂Cl₂

-continued

R:

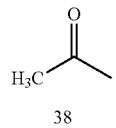

38

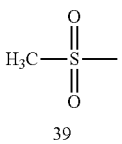

39

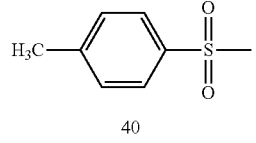

40

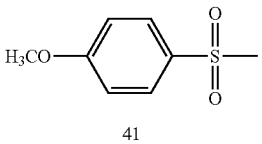

41

[(1S,4aS,7R)-1,4a,7-Trimethyl-7-vinyl-1,2,3,4,4a,6,7,8,8a,9,10,10a-dodecahydro-1-phenanthrenyl]methyl 2-bromoacetate (36)

To a solution of the analog 17 (107 mg, 0.37 mmol) in CH₂Cl₂ (10 ml) at 0° C. were added Et₃N (0.15 mL, 1.1 mmol) and bromoacetyl bromide (0.064 mL, 0.74 mmol). The reaction mixture was stirred for 10 min., quenched with aqueous NaHCO₃ solution (5 ml) and extracted with CH₂Cl₂ (10 ml). The organic layer was dried over magnesium sulfate and concentrated under reduced pressure and the residue was purified by silica gel column chromatography (ethyl acetate: hexane=1:10) to afford 11 mg of the analog 36 (93%).
¹H-NMR (CDCl₃, 300MHz) δ 5.79 (dd, 1H, J=17.6, 10.8 Hz), 5.35 (m, 1H), 4.93 (dd, 1H, J=10.8, 1.4 Hz), 4.83 (dd, 1H, J=5.5, 1.4 Hz), 4.43 (d, 1H, J=10.9 Hz), 4.10 (d, 1H, J=10.9 Hz), 3.81 (s, 2H), 0.79-2.03 (m, 16H), 1.10 (s, 3H), 1.05 (s, 3H), 0.97 (s, 3H)

[(1S,4aS,7R)-1,4a,7-Trimethyl-7-vinyl-1,2,3,4,4a,6,7,8,8a,9,10,10a-dodecahydro-1-phenanthrenyl]methyl 2-piperazinoacetate (37) (SP148)

To a solution of the analog 36 (108 mg, 0.26 mmol) in CH₂Cl₂ (10 ml) was added piperazine (68 mg, 0.80 mmol). The reaction mixture was stirred for 4 h at room temperature and washed with brine. The organic layer was dried over magnesium sulfate. The organic layer was concentrated under reduced pressure and the residue was purified by silica gel column chromatography (ethyl acetate:hexane=3:1) to afford 102 mg of the analog 37 (93%).
¹H-NMR (CDCl₃, 300MHz) δ 5.79 (dd, 1H, J=17.6, 10.8 Hz), 5.34 (m, 1H), 4.87 (dd, 1H, J=10.8, 1.4 Hz), 4.82 (dd, 1H, J=5.5, 1.4 Hz), 4.37 (d, 1H, J=10.9 Hz), 4.04 (d, 1H, J=10.9 Hz), 3.19 (s, 2H), 2.57-2.97 (m, 8H), 0.76-2.03 (m, 16H), 1.05 (s, 3H), 0.94 (s, 3H), 0.93 (s, 3H); IR (neat) 3396, 2926, 1741, 1622, 1456 cm⁻¹; LRMS (EI) m/z 414 (M⁺).

[(1S,4aS,7R)-1,4a,7-Trimethyl-7-vinyl-1,2,3,4,4a,6,7,8,8a,9,10,10a-dodecahydro-1-phenanthrenyl]methyl 2-(4-acetylpiperazino) acetate (38) (SP152)

To a solution of the analog 37 (15 mg, 0.04 mmol) in CH₂Cl₂ (3 ml) were added Et₃N (0.01 mL, 0.07 mmol) and acetyl chloride (0.003 mL, 0.04 mmol). The reaction mixture was stirred for 2 h at room temperature and quenched with aqueous $NaHCO_3$ solution (1 ml). The resulting mixture was extracted with $CH_2Cl_2$ (10 ml). The organic layer was washed with brine, dried over magnesium sulfate, and concentrated under reduced pressure. The residue was purified by silica gel column chromatography (chloroform:methanol=10:1) to afford 15 mg of the analog 38 (94%).

$^1$H-NMR (CDCl$_3$, 300MHz) δ 5.79 (dd, 1H, J=17.6, 10.8 Hz), 5.34 (m, 1H), 4.87 (dd, 1H, J=10.8, 1.4 Hz), 4.82 (dd, 1H, J=5.5, 1.4 Hz), 4.37 (d, 1H, J=10.9 Hz), 4.04 (d, 1H, J=10.9 Hz), 3.49-3.66 (m, 4H), 3.26 (s, 2H), 2.48-2.61 (m, 4H), 0.76-2.03 (m, 16H), 2.02 (s, 3H), 1.05 (s, 3H), 0.95 (s, 3H), 0.94 (s, 3H); IR (neat) 2926, 1741, 1645, 1434 cm$^{-1}$; LRMS (EI) m/z 456 (M$^+$).

[(1S,4aS,7R)-1,4a,7-Trimethyl-7-vinyl-1,2,3,4,4a,6, 7,8,8a,9,10,10a-dodecahydro-1-phenanthrenyl]methyl 2-[(4-(methylsulfonyl) piperazino) acetate (39) (SP149)

The analog 39 was prepared (93% yield) according to the same procedure for the analog 38, using methanesulfonyl chloride instead of acetyl chloride.

$^1$H-NMR (CDCl$_3$, 300 MHz) δ 5.79 (dd, 1H, J=17.6, 10.8 Hz), 5.34 (m, 1H), 4.93 (dd, 1H, J=10.8, 1.4 Hz), 4.84 (dd, 1H, J=5.5, 1.4 Hz), 4.40 (d, 1H, J=10.9 Hz), 4.08 (d, 1H, J=10.9 Hz), 3.35 (m, 4H), 2.81 (s, 2H), 2.78-2.80 (m, 9H), 2.48-2.61 (m, 4H), 0.76-2.03 (m, 16H), 2.02 (s, 3H), 1.05 (s, 3H), 0.95 (s, 3H), 0.94 (s, 3H); IR (neat) 2925, 1735, 1642, 1539, 1182 cm$^{-1}$; LRMS (EI) m/z 492 (M$^+$).

[(1S,4aS,7R)-1,4a,7-Trimethyl-7-vinyl-1,2,3,4,4a,6, 7,8,8a,9,10,10a-dodecahydro-1-phenanthrenyl]methyl 2-{4-[(4-(methylphenyl) sulfonyl)piperazino] acetate (40) (SP150)

The analog 40 was prepared (93% yield) according to the same procedure for the analog 38, using p-toluenesulfonyl chloride instead of acetyl chloride.

$^1$H-NMR (CDCl$_3$, 300 MHz) δ 7.62 (m, 2H), 7.31 (m, 2H), 5.79 (dd, 1H, J=17.6, 10.8 Hz), 5.34 (m, 1H), 4.93 (dd, 1H, J=10.8, 1.4 Hz), 4.84 (dd, 1H, J=5.5, 1.4 Hz), 4.37 (d, 1H, J=10.9 Hz), 4.08 (d, 1H, J=10.9 Hz), 2.64-3.18 (m, 10H), 2.41 (s, 3H), 0.74-1.97 (m, 16H), 1.08 (s, 3H), 0.95 (s, 3H), 0.93 (s, 3H); IR (neat) 2924, 1742, 1455, 1351, 1166 cm$^{-1}$; LRMS (EI) m/z 568 (M$^+$).

[(1S,4aS,7R)-1,4a,7-Trimethyl-7-vinyl-1,2,3,4,4a,6, 7,8,8a,9,10,10a-dodecahydro-1-phenanthrenyl]methyl 2-{4-[(4-(methoxyphenyl) sulfonyl)piperazino] acetate (41) (SP151)

The analog 41 was prepared (92% yield) according to the same procedure for the analog 38, using 4-(methoxy)benzenesulfonyl chloride instead of acetyl chloride.

$^1$H-NMR (CDCl$_3$, 300MHz) δ 7.82 (m, 2H), 7.65 (m, 2H), 5.79 (dd, 1H, J=17.6, 10.8 Hz), 5.34 (m, 1H), 4.93 (dd, 1H, J=10.8, 1.4 Hz), 4.84 (dd, 1H, J=5.5, 1.4 Hz), 4.37 (d, 1H, J=10.9 Hz), 4.03 (d, 1H, J=10.9 Hz), 3.85 (s, 3H), 2.66-3.19 (m, 10H), 0.74-1.97 (m, 16H), 1.03 (s, 3H), 0.94 (s, 3H), 0.88 (s, 3H); IR (neat) 2926, 1742, 1450, 1065 cm$^{-1}$; LRMS (EI) m/z 584 (M$^+$).

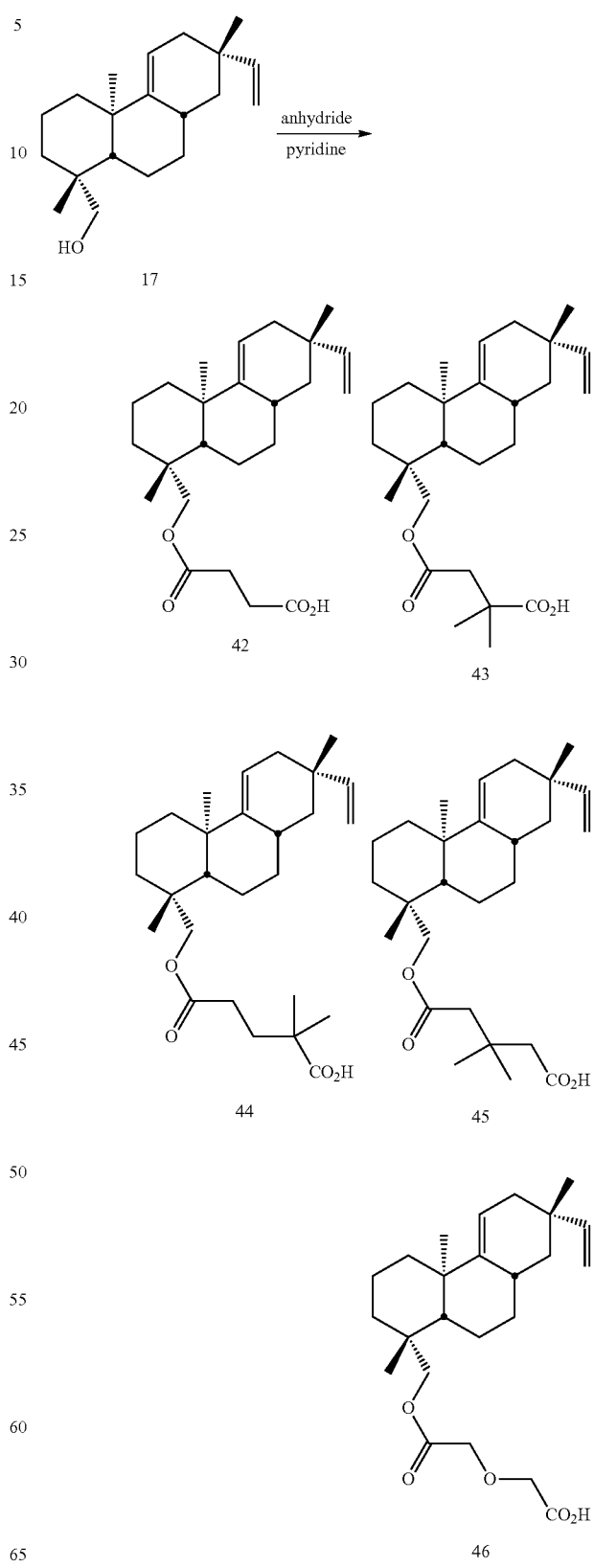

Scheme 8. Synthesis of the acanthoic acid analogs possessing ester functionality

4-[(1S,4aS,7R)-1,4a,7-Trimethyl-7-vinyl-1,2,3,4,4a, 6,7,8,8a,9,10,10a-dodecahydro-1-phenanthrenyl] methoxy-4-oxobutanoic acid (42) (SP117)

To a solution of the analog 17 (30 mg, 0.10 mmol) in pyridine 3 ml) was added succinic anhydride (12 mg, 0.12 mmol). The reaction mixture was refluxed for 3 h and cooled to room temperature. The resulting mixture was diluted with ethyl acetate (10 ml) and washed with brine. The organic layer was dried over magnesium sulfate, concentrated under reduced pressure. The residue was purified by silica gel column chromatography (ethyl acetate: n-hexane=2:1) to afford 26 mg of the analog 42 (67%).

$^1$H-NMR (CDCl$_3$, 300MHz) δ 5.79 (dd, 1H, J=17.6, 10.8 Hz), 5.31 (m, 1H), 4.89 (dd, 1H, J=10.8, 1.4 Hz), 4.84 (dd, 1H, J=5.5, 1.4 Hz),), 4.37 (d, 1H, J=10.9 Hz), 3.98 (d, 1H, J=10.9 Hz), 2.64 (m. 4H), 0.80-2.22 (m, 16H), 1.00 (s, 3H), 0.89 (s, 3H), 0.87 (s, 3H); IR (neat) 2928, 1732, 1708, 1459 cm$^{-1}$; LRMS (EI) m/z 388 (M$^+$).

4-[(1S,4aS,7R)-1,4a,7-Trimethyl-7-vinyl-1,2,3,4,4a, 6,7,8,8a,9,10,10a-dodecahydro-1-phenanthrenyl] methoxy-2,2-dimethyl-4-oxobutanoic acid (43) (SP118)

The analog 43 was prepared (79% yield) according to the same procedure for the analog 42, using 2,2-dimethyl succinic anhydride instead of succinic anhydride.

$^1$H-NMR (CDCl$_3$, 300MHz) δ 5.79 (dd, 1H, J=17.6, 10.8 Hz), 5.31 (m, 1H), 4.87 (dd, 1H, J=10.8, 1.4 Hz), 4.83 (dd, 1H, J=5.5, 1.4 Hz),), 4.30 (d, 1H, J=10.9 Hz), 3.94 (d, 1H, J=10.9 Hz), 2.56 (s, 2H), 0.81-2.25 (m, 16H), 1.23 (s, 6H), 1.00 (s, 3H), 0.90 (s, 3H), 0.89 (s,3H); IR (neat) 2926, 1735, 1706, 1467 cm$^{-1}$; LRMS (EI) m/z 416 (M$^+$).

5-[(1S,4aS,7R)-1,4a,7-Trimethyl-7-vinyl-1,2,3,4,4a, 6,7,8,8a,9,10,10a-dodecahydro-1-phenanthrenyl] methoxy-2,2-dimethyl-5-oxopentanoic acid (44) (SP119)

The analog 44 was prepared (99% yield) according to the same procedure for the analog 42, using 2,2-dimethyl glutaric anhydride instead of succinic anhydride.

$^1$H-NMR (CDCl$_3$, 300MHz) δ 5.79 (dd, 1H, J=17.6, 10.8 Hz), 5.31 (m, 1H), 4.88 (dd, 1H, J=10.8, 1.4 Hz), 4.83 (dd, 1H, J=5.5, 1.4 Hz),), 4.27 (d, 1H, J=10.9 Hz), 3.95 (d, 1H, J=10.9 Hz), 2.78 (t, 2H, J=6.96 Hz), 1.82 (t, 2H, J=6.96 Hz), 0.68-2.30 (m, 16H), 1.29 (s, 6H), 1.15 (s, 3H), 1.01 (s, 3H), 0.90 (s, 3H); IR (neat) 2927, 1735, 1714 cm$^{-1}$; LRMS (EI) m/z 430 (M$^+$).

5-[(1S,4aS,7R)-1,4a,7-Trimethyl-7-vinyl-1,2,3,4,4a, 6,7,8,8a,9,10,10a-dodecahydro-1-phenanthrenyl] methoxy-3,3-dimethyl-5-oxopentanoic acid (45) (SP120)

The analog 45 was prepared (74% yield) according to the same procedure for the analog 42, using 3,3-dimethyl glutaric anhydride instead of succinic anhydride.

$^1$H-NMR (CDCl$_3$, 300 MHz) δ 5.80 (dd, 1H, J=17.6, 10.8 Hz), 5.31 (m, 1H), 5.23 (s, 2H), 4.89 (dd, 1H, J=10.8, 1.4 Hz), 4.82 (dd, 1H, J=5.5, 1.4 Hz), 4.43 (d, 1H, J=10.9 Hz), 4.20 (s, 2H), 4.09 (d, 1H, J=10.9 Hz), 0.71-2.25 (m, 16H), 0.96 (s, 6H), 1.01 (s, 3H), 0.89 (s, 3H), 0.87 (s, 3H); IR (neat) 2925, 1748, 1455 cm$^{-1}$; LRMS (EI) m/z 430 (M$^+$).

2-(2-[(1S,4aS,7R)-1,4a,7-Trimethyl-7-vinyl-1,2,3,4, 4a,6,7,8,8a,9,10,10a-dodecahydro-1-phenanthrenyl] methoxy-2-oxoethoxy)acetic acid (46) (SP121)

The analog 46 was prepared (72% yield) according to the same procedure for the analog 42, using diglycolic anhydride instead of succinic anhydride.

$^1$H-NMR (CDCl$_3$, 300MHz) δ 5.74 (dd, 1H, J=17.6, 10.8 Hz), 5.26 (m, 1H), 4.84 (dd, 1H, J=10.8, 1.4 Hz), 4.78 (dd, 1H, J=5.5, 1.4 Hz), 4.24 (d, 1H, J=10.9 Hz), 3.89 (d, 1H, J=10.9 Hz), 2.35 (m, 4H), 0.82-1.93 (m, 16H), 0.96 (s, 3H), 0.85 (s, 3H), 0.82 (s, 3H); IR (neat) 2930, 1765, 1704, 1020 cm$^{-1}$; LRMS (EI) m/z 404 (M$^+$).

Synthesis and Purification of NPI-1387 and NPI-1388

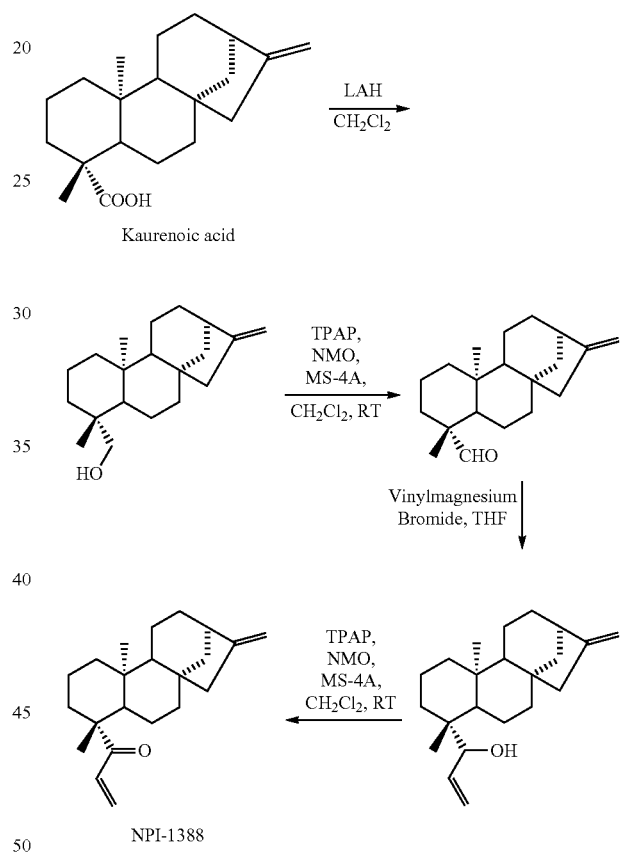

Scheme-9

A mixture of acanthoic acid (1) and kaurenoic acid were treated with lithium aluminium hydride to yield their corresponding hydroxy derivatives which were oxidized with TPAP to give aldehyde mixtures. The aldehyde mixtures of acanthoic acid and kaurenoic acid derivatives were treated with vinyl magnesium bromide to yield their corresponding vinyl alcohol derivatives, which were oxidized to yield a mixture of NPI-1387 (24) and NPI-1388 (see scheme-II for conversion of kaurenoic acid to NPI-1388); the analogous conversion of acanthoic acid (1) to NPI-1387 (24) is shown in schemes 3 and 4).

Purification of NPI-1387 (24) and NPI-1388: The mixture of NPI-1387 (24) and NPI-1388 was dissolved in acetone (20 mg/mL) and purified by preparative HPLC as described below:

| | |
|---|---|
| Column | Ace C18 5u |
| Dimensions | 15 cm × 21 mm ID |
| Flow rate | 14.5 ml/min |
| Detection | DAD |
| Solvent | Gradient of 50% to 90% CH₃CN/water in 8 min, 90% CH₃CN/water for 10 min, 90-100% CH₃CN/water in 1 min then 100% CH₃CN for 10 min |

Compounds NPI-1387 (24) and NPI-1388 were eluted at 23.5 min and 25.5 min, respectively. Fractions containing Compound NPI-1387 and NPI-1388 were pooled based on composition of compounds present, and evaporated under reduced pressure on a rotary evaporator. This process yielded pure Compound NPI-1387 and NPI-1388.

¹H-NMR (CDCl₃, 500 MHz) for NPI-1387 see Fig-VI
¹³C-NMR (CDCl₃, 125 MHz) for NPI-1387 see Fig-VII
¹H-NMR (CDCl₃, 500 MHz) for NPI-1388 see Fig-VIII Methods of Making Compounds of Formula IIA-b Compounds of Formula IIA-b are made following the above-procedure for making compounds of Formula II-b except that as the starting material in place of Acanthoic acid (1), Kaurenoic acid is used:

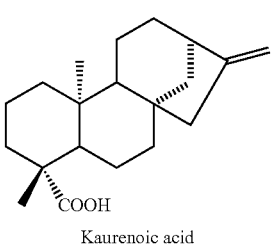

Kaurenoic acid

Methods of Making Compounds of Formula IIB-b

Compounds of Formula IIB-b are made following the above-procedure for making compounds of Formula II-b except that as the starting material in place of Acanthoic acid (1), a TTL compound is used, for example, TTL-1, TTL-2, TTL-3, TTL-4, etc.

Methods of Making NPI-1390

Compound NPI-1390 (Vinylketone derivative of TTL3) were made as shown in Scheme 9:

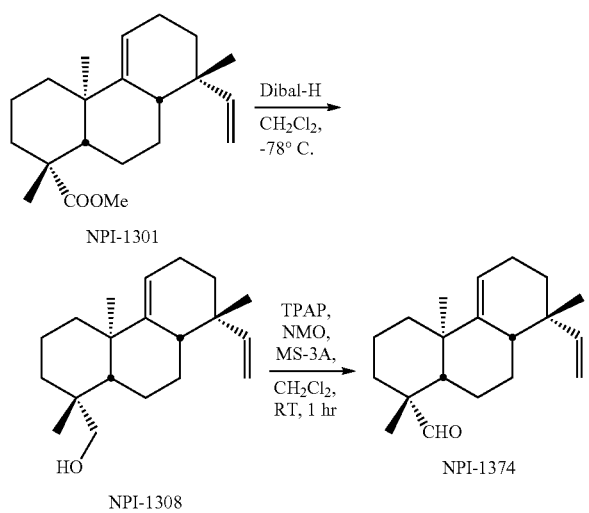

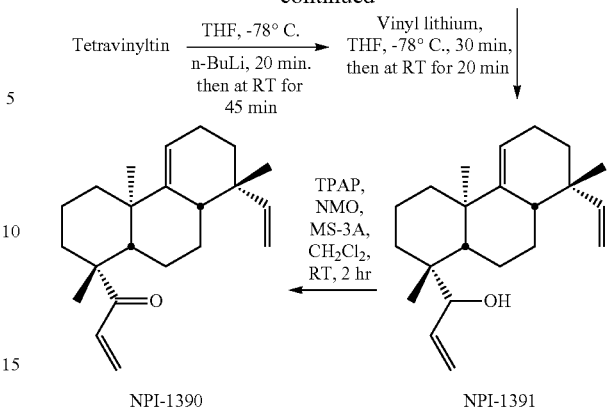

NPI-1390         NPI-1391

Compound NPI-1308: To a solution of compound NPI-1301 (315 mg, 1 mmol) in CH₂Cl₂ (15 mL) was added DIBAL-H (3.0 mL, 1 M in hexane, 3 mmol) slowly at −78° C. The reaction mixture was stirred at −78° C. for an hour and quenched with MeOH (2 mL). Then the reaction mixture was allowed to warm up to room temperature, added 1N HCl (30 mL) and stirred for about 30 min. The resulting mixture was extracted with CH₂Cl₂ (3×50 mL) and the organic layers were combined and concentrated under reduced pressure to yield NPI-1308 (275 mg, 96% yield)

¹H-NMR (CDCl₃, 500 MHz) see Fig-IV
¹³C-NMR (CDCl₃, 125 MHz) see Fig-V

Compound NPI-1374: To a solution of compound NPI-1308 (40 mg, 0.14 mmol) in CH₂Cl₂ (3 ml) were added NMO (116 mg, 0.36 mmol) and a catalytic amount of TPAP in the presence of molecular sieves (3A). The reaction mixture was stirred for 1 h at room temperature and poured onto a silica column (15×30 mm). The column was eluted with 0-15% EtOAc/hexanes to yield NPI-1374 (38 mg, 96% yield).

Compound NPI-1391: A solution of n-butyllithium (0.2 mL, 2.5M in hexane, 0.5 mmol) was added to a solution of tetravinyl tin (35 mg, 0.15 mmol) in THF (1.5 mL) at −78° C. under N₂. The mixture was stirred at same temperature for about 20 min and then at room temperature for about 45 min. A solution of aldehyde NPI-1374 (115 mg, 0.04 mmol) in THF (0.6 mL) was added to the reaction mixture at −78° C. and the reaction mixture was stirred at −78° C. for about 30 min and then at room temperature about 20 min. Then the reaction mixture was quenched with saturated NH₄Cl solution (8 mL) and extracted with ethyl ether (3×25 mL). The combined organic layer was concentrated under reduced pressure and the resulting residue was purified by silica column chromatography (15×30 mm; 0-10% EtOAc/hexane) to yield NPI-1391 (10.3 mg, 83% yield).

¹H-NMR (CDCl₃, 500 MHz) see Fig-III

Compound NPI-1390: To a solution of compound NPI-1391 (8.3 mg, 0.026 mmol) in CH₂Cl₂ (1.5 ml) were added NMO (10 mg, 0.09 mmol) and catalytic amount of TPAP in the presence of molecular sieves (3A). The reaction mixture was stirred for 2 h at room temperature and filtered through a silica gel plug. The filtrate was concentrated under reduced pressure and the residue was purified by silica gel column chromatography (10×200 mm; 0-3% EtOAc/hexanes) to yield NPI-1390 (2.2 mg).

¹H-NMR (CDCl₃, 500 MHz) see Fig-I
¹³C-NMR (CDCl₃, 125 MHz) see Fig-II

Methods of Using the Invention

The in vitro and in vivo methods described above as part of the present invention also establish the selectivity of a TNF-α or IL-1 modulator. It is recognized that chemicals can modulate a wide variety of biological processes or be selective. Panels of cells based on the present invention can be used to determine the specificity of the candidate modulator. Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a candidate modulator can be established in vitro by testing the toxicity and effect of a candidate modulator on a plurality of cell lines that exhibit a variety of cellular pathways and sensitivities. The data obtained from these in vitro toxicity studies may be extended to animal models, including accepted animal model studies and human clinical trials, to determine toxicity, efficacy, and selectivity of the candidate modulator.

The present invention also encompasses the compositions, produced by the methods, in pharmaceutical compositions comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

These TNF-α or IL-1 modulator compositions may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the TNF-α or IL-1 modulator composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration is preferably oral on a daily or twice daily basis.

The exact formulation, route of administration, scheduling and dosage can be chosen by the individual physician in view of the patient's condition. See for example, Fingl et al., in The Pharmacological Basis of Therapeutics, 1975. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. A variety of techniques for formulation and administration may be found in Remington's Pharmaceutical Sciences, 18th Ed., Mack Publishing Co., Easton, Pa. (1990). Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use as herein described include compositions wherein the TNF-α or IL-1 modulators are contained in an effective amount to achieve the TNF-α or IL-1 modulatory purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, for example, by means of conventional mixing, dissolving, granulating, dragee-making, levitating, emulsifying, encapsulating, entrapping, or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations).

Compounds of the present invention can be evaluated for efficacy and toxicity using known methods. For example, the toxicology of a particular compound of the present invention, or of a subset of the compounds of the present invention sharing certain chemical moieties, can be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds of the present invention in an animal model, such as mice, rats, rabbits, or monkeys, may be determined using known methods. The efficacy of a particular compound of the present invention may be established using several art recognized methods, such as in vitro methods, animal models, or human clinical trials. Art-recognized in vitro models exist for nearly every class of condition, including the conditions abated by the present invention, including cancer, cardiovascular disease, and various immune disfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound of the present invention in humans.

When used as an anti-inflammatory agent, an anti-cancer agent, a tumor-growth-inhibiting compound, or as a means of treating cardiovascular disease, the compounds of Formulae (II), (IIA) can be administered by either oral or a non-oral pathways. In some aspects the compounds of Formulae (IIB), including for example, IIB-a,b, IIA-a,b, and II-a,b) and (II2) can be administered by such pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intreperitoneally, intravenously, intramuscularly, intradermally, or the like. Similarly, it may be administered topically, rectally, or vaginally, as deemed appropriate by those of skill in the art for bringing the compound into optimal contact with a tumor, thus inhibiting the growth of the tumor. Local administration at the site of the tumor or other disease condition is also contemplated, either before or after tumor resection, or as part of an art-recognized treatment of the disease condition. Controlled release formulations, depot formulations, and infusion pump delivery are similarly contemplated.

The compounds described herein, including Formulae (II) and (IIA), and preferably (IIB), when used as an antitumor agent or as a treatment for any other above-identified disease condition, may be orally or non-orally administered to a human patient in the amount of about 0.0007 mg/day to about 7,000 mg/day of the active ingredient, and more preferably about 0.07 mg/day to about 70 mg/day of the active ingredient at, preferably, one time per day or, less preferably, over two to about ten times per day. Alternatively and also preferably, the compound may preferably be administered in the stated amounts continuously by, for example, an intravenous drip. Thus, for a patient weighing 70 kilograms, the preferred daily dose of the active anti-tumor ingredient would be about 0.0007 mg/kg/day to about 35 mg/kg/day, and more preferable, 0.007 mg/kg/day to about 0.035 mg/kg/day. Nonetheless, as will be understood by those of skill in the art, in certain situations it may be necessary to administer the anti-tumor compound in amounts that excess, or even far exceed, the above-stated, preferred dosage range to effectively and aggressively treat particularly advanced or lethal tumors.

To formulate the compounds described herein, including those of Formula (II), the compound of Formula (IIA), or the compound of Formula (IIB), as a tumor-growth-inhibiting or anti-viral compound, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound, particularly when the compound is to be administered orally.

In the case of using the compound of Formula (II), Formula (IIA), and/or Formula (IIB) as a means of treating skin redness, the compound may alternatively be administered topically as a salve or ointment, in conjunction with a pharmaceutically acceptable carrier.

In the case of using the compound of Formula (II), Formula (IIA), and or Formula (IIB) as a biochemical test reagent, as described above, the compound may be dissolved in an organic solvent or hydrous organic solvent and directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound for use as a cell cycle inhibitor is generally in the range of about 1 to about 100 µg/ml, the most appropriate use amount varies depending on the type of cultured cell system and the purpose of use, as will be appreciated by persons of ordinary skill in the art. Also, in certain applications it may be necessary or preferred to persons of ordinary skill in the art to use an amount outside the foregoing range.

The present invention also encompasses the compositions of Formula (II), Formula (IIA), and/or Formula (IIB) in a pharmaceutical compositions comprising a pharmaceutically acceptable carrier. Such compositions may be prepared for storage and for subsequent administration. Acceptable carriers or diluents for therapeutic use are well known in the pharmaceutical art, and are described, for example, in Remington's Pharmaceutical Sciences, Mack Publishing Co. (A.R. Gennaro edit. 1985). For example, such compositions may be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions, as described above, may be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions of the present invention may be formulated and administered either systemically or locally. A variety of techniques for formulation and administration may be found in Remington's Pharmaceutical Sciences, 18th ed., Mack Publishing Co., Easton, Pa. (1990).

Various references, publications, and patents are cited herein. To the extent permitted by law, each of these references, publications, and patents is hereby incorporated by reference herein in its entirety.

EXAMPLES

The following examples are meant to illustrate specific, preferred embodiments of the invention, and are not meant to limit the scope of protection afforded by the invention. The following examples, specifically Example 1-8, demonstrate that representative compounds of the classes of compounds described herein have been synthesized. Examples 9-17 exhibit, in mammalian cells which present an acceptable preliminary model for human efficacy and safety, treated with increasing doses of the compound of Formula (I), as synthesized in Example 1, and compounds of Formula (IIB), as herein designated TTL1 through TTL4, as synthesized in accordance with the processes of Example 1, and, more particularly, as in Examples 2-5, at concentrations as high as 10 µg/ml showed similar viability compared to untreated controls indicating that the inhibitory effects of the evaluated compounds on TNF-α synthesis were not mediated by a direct cytotoxic effect.

Subsequent studies with certain preferred compounds demonstrated that TTL1 exhibited approximately ten (10) fold greater activity compared to THE SYNTHETIC COMPOUND OF FORMULA (I) in inhibiting TNF-α and IL-1 synthesis. TTL3 which contains an additional chemical modification exhibited approximately 100 times greater activity than TTL1. It is important to note that similar to the compound of Formula (I), neither TTL1 nor TTL3 significantly inhibited IL-6 synthesis.

Example 1

Stereoselective Synthesis of Compounds of Formulae (I) and (II)

Figure 18:
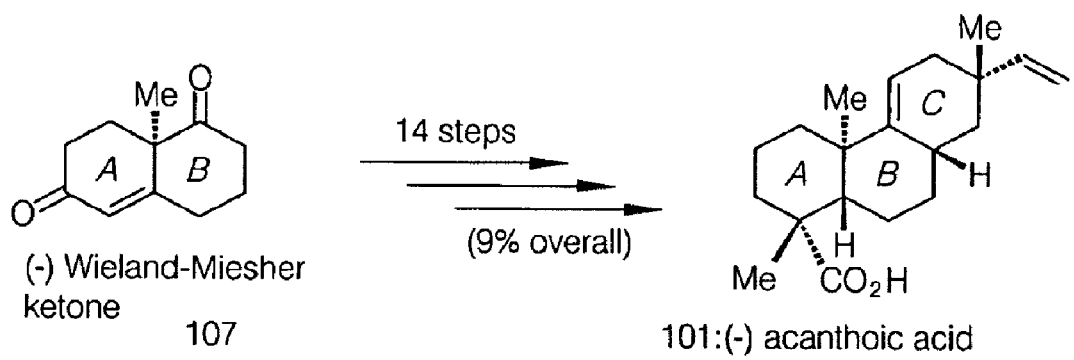
FIG. 18 depicts a summary of the synthesis of Example 1.
Figure 19:
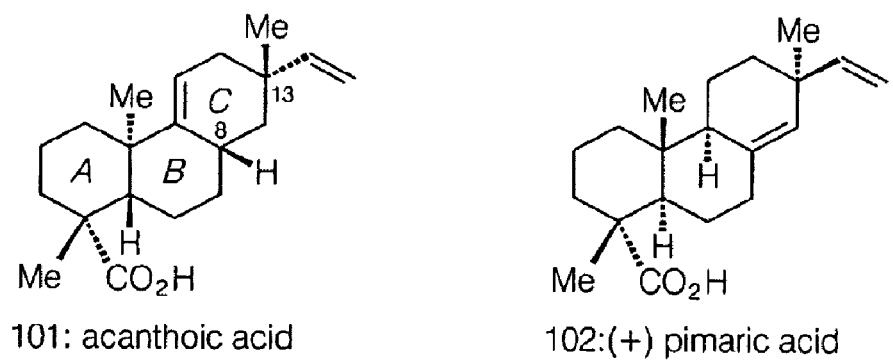
FIG. 19 depicts the structures of (−) acanthoic acid and (+) pimaric acid.

The first stereoselective synthesis of Compound of Formula (I) has been accomplished. Our synthetic plan departs from (−) Wieland-Miesher ketone (107), see FIG. 18, and calls upon a Diels-Alder cycloaddition reaction for the construction of the C ring of 101. The described synthesis confirms the proposed stereochemistry of 101 and represents an efficient entry into an unexplored class of biologically active diterpenes.

The root bark of *Acanthopanax koreanum* Nakai (Araliaceae), a deciduous shrub that grows in The Republic of Korea, has been used traditionally as a tonic, sedative, and as a remedy for rheumatism and diabetes. (*Medicinal Plants of East and Southeast Asia*, Perry, L. M.; Metzger, J. Eds.; MIT Press, Cambridge, Mass. and London, 1980). In their study of the pharmacologically active extracts of this folk medicine, Chung and co-workers have isolated and structurally characterized a novel diterpene, that was subsequently named acanthoic acid (101). ((a) Kim, Y.-H.; Chung, B. S.; Sankawa, U. *J. Nat. Prod.* 1988, 51, 1080-1083; (b) Kang, H.-S.; Kim, Y.-H.; Lee, C.-S.; Lee, J.-J.; Choi, I.; Pyun, K.-H. *Cellular Immunol.* 1996, 170, 212-221; (c) Kang, H.-S.; Song, H. K.; Lee, J.-J.; Pyun, K.-H.; Choi, I. *Mediators Inflamm.* 1998, 7, 257-259).

From the biosynthesis standpoint, 101 belongs to a rather large family of pimaradiene diterpenes, which may be best represented by pimaric acid (102). (Ruzicka, L.; Sternbach, L.; *J. Am. Chem. Soc.* 1948, 70, 2081-2085; Ireland, R. E.; Schiess, P. W. *Tetrahedron Lett.* 1960, 25, 37-43; Wenkert, E.; Buckwalter, B. L. *J. Am. Chem. Soc.* 1972, 94, 4367-4372; Wenkert, E.; Chamberlin, J. W. *J. Am. Chem. Soc.* 1959, 81, 688-693). The structure of the compound of Formula (I) is distinguished by an uncommon connectivity across the rigid tricyclic core, which may be held accountable for its pharmacological profile. Indeed, the recent isolation of this compound has allowed studies into its biological activity and verified its medicinal potential. (Kang, H.-S.; Kim, Y.-H.; Lee, C.-S.; Lee, J.-J.; Choi, I.; Pyun, K.-H. *Cellular Immunol.* 1996, 170, 212-221; Kang, H.-S.; Song, H. K.; Lee, J.-J.; Pyun, K.-H.; Choi, I. *Mediators Inflamm.* 1998, 7, 257-259)).

More specifically, acanthoic acid was found to exhibit promising anti-inflammatory and antifibrotic activities that presumably arise by inhibiting the production of the pro-inflammatory cytokines: tumor necrosis factor-alpha (TNF-α) and interleukin-1 (IL-1). See *Tumor Necrosis Factors. The Molecules and their Emerging Role in Medicine*, B. Beutler, Ed.; Raven Press, N.Y. 1992; Aggarwal, B.; Puri, R. *Human Cytokines: Their Role in Disease and Therapy*; Blackwell Science, Inc.: U.S.A., 1995; Thorpe, R.; Mire-Sluis, A. *Cytokines*; Academic Press: San Diego, 1998; Kurzrock, R.; Talpaz, M. *Cytokines: Interleukins and Their Receptors*; Kluwer Academic Publishers: U.S.A., 1995; Szekanecz, Z.; Kosh, A. E.; Kunkel, S. L.; Strieter, R. M. *Clinical Pharmacol.* 1998, 12, 377-390; Camussi, G.; Lupin, E. *Drugs* 1998, 55, 613-620; Newton, R. C.; Decicco, C. P. *J. Med. Chem.* 1999, 42, 2295-2314.

This inhibition was concentration dependent and cytokine-specific since under the same conditions the production of IL-6 or IFN-γ (interferon-gamma) were not affected. In addition, acanthoic acid was found to be active upon oral administration and showed minimal toxicity in experiments performed in mice and rats.

The combination of uncommon structure and promising pharmacological activity displayed by 101 prompted us to extend our synthetic studies, see Xiang, A. X.; Watson, D. A.; Ling. T.; Theodorakis, E. A. *J. Org. Chem.* 1998, 63, 6774-6775; Ling, T.; Xiang, A. X.; Theodorakis, E. A. *Angew. Chem. Int. Ed. Engl.* 1999, 38, 3089-3091, to this family of biologically important metabolites. This example provides a stereoselective total synthesis of (−) acanthoic acid and the compounds of Formula (II) and, as shown in Examples 2-6, provides the basis for the total synthesis of the compounds of Formula (IIB). This Example also confirms the structure and absolute stereochemistry of 101.

Figure 20:
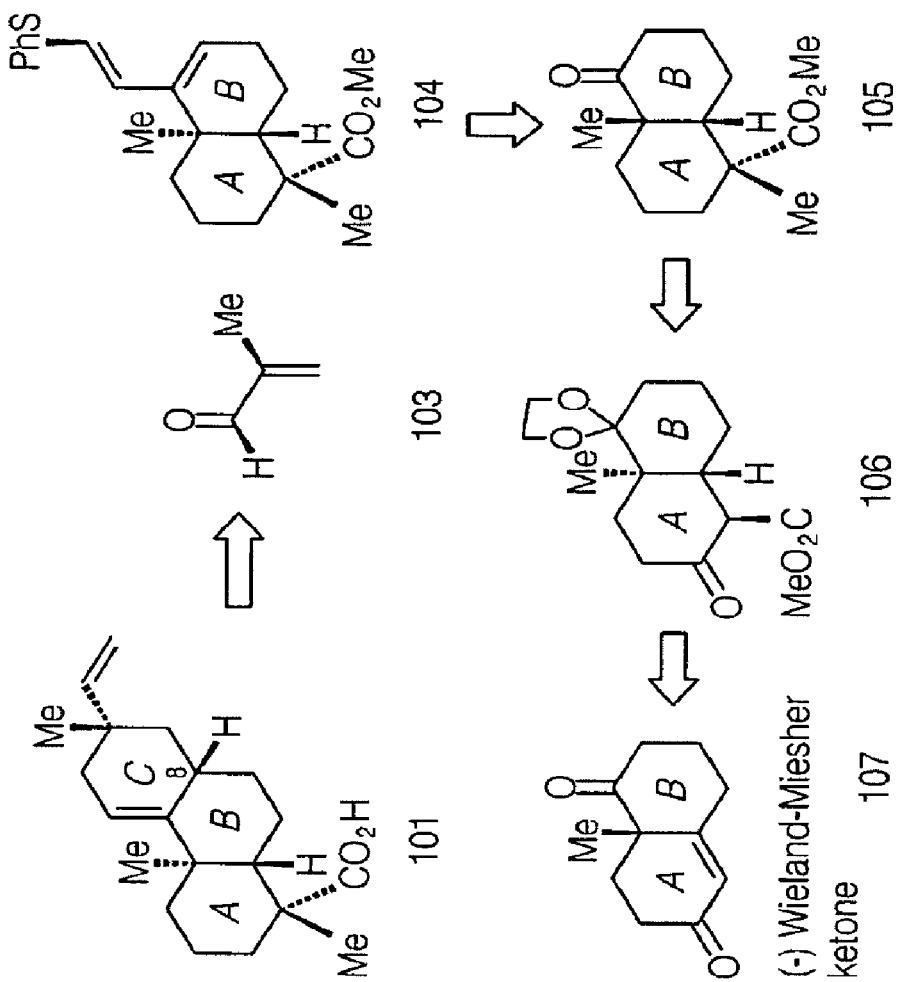
FIG. 20 depicts the retrosynthetic analysis of (−) acanthoic acid of Example 1.
Figure 21:
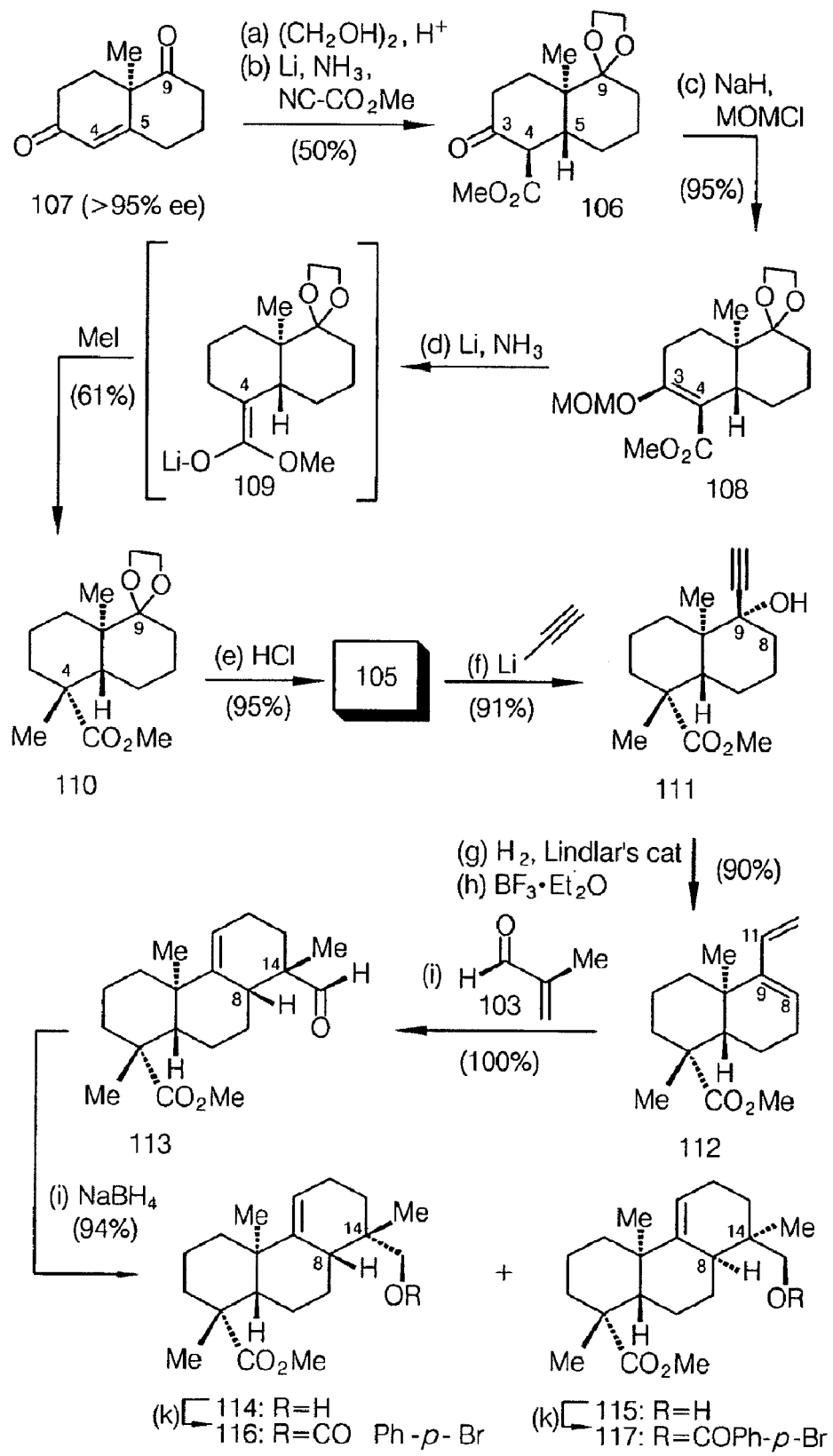
FIG. 21 depicts the synthetic scheme (Scheme 5) of preferred compounds of Formula (IIB) as described in Examples 1-6. The regents, conditions, and percentage yields of each step were as follows: (a) 0.1 equiv PTSA (CH$_2$OH)$_2$, benzene, 80° C., 4 h, 90%; (b) 2.2 equiv Li, liquid NH$_3$, 1.0 equiv tBuOH, −78 to −30° C., 30 minu then isoprene (excess), −78 to 50° C.; 1.1 equiv NC—CO$_2$Me, Et$_2$O, −78 to 0° C., 2 h, 55%; (c) 1.1 equiv NaH, HMPA, 25° C., 3 h; 1.1 equiv MoMCl, 25° C., 2 h, 95%; (d) 7.0 equiv Li, liquid NH$_3$, −78 to −30° C., 20 min; CH$_3$I (excess), −78 to −30° C., 1 h, 61%; (e) 1N HCl, THF, 25° C., 15 min, 95%; (f) 1.6 equiv Li acetylide, Et$_2$O, 25° C., 1 h, 91%; (g) Lindlar's catalyst (20% per weight), H$_2$, dioxane/pyridine 10/1. 25°, 10 min 95%; (h) 4.4 equiv BF$_3$.Et$_2$O, benzene/THF4/1. 80° C., 5 h, 95%; (i) 13 equiv compound 103, neat, 8 h, 25° C., 100%; (j) 1.4 equiv NaBH$_4$, THF MeOH: 10/1, 30 min, 25° C., 94%; (k) 1.1 equiv p-Br—C$_6$H$_4$COCl, 1.5 equiv pyridine, 0.1 equiv DMAP, CH$_2$Cl$_2$, 25°, 2 h, 95% for compound 116, 97% for compound 117.
Figure 23:
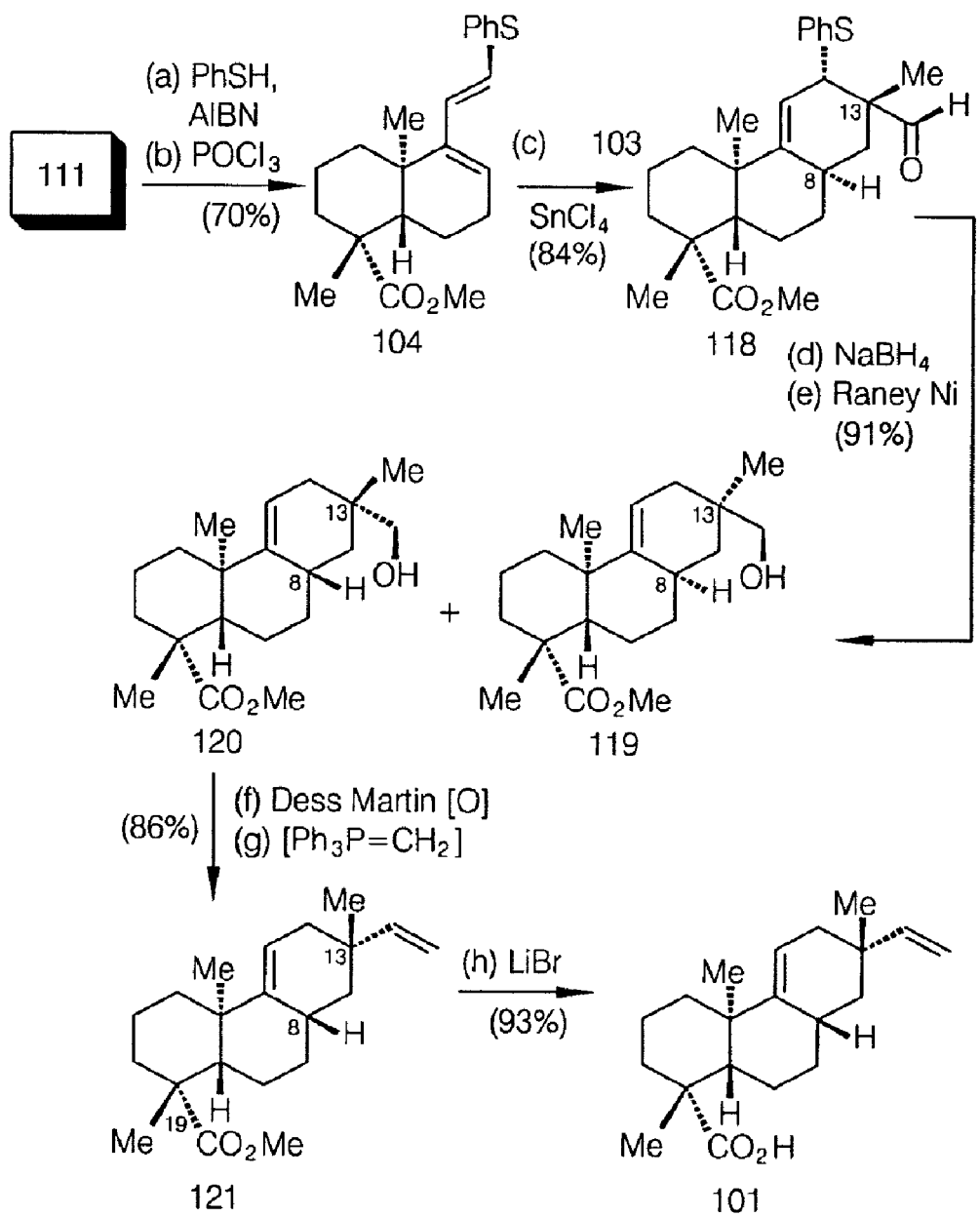
FIG. 23 depicts the synthetic scheme (Scheme 6) of the tricyclic core of (−) acanthoic acid of Example 1. The reagents, conditions, and percentage yields of each step were as follows: (a) 3.0 equiv PhSH, 0.05 equiv AIBN, xylenes, 120° C., 18 h, 86%, (b) 1.1 equiv. POCl$_3$, HMPA, 25° C., 1 h; 1.1 equiv pyridine, 150° C., 18 h 81%; (c) 3.0 equiv compound 103, 0.2 equiv SnCl$_4$ (1 M in CH$_2$Cl$_2$), CH$_2$Cl$_2$, −20 to 0° C., 20 h, 84%; (d) 1.4 equiv NaBH$_4$, EtOH, 25° C., 30 min; (e) RaneyNi (excess), THF, 65° C., 10 min 91% (over two steps); (f) 1.3 equiv Dess-Martin periodinane, CH$_2$Cl$_2$, 25° C., 30 min; (g) 2.7 equiv P$_3$PhCH$_3$Br, 2.2. equiv NaHMDS (1.0 in THF), THF, 25° C., 18 h, 86% (over two steps); (h) 3.0 LiBr, DMF, 160° C., 3 h, 93%.
Figure 24:
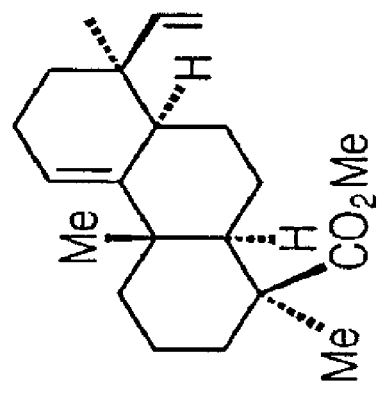
FIG. 24 depicts two enantiomers of the compounds designated TTL herein, exhibiting the ability to locate the moiety designated R$_6$ stereo-selectively.
Figure 24:
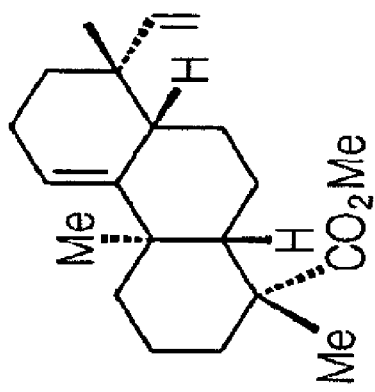
Figure 25:
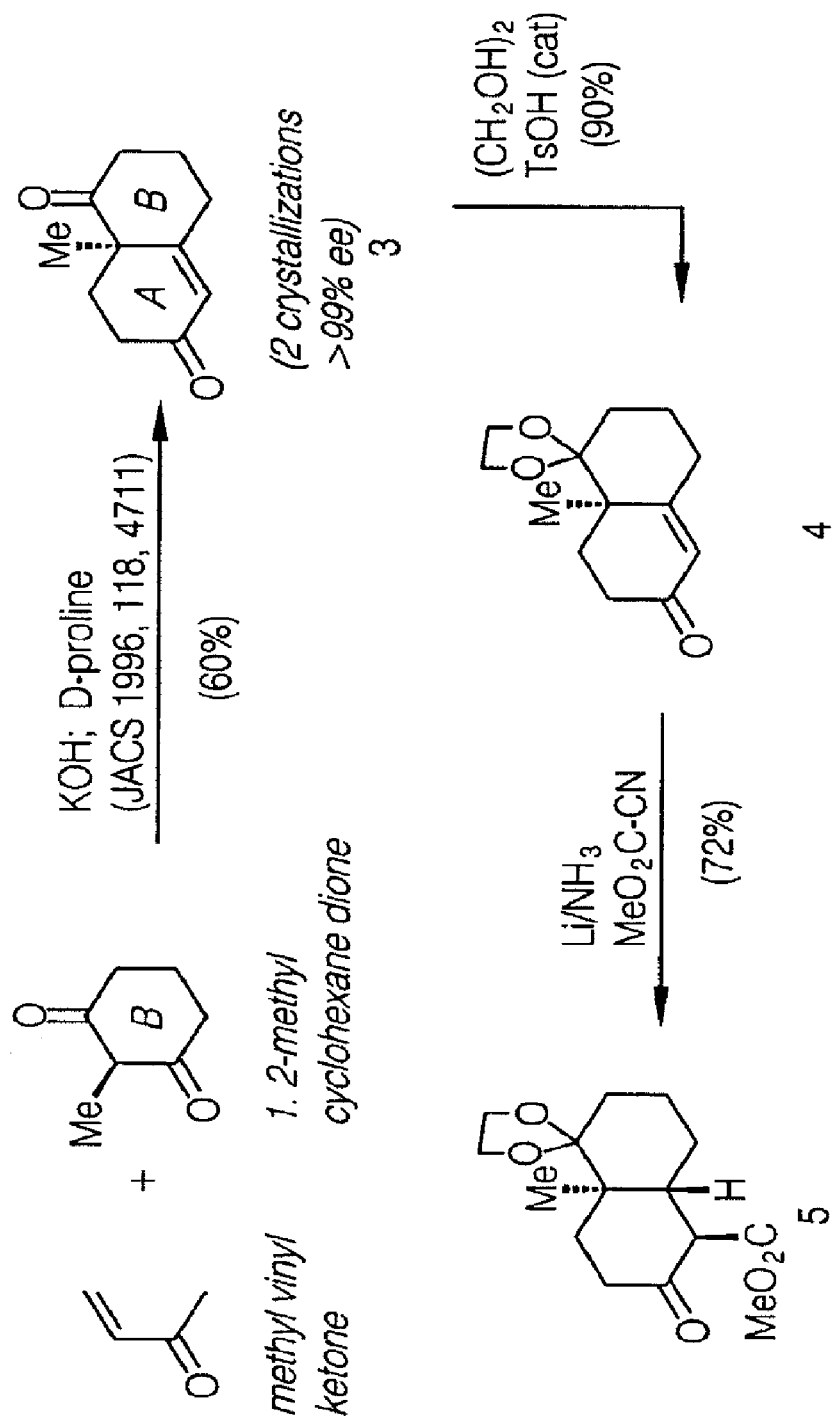
FIG. 25 depicts a method of synthesizing the (−) enantiomer depicted in FIG. 23; the (+) enantiomer depicted in FIG. 23 may be synthesized by using (L)-proline in place of (D)-proline.
Figure 26:
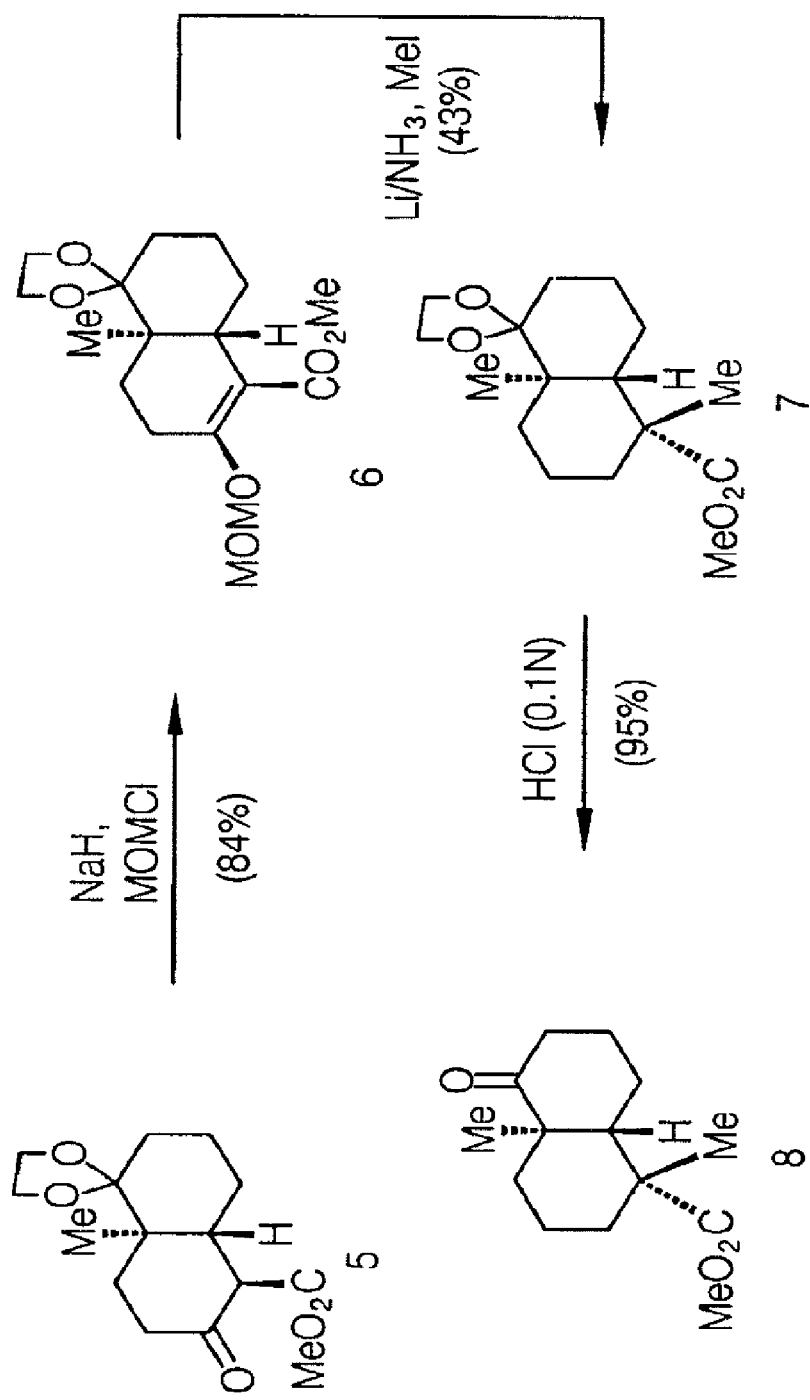
FIG. 26 depicts synthetic steps subsequent to those depicted in FIG. 24.
Figure 27:
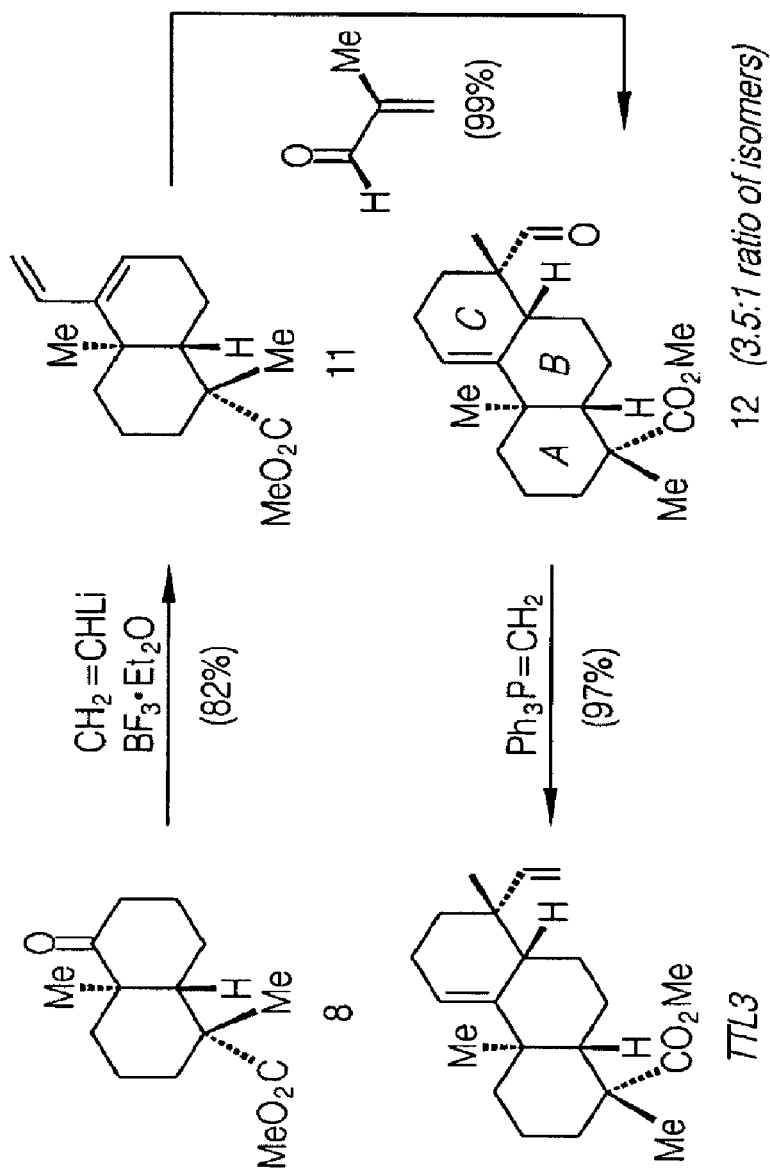
FIG. 27 depicts the use of the synthetic route disclosed to locate the moieties designated $R_9$, $R_{10}$ and $R_{11}$ in the compound of Formula IIB and its stereo-isomers in a stereo-specific manner on the ring.
Figure 28:
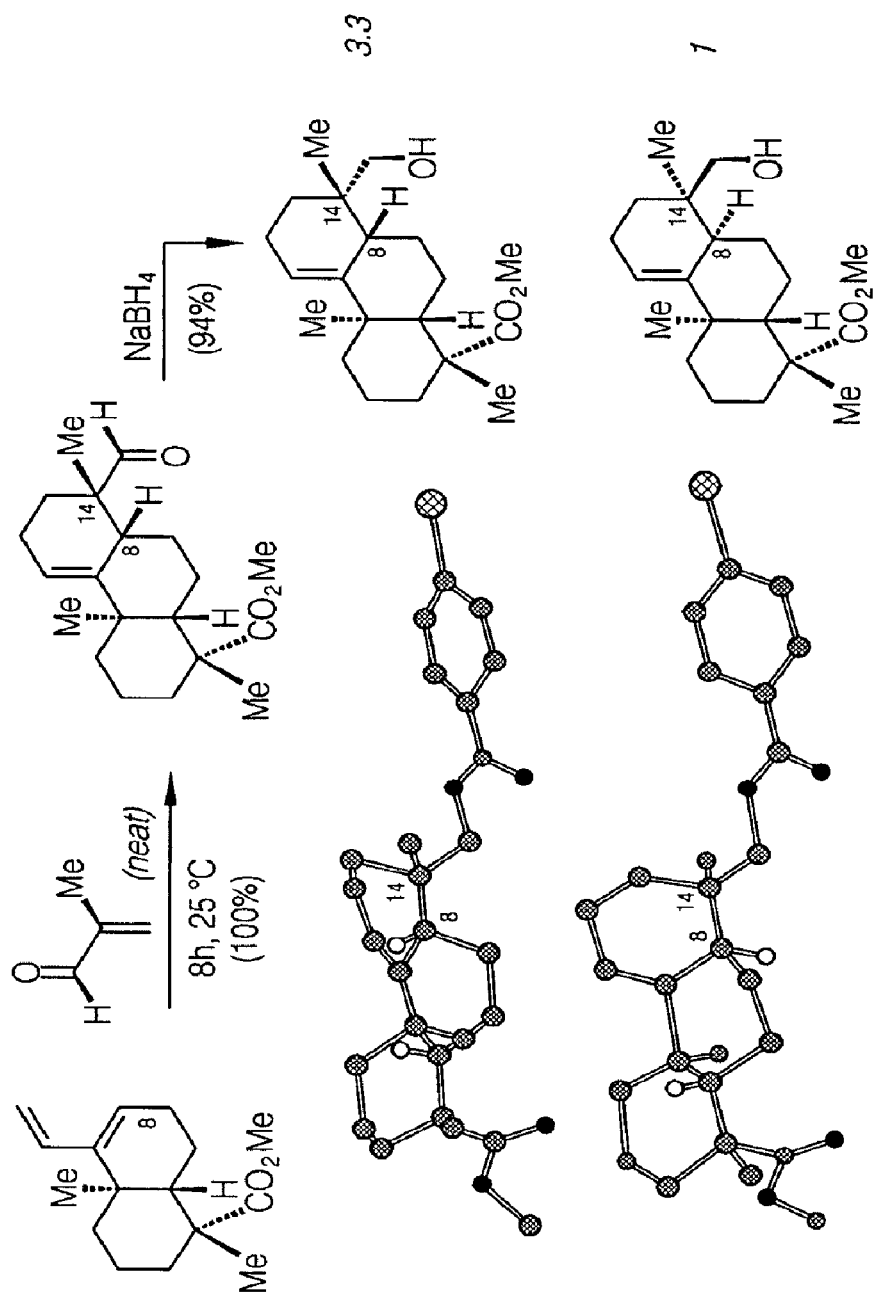
FIG. 28 depicts the synthesis, isolation and purification of the compound of Formula IIB and its stereo-isomers, showing how to purify compounds in which to locate the moieties designated $R_9$, $R_{10}$ and $R_{11}$ of in the compounds of Formula IIB and its stereo-isomers, in a stereo-specific manner on the ring.
Figure 29:
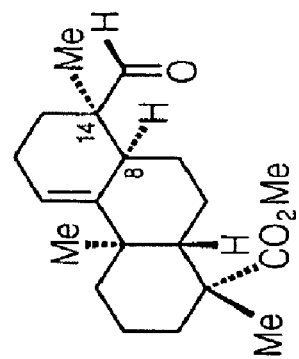
FIG. 29 also depicts the synthesis, isolation and purification of the compound of Formula IIB and its stereo-isomers, showing how to purify compounds in which to locate the moieties designated R9, R10 and R11 of in the compounds of Formula IIB and its stereo-isomers, in a stereo-specific manner on the ring.
Figure 29:
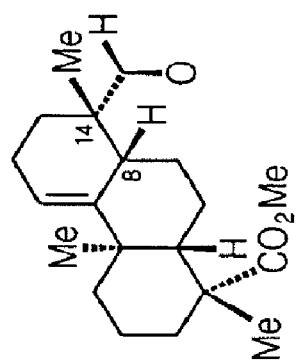
Figure 29:
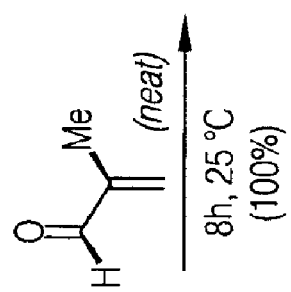
Figure 29:
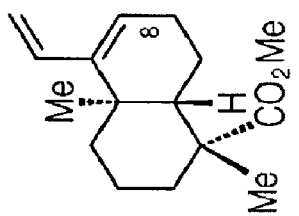

The retrosynthetic strategy towards acanthoic acid is illustrated in FIG. 20. The C ring of 101 is envisioned to be constructed by a Diels-Alder cycloaddition reaction, thereby revealing dienophile 103 and an appropriately substituted diene, such as 104, as ideal coupling partners. See Oppolzer, W in *Comprehensive Org. Synthesis*, Trost, B. M. Ed.; Oxford, N.Y.; Pergamon Press, 1991, 315-399. This reaction introduces both the unsaturation at the C9-C11 bond and the desired stereochemistry at the C8 and C13 carbons, permitting a convenient branch point between the syntheses of the compounds of Formula (II) and the compounds of Formula (IIB). Diene 104 could be produced by functionalization of ketone 105, whose C4 quaternary center was projected to be formed by a stereocontrolled alkylation of β-ketoester 107. This analysis suggested the use of (−) Wieland-Miesher ketone 107 as a putative starting material. Application of such a plan to the synthesis of acanthoic acid is depicted in FIGS. 21 and 23, as Schemes 5 and 6. All compounds exhibited satisfactory spectral and analytical data.

The synthesis began with optically pure enone 107, which was readily available through a D-proline-mediated asymmetric Robinson annulation (75-80% yield, >95% ee). See Buchschacher, P.; Fuerst, A.; Gutzwiller, J. *Org. Synth. Coll. Vol. VII* 1990, 368-3372.). Selective ketalization of the C9 ketone group of 107, followed by reductive alkylation across the enone functionality with methyl cyanoformate afforded ketoester 106 in 50% overall yield. See Crabtree, S. R.; Mander, L. N.; Sethi, P. S. *Org. Synth.* 1992, 70, 256-263. To introduce the desired functionalization at the C4 position, a second reductive alkylation procedure was implemented, see Coates, R. M.; Shaw, J. E. *J. Org. Chem.* 1970, 35, 2597-2601; Coates, R. M.; Shaw, J. E. *J. Org. Chem.* 1970, 35, 2601-2605. Compound 106 was first transformed to the corresponding methoxymethyl ether 108, which upon treatment with lithium in liquid ammonia and iodomethane gave rise to ester 110 in 58% overall yield and as a single diastereomer. See Welch, S.C.; Hagan, C. P. *Synthetic Comm.* 1973, 3, 29-32; Welch, S.C.; Hagan, C. P.; Kim, J. H.; Chu, P. S. *J. Org. Chem.* 1977, 42, 2879-2887; Welch, S.C.; Hagan, C. P.; White, D. H.; Fleming, W. P.; Trotter, J. W. *J. Amer. Chem. Soc.* 1977, 99, 549-556. The stereoselectivity of this addition arose from the strong preference of the intermediate enolate 109 to undergo alkylation at the less hindered equatorial side.

Figure 22:
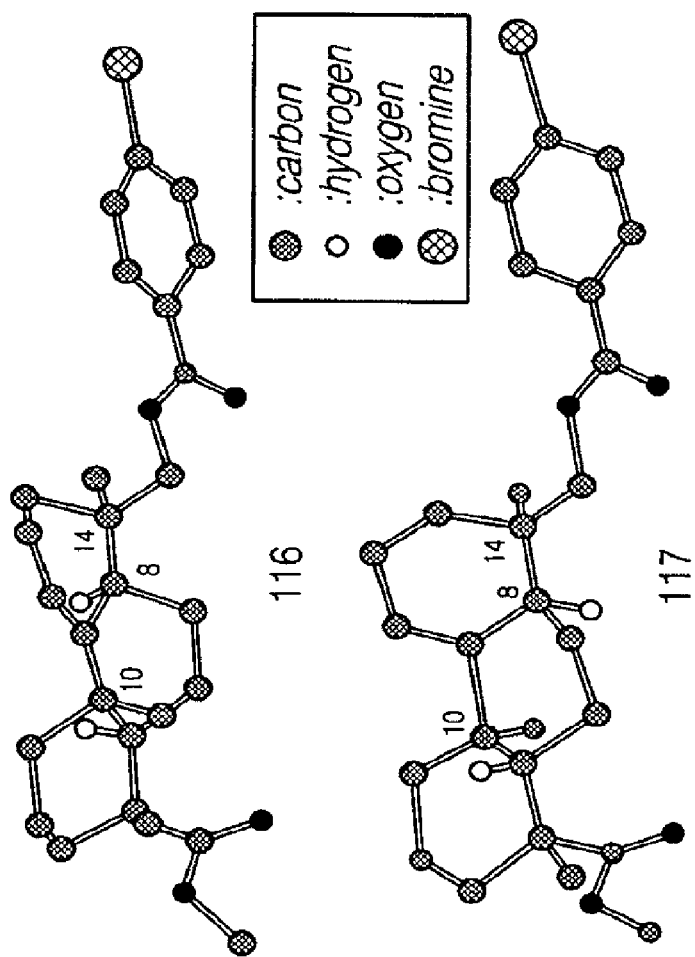
FIG. 22 depicts the Chem3D representation of ORTEP drawings of compound 116 and 117, showing only selected hydrogen atoms for sake of clarity.

With the bicyclic core at hand, the C ring was constructed. The C-ring was formed via a Diels-Alder reaction between methacrolein 103, see for example, FIG. 21, and the sulfur-containing diene 104. The synthesis of 104 was initiated with an acid-catalyzed deprotection of the C9 ketal of 110, followed by alkylation of the resulting ketone 105 with lithium acetylide.ethylene diamine complex. See Das, J.; Dickinson, R. A.; Kakushima, M.; Kingston, G. M.; Reid, G. R.; Sato, Y.; Valenta, Z. *Can. J. Chem.* 1984, 62, 1103-1111). This sequence afforded alkyne 111 as an 8:1 diasteromeric mixture at C9 (in favor of the isomer shown) and in 86% overall yield. At this point, the diastereofacial selectivity of the Diels-Alder reaction was evaluated, as was the overall feasibility of using a non-functionalized diene, such as 112. To this end, the diastereomeric mixture of propargyl alcohols 111 was partially reduced ($H_2$, Lindlar's catalyst) and dehydrated ($BF_3.Et_2O$) to produce diene 112 in 90% yield. (Coisne, J.-M.; Pecher, J.; Declercq, J.-P.; Germain, G.; van Meerssche, M. *Bull. Soc. Chim. Belg.* 1980, 89, 551-557). The Diels-Alder cycloaddition between 112 and methacrolein (103) under neat conditions at 25° C., afforded in quantitative yield a mixture of two diastereomeric aldehydes that were separated after reduction with sodium borohydride. The resulting alcohols 114 and 115 were transformed to the corresponding p-bromobenzoate esters (compounds 116 and 117 respectively), which upon recrystallization with dichloromethane/ethanol yielded crystals suitable for X-Ray analysis (FIG. 22).

The results of the X-ray analyses established that the tricyclic system had the expected stereochemistry at the C4 position and confirmed that the Diels-Alder reaction proceeded with exclusive endo orientation. Methacrolein was shown to produce exo Diels Alder products when reacting with cyclopentadiene: Kobuke, Y.; Fueno, T.; Furukawa, J. *J. Am. Chem. Soc.* 1970, 92, 6548-6553. This surprising observation was rationalized based on the steric repulsion exhibited by the methyl group: Yoon, T.; Danishefsky, S. J.; de Gala, S. *Angew. Chem. Int. Ed. Engl.* 1994, 33, 853-855). Second, after reduction, the major product of the cycloaddition was shown to be alcohol 114, which had the desired stereochemistry at the C8 center, thereby demonstrating a strong preference of diene 112 to undergo reaction with 103, see for example, FIG. 21, from the α-face (bottom side attack). Moreover, these data indicated that synthesis of acanthoic acid would require an inversion in the orientation of the incoming dienophile.

As discussed in Example 2-8, below, absent inversion of the incoming dienophile, the wholly novel compounds of Formula (IIB) were synthesized. The choice of an appropriate substituted dienophile allows essentially limitless selection of the $R_{11}$ and $R_{12}$ groups of the compounds of Formula (IIB).

The inversion of the dienophile required for the synthesis of the compound of Formula (I), its naturally occurring analogs, and the compounds of Formula (II) and (IIA), was accomplished by altering the atomic orbital coefficients at the termini of the diene, supporting the use of a heteroatom-containing diene, such as 104, during the cycloaddition. See generally Overman, L. E.; Petty, C. B.; Ban, T.; Huang, G. T. *J. Am. Chem. Soc.* 1983, 105, 6335-6338; Trost, B. M.; Ippen, J.; Vladuchick, W. C. *J. Am. Chem. Soc.* 1977, 99, 8116-8118; Cohen, T.; Kozarych, Z. *J. Org. Chem.* 1982, 47, 4008-4010; Hopkins, P. B.; Fuchs, P. L. *J. Org. Chem.* 1978, 43, 1208-1217; Petrzilka, M.; Grayson, J. I. *Synthesis,* 1981, 753-786). The construction of diene 104 and its utilization for the synthesis of 101 is shown in FIG. 23, Scheme 6.

Compound 104 was produced by a radical addition of thiophenol onto alkyne 111 (Greengrass, C. W.; Hughman, J. A.; Parsons, P. J. *J. Chem. Soc. Chem. Commun.* 1985, 889-890), followed by $POCl_3$-mediated dehydration of the resulting allylic alcohol (Trost, B. M.; Jungheim, L. N. *J. Am. Chem. Soc.* 1980, 102, 7910-7925; Mehta, G.; Murthy, A. N.; Reddy, D. S.; Reddy, A. V. *J. Am. Chem. Soc.* 1986, 108, 3443-3452) (2 steps, 70% yield). Interestingly, this dehydration was also attempted with $BF_3.Et_2O$, but proved ineffective in this case. With a substantial amount of 104 at hand, we investigated the Diels-Alder reaction, using 103 as the dienophile. Several thermal—(−78 to 80° C.) and Lewis Acid— ($BF_3.Et_2O$, $TiCl_4$, $AlCl_3$ and $SnCl_4$) catalyzed Diels-Alder conditions were tested. Best results were obtained with $SnCl_4$ in methylene chloride at −20° C. and afforded aldehyde 118 in 84% yield as a 4.2:1 mixture of diastereomers. To simplify the product characterization and allow adequate separation, this mixture was reduced with $NaBH_4$ and reductively desulfurized using Raney Ni. Alcohols 119 and 120 were thus obtained in 91% overall yield. The structure of these compounds was assigned by comparison to the products isolated from the reaction between 103 and 112. Treatment of the major diastereomer 120 with Dess-Martin periodinane, followed by Wittig methylenation installed the alkene functionality at the C13 center and produced 121 in 86% overall yield. The C-19 carboxylic acid was then deprotected. Exposure of 121 to LiBr in refluxing DMF gave rise to acanthoic acid 101 in 93% yield via an $S_N^2$-type displacement of the acyloxy functionality. See Bennet, C. R.; Cambie, R. C. *Tetrahedron* 1967, 23, 927-941. Synthetic 101 had identical spectroscopic and analytical data with those reported for the natural product.

This Example provides a concise, stereoselective synthesis of Compound 101. The synthetic strategy is highlighted by the implementation of a Diels-Alder reaction between diene 104 and methacrolein (103), which set the stereochemistry at the C13 and C8 carbon centers. The described synthesis of 101 requires fourteen steps (starting with enone 107) and proceeds in approximately 9% overall yield. The overall efficiency and versatility of our strategy sets the foundation for the preparation of designed analogs with improved pharmacological profiles.

Examples 2-8

Stereoselective Synthesis of Compounds of Formula (IIB)

The procedure outline in Example 1, and depicted in FIG. 23, Scheme 6, may be modified or truncated to yield the compounds of Formula (II) or Formula (IIB).

Example 2

The compound herein designated TTL4 was synthesized by following the procedures of Example 1, as depicted in FIG. 21, to yield compound 114, herein designated TTL4.

Example 3

The compound herein designated TTL2 was synthesized by following the procedures of Example 1, as depicted in FIG.

21, to yield compound 114. Similar to the reaction depicted in FIG. 23, step (h), the compound 114 was then reacted with 3.0 equivalents LiBr, in DMF, at 160° C., for approximately three hours, to a yield of approximately 93% of the compound herein designated TTL2.

Example 4

Figure 14:
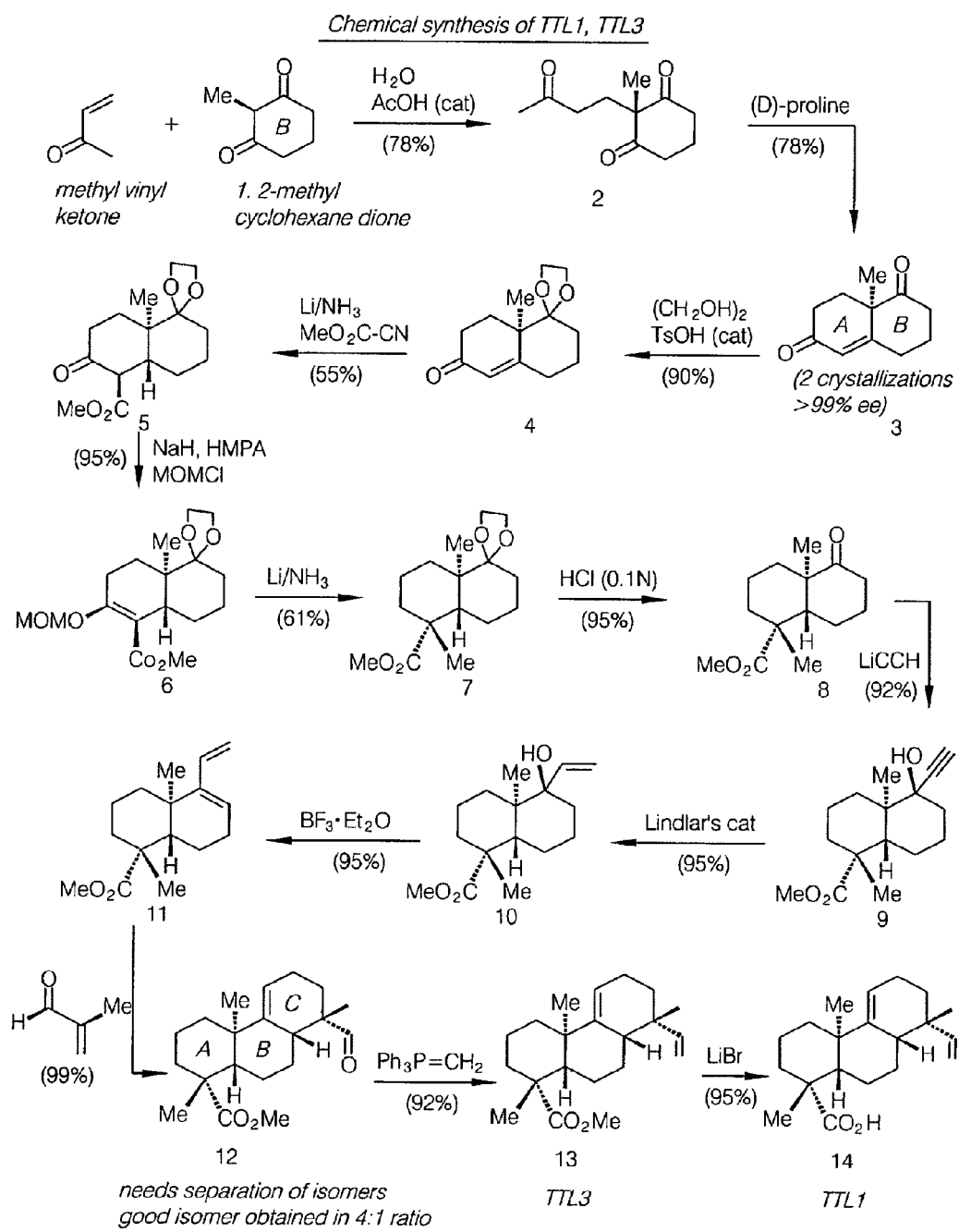
FIG. 14 depicts a complete chemical synthesis of certain compounds, identified herein as TTL1 and TTL3 in FIG. 17.
Figure 15:
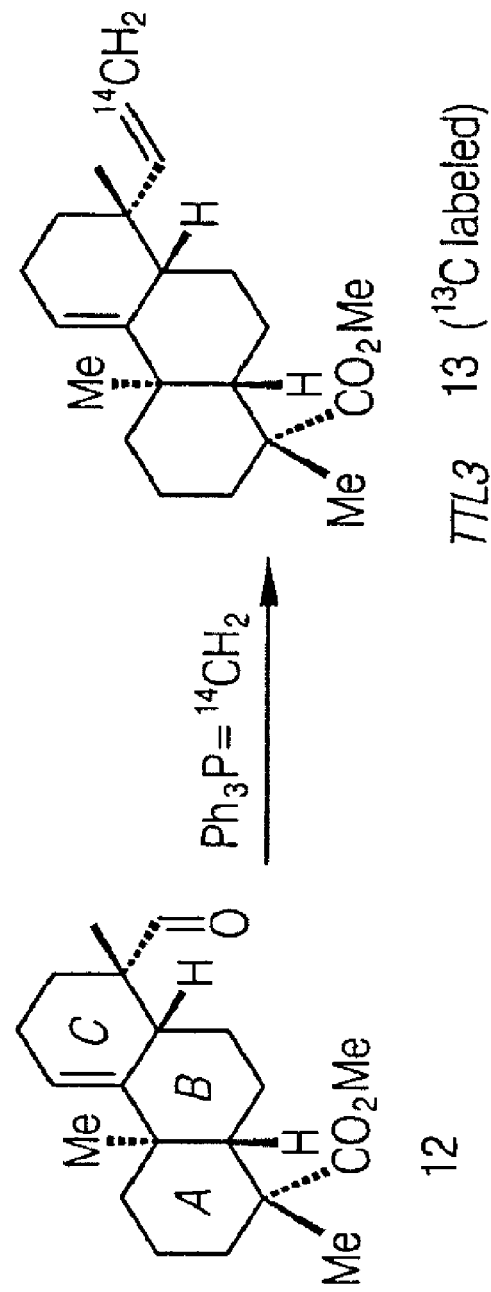
FIG. 15 depicts a chemical synthesis of a preferred $^{14}$C-labeled compound, identified as TTL3 in FIG. 17.
Figure 16:
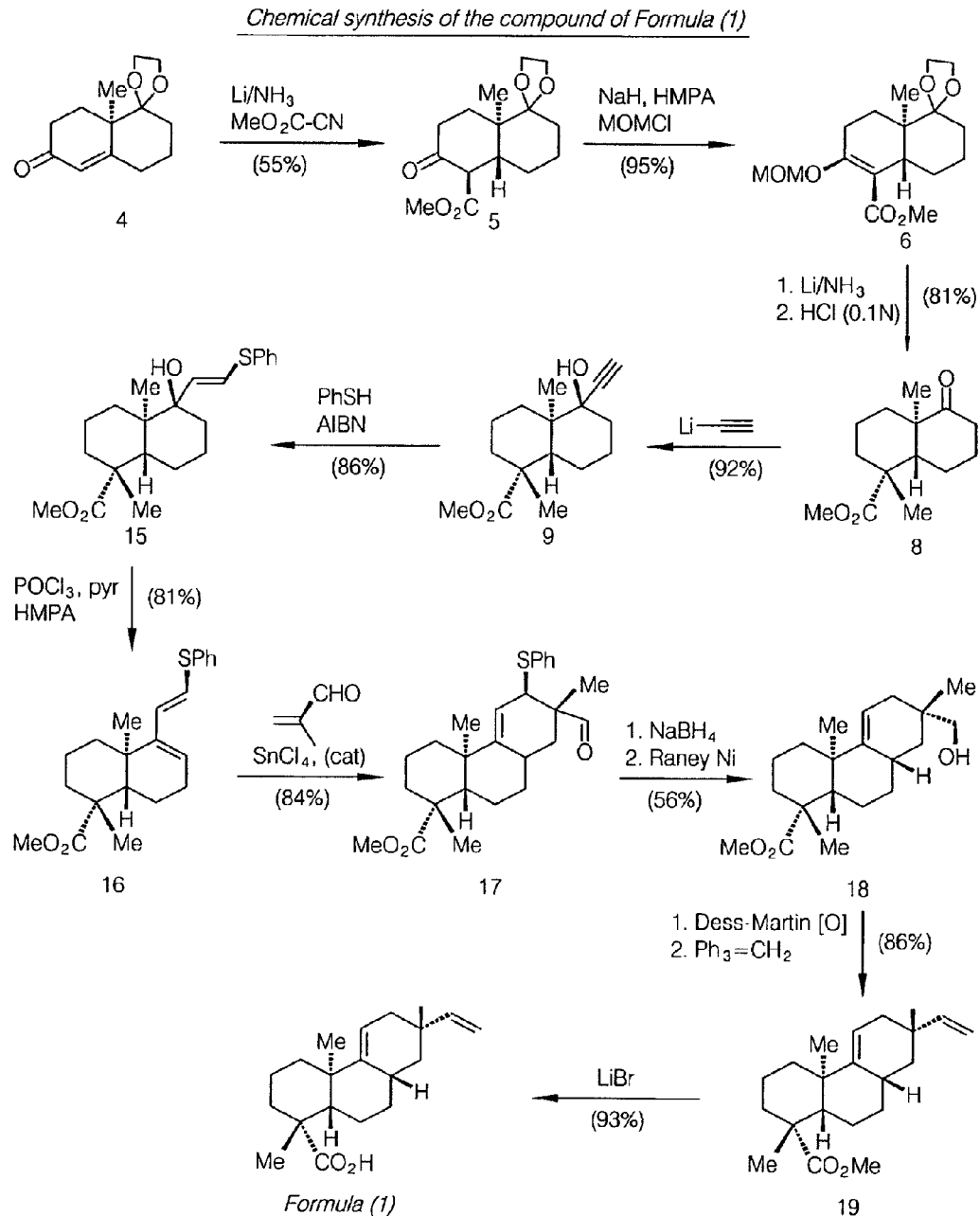
FIG. 16 depicts the complete chemical synthesis of the compound of Formula (I).

The compound herein designated TTL3 was synthesized by following the procedures as depicted in FIG. 14, to yield compound 13. This compound is herein designated TTL3.

Example 5

The compound herein designated TTL1 was synthesized by following the procedures as depicted in FIG. 14, to yield compound 13. This compound is herein designated TTL1.

Example 6

A compound of Formulae (IIB) wherein $R_{15}$ is a hydrogen and $R_9$ and $R_{15}$ are separately selected from the group consisting of $C_1$-$C_6$ alkyl, and $C_1$-$C_6$ substituted alkyl is synthesized by following the procedures therefor of Example 1, except that the dienophile is selected from one of the compound of Formulae (III) wherein $R_{15}$ is a hydrogen and $R_9$ and $R_{15}$ are separately selected from the group consisting of $C_1$-$C_6$ alkyl, and $C_1$-$C_6$ substituted alkyl, as in this Example.

Example 7

Specifically, a compound of Formulae (IIB) wherein $R_{14}$ is a hydrogen and $R_9$ and $R_{15}$ are separately selected from the group consisting of $C_1$-$C_6$ alkyl, and $C_1$-$C_6$ substituted alkyl is synthesized by following the procedures therefor of Example 1, except that the dienophile is selected from one of the compound of Formulae (III) wherein $R_{14}$ is a hydrogen and $R_9$ and $R_{15}$ are separately selected from the group consisting of $C_1$-$C_6$ alkyl, and $C_1$-$C_6$ substituted alkyl, as in this Example.

Example 8

A compound of Formulae (IIB) wherein $R_{14}$ is a hydrogen, and $R_9$ and $R_{15}$ are separately selected from $C_2$-$C_6$ alkenyl, $C_2$-$C_6$ substituted alkenyl, $C_1$-$C_6$ alcohol, and $C_5$-$C_6$ aryl, is synthesized by following the procedures therefor of Example 1, except that the dienophile is selected from one of the compound of Formulae (III) wherein $R_{14}$ is a hydrogen and $R_9$ and $R_{15}$ are separately selected from $C_2$-$C_6$ alkenyl, $C_2$-$C_6$ substituted alkenyl, $C_1$-$C_6$ alcohol, and $C_5$-$C_6$ aryl, as in this Example.

Examples 9-17

Materials and Methods

Murine macrophage cells RAW 264.7 (1×10$^6$/ml) were pretreated for 30-60 minutes with varying doses of the synthetic compound of Formula (I) and a panel of analogs (diluted in 0.5% DMSO) prior to stimulation with various agents such as lipopolysaccharide (LPS) or a gram positive agent like heat-killed *Staph aureus* (SAC). Supernatants collected over a 72-hour period will be assayed for the levels of TNF-α, IL-6, IL-10, IL-12 and other cytokines either by elisa or bioassay. Additional studies to evaluate the effects of the synthetic compound of Formulae (I), (II), (IIA) and (IIB) on cytokine signaling pathways such as, for example, Caspase-activity (Nr-1, Nr.3), transcription factors such as NF-κB, MAP-kinase activity (p38, ERK and JNK) will also be performed.

Results

Preclinical studies demonstrated that murine RAW 264.7 cells treated with increasing doses of the synthetic compounds of Formulae (I) and (IIB), specifically those designated TTL1 and TTL3 herein, at concentrations as high as 10 ug/ml showed similar viability compared to untreated controls indicating that the inhibitory effects of the synthetic compounds of Formulae (I) and (IIB) on TNF-α synthesis were not mediated by a direct cytotoxic effect.

Subsequent studies with the compound of Formula (I) as synthesized according to Example 1, TTL1 (as synthesized according to Example 2) and TTL3 (as synthesized according to Example 4) demonstrated that TTL1 exhibited approximately 10 fold greater activity compared to the compound of Formula (I) as synthesized according to Example 1 in inhibiting TNF-α and IL-1 synthesis. TTL3, as synthesized according to Example 4, contains an additional chemical modification exhibited approximately 100 times greater activity than TTL1, as synthesized according to Example 2. It is noted that similar to the compound of Formula (I) as synthesized according to Example 1, neither analog TTL1 nor TTL3 significantly inhibited IL-6 synthesis. TTL1 exhibited a ten (10)-fold greater activity compared to the compound of Formula (I) as synthesized according to Example 1 in inhibiting TNF-α and IL-1 synthesis.

TTL3 which contains an additional chemical modification exhibited approximately 100 times greater activity than TTL1. It is again important to note that similar to the compound of Formula (I) as synthesized according to Example 1, neither analog significantly inhibited IL-6 synthesis.

Example 18

Synthesis of compounds have alternative stereo-structure at ring position covalently bound to $R_6$. Various diastereomers of the compounds designated TTL1-TTL5 herein designated were prepared and isolated by (a) using L-proline in place of D-proline in the Robinson cyclization of triketone 2 to enone 3 and/or (b) purifying the stereoisomers at position C14 that were produced via the Diels-Alder reaction between diene 104 and methacrolein (103). Selection of the stereo-structure at these two chiral centers allows for the selection and isolation of four distinct diasteriomers corresponding to each TNF-α modulator herein described.

More specifically, the enantiomers at the ring position covalently linked to the R6 moiety, were synthesized by modifying the procedures depicted in FIG. 14 as follows: (L)-proline replaced (D)-proline in the Robinson cyclization of triketone 2 to enone 3. The cyclization utilizing L-proline thus afforded the (+) enantiomer of enone 3. FIG. 14 was otherwise followed using the same reactions and conditions as shown. The resulting product was the (+) enantiomer of TTL3.

Similarly, as noted above, the Diels-Alder reaction between diene 104 and methacrolein (103) sets the stereochemistry at the C13 and C8 carbon centers, or the C14 and C8 carbon centers depending on the orientation of the dienophile. Accordingly, the methods disclosed herein permit the synthesis and purification, and hence the use, of at least the diasteromers of the following compounds:

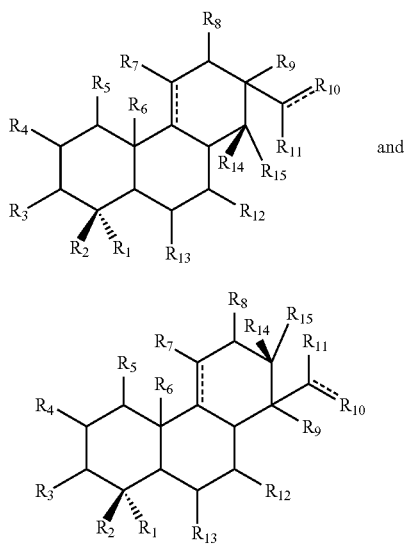

wherein $R_1$-$R_{15}$ are as defined previously, and the chirality at the ring position directly covalently bound to $R_6$ and at the ring position designated $C_{14}$ (directly covalently bound to $R_{14}$ and $R_{15}$ in the former structure and to $R_9$ in the latter) may be separately selected from either (−) or (+), or may represent a racemic mixture of enantiomers. These structures are to be understood as within the meaning of the structures of Formulae (II) and (IIB), as those term are used herein.

Exemplary of the synthetic routes and routes of isolation, as well as certain of the disclosed diastereomers, are depicted in FIGS. 24, 25, 26, 27, 28 and 29.

Examples 19-21

Murine Macrophage and Human Macrophage cell-based assays were completed to test the activity of stereo-isomers, produced and isolated as described in Example 19, of the compound TTL3.

Example 19

LPS Stimulation of Human Macrophage Cell Line THP-1. Human monocytic THP-1 cells were washed in complete RPMI-1640 medium (CRPMI; contains 10% heat inactivated fetal calf serum, with 2 mM L-glutamine, 10 mM Hepes, 1 mM sodium pyruvate, 4.5 g/L glucose, 1.5 gL bicarbonate and 0.05 mM 2-mercaptoethanol) at 1000 rpm for 5 minutes and counted. To induce maturation, THP-1 cells were plated at a density of 1×10⁶ cells/ml in either 24 or 96 well plates (Costar) and pretreated with 5 nM phorbol myristate acetate (PMA) for three days. After three days, the CRPMI was discarded and new medium added. Lipopolysaccharide (LPS, E. coli serotype 0111:B4 or 055:B5), was diluted to a 1 mg/ml stock in phosphate-buffered saline and stored at −80° C. Prior to use, the LPS was thawed and vortexed for 30 minutes. To evaluate the effect of different isoforms of TTL3 (including enantiomers, analogs, diastereomers) on LPS induced TNF-α production, cells were treated with the compounds for 1 hour, followed by a 5 hour incubation with 2 ug of LPS. A p38 kinase inhibitor SB203580 (Sigma) was used as a positive control.

Example 20

LPS Stimulation of Murine Macrophage Cell Line RAW-264.7. RAW 264.7 cells were plated at 1×10⁵ cells/well of a 24 well plate and allowed to adhere and spread overnight at 37° C. The next day, the media was replaced with fresh media (1 ml/well), and the cells were allowed to incubate for 15 to 20 minutes prior to pretreatment with inhibitors. Inhibitors tested include TTL3 enantiomer peaks A and B and a control inhibitor of p38 MAP kinase, SB203580. A 200× stock of each inhibitor was prepared in 100% DMSO in borosilicate glass vials, and 5u1 of this solution was added per well and mixed immediately. DMSO alone (0.5% DMSO in media) served as the vehicle control. The cells were pretreated with the inhibitors for 1 hour at 37° C. at concentrations ranging from 10 pg/ml to 10 ug/ml final concentration. A 100× stock of the LPS was prepared in media and added to the cells at a final concentration of 1 ug/ml. The cells were stimulated for 12 to 24 hours after which the supernatants were harvested and assayed for TNF-α by ELISA (Biosource).

Example 21

Example of human TNF-α ELISA Methodology. Supernatants were collected and stored at −80° C. until testing in a specific TNF-α ELISA. ELISA plates were coated with 100 uL/well of TNF-α capture antibody at 5 ug/ml for 20 hours at 4° C. Plates were washed 2 times with wash buffer and blocked by adding 300 uL/well of blocking solution for 2 hours at room temperature. Plates were washed 4 times and reconstituted with standards and samples added at 100 uL/well. At the same time 50 uL/well of biotinylated antibody (4 ug/mL) were added and incubated for 2 hours at room temperature with continual shaking (700 rpm). Plates were washed 4 times and strepavidin-HRP working solution was added for 30 minutes at room temperature. 100 uL/well of TMB was added for 30 minutes and the reaction was stopped by adding 50 uL/well of 1.8 $NH_2SO_4$.

Examples 19-21 also demonstrate the surprising ability of both the A and B enantiomers of TTL3 to inhibit TNF-α synthesis. In the above assays of Examples 19-21, no significant differences were observed with respect to the ability of these stereo-isomer to inhibit TNF-α synthesis.

Example 22

Strategy for Synthesis of TTL3 Analogs

Figure 30:
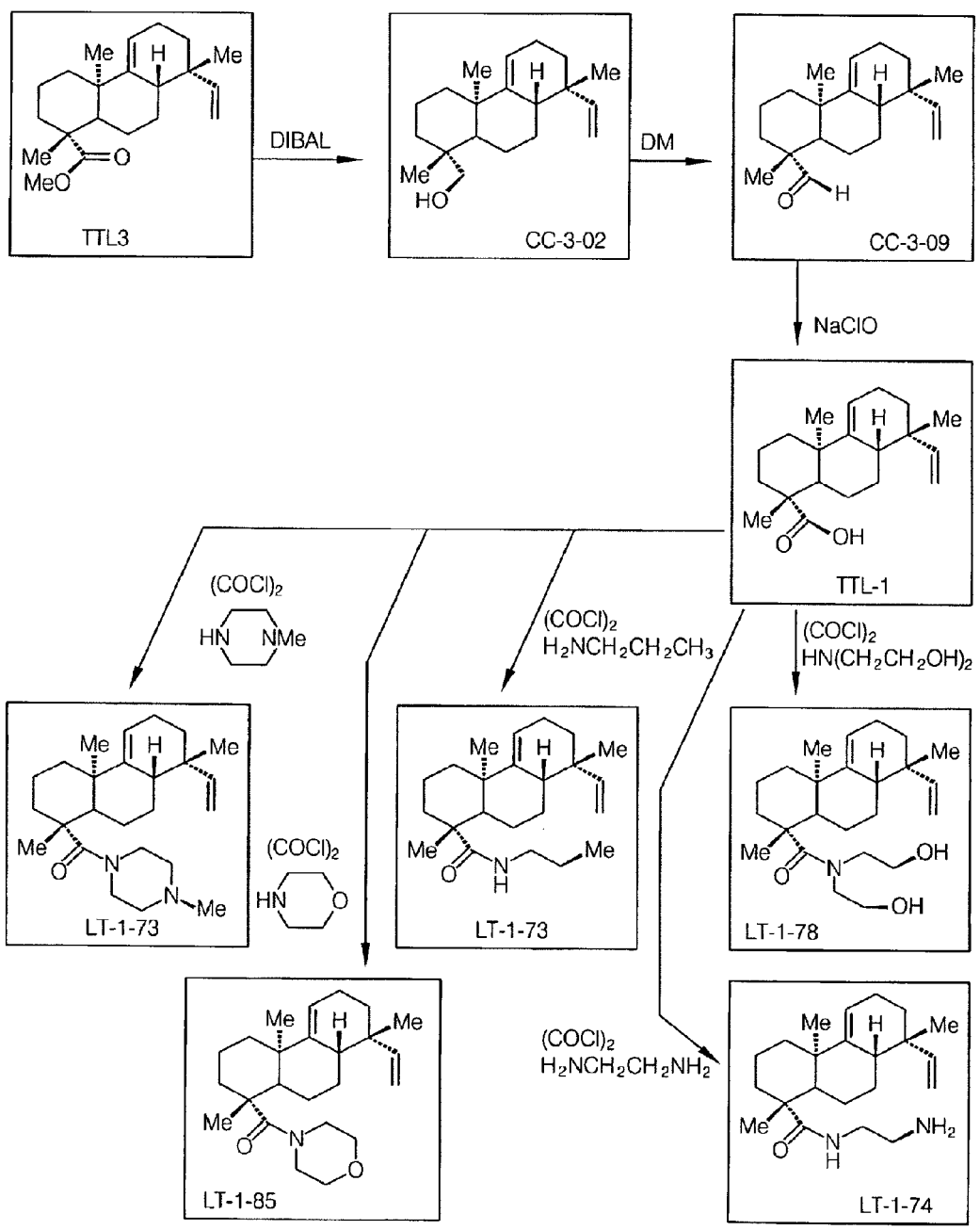
FIG. 30 depicts a strategy (Strategy 1) of the synthesis of TTL3 analogs, CC-3-02, CC-3-09, TTL-1, LT-1-73, LT-1-78, LT-1-85, and LT-1-74.

A. Strategy 1
The compounds herein designated as CC-3-02, CC-3-09, TTL-1, LT-1-73, LT-1-73, LT-1-78, LT-1-85, and LT-1-74 were synthesized by following the strategy as depicted in FIG. 30.

Figure 31:
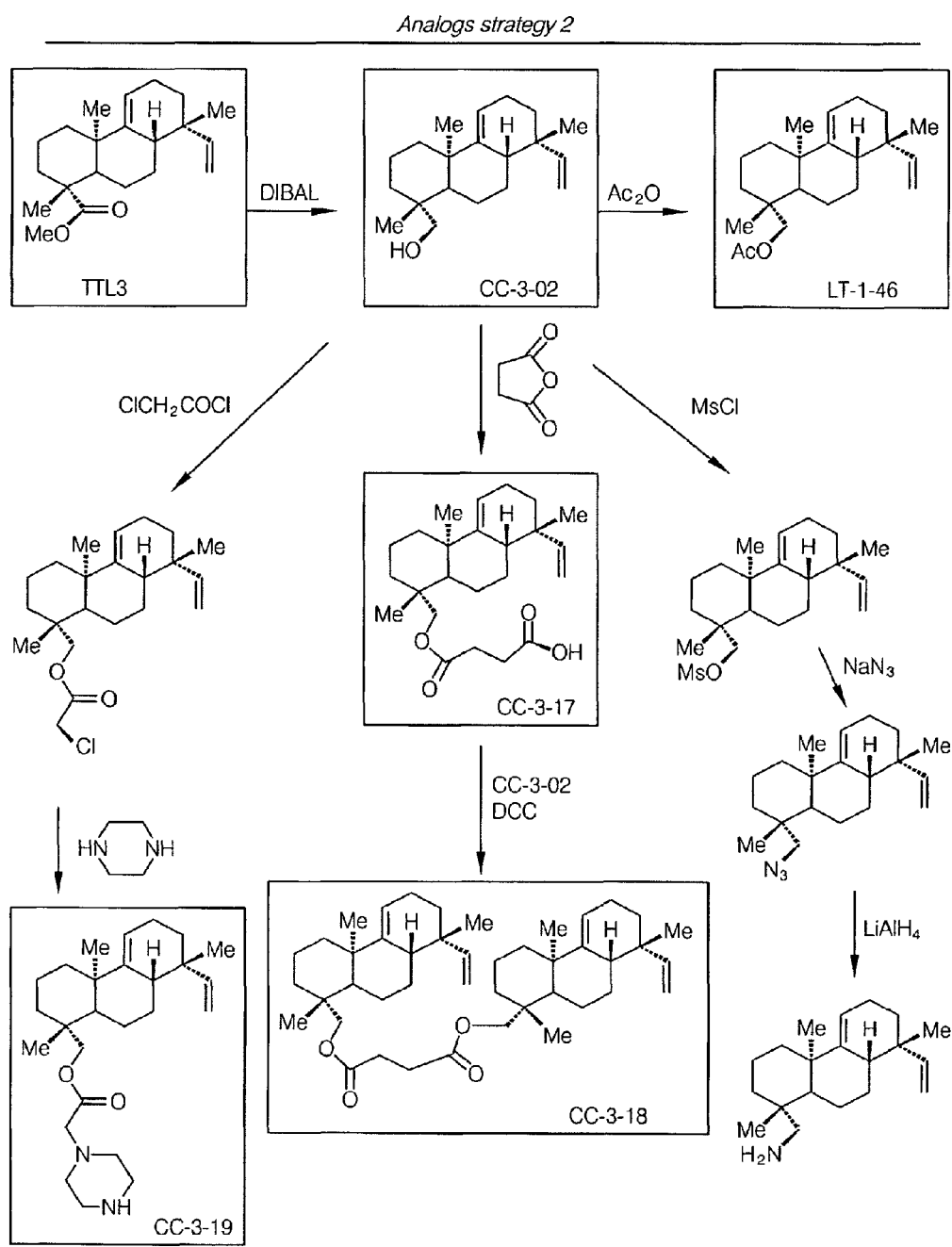
FIG. 31 depicts a strategy (Strategy 2) of the synthesis of TTL3 analogs, CC-3-02, LT-1-46, CC-3-19, CC-3-17, and CC-3-18.

B. Strategy 2
The compounds herein designated as CC-3-02, LT-1-46, CC-3-19, CC-3-17, and CC-3-18 were synthesized by following the strategy as depicted in FIG. 31.

Figure 32:
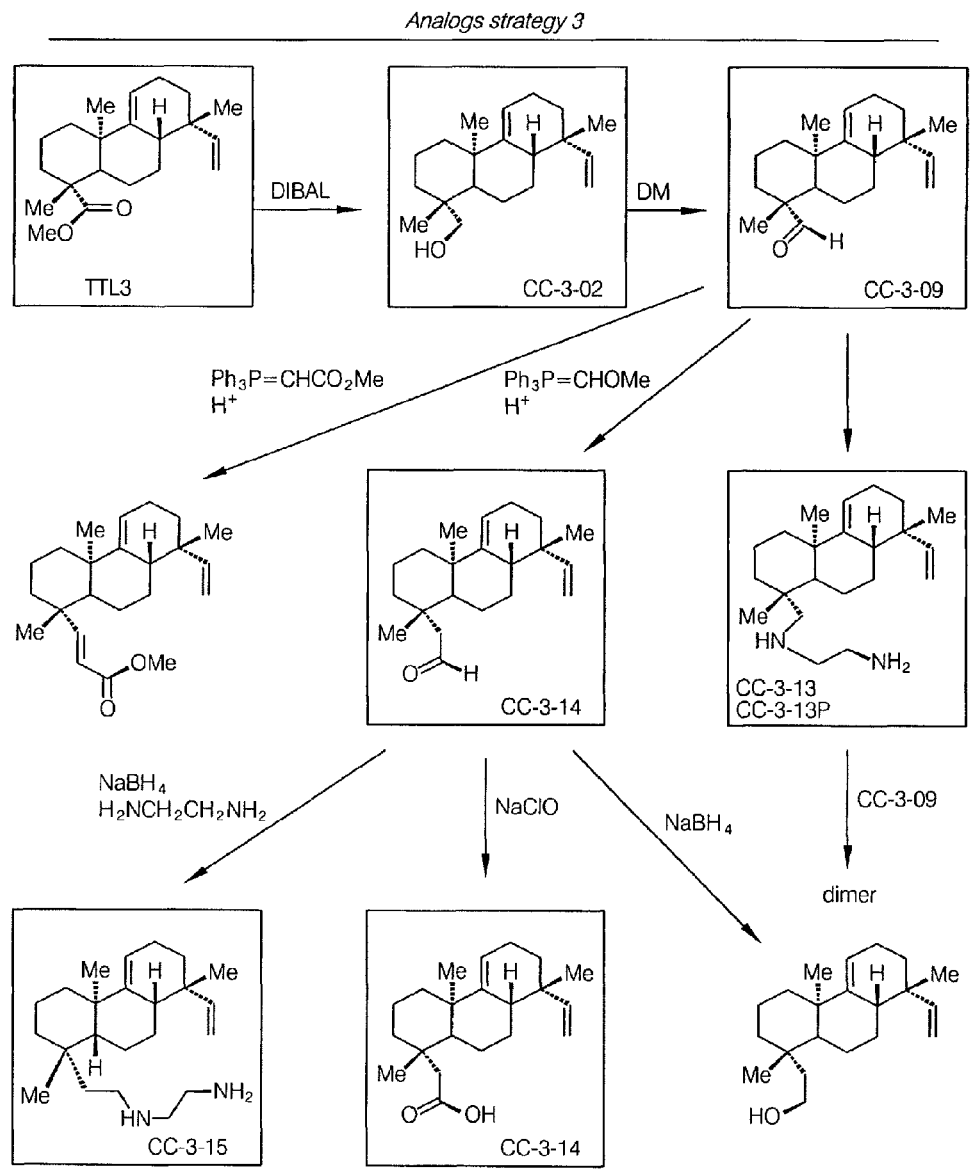
FIG. 32 depicts a strategy (Strategy 3) of the synthesis of TTL3 analogs, CC-3-02, CC-3-09, CC-3-14. CC-3-13, CC-3-13P, CC-3-15, and CC-3-14x.
Figure 33:
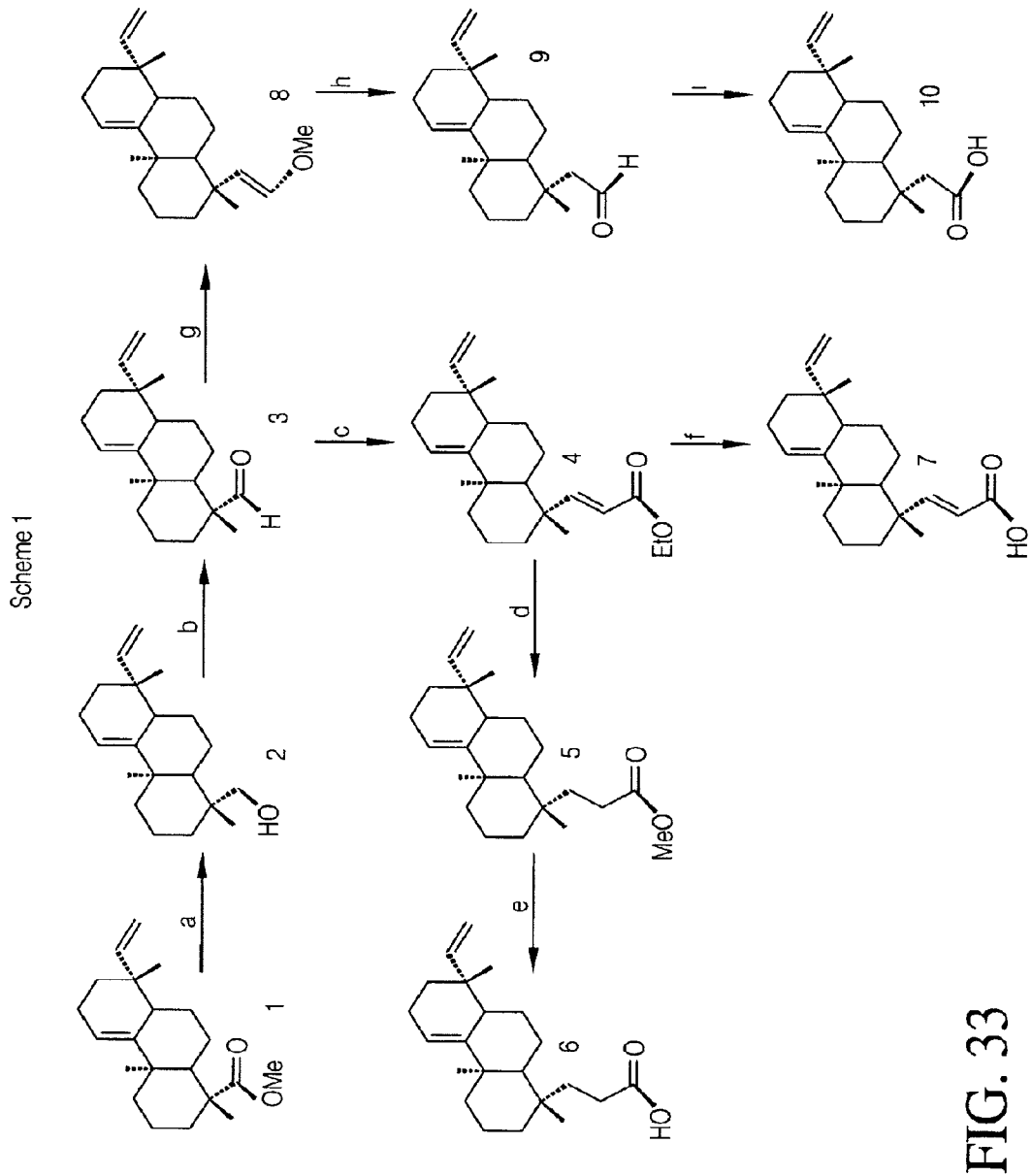
FIG. 33 depicts a schematic synthetic scheme (Scheme 1) of the synthesis of TTL3 analogs and certain compounds.
Figure 34:
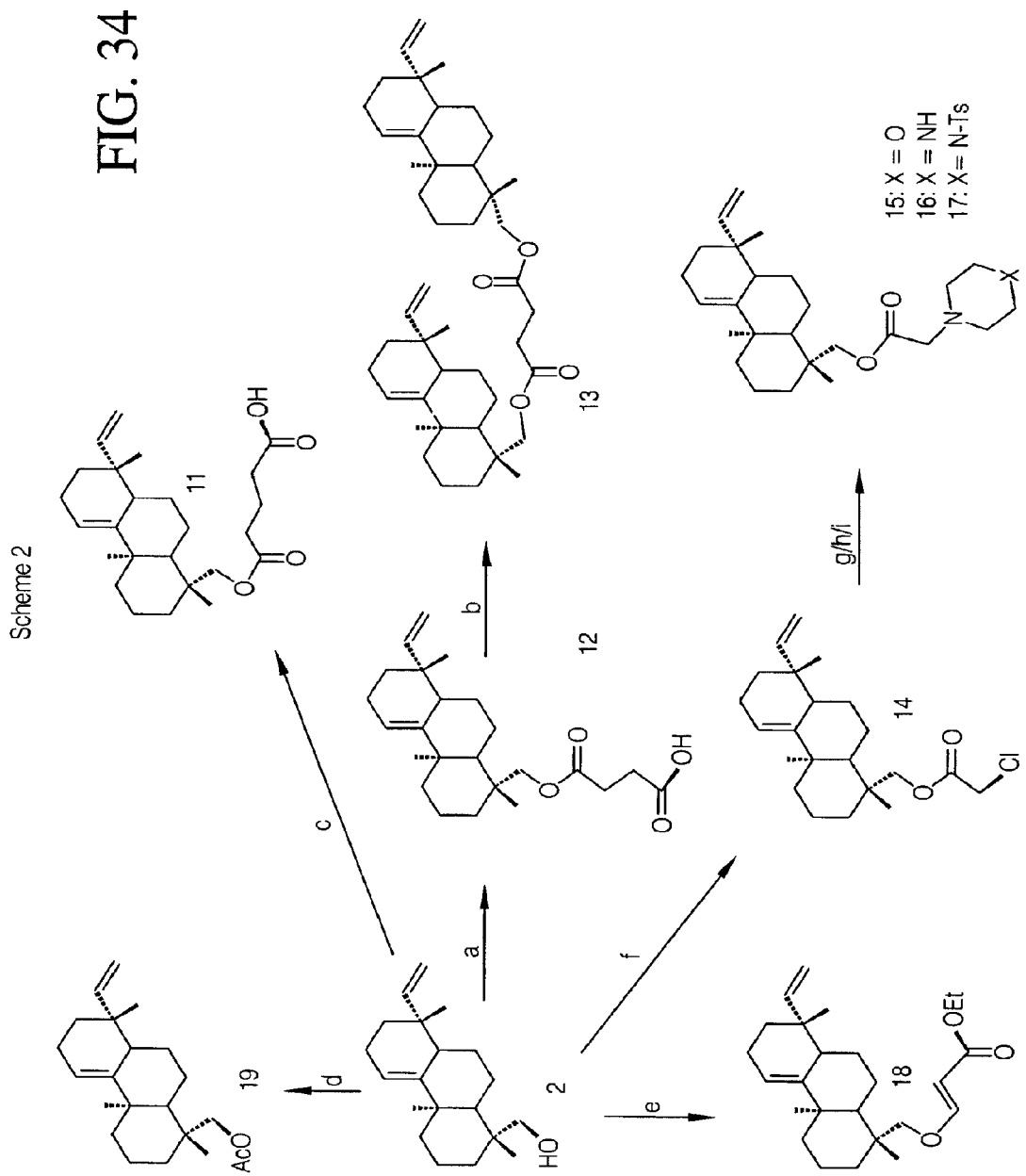
FIG. 34 depicts a schematic synthetic scheme (Scheme 2) of the synthesis of TTL3 analogs and certain compounds.
Figure 35:
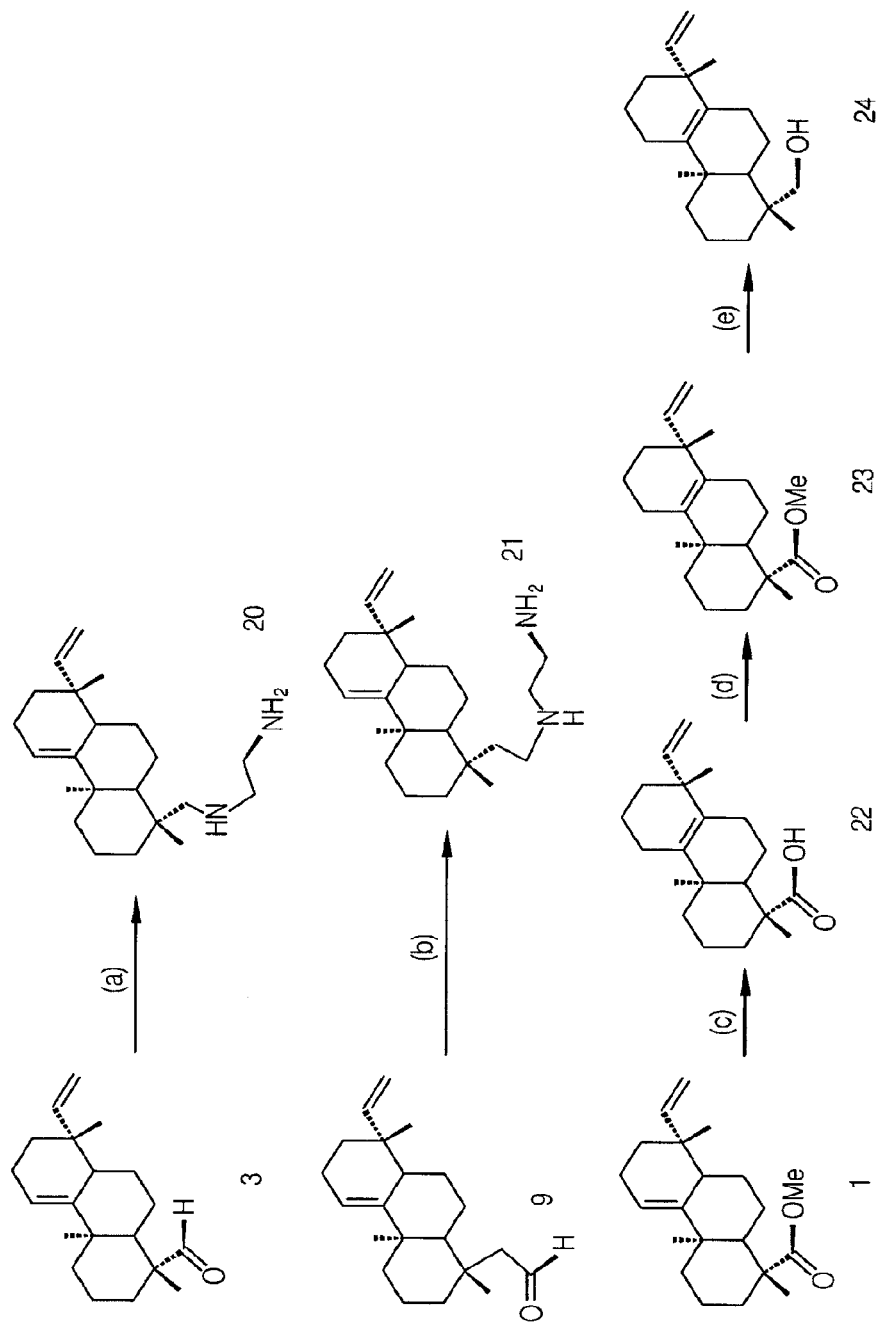
FIG. 35 depicts a schematic synthetic scheme (Scheme 3) of the synthesis of TTL3 analogs and certain compounds.
Figure 36:
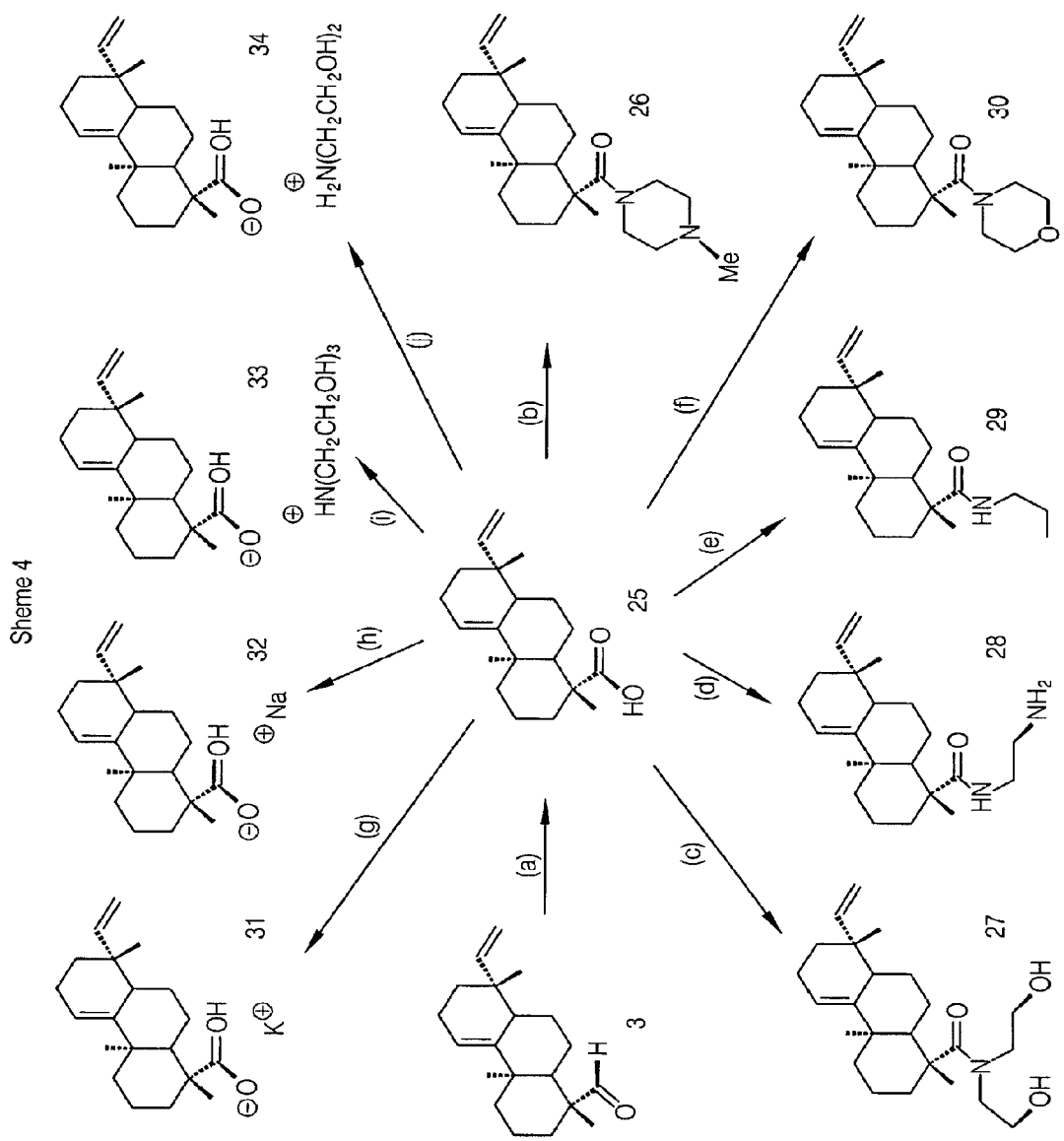
FIG. 36 depicts a schematic synthetic scheme (Scheme 4) of the synthesis of TTL3 analogs and certain compounds.
Figure 37:
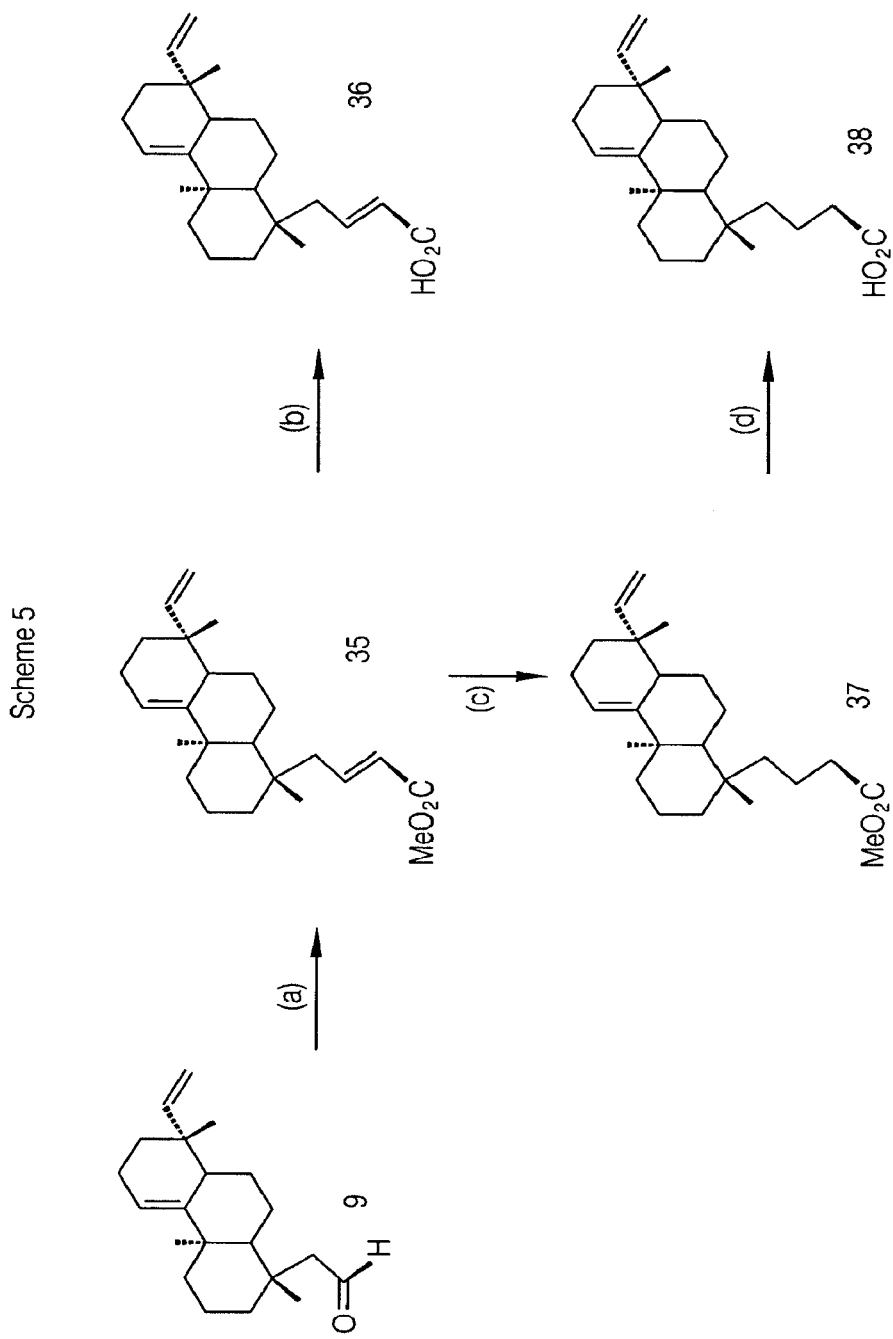
FIG. 37 depicts a schematic synthetic scheme (Scheme 5) of the synthesis of TTL3 analogs and certain compounds.

C. Strategy 3
The compounds herein designated as CC-3-02, CC-3-09, CC-3-14, CC-3-13, CC-3-13P, CC-3-15, and CC-3-14× were synthesized by following the strategy as depicted in FIG. 32.

Example 23

Scheme for Synthesis of TTL3 Analogs

The synthesis of TTL3 analogs are demonstrated in FIGS. 33-37 and further detailed with the following descriptions:
Compound 1 (TTL3): colorless oil; $R_f$=0.75 (silica, 25% ether in hexanes); ¹H NMR (400 MHz, CDCl₃) δ 5.96 (dd, 1H, J=16.8, 11.6 Hz), 5.50 (m, 1H), 4.98 (m, 2H), 3.62 (s, 3H), 2.20-2.11 (m, 1H), 2.10-1.91 (m, 4H), 1.90-1.70 (m, 4H), 1.69-1.51 (m, 3H), 1.50-1.38 (m, 3H), 1.36-1.24 (m, 1H), 1.17 (s, 3H), 1.04 (s, 3H), 0.90 (s, 3H); $^{13}$C NMR (100 MHz, CDCl$_3$) δ 177.9, 149.1, 143.8, 117.9, 111.7, 51.2, 47.7, 44.4, 41.4, 41.2, 38.9, 38.3, 37.7, 34.8, 30.4, 28.4, 24.8, 23.1, 22.3, 22.2, 20.6, 19.8.

Compound 2: To a well stirred solution of ester 1 (480 mg, 1.50 mmol) in CH$_2$Cl$_2$ (10 ml) was treated with DIBAL (6.0 mmol, 6.0 ml, 1M in CH$_2$Cl$_2$) at −78° C. After stirring for 30 min, the whole reaction mixture was allowed to warm up to rt for another 2 h. Methanol (5 ml) was added to quench the reaction mixture and the whole reaction mixture was diluted with ether (30 ml) and Rochelle salt (20 ml, 1N water solution). After stirring vigorously another 2 h at rt, the organic layer was extracted with ether (3×40 ml) and concentrated. The brown residue was purified through flash chromatography over silica gel using 20% ether in hexane as eluant to afford the desired product 2 (372 mg, 86%). White solid, $[\alpha]^D$=+70 (c=1, benzene). $^1$H NMR (CDCl$_3$, 400 MHz) δ 5.95 (dd, J=11.2 Hz, J=12 Hz, 1H), 5.46 (m, 1H), 4.98 (t, J=8 HZ, 2H), 3.82 (d, J=12 Hz, 1H), 3.52 (d, J=12 Hz, 1H), 2.07-1.57 (m, 6H), 1.51-1.42 (m, 5H), 1.27-1.23 (m, 6H), 1.05 (s, 3H), 1.02 (s, 3H), 0.95 (s, 3H); $^{13}$C NMR (CDCl$_3$, 100 MHz) δ 150.39, 142.47, 117.05, 112.34, 64.85, 45.74, 42.11, 41.10, 38.46, 37.46, 35.36, 29.78, 26.32, 26.02, 24.95, 23.36, 19.14, 18.49; HRMS calcd. for C$_{20}$H$_{32}$O: 288.24; Found 288 (GC-MS).

Compound 3: To a well stirred solution of alcohol 2 (360 mg, 1.23 mmol) in CH$_2$Cl$_2$, was added portionwise Dess-Martin reagent (483 mg, 1.61 mmol) and the mixture was allowed to stir for 3 h at rt until tlc indicated complete consumption of starting material. The whole reaction mixture was extracted with CH$_2$Cl$_2$ (3×50 ml), washed with NaHCO$_3$ and concentrated. The brown residue was purified through silica gel chromatography over silica gel using 15% ether in hexane (v/v) as eluent to afford the desired product 3 (266 mg, 74%). 3: White solid, $[\alpha]^D$=−142.2 (c=1, benzene). $^1$H-NMR (CDCl$_3$, 400 MHz) δ 9.94 (s, 1H), 5.94 (dd, J=11.6 Hz, J=12 Hz, 1H), 5.53 (m, 1H), 4.96 (t, J=8 Hz, 2H), 2.10-2.03 (m, 4H), 1.95-1.86 (m, 3H), 1.71-1.42 (m, 7H), 1.28-1.23 (m, 2H), 1.07 (s, 3H), 1.02 (s, 3H), 0.96 (s, 3H); $^{13}$C-NMR (CDCl$_3$, 100 MHz) δ 206.39, 148.13, 142.42, 118.10, 112.39, 48.22, 46.55, 41.80, 40.67, 37.70, 36.70, 35.05, 24.96, 24.47, 23.92, 23.27, 20.54, 19.64, 18.47 HRMS calcd. for C$_{20}$H$_{30}$O: 309.21 (M+Na)$^+$ found 309 (ESI Mass Spec).

Ethyl Ester 4: To a well stirred solution of NaH (67 mg, 0.43 mmol) in THF (20 ml) at 0° C. was added triethyl phosphonoacetate (500 mg, 0.60 mmol). The reaction mixture was allowed to attend rt over a period of 4 h and treated with a solution (THF, 10 ml) of aldehyde 3 (76 mg, 0.27 mmol) and then the reaction mixture was heated under reflux for 16 h. After quenching with water, the organic layer was extracted with ether (2×60 ml). The ether extract was concentrated and purified over silica gel (5% ether/hexane, v/v) to afford the desired ester 4 (68 mg, 70%). 4: Oil (R$_f$=0.4, 10% ether/hexane, v/v), $^1$H-NMR (CDCl$_3$, 400 MHz) δ 7.34 (d, J=16 Hz, 1H), 5.90 (dd, J=11.6 Hz, J=12 Hz, 1H), 5.76 (d, J=16 Hz, 1H), 5.48 (m, 1H), 4.97 (m, 2H), 4.18 (q, J=8 Hz, 2H), 2.09-1.74 (m, 6H), 1.66-1.42 (m, 8H), 1.30-1.17 (m, 5H), 1.06 (s, 3H), 0.98 (s, 3H), 0.95 (s, 3H); $^{13}$C-NMR (CDCl$_3$, 100 MHz) δ 167.10, 154.47, 149.15, 142.41, 118.13, 117.43, 112.33, 60.18, 46.75, 42.38, 41.07, 39.93, 38.66, 37.74, 37.03, 29.67, 25.04, 24.81, 23.35, 20.19, 19.11, 14.45; HRMS calcd. for C$_{24}$H$_{36}$O$_2$ 356.54 Found 356.54.

Methyl Ester 5: To a well stirred solution of ester 4 (60 mg, 0.168 mmol) in methanol (10 ml), magnesium powder (50 mg, 6.25 mmol) was added and the whole reaction mixture was stirred at room temp. for 12 h. HCl (10 ml, 2M) was added to the reaction mixture to dissolve the remaining magnesium. The reaction mixture was concentrated under reduced pressure and extracted with ether (2×50 ml) and the organic layer concentrated. The desired product 5 was purified through column chromatography using 10% ether/hexane (v/v) as eluent. 5: Oil (50 mg, 87% yield); $^1$H-NMR (CDCl$_3$, 400 MHz) δ 5.95 (dd, J=11.2 Hz, J=12 Hz, 1H), 5.45 (m, 1H), 4.98 (m, 2H), 3.66 (s, 3H), 3.26-1.87 (m, 7H), 1.69-1.51 (m, 11H), 1.24-1.19 (m, 2H), 1.09 (s, 3H), 1.04 (s, 3H), 0.93 (s, 3H); HRMS Calcd. for C$_{23}$H$_{36}$O$_2$ 344.56; Found 344.56.

Acid 6: Ester 5 (50 mg, 0.14 mmol) was dissolved in a mixed solution of THF/H$_2$O (v/v, 1:1, 4 ml) and LiOH (30 mg) was added. After stirring for 30 min the reaction mixture was heated under reflux for 12 hours. The reaction mixture was diluted with water, acidified with HCl solution (3 N) and extracted with ether (2×50 ml). The desired product 6 was purified through column chromatography over silica gel using 50% ether/hexane (v/v). 6: White solid (34 mg, 71%); $^1$H-NMR (CDCl$_3$, 400 MHz) δ 5.95 (dd, J=11.2 Hz, J=12 Hz, 1H), 5.46 (m, 1H), 5.00-4.95 (m, 2H), 2.27-2.17 (m, 3H), 2.09-1.88 (m, 10H), 1.69-1.37 (m, 7H), 1.24-1.18 (m, 1H), 1.09 (s, 3H), 1.04 (s, 3H), 0.83 (s, 3H); $^1$C-NMR (CDCl$_3$, 100 MHz) δ 178.62, 152.06, 143.69, 118.13, 113.52, 67.09, 48.16, 43.67, 42.52, 39.42, 38.38, 36.98, 31.02, 30.45, 29.48, 28.43, 27.33, 26.26, 24.64, 21.17, 20.41, 19.86, 16.62; HRMS Calcd. for C$_{22}$H$_{34}$O$_2$ 329.24 (M−H)$^+$, found 329.20.

Unsaturated Acid 7: To a solution of methyl ester 4 (60 mg, 0.17 mmol) in THF/H$_2$O (1:1, v/v, 8 ml), LiOH (40 mg, excess) was added at rt. After stirring for 30 min the reaction mixture was allowed to reflux for 12 h. The reaction mixture was diluted with water and acidified with HCl solution (3 N, 40 ml) and extracted with ether (2×50 ml). The desired product was purified through column chromatography over silica gel using ether/hexane (1:1, v/v). 7: White solid (42 mg, 76%), $^1$H NMR (CDCl$_3$, 400 MHz) δ 7.45 (d, J=16 Hz, 1H), 5.94 (dd, J=11.2 Hz, J=12 Hz, 1H), 5.76 (d, J=16 Hz, 1H), 5.48 (m, 1H), 5.00-4.95 (m, 2H), 2.15-1.74 (m, 5H), 1.64-1.50 (m, 7H), 1.47-1.42 (m, 5H), 1.06 (s, 3H), 0.99 (s, 3H), 0.95 (s, 3H); $^{13}$C NMR (CDCl$_3$, 100 MHz) δ 171.03, 157.41, 149.02, 142.37, 117.55, 117.20, 112.37, 46.82, 42.36, 41.01, 40.18, 38.50, 38.21, 37.75, 37.01, 29.82, 25.04, 24.75, 23.35, 20.18, 19.11; HRMS Calcd for C$_{22}$H$_{32}$O$_2$ 351 (M+Na)$^+$ Found 351 (ESI Mass Spec.).

Vinyl ether 8: Methoxy methyl triphenyl phosphonium chloride was stirred in THF (476.1 mg, 1.39 mmol) and treated with 4.8 equivalent of potassium t-butoxide, followed by addition of aldehyde 3 (80 mg, 0.28 mmol). The reaction was completed within 30 minutes. After the reaction mixture was concentrated, the residue was redissolved in ethyl ether and extracted with NaCl solution. After the chromatography column purification, 87 mg of the product was obtained (99% yield).

Aldehyde 9: To a well stirred solution of compound 8 (50 mg, 0.159 mmol) in acetone (10 ml), was added p-toluene sulphonic acid (50 mg, 0.26 mmol) and the reaction was allowed to stir for 2 h at rt. TLC indicated the complete formation of desired product. Solvent was removed and the reaction mixture was extracted with ether (3×40 ml) and washed with sat. NaHCO$_3$ and sat. NaCl solution. The crude product was purified through column chromatography using 4% ether hexane as eluent. 9: Oil (88%), $[\alpha]^D$=+4.4 (c=1, benzene), $^1$H-NMR (CDCl$_3$, 400 MHz) δ 5.94 (dd, J=11.2 Hz, J=12 Hz, 1H), 5.48 (m, 1H), 5.01-4.96 (m, 2H), 2.55 (d, J=12 Hz, 1H), 2.37 (d, J=12 Hz, 1H), 2.09-1.93 (m, 3H), 1.76-1.71 (m, 2H), 1.63-1.13 (m, 12H), 1.09 (s, 3H), 1.07 (s, 3H), 1.06 (s, 3H); $^{13}$C-NMR (CDCl$_3$, 100 MHz) δ 204.26, 150.23, 142.24, 117.26, 112.46, 47.22, 42.43, 40.81, 39.02, 38.08, 37.03, 29.06, 25.59, 25.00, 23.39, 19.90, 19.07; HRMS calcd for C$_{21}$H$_{32}$O 323.25 Found 323.23.

Acid 10: To a solution of 17 mg of aldehyde 10 (0.056 mmol) in tBuOH/H$_2$O (3:1) was added 23.3 mg of NaH$_2$PO$_4$.H$_2$O (0.17 mmol) and the reaction mixture was stirred to completely dissolve the salt before adding 84.5 μl of 2M 1-methyl-2-butene in THF. The reaction was stirred for 30 minutes, then it was treated with 15.3 mg of NaClO$_2$ (0.17 mmol). When the reaction was done, it was neutralized with NH$_4$Cl. The product was collected via the extraction with CH$_2$Cl$_2$ and purified through chromatography column to produce 17.0 mg of acid 10 (96%). 10: $^1$H-NMR (CDCl$_3$, 300 MHz) δ 6.00-5.90 (m, 1H), 5.48 (d, J=3 Hz, 1H), 5.02-4.95 (m, 2H), 2.58 (d, J=12.6 Hz, 1H), 2.30 (d, J=12.6 Hz, 1H), 1.25 (s, 3H), 1.07 (s, 3H), 1.02 (s, 3H).

Acid 12: To a well stirred solution of alcohol 2 (70 mg, 0.24 mmol) in DCM (8 ml), DMAP (5 mg, cat.) and succinic anhydride (30 mg, 0.28 mmol) were added and the reaction mixture was allowed to stir for 8 h at rt. The reaction mixture was extracted with DCM (2×40 ml) and washed with water (30 ml). The desired product was purified through column chromatography over silica gel using 12-16% ether in hexane to afford acid 12. 12: Solid (73 mg, 78%). IR (neat) 3312 2920, 1732, 1708 cm$^{-1}$; $^1$H-NMR (CDCl$_3$, 400 MHz) δ 5.95 (dd, J=11.2 Hz, 12 Hz, 1H), 5.48 (m, 1H), 5.0-4.96 (m, 2H), 4.34 (d, J=12 Hz, 1H), 4.03 (d, J=12 Hz, 1H), 2.70-2.61 (m, 4H), 2.09-1.91 (m, 4H), 1.80-1.39 (m, 10H), 1.25-1.08 (m, 6H), 1.05 (s, 3H), 0.91 (s, 3H); $^{13}$C-NMR (CDCl$_3$, 100 MHz) δ 177.32, 172.02, 150.09, 142.32, 117.24, 112.41, 67.12, 45.88, 42.19, 40.99, 37.97, 37.21, 36.11, 29.80, 29.01, 26.77, 25.97, 25.00, 23.39, 19.94, 19.10, 18.78; HRMS Calcd for C$_{24}$H$_{36}$O$_4$ 411.25 (M+Na)$^+$ Found 411.25.

Acid 11: This compound was prepared using the procedure described above for acid 12. In this case maleic anhydride was used instead of succinic anhydride. 11: (68 mg, 71%); $^1$H-NMR (CDCl$_3$, 500 MHz) δ 6.01 (dd, J=11.2 Hz, J=12 Hz, 1H), 5.46 (brd, 1H), 5.09-4.95 (m, 2H), 4.36 (d, J=8 Hz, 1H), 4.02 (d, J=8 Hz, 1H), 2.48-2.36 (m, 3H), 2.16-1.92 (m, 5H), 1.86-1.38 (m, 9H), 1.35-1.11 (m, 10H), 0.98-0.81 (m, 5H); $^{13}$C-NMR (CDCl$_3$, 100 MHz) δ 173.96, 169.08, 146.28, 138.46, 113.29, 108.44, 93.15, 88.18, 62.60, 41.65, 37.95, 36.75, 33.71, 32.93, 29.11, 28.66, 25.54, 25.46, 25.43, 22.54, 20.69, 19.06, 15.61, 14.45; HRMS Calcd for C$_{25}$H$_{38}$O$_4$ 425.26 Found 425.26.

Ester 13: To a well stirred solution of alcohol 2 (22 mg, 0.079 mmol) and acid 12 (24 mg, 0.0617 mmol) in DCM (10 ml), was added DCC (17 mg, 0.080 mmol) and DMAP (5 mg, cat.) and the reaction mixture was allowed to stir at rt for 12 h. The mixture was extracted with DCM (20×2 ml) and washed with water (15 ml). The desired product was isolated through silica gel chromatography. 13: Solid (30 mg, 70%); $^1$H-NMR (CDCl$_3$, 400 MHz) δ 5.95 (dd, J=11.2 Hz, J=12 Hz, 2H), 5.48 (m, 2H), 5.00-4.95 (m, 4H), 4.32 (d, J=12 Hz, 2H), 4.03 (d, J=12 Hz, 2H), 2.62 (s, 4H), 2.05-1.70 (m, 6H), 1.76-1.70 (m, 3H), 1.56-1.42 (m, 23H), 1.20 (s, 6H), 0.98 (s, 6H), 0.93 (s, 6H); $^{13}$C-NMR (CDCl$_3$, 100 MHz) δ 172.18, 150.10, 142.32, 117.23, 112.41, 66.95, 45.87, 42.18, 40.99, 37.97, 37.19, 36.13, 29.40, 26.82, 25.98, 25.00, 23.39, 19.95, 19.13, 18.77; HRMS Calcd for C$_{44}$H$_{66}$O$_4$ 681.48 (M+Na)$^+$ Found 681.48.

Chloro Acetyl Derivative 14: To a well stirred solution of alcohol 2 (40 mg, 0.1389 mmol) and DMAP (10 mg, cat.) in DCM (10 ml) at 0° C., was added chloroacetyl chloride (23 mg, 0.20 mmol). The reaction mixture was allowed to stir at rt for another 2 h and then quenched with water and extracted with ether (2×40 ml). The combined ether layer was concentrated and purified through column chromatography. The desired product was eluted with 8% ether/hexane. 14: Solid (39 mg, 82%). $^1$H-NMR (CDCl$_3$, 400 MHz) δ 5.93 (dd, J=11.2 Hz, J=13 Hz, 1H), 5.48 (brd, 1H), 5.01-4.96 (m, 2H), 4.43 (d, J=8 Hz, 1H), 4.13 (d, J=8 Hz, 1H), 4.06 (s, 2H), 2.09-1.96 (m, 3H), 1.92-1.71 (m, 2H), 1.65-1.42 (m, 14H), 1.22 (s, 3H), 1.14 (s, 3H) 0.97 (s, 3H); $^{13}$C-NMR (CDCl$_3$, 100 MHz) δ 167.28, 149.96, 142.26, 117.37, 112.47, 68.58, 45.91, 42.19, 41.06, 40.93, 37.95, 37.70, 37.37, 36.04, 29.80, 26.69, 25.95, 25.01, 23.39, 19.94, 19.09, 18.82.

Morpholine Derivative 15: To a well stirred solution chloro acetyl derivative 14 (24 mg, 0.066 mmol) in DCM, was added morpholine (15 mg, 0.17 mmol). The reaction mixture was heated under reflux for 12 h and the reaction mixture was extracted with DCM (2×30 ml) and washed with water (15 ml). The desired product was purified through column chromatography over silica gel. 15: Oil (20 mg, 71%); $^1$H-NMR (CDCl$_3$, 400 MHz) δ 5.94 (dd, J=11.2 Hz, J=12 Hz, 1H), 5.47 (m, 1H), 5.00-4.95 (m, 2H), 4.36 (d, J=12 Hz, 1H), 4.05 (d, J=12 Hz, 1H), 3.75-3.73 (m, 4H), 3.20 (s, 2H), 2.58-2.56 (m, 4H), 2.08-1.42 (m, 16H), 1.24 (s, 3H), 1.05 (s, 3H), 0.92 (s, 3H); $^{13}$C-NMR (CDCl$_3$, 100 MHz) δ 170.15, 150.02, 142.27, 117.28, 112.43, 81.54, 66.82, 59.62, 53.32, 52.0, 45.87, 42.17, 37.96, 37.67, 37.18, 29.78, 26.89, 25.95, 24.99, 19.93, 19.10., 18.79; HRMS Calcd. for C$_{26}$H$_{41}$NO$_3$ 416.31 (M+H)$^+$ Found 416.31.

Piperazine Derivative 16: Compound 16 was prepared according to the procedure described above, using piperazine instead of morpholine. 16: Oil (77%), $^1$H-NMR (CDCl$_3$, 400 MHz) δ 5.93 (dd, J=11.2 Hz, J=12 Hz, 1H), 5.48 (brd, 1H), 5.00-4.95 (m. 2H), 4.37 (d, J=10 Hz, 1H), 4.05 (d, J=10 Hz, 1H), 3.20 (s, 2H), 2.63 (brd, 2H), 2.60-2.57 (m, 5H), 2.4-2.2 (brd, 3H), 2.08-1.94 (m, 5H), 1.71-1.42 (m, 10H), 1.20 (s, 3H), 1.05 (s, 3H), 0.87 (s, 3H); $^{13}$C-NMR (CDCl$_3$, 100 MHz) δ 170.90, 150.28, 117.21, 112.39, 66.71, 59.78, 53.75, 53.47, 51.58, 51.25, 45.84, 42.15, 40.94, 37.93, 37.66, 37.17, 36.16, 29.78, 26.88, 25.95, 24.96, 23.25, 19.92, 19.10, 18.76; HRMS Calcd. for C$_{26}$H$_{42}$N$_2$O$_2$ 415.33 (M+H)$^+$, Found 415.33.

Compound 17: To a well stirred solution of product 16 (30 mg, 0.072 mmol) in DCM, was added triethyl amine (0.4 ml) and tosyl chloride (19 mg, 0.1 mmol). The reaction mixture was allowed to stir at rt for 15 h and was then quenched with water and extracted with methylene chloride (3×30 ml). The desired product was purified over silica gel using 25-30% ether/hexane as eluent. 17: White solid (40 mg, 69%); $^1$H-NMR (CDCl$_3$, 400 MHz) δ 7.62 (d, J=8 Hz, 2H), 7.31 (d, J=8 Hz, 2H), 5.92 (dd, J=11.2 Hz, 12 Hz, 1H), 5.47 (m, 1H), 5.0-4.95 (m, 2H), 4.36 (d, J=12 Hz, 1H), 4.03 (d, J=12 Hz, 1H), 3.24 (brd, 1H), 3.08 (brd, 4H), 2.72 (brd, 3H), 2.44 (s, 3H), 2.42-1.90 (m, 4H), 1.63-1.40 (m, 10H), 1.24-1.05 (m, 4H), 1.05 (s, 3H), 1.03 (s, 3H), 0.89 (s, 3H); $^{13}$C-NMR (CDCl$_3$, 100 MHz) δ 194.25, 149.93, 142.28, 131.92, 129.56, 127.72, 117.32, 112.45, 55.87, 51.90, 45.50, 42.15, 40.89, 37.93, 37.68, 36.15, 29.80, 26.85, 25.94, 24.98, 23.37, 19.92, 19.08, 18.79. HRMS Calcd for C$_{33}$H$_{48}$N$_2$O$_4$S 591.32 Found 591.32.

Ester 18: A solution of alchohol 2 (20 mg, 0.069 mmol) and 4-methyl morpholine (20 mg, 0.173 mmol) in methylene chloride (10 ml) was cooled to 0° C. and treated with ethyl propiolate (10 mg, 0.10 mmol). The whole reaction mixture was allowed to stir for overnight. Water (25 ml) was added in the reaction mixture and extracted with methylene chloride (2×30 ml). The combined organic extracts were combined and concentrated. Finally the desire product was purified through silica gel chromatography using 20% ether/hexane (v/v) as eluent. Oil (18 mg, 64%), $^1$H-NMR (CDCl$_3$, 400

MHz) δ 7.61 (d, J=12 Hz, 1H), 5.93 (dd, J=11.2 Hz, J=13 Hz, 1H), 5.48 (brd, 1H), 5.16 (d, J=13 Hz, 1H), 5.02-4.96 (m, 2H), 4.13 (q, J=8 Hz, 2H), 3.99 (d, J=8 Hz, 1H), 3.69 (d, J=8 Hz, 1H), 2.09-1.78 (m, 6H), 1.62-1.40 (m, 15H), 1.06 (s, 3H), 1.04 (s, 3H), 0.97 (s, 3H); $^{13}$C-NMR (CDCl$_3$, 100 MHz) δ 167.80, 163.03, 149.96, 142.25, 117.39, 112.46, 95.71, 73.70, 59.72, 45.76, 42.15, 40.90, 37.94, 37.60, 35.87, 26.70, 25.96, 24.98, 23.37, 19.93, 19.09, 18.79, 14.52.

Acetate 19: 8.7 mg of alcohol 2 was dissolved in 0.5 ml CH$_2$Cl$_2$, and treated with 5 equiv of pyridine, and 2.5 equiv of acetic anhydride. The reaction was stirred at room temperature for two hours and was then quenched with NaHCO$_3$/H$_2$O and extracted with ether. After chromatography column, 8.3 mg of pure product 19 was obtained (84%). 19: $^1$H-NMR (CDCl$_3$, 400 MHz) δ 5.95 (q, J=11.6 Hz, 1H), 5.48 (d, J=4.4 Hz, 1H), 5.01-4.96 (m, 2H), 4.29 (d, J=11.2 Hz, 1H), 4.01 (d, J=10.8 Hz, 1H), 2.05 (s, 3H), 1.25 (s, 3H), 1.06 (s, 3H), 0.94 (s, 3H); $^{13}$C-NMR (CDCl$_3$, 100 MHz) δ 18.77, 19.14, 19.95, 21.17, 23.39, 25.00, 25.99, 26.83, 29.81, 36.14, 37.11, 37.22, 37.70, 41.01, 42.20, 45.86, 66.67, 112.42, 117.23, 142.36, 150.15, 171.22.

Amine 20: A solution of aldehyde 3 (40 mg, 0.14 mmol) in dry MeOH (12 ml) was treated with ethylene diamine (0.4 ml, 3.36 mmol) at rt. The reaction was allowed to stir at rt for 4 h until tlc confirmed the disappearance of starting material. The mixture was then cooled to 0° C. and NaBH$_4$ (11 mg, 0.28 mmol) was added portionwise. The reaction mixture again allowed to stir for overnight and it was then quenched with saturated ammonium chloride solution (25 ml). Extraction was made with methylene chloride (2×35 ml). The desired product was purified through silica gel column chromatography. 20: Oil (42 mg, 90%); IR (neat) 3382, 2924 cm$^{-1}$; $^1$H-NMR (CDCl$_3$, 400 MHz) δ 5.95 (dd, J=11.2 Hz, J=12 Hz, 1H), 5.45 (brd, 1H), 5.00-4.95 (m, 2H), 2.78-2.75 (m, 3H), 2.66-2.63 (m, 2H), 2.47 (d, J=11.6 Hz, 1H), 2.10-1.83 (m, 6H), 1.63-1.44 (m, 10H), 1.42 (s, 3H), 1.05 (s, 3H), 0.85 (s, 3H); $^{13}$C-NMR (CDCl$_3$, 100 MHz) δ 150.69, 142.47, 116.85, 112.24, 53.38, 51.68, 46.35, 42.24, 41.31, 38.14, 37.34, 37.24, 36.54, 30.38, 27.64, 26.18, 24.98, 23.38, 20.00, 19.33, 18.54; HRMS Calcd for C$_{22}$H$_{38}$N$_2$ 331.31 (M+H)$^+$, Found 331.31.

Amine 21: Amine 21 was synthesized according to the same procedure described above for amine 19, using aldehyde 9 as starting material. 21: $^1$H-NMR (CDCl$_3$, 400 MHz) δ 5.98 (dd, J=11.2 Hz, J=12 Hz, 1H), 5.45 (brd, 1H), 5.00-4.95 (m, 2H), 2.94 (brd, 1H), 2.80 (brd, 1H), 2.82-2.79 (m, 2H), 2.60-2.35 (brd, 4H), 2.09-1.90 (m, 6H), 1.67-1.42 (m, 7H), 1.24-1.17 (m, 5H), 1.24 (s, 3H), 1.10 (s, 3H), 0.85 (s, 3H); $^{13}$C-NMR (CDCl$_3$, 100 MHz) δ 150.82, 142.46, 125,38, 116.89, 112.31, 51.47, 47.14, 45.82, 42.46, 41.28, 38.23, 37.73, 37.28, 35.65, 31.22, 30.41, 28.63, 26.11, 25.03, 23.43, 19.99, 19.36, 18.76; HRMS Calcd for C$_{23}$H$_{40}$N$_2$ 344.55 Found 344.31.

Compound 22. 150 mg of ester 1 (0.475 mmol) and 173 mg of LiBr were dissolved in DMF and heated at 165° C. for two days. The reaction was quenched with H$_2$O and the product extracted with ethyl ether and purified using chromatography column. The reaction yielded 74.6 mg of white crystal product 22 (52%). $^1$H-1-NMR (CDCl$_3$, 400 MHz) δ 5.60 (q, J=10.4 Hz, 1H), 4.98 (dd, J=8.4 Hz, 1H), 4.76 (dd, J=15.2 Hz, 1H), 1.26 (s, 3H), 1.05 (s, 3H), 0.93 (s, 3H); α$_D$=−144.06.

Compound 23: 10 mg of compound 22 (0.33 mmol) were dissolved in 2.5 ml of methanol, and treated with 2.5 ml of (trimethylsilyl) diazomethane, and 2.5 ml of benzene. The reaction was stirred at room temperature for 20 minutes, then worked up with H$_2$O, and extracted with ether. The mixture was purified by silica gel column purification to afford 8.2 mg of compound 23. 23: white solid (82% yield). $^1$H-NMR (CDCl$_3$, 300 MHz) δ 5.61 (q, J=10.2 Hz, 1H), 4.97 (dd, J=8.7 Hz, 1H), 4.76 (dd, J=15.3 Hz, 1H), 3.63 (s, 3H), 1.19 (s, 3H), 1.05 (s, 3H), 0.82 (s, 3H); $^{13}$C-NMR (CDCl$_3$, 100 MHz) δ 19.22, 20.22, 20.93, 22.20, 26.29, 27.44, 29.73, 30.00, 37.76, 38.86, 39.00, 40.25, 42.56, 45.13, 52.42, 54.81, 113.80, 131.17, 140.28, 147.83, 179.27; α$_D$=−121.6.

Compound 24: 7.8 mg of ester 23 (0.025 mmol) was dissolved in dry CH$_2$Cl$_2$ and treated at −78° C. with 4.0 equivalent DIBALH for 10 minutes. The reaction was quenched with Rochelle salt solution and the product was collected by extraction with ether and purified through chromatography column. 24: (6.5 mg, 94% yield). $^1$H-1-NMR (CDCl$_3$, 300 MHz) δ 5.62 (q, J=10.5 Hz, 1H), 4.96 (dd, J=8.4 Hz, 1H), 4.75 (dd, J=15.3 Hz, 1H), 3.78 (d, J=10.8 Hz, 1H), 3.48 (d, J=10.8 Hz, 1H), 1.25 (s, 3H), 1.04 (s, 3H), 0.99 (s, 3H); $^{13}$C-NMR (CDCl$_3$, 100 MHz) δ 14.15, 14.37, 14.75, 16.09, 20.27, 21.57, 22.09, 23.75, 30.75, 31.70, 32.97, 33.77, 34.03, 36.48, 61.10, 107.97, 124.66, 135.63, 142.29; α$_D$=−53.8.

Compound 25. 53.2 mg of aldehyde 3 (0.19 mmol) was dissolved in tBuOH/H$_2$O (3:1), and treated with 76.45 mg of NaH$_2$PO$_4$.H$_2$O (0.56 mmol). The reaction mixture was stirred to completely dissolve the salt before the addition of 277.5 μl of 2M 1-methyl-2-butene in THF. The reaction was stirred for 30 minutes, then it was treated with 50.2 mg of NaClO$_2$ (0.56 mmol). When the reaction was done, it was neutralized with NH$_4$Cl. The product was collected via the extraction with CH$_2$Cl$_2$ and purified through chromatography column to produce 44 mg of compound 25 (78%). 25: white solid; R$_f$=0.30 (silica, 30% ether in hexanes); $^1$H NMR (400 MHz, CDCl$_3$) δ 5.96 (dd, 1H, J=14.4, 9.6 Hz), 5.52 (m, 1H), 4.98-4.95 (m, 2H), 2.20-1.72 (m, 10H), 1.64-1.58 (m, 3H), 1.57-1.37 (m, 4H), 1.22 (s, 3H), 1.04 (s, 3H), 0.99 (s, 3H); $^{13}$C NMR (100 MHz, CDCl$_3$) δ 182.9, 149.3, 143.9, 118.1, 111.9, 47.5, 44.2, 41.3, 41.2, 38.9, 38.0, 37.6, 34.8, 28.4, 24.7, 23.0, 22.4, 21.9, 20.3, 19.5.

Compound 26. 3.5 mg of acid 25 (0.012 mmol) was dissolved in dry CH$_2$Cl$_2$ and treated with 10 equivalents of (COCl)$_2$ followed by two drops of DMF. When the reaction stopped bubbling, the CH$_2$Cl$_2$ solvent and excess (COCl)$_2$ were evaporated under vacuum and the reaction residue was redissolved in dry benzene and then treated with 5 equivalent of N-methyl piperazine. When the reaction was done, the solvent was evaporated under vacuum, and the product was collected by the extraction with ether and NH$_4$Cl solution. After the chromatography column, 3.0 mg of pure product 26 was obtained (65% yield). 26: $^1$H-NMR (CDCl$_3$, 300 MHz) δ 5.95 (q, J=11.6 Hz, 1H), 5.46 (d, J=2.4 Hz, 1H), 5.00-4.94 (m, 2H), 3.73-3.68 (m, 4H), 2.48 (s, 3H), 2.10-2.03 (m, 4H), 1.25 (s, 3H), 1.09 (s, 3H), 1.03 (s, 3H); α$_D$=+ 8.6.

Compound 27. 10 mg of acid 25 (0.033 mmol) was dissolved in dry CH$_2$Cl$_2$ and treated with 10 equivalents of (COCl)$_2$ followed by two drops of DMF. When the reaction stopped bubbling, the CH$_2$Cl$_2$ solvent and excess (COCl)$_2$ were evaporated under vacuum and the reaction residue was redissolved in dry benzene and then treated with 5 equivalent of diethanolamine. When the reaction was done, the solvent was evaporated under vacuum, and the product was collected by the extraction with ether and NH$_4$Cl solution. After the chromatography column, 9.2 mg of pure product was obtained (75% yield). $^1$H-NMR (CDCl$_3$, 300 MHz) δ 5.95 (q, J=11.6 Hz, 1H), 5.46 (s, 1H), 4.96 (m, 2H), 2.99 (s, 7H), 2.37 (d, 1H), 1.29 (s, 3H), 1.09 (s, 3H), 1.02 (s, 3H); α$_D$=−41.2.

Amine 28: 5.0 mg of acid 25 (0.017 mmol) was dissolved in dry CH$_2$Cl$_2$ and treated with 10 equivalents of (COCl)$_2$ followed by two drops of DMF. When the reaction stopped bubbling, the CH$_2$Cl$_2$ solvent and excess (COCl)$_2$ were evaporated under vacuum and the reaction residue was redissolved in dry benzene and then treated with 5 equivalent of ethylene diamine. When the reaction was done, the solvent was evaporated under vacuum, and the product was collected by the extraction with ether and $NH_4Cl$ solution. After the chromatography column, 3.0 mg of pure product was obtained (52% yield).

Compound 29. 5.0 mg of acid 25 (0.017 mmol) was dissolved in dry $CH_2Cl_2$ and treated with 10 equivalents of $(COCl)_2$ followed by two drops of DMF. When the reaction stopped bubbling, the $CH_2Cl_2$ solvent and excess $(COCl)_2$ were evaporated under vacuum and the reaction residue was redissolved in dry benzene and then treated with 5 equivalent of propylamine. When the reaction was done, the solvent was evaporated under vacuum, and the product was collected by the extraction with ether and $NH_4Cl$ solution. After the chromatography column, 3.7 mg of pure product was obtained (63% yield).

Compound 30. 4.5 mg of acid 25 (0.015 mmol) was dissolved in dry $CH_2Cl_2$ and treated with 10 equivalents of $(COCl)_2$ followed by two drops of DMF. When the reaction stopped bubbling, the $CH_2Cl_2$ solvent and excess $(COCl)_2$ were evaporated under vacuum and the reaction residue was redissolved in dry benzene and then treated with 5 equivalent of morpholine. When the reaction was done, the solvent was evaporated under vacuum, and the product was collected by the extraction with ether and $NH_4Cl$ solution. After the chromatography column, 5.0 mg of pure product was obtained (89% yield). $^1$H-NMR ($CDCl_3$, 400 MHz) δ 5.95 (q, J=11.6 Hz, 1H), 5.47 (s, 1H), 4.99-4.95 (m, 2H), 3.64-3.60 (m, 8H), 1.29 (s, 3H), 1.11 (s, 3H), 1.03 (s, 3H); $^{13}$C-NMR ($CDCl_3$, 100 MHz) δ 21.24, 22.82, 23.22, 24.90, 25.16, 27.35, 34.36, 37.65, 39.71, 40.37, 41.42, 41.62, 46.32, 46.47, 46.71, 51.29, 67.02, 111.68, 117.10, 143.89, 149.84; $α_D$=-47.1.

Compound 31. To a solution of 14.5 mg of acid 25 (0.048 mmol) in THF was added 1 equivalent of KOH dissolved in 200 µl of water and the mixture was stirred for 1 h. Evaporation of the solvent afforded pure salt 31 (100%).

Compound 31. To a solution of 24.5 mg of acid 25 (0.072 mmol) in THF was added 1 equivalent of NaOHOH dissolved in 200 µl of water and the mixture was stirred for 1 h. Evaporation of the solvent afforded pure salt 32 (100%).

Compound 33. To a solution of 20.1 mg of acid 25 (0.052 mmol) in THF was added 1 equivalent of triethanolamine dissolved in 200 µl of methanol and the mixture was stirred for 1 h. Evaporation of the solvent afforded pure salt 33 (100%).

Compound 34. To a solution of 20.1 mg of acid 25 (0.052 mmol) in THF was added 1 equivalent of diethanolamine dissolved in 200 µl of methanol and the mixture was stirred for 1 h. Evaporation of the solvent afforded pure salt 34 (100%).

Ester 35. Methyl (triphenylplhosphoranylidene) acetate (90.7 mg, 0.27 mmol) and aldehyde 9 (27.3 mg, 0.09 mmol) were dissolved in dried $CH_2Cl_2$ and stirred at room temperature. The reaction was completed within one day and then neutralized with $NH_4Cl$. Both trans and cis products were collected by the extraction with $CH_2Cl_2$. They were separated through the chromatography column. 24.4 mg and 2.5 mg of trans and cis ester were obtained and were separable by column chromatography (84% total yield). Trans 35: $^1$H-NMR ($CDCl_3$, 400 MHz) δ 7.00-6.92 (m, 1H), 5.96 (q, J=11.6 Hz, 1H), 5.80 (d, J=15.2 Hz, 1H), 4.47 (d, J=4.4 Hz, 1H), 5.00-4.96 (m, 2H), 3.72 (s, 3H), 2.45 (m, 1H), 2.35 (m, 1H), 1.08 (s, 3H), 1.06 (s, 3H), 0.89 (s, 1H); $^{13}$C-NMR ($CDCl_3$, 100 MHz) δ 18.82, 19.01, 19.90, 23.37, 24.97, 28.84, 35.94, 37.15, 37.22, 37.69, 37.85, 38.11, 40.98, 42.40, 46.55, 51.42, 112.38, 117.04, 122.38, 142.45, 148.03, 150.67, 166.73; $α_D$=-12.02. Cis: $^1$H-NMR ($CDCl_3$, 400 MHz) δ 6.32-6.25 (m, 1H), 5.97 (q, J=11.6 Hz, 1H), 5.83 (d, J=11.6 Hz, 1H), 5.47 (d, J=8 Hz, 1H), 5.00-4.96 (m, 2H), 3.71 (s, 3H), 3.19-3.13 (m, 1H), 2.61-2.55 (m, 1H), 1.15 (s, 3H), 1.07 (s, 3H), 0.90 (s, 3H).

Acid 36. 8 mg of trans ester 35 (0.023 mmol) and 2.70 mg of LiOH (0.113 mmol) were dissolved in 1 ml of $THF/H_2O$ (1:1). The reaction mixture was refluxed at 60° C. overnight. The completed reaction was neutralized with HCl (1M) and extracted with $CH_2Cl_2$. After the purification by chromatography column, 7.3 mg of pure product 36 was obtained (95%). 36: $^1$H-NMR ($CDCl_3$, 400 MHz) δ 7.12-7.04 (m, 1H), 5.96 (q, J=11.6 Hz, 1H), 5.82 (d, J=15.6 Hz, 1H), 5.48 (d, J=4.4 Hz, 1H), 5.01-4.97 (m, 2H), 2.53-2.46 (m, 1H), 2.23-2.19 (m, 1H), 1.09 (s, 3H), 1.07 (s, 3H), 0.88 (s, 3H); $^{13}$C-NMR ($CDCl_3$, 100 MHz) δ 38.12, 42.76, 42.93, 43.82, 47.29, 48.87, 48.91, 49.74, 52.77, 53.70, 60.01, 61.21, 61.64, 61.84, 6 2.05, 64.90, 66.35, 70.54, 136.46, 141.09, 141.19, 146.10; $α_D$=-15.17.

Ester 37. In a moisture-free flask, 5 mg of trans ester 35 (0.14 mmol) were dissolved in dry methanol. 1.7 mg Mg (0.07 mmol), which was freshly activated by heat, was added into the reaction flask. The reaction was stirred at room temperature overnight. When the reaction was done, the remaining Mg was dissolved by HCl (2M), and the mixture was then extracted with ether. 2.9 mg of yellow solid was obtained after the chromatography column (54% yield). 36: $^1$H-NMR ($CDCl_3$, 400 MHz) δ 5.96 (q, J=11.6 Hz, 1H), 5.45 (d, J=4 Hz, 1H), 5.00-4.95 (m, 2H), 3.67 9s, 3H), 2.27 (m, 2H), 1.25 (s, 3H), 1.05 (s, 3H), 0.83 (s, 3H); $^{13}$C-NMR ($CDCl_3$, 100 MHz) δ 18.59, 19.31, 19.99, 20.26, 23.44, 25.05, 26.16, 28.58, 29.81, 32.01, 35.25, 36.11, 37.3, 37.35, 37.75, 38.28, 41.41, 42.46, 46.94, 112.25, 116.75, 116.73, 142.60, 151.09; $α_D$=-22.1.

Acid 38. 5 mg of ester 37 (0.014 mmol) and 1.70 mg of LiOH (0.07 mmol) were dissolved in 1 ml of $THF/H_2O$ (1:1). The reaction mixture was refluxed at 65° C. overnight. The completed reaction was neutralized with HCl (1M) and extracted with $CH_2Cl_2$. After the purification by chromatography column, 3.9 mg of pure product 38 was obtained (81%). $^1$H-NMR ($CDCl_3$, 400 MHz) δ 5.96 (q, J=11.6 Hz, 1H), 5.45 (d, J=4 Hz, 1H0, 5.00-4.95 (m, 2H), 2.37 (m, 2H), 1.25 (s, 3H), 1.05 (s, 3H), 0.84 (s, 3H); $^{13}$C-NMR ($CDCl_3$, 100 MHz) δ 18.58, 19.28, 19.98, 23.42, 25.03, 26.12, 28.55, 29.79, 30.40, 31.94, 34.91, 36.09, 37.32, 37.73, 38.25, 41.38, 42.44, 46.93, 112.24, 116.73, 116.75, 142.55, 151.04; $α_D$=+3.4.

Example 24

The effects of seven different TTL3 analogs on viability and TNF-α synthesis of THP-1 cells was analyzed.

The ability to inhibit TNF-α production was analyzed in THP-1 cells, a human acute monocytic leukemia cell line that is widely used to assess monocyte functions. In order to induce maturation, THP-1 cells were plated at $1×10^6$ cells/ml and pretreated with 5 nM PMA for two days. Differentiated THP-1 cells were pretreated with various concentrations of TTL3 or its analogs for 1 hour, followed by a 4 hour incuba tion with 1 of LPS (Sigma, St. Louse, Mo.). The p38 inhibitor (SB 203580; Sigma, St. Louis, Mo.) was used as a positive control. Supernatants were collected and stored at −80° C. until assayed for TNF-α activity. A resazurin assay was performed for each analog to evaluate the effects on cell metabolism and viability.

A preparation of the dye resazurin, commercially-available as alamarBlue™ (Biosource International Inc., 820 Flynn Road, Camarillo, Calif.), was used for the cytotoxicity assays described herein. The assays and experiments described herein were conducted in substantially the same manner as described in the scientific literature, for example, in Magnani, E. and Bettini, E., "Resazurin detection of energy metabolism changes in serum-starved PC12 cells and of neuroprotective agent effect," Brain Res Protoc., 2000 July; 5(3):266-72 and in Nociari M. M., Shalev A., Benias P., and Russo C. J, "A novel one-step, highly sensitive fluorometric assay to evaluate cell-mediated cytotoxicity," Immunol. Methods 213, 157-167 (1998), see also U.S. Pat. No. 5,501,959, entitled "Antibiotic and Cytotoxic Drug Susceptibility Assays using Resazurin and Poising Agents," the entire specification of which is incorporated herein by reference.

To detect the presence of human TNFα, fluorescent linked immunosorbent assay or FLISA was developed and optimized. 100 μl of beads (6 μm, Spherotech) coated with goat anit-mouse IgG (1 mg/ml, R and D Systems) were mixed with 4 μl of biotin-anti-hTNFα mouse IgG (0.1 mg/ml, R and D Systems) and 2 μl of FMAT Blue-streptavidin (0.1 mg/ml, Applied Biosystems). 50 μl of the mixtures was combined with 50 μl of the supernatant isolated from treated THP-1 cells and added to the black wall FLISA plates (Applied Biosystems) and incubated overnight. The plates were scanned at factory set PMT setting, and the values were plotted and analyzed by Applied Biosystems software.

Tables 10-23 also summarize the effects of seven TTL3 analog families on viability and TNF-α synthesis of THP-1 cells.

Example 25

Reduction of TNF-α Levels by Formula (IIB-A1) and Analogs in LPS-Stimulated Human Peripheral Blood Mononuclear Cells Eighty μl of $3.1 \times 10^5$/ml Human Peripheral Blood Mononuclear cells (HPBMC) were seeded in Costar 3904 96-well plate in LGM-3 medium and cultured for 12 hr at 37° C., 5% $CO_2$ and 95% humidified air. 10 μl of 8-point half-log serial dilutions of LT-1-85, CC-3-19, CC-3-13P, formula (IIB-A1) and CC-3-22 prepared in LGM-3 medium was added to the cells and incubated for 1 hr. Subsequently, 10 μl of 500 ng/ml lipopolysaccharide (LPS) diluted in LGM-3 medium from 1 mg/ml stock solution was added to the cells and incubation proceeded for another 4 hr at 37° C., 5% $CO_2$ and 95% humidified air. SB203580, a known p38 MAP kinase inhibitor and DMSO were used as positive and negative controls, respectively. After 4 hr stimulation with LPS, the level of TNF-α from each sample was analyzed by using the human TNF-α cytoset ELISA kit. $EC_{50}$ values (the drug concentration at which 50% of the maximal observed TNF-α production is inhibited) were determined using a standard sigmoidal dose response curve fitting algorithm (Prism 2.0, GraphPad Software Inc). A duplicate set of cell plates were assayed for cell viability using the Resazurin dye after the cells were incubated with test compounds for 24 hr. The fluorescence of the reduction product of Resazurin was measured using a Fusion microplate fluorometer (Packard Bioscience) with $\lambda_{ex}=535$ nm and $\lambda_{em}=590$ nm filters. $EC_{50}$ values (the drug concentration at which 50% of the maximal observed growth inhibition is established) were determined using a standard sigmoidal dose response curve fitting algorithm (Prism 2.0, GraphPad Software Inc).

The effects on TNF-α production and cell viability in HPBMC by LT-1-85, CC-3-19, CC-3-13P, formula (IIB-A1) and CC-3-22 are summarized in Table 24. The results indicate that with an EC50 of 1.4 μM, formula (IIB-A1) is effective in the inhibition of TNF-α production in LPS-stimulated HPBMC. Under the condition tested, formula (IIB-A1) did not inhibit the cell growth of HPBMC at concentrations up to 26 μM.

TABLE 24

The effects on LPS-stimulated TNF-α production and cell viability in HPBMC by LT-1-85, CC-3-19, CC-3-13P, formula (IIB-A1) and CC-3-22 compounds

| Compound | Structure | $EC_{50}$ (μM) | |
|---|---|---|---|
| | | Inhibition of TNF-α production* | Inhibition of cell growth[#] |
| LT-1-85 | 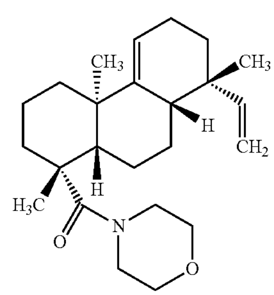 | 1.9 2.3 | 3.8 3.6 |

TABLE 24-continued

The effects on LPS-stimulated TNF-α production and cell viability in HPBMC
by LT-1-85, CC-3-19, CC-3-13P, formula (IIB-A1) and CC-3-22 compounds

| Compound | Structure | EC$_{50}$ (μM) | |
|---|---|---|---|
| | | Inhibition of TNF-α production* | Inhibition of cell growth# |
| CC-3-19 | 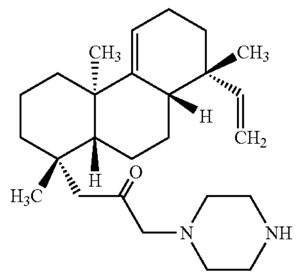 | 3.3 | 3.0 |
| CC-3-13P | 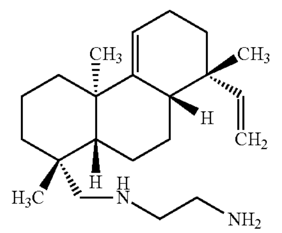 | 0.5<br>0.4 | 0.9<br>0.7 |
| Formula (IIB-A1) | 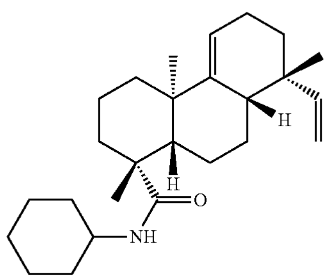 | 1.4 | >26 |
| CC-3-22 | 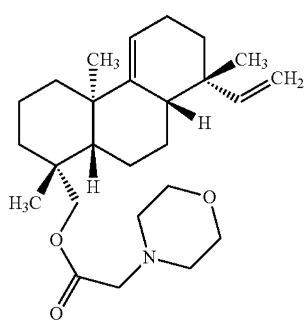 | 7.4 | 24 |

*5 hr drug exposure
24 hr drug exposure

Example 26

Formula (IIB-A1) Decreases the Phosphorylation Level of IκBα in Lps-Stimulated Human Peripheral Blood Mononuclear Cells One ml/well of 3×10$^6$/ml HPBMC were seeded in 6-well plate in LGM-3 medium and cultured for 12 hr at 37° C., 5% CO$_2$ and 95% humidified air. Final concentration of 13 μM for formula (IIB-A1) (or 10 μM for TTL3) was added to HPBMC for 1 hr. DMSO was used as a control. Cells were then stimulated with 20 ng/ml LPS diluted in LGM-3 medium from 1 mg/ml stock solution for 30 min, 1 hr, 2 hr and 4 hr. At the end of each time point, cells were harvested by centrifugation and cell pellets were washed once in ice-cold 1×Dulbecco's Phosphate buffered Saline (DPBS). To prepare samples for SDS Polyacrylamide Gel Electrophoresis (SDS-PAGE), cells were lysed in RIPA buffer (50 mM Tris-HCl, pH7.4, 0.9% NaCl, 1% Triton X-100, 0.25% Na-deoxycholate, 1 mM EDTA, 2 mM Na$_3$VO$_4$ and 1× protease inhibitors cocktail) for 15 min on ice. Cell lysates were cleared by centrifugation at 14,000 rpm, 4° C. for 10 min. Protein concentrations of cell lysates were determined by BCA protein assay kit prior to SDS-PAGE. Equal amount of proteins from various cell lysates were resolved on 10% NuPage IVIES precast gels and transferred to nitrocellulose membranes according to the manufacturer's instructions. After transfer, membranes were first blocked in BLOTTO (5% Non-fat dry milk in 1×DPBS buffer containing 0.1% Tween-20) at room temperature for 2 hr and then incubated with appropriate primary antibodies: anti-phospho-IκBa (1:1000) or anti-Tubulin (1:2000) for 2 hr. Antibody against tubulin was used as a control to confirm the equal loading of each sample. After the primary antibody incubation, membranes were washed briefly 2-3 times for 10 min each with BLOTTO and again incubated with sheep anti-mouse HRP conjugated secondary antibody for 1 hr. Following the secondary antibody incubation, membranes were washed extensively 4 times for 15 min each with PBST (1×DPBS plus 0.1% Tween-20). HRP activity was visualized by the enhanced chemiluminescence (ECL) detection system.

Figure 38:
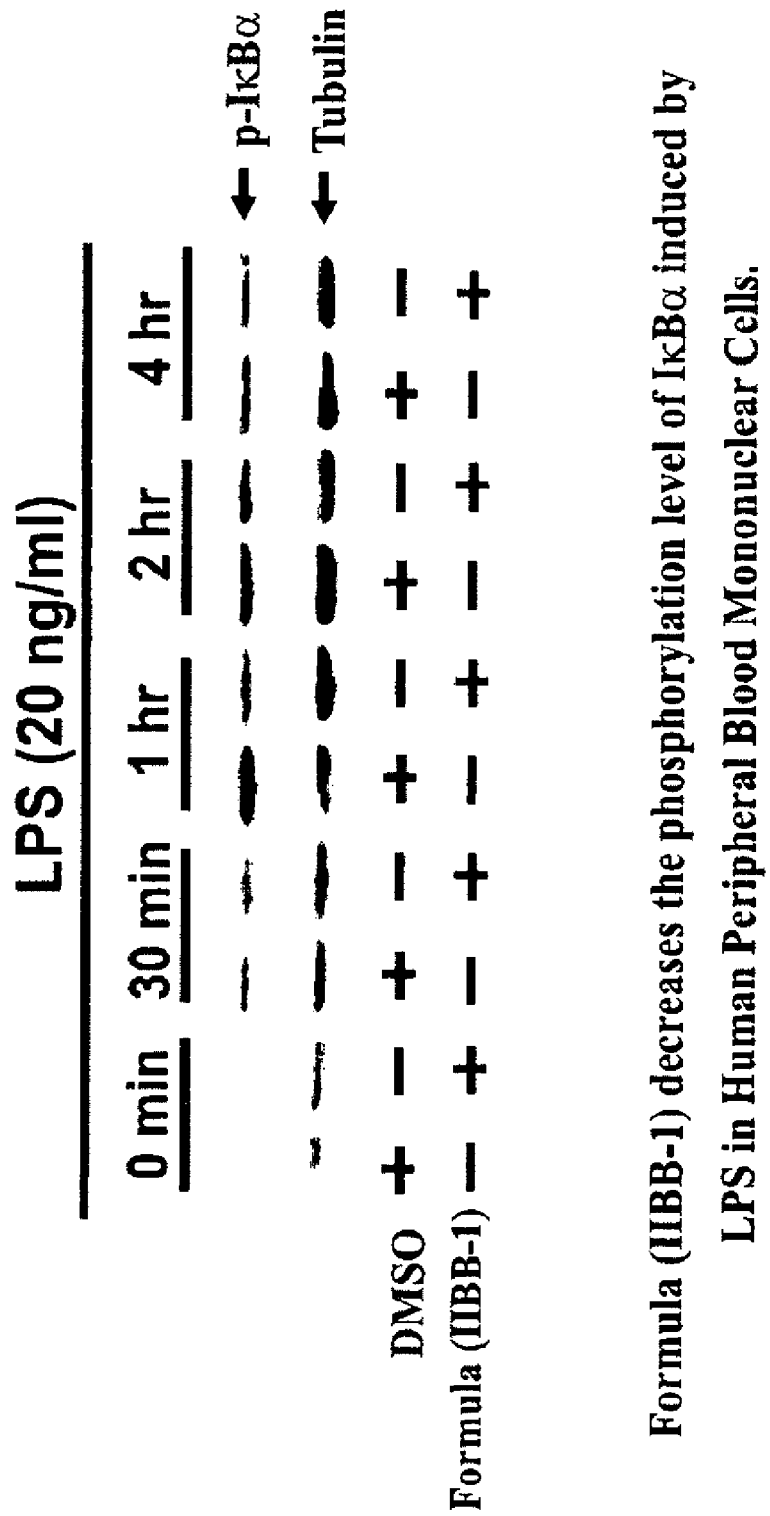
FIG. 38 depicts the decrease caused by Formula (IIB-a1) in the phosphorylation level of IκBα induced by LPS in Human Peripheral Blood Mononuclear Cells.

FIG. 38 demonstrates that formula (IIB-A1) effectively inhibited the level of IxBa phosphorylation in LPS-stimulated HPBMC as compared with DMSO control.

Example 27

Formula (IIB-A1) Reduces the Phosphorylation Level of IκBα Induced b LPS in RPMI 8226 Cells One ml/well of $2 \times 10^6$/ml RPMI 8226 cells (#CCL-155C, American Type Culture Collection) were seeded in 6-well plate in LGM-3 medium and cultured for overnight at 37° C., 5% $CO_2$ and 95% humidified air. TTL3 and formula (IIB-A1) were added to RPMI 8226 cells at the final concentration of 10 μM and 13 μM for 1 hr, respectively. DMSO was used as a control. Cells were then stimulated with 50 ng/ml LPS diluted in LGM-3 medium from 1 mg/ml stock solution for 30 min, 1 hr, 2 hr and 4 hr. At the end of each time point, cells were harvested by centrifugation and cell pellets were washed once in ice-cold 1×DPBS. To prepare samples for SDS-PAGE, cells were lysed in RIPA buffer (50 mM Tris-HCl, pH7.4, 0.9% NaCl, 1% Triton X-100, 0.25% Na-deoxycholate, 1 mM EDTA, 2 mM $Na_3VO_4$ and 1× protease inhibitors cocktail) for 15 min on ice. Cell lysates were cleared by centrifugation at 14,000 rpm, 4° C. for 10 min. Protein concentrations of cell lysates were determined by BCA protein assay kit prior to SDS-PAGE. Equal amount of proteins from various cell lysates were resolved on 10% NuPage IVIES precast gels and transferred to nitrocellulose membranes according to the manufacturer's instructions. After transfer membranes were first blocked in BLOTTO (5% Non-fat dry milk in 1×DPBS buffer containing 0.1% Tween-20) at room temperature for 2 hr and then incubated with appropriate primary antibodies: anti-phospho-IκBα (1:1000) or anti-Tubulin (1:2000) for 2 hr. Antibody against tubulin was used as a control to confirm the equal loading of each sample. After the primary antibody incubation, membranes were washed briefly 2-3 times for 10 min each with BLOTTO and again incubated with sheep anti-mouse HRP conjugated secondary antibody for 1 hr. Following the secondary antibody incubation, membranes were washed extensively 4 times for 15 min each with PBST (1×DPBS plus 0.1% Tween-20). HRP activity was visualized by the enhanced chemiluminescence (ECL) detection system.

Figure 39:
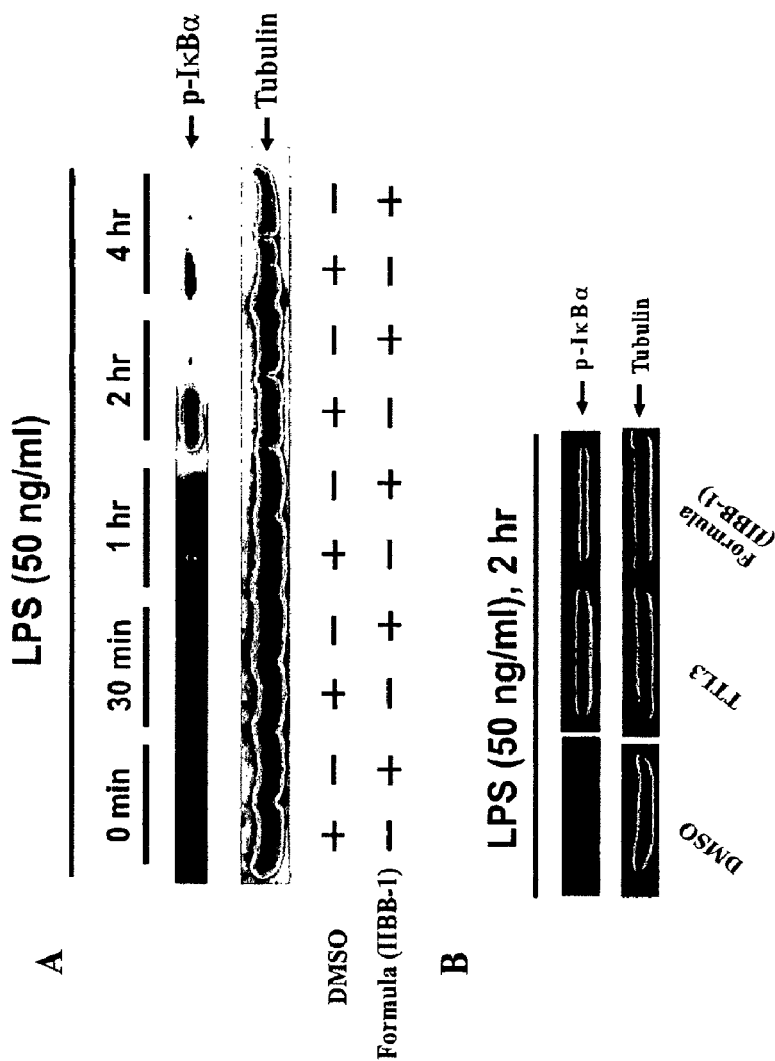
FIG. 39 depicts the decrease caused by Formula (IIB-A1) in the phosphorylation level of IκBα induced by LPS in RPMI 8226 cells.

FIG. 39 demonstrates that after the formula (IIB-A1) treatment, the level of IκBα phosphorylation induced by LPS stimulation in RPMI 8226 cells was greatly reduced as compared with DMSO control treated cells. The inhibitory effect on the phosphorylation level of IκBα by LPS in the presence of TTL3 was minimal (FIG. 39B).

Example 28

Formula (IIB-A1) Specifically Inhibits LPS-Induced Phosphorylation of IκBα and p38 MAP Kinase in RPMI 8226 Cells One ml/well of $2 \times 10^6$/ml RPMI 8226 cells (#CCL-155C, American Type Culture Collection) were seeded in 6-well plate in LGM-3 medium and cultured for overnight at 37° C., 5% $CO_2$ and 95% humidified air. Formula (IIB-A1) was added to RPMI 8226 cells at the final concentration of 13 μM for 1 hr. DMSO was used as a control. Cells were then either stimulated by LPS (50 ng/ml) or by TNF-α (10 ng/ml) for various length of time. At the end of each period of stimulation, cells were harvested by centrifugation and cell pellets were washed once in ice-cold 1×Dulbecco's Phosphate buffered Saline (DPBS). To prepare samples for SDS-PAGE, cells were lysed in RIPA buffer (50 mM Tris-HCl, pH7.4, 0.9% NaCl, 1% Triton X-100, 0.25% Na-deoxycholate, 1 mM EDTA, 2 mM $Na_3VO_4$ and 1× protease inhibitors cocktail) for 15 min on ice. Cell lysates were cleared by centrifugation at 14,000 rpm, 4° C. for 10 min. Protein concentrations of cell lysates were determined by BCA protein assay kit prior to SDS-PAGE. Equal amount of proteins from various cell lysates were resolved on 10% NuPage IVIES precast gels and transferred to nitrocellulose membranes according to the manufacturer's instructions. After transfer membranes were first blocked in BLOTTO (5% Non-fat dry milk in 1×DPBS buffer containing 0.1% Tween-20) at room temperature for 2 hr and then incubated with appropriate primary antibodies: anti-phospho-IκBα, anti-p38 and anti-phopho-p38 (1:1000) or anti-Tubulin (1:2000) for 2 hr. Antibody against tubulin was used as a control to confirm the equal loading of each sample. After the primary antibody incubation, membranes were washed briefly 2-3 times for 10 min each with BLOTTO and again incubated with either sheep anti-mouse or goat anti-rabbit-HRP conjugated secondary antibody for 1 hr. Following the secondary antibody incubation, membranes were washed extensively 4 times for 15 min each with PBST (1×DPBS plus 0.1% Tween-20). HRP activity was visualized by the enhanced chemiluminescence (ECL) detection system.

Figure 40:
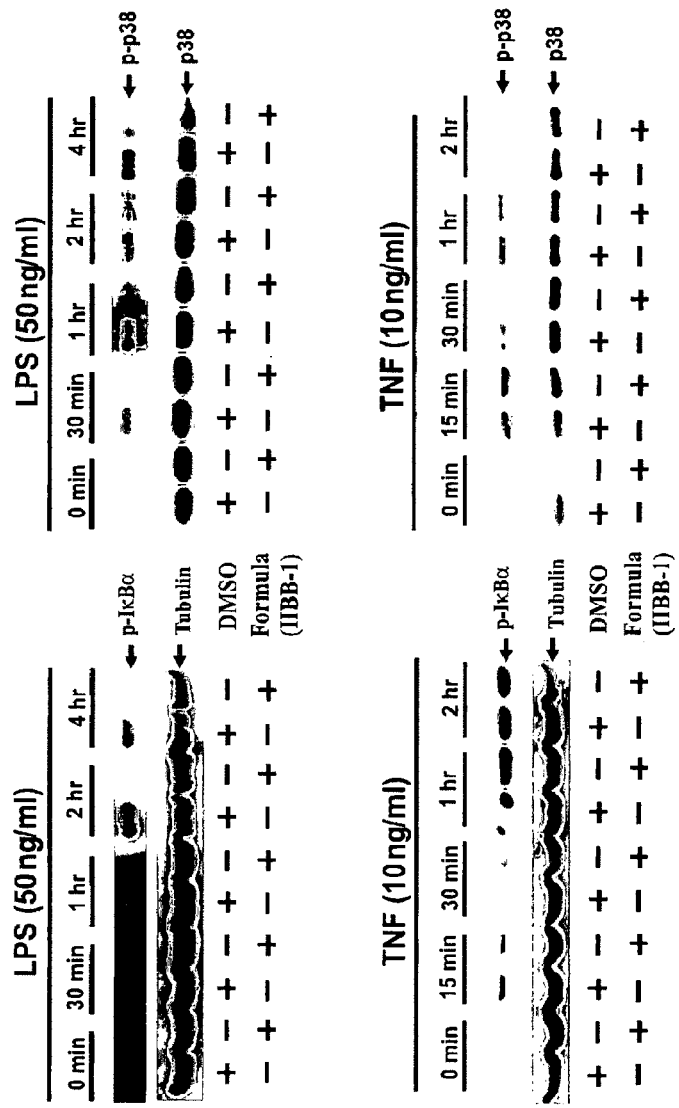
FIG. 40 shows that Formula (IIB-A1) specifically inhibits LPS-induced phosphorylation of IκBα and p38 MAP kinase in RPMI 8226 cells.

Comparing the effects of formula (IIB-A1) treatment on the phosphorylation levels of IxBa and p38 MAP kinase induced by LPS and TNF-α in RPMI 8226 cells (FIG. 40), the data indicate that formula (IIB-A1) specifically decreases LPS-induced phosphorylation of IκBα and p38 MAP kinase.

Example 29

Formula (IIB-A1) Inhibits the Phosphorylation of IκBα Induced b Toll-Like Receptor Ligands in RPMI 8226 Cells One ml/well of $2 \times 10^6$/ml RPMI 8226 cells (#CCL-155C, American Type Culture Collection) were seeded in 6-well plate in LGM-3 medium and cultured for overnight at 37° C., 5% $CO_2$ and 95% humidified air. Formula (IIB-A1) was added to RPMI 8226 cells at the final concentration of 13 μM for 1 hr. DMSO was used as a control. Cells were then stimulated with 50 ng/ml LPS, 2 μg/ml Lipoteichoic acid (LTA) and CpG DNA for various length of time. At the end of each period of stimulation, cells were harvested by centrifugation and cell pellets were washed once in ice-cold 1×Dulbecco's Phosphate buffered Saline (DPBS). To prepare samples for SDS-PAGE, cells were lysed in RIPA buffer (50 mM Tris-HCl, pH7.4, 0.9% NaCl, 1% Triton X-100, 0.25% Na-deoxycholate, 1 mM EDTA, 2 mM $Na_3VO_4$ and 1× protease inhibitors cocktail) for 15 min on ice. Cell lysates were cleared by centrifugation at 14,000 rpm, 4° C. for 10 min. Protein concentrations of cell lysates were determined by BCA protein assay kit prior to SDS-PAGE. Equal amount of proteins from various cell lysates were resolved on 10% NuPage IVIES precast gels and transferred to nitrocellulose membranes according to the manufacturer's instructions. After transfer membranes were first blocked in BLOTTO (5% Non-fat dry milk in 1×DPBS buffer containing 0.1% Tween-20) at room temperature for 2 hr and then incubated with appropriate primary antibodies: anti-phospho-IκBα (1:1000) or anti-Tubulin (1:2000) for 2 hr. Antibody against tubulin was used as a control to confirm the loading of each sample. After the primary antibody incubation, membranes were washed briefly 2-3 times for 10 min each with BLOTTO and again incubated with sheep anti-mouse HRP conjugated secondary antibody for 1 hr. Following the secondary antibody incubation, membranes were washed extensively 4 times for 15 min each with PBST (1×DPBS plus 0.1% Tween-20). HRP activity was visualized by the enhanced chemiluminescence (ECL) detection system.

Figure 41:
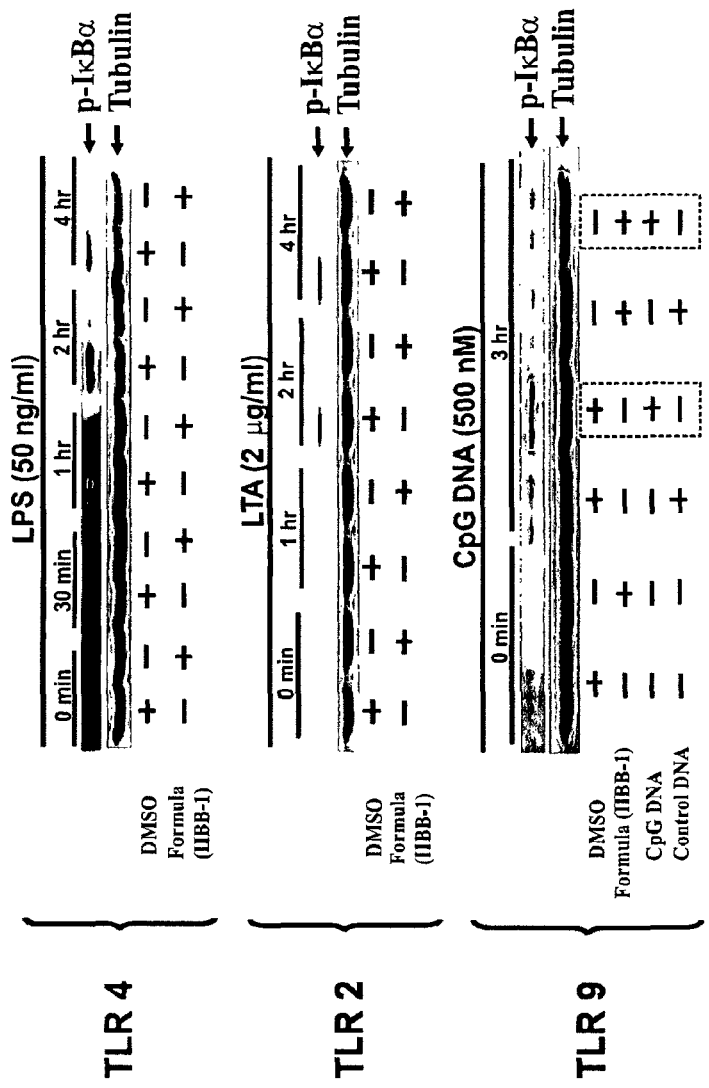
FIG. 41 shows that Formula (IIB-A1) inhibits the phosphorylation of IκBα induced by Toll-like receptor ligands in RPMI 8226 cells.

In addition to the already demonstrated effect of formula (IIB-A1) on the phosphorylation of IκBα induced by LPS through the well characterized Toll-like receptor 4 (TLR4) in HPBMC and RPMI 8226 cells (FIGS. 38, 39 and 40), formula (IIB-A1) also inhibits the phosphorylation of IκBα induced by other Toll-like receptor ligands. As shown in FIG. 41, formula (IIB-A1) inhibits the phosphorylation of IxBa induced by LTA and CpG DNA which are thought to function through the Toll-like receptor 2 (TLR2) and Toll-like receptor 9 (TLR9), respectively.

Example 30

Formula (IIB-A1) Reduces LPS-Stimulated IL-8 and IL-10 Levels in RPMI 8226 Cells Ninety µl of $2.8×10^5$/ml and 0.5 ml of $5×10^5$/ml RMPI 8226 cells (#CCL-155C, American Type Culture Collection) were seeded in 96-well and 6-well plate in LGM-3 medium, respectively. Cells were cultured overnight at 37° C., 5% $CO_2$ and 95% humidified air. 8-point serial dilution of TTL3 or formula (IIB-A1) was added to cells for 1 hr at the final concentration ranging from 20 µM to 0.16 DMSO was used as control. After 1 hr, 50 ng/ml of LPS diluted in LGM-3 medium from 1 mg/ml stock solution was added to stimulate the cells for additional 10 hr. Supernatants were collected and IL-8 and IL-10 levels were analyzed by using the human IL-8 and IL-10 cytoset ELISA kits.

Figure 42:
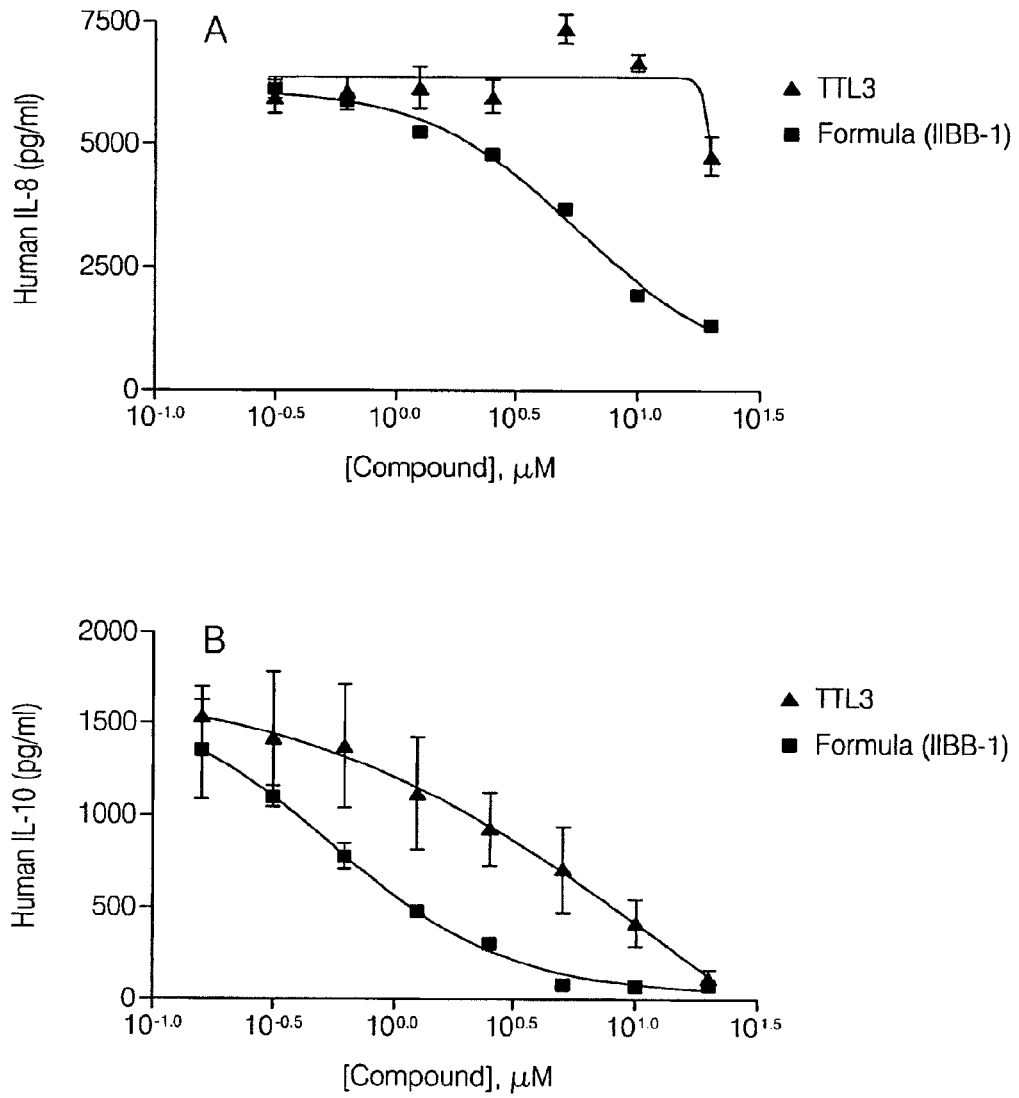
FIG. 42 shows that Formula (IIB-A1) reduces LPS-induced IL-8 and IL-10 production in a dose-dependent manner in RPMI 8226 cells.

FIGS. 42A and 42B both demonstrate that formula (IIB-A1) inhibits the LPS-induced IL-8 and IL-10 production in RPMI 8226 in a dose-dependent manner. TTL3 inhibits the IL-10 production in a dose-dependent manner in RPMI 8226 cells.

Example 31

Growth Inhibition of Cell Lines

Human prostate adenocarcinoma (PC-3; CRL-1435), multiple myeloma (RPMI 8226; CCL-155) and embryonic kidney (HEK-293; CRL-1573) cells were all purchased from ATCC and maintained in appropriate culture media. The cells were cultured in an incubator at 37° C. in 5% CO2 and 95% humidified air.

For cell growth inhibition assays, PC-3 and HEK-293 cells were seeded at $5×10^3$ and $1.5×10^3$ cells/well respectively in 90 µl media containing 1% (v/v) FBS into 96 well (Corning; 3904) black-walled, clear-bottom tissue culture plates and the plates were incubated overnight to allow cells to establish and enter log phase growth. RPMI 8226 cells were seeded at $2×10^4$ cells/well respectively in 90 µl media containing 1% (v/v) FBS into 96 well plates on the day of the assay. 4 mg/ml stock solutions of the compounds were prepared in 100% DMSO and stored at −20° C. The compounds were serially diluted and added in triplicate to the test wells. LT-1-85 was tested at concentrations ranging from 27 µM to 8.6 nM. Concentrations ranging from 30 µM to 9.7 nM were tested for CC-3-13P. Formula (IIB-A1) was tested at concentrations ranging from 26 µM to 8.4 nM. The plates were returned to the incubator for 48 hours. The final concentration of DMSO was 0.25% in all samples.

Following 48 hours of drug exposure, 10 µl of 0.2 mg/ml Resazurin in Mg2+, Ca2+ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with λex=535 nm and λem=590 nm filters. Resazurin dye in medium without cells was used to determine the background, which was subtracted from the data for all experimental wells. The data were normalized to the average fluorescence of the cells treated with media+0.25% DMSO (100% cell growth) and $EC_{50}$ values (the drug concentration at which 50% of the maximal observed growth inhibition is established) were determined using a standard sigmoidal dose response curve fitting algorithm (Prism 2.0, GraphPad Software Inc). Where the maximum inhibition of cell growth was less than 50%, an $EC_{50}$ value was not determined. The data in Table 25 summarize the growth inhibitory effects of LT-1-85, CC-3-13P and formula (IIB-A1) against HEK-293, PC-3 and RPMI 8226 cells. The $EC_{50}$ values indicate that LT-1-85 and CC-3-13P are cytotoxic against HEK-293, PC-3 and RPMI 8226 cells. Formula (IIB-A1) is cytotoxic against RPMI 8226 cells.

TABLE 25

$EC_{25}$ values of LT-1-85, CC-3-13P and formula (IIB-A1) against HEK-293, PC-3 and RPMI 8226 cells

| Compound | $EC_{50}$ (µM) | | |
|---|---|---|---|
| | HEK-293 | PC-3 | RPMI 8226 |
| LT-1-85 | 23 | 22 | 14 |
| | 22 | 19 | 13 |
| CC-3-13P | 2.6 | 4.0 | 2.7 |
| | 1.2 | 3.7 | 2.3 |
| Formula (IIB-A1) | >26 | >26 | 21 |
| | >26 | >26 | 21 |

Cell viability determined after 48 hr of drug exposure

Example 32

TTL3, TTL1, LT-1-45, LT-1-85 and Formula (IIB-A1) Inhibit the Expression of Genes Mediating Inflammation in the Murine Macrophage Cell Line RAW264.7

RAW 264.7 cells were seeded at $6-8×10^4$ cells/cm2 in RPMI 1640 medium containing 2 mM glutamine, 10% fetal calf serum (FCS) and 50 µg/ml penicillin, streptomycin and gentamicin. After 2 days in culture the medium was replaced by phenol-red free RPMI 1640 medium supplemented with 0.5 mM arginine and 2% FCS followed by the addition of the indicated stimuli. TTL3, TTL1, LT-1-45, LT-1-85 and formula (IIB-A1) were added to cells at the final concentration of 10 µM for 15 min. DMSO was used as a control. Cells were then stimulated with 200 ng/ml of LPS and 20 units/ml of IFNγ for 18 hr. NO release was measured as the accumulation of nitrite and nitrate in the incubation medium (phenol-red free). Nitrate was reduced to nitrite with nitrate reductase and was determined spectrophotometrically with Griess reagent. To determine the protein levels of COX-2 and NOS-2, cells ($1.5 \times 10^6$) were washed with PBS and collected by centrifugation. Cell pellets were homogenized with 100 µl of buffer A (10 mM Hepes; pH 7.9, 1 mM EDTA, 1 mM EGTA, 100 mM KCl, 1 mM dithiothreitol, 0.5 mM phenylmethylsulfonyl fluoride, 2 µg/ml aprotinin, 10 µg/ml leupeptin, 2 µg/ml Na-p-tosyl-L-lysine chloromethyl ketone, 5 mM NaF, 1 mM $Na_3VO_4$, 10 mM $Na_2MoO_4$). After 10 min at 4° C., Nonidet P-40 was added to reach a 0.5% concentration. The tubes were gently vortexed for 15 sec and centrifuged at 8,000×g for 15 min. The supernatants were stored at −80° C. until use. Protein content was assayed using the Bio-Rad protein reagent. Protein extracts were separated by 10% SDS-polyacrylamide gel electrophoresis. The gels were blotted onto a Hybond P membrane and then incubated with appropriate primary antibodies: anti-NOS-2 or anti-cyclooxygenase-2. Antibody against β-actin was used as a control to confirm the loading of each sample. The blots were revealed by ECL. Different exposure times of the films were used to ensure that bands were not saturated. Quantification of the films was performed by laser densitometry.

To determine whether the test compounds induce apoptosis, flow cytometric measurement of propidium iodide (PI) staining was performed after incubation of the cells with 0.005% PI, following published protocols. Cells were analyzed in a FACScan cytometer equipped with a 25-mW argon laser. The quantification of the percentage of apoptotic cells was calculated using a dot plot of the forward scatter against the PI fluorescence. Cell sorting and analysis of viable and apoptotic populations was performed to confirm the criteria of gating.

Figure 43:
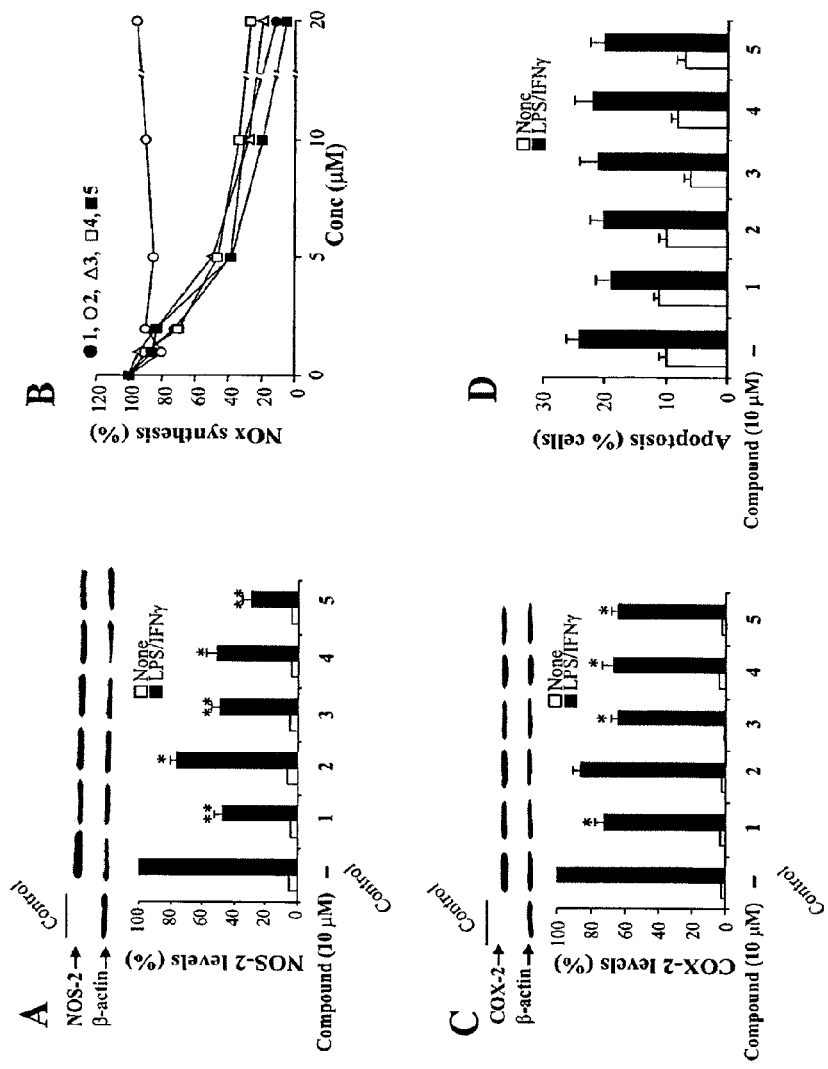
FIG. 43 depicts the effect of TTL3 and its analogs on NOS-2, COX-2 and NO in RAW264.7 cells stimulated with LPS/IFNγ.

As shown in FIG. 43A, the protein levels of NOS-2 in LPS/IFNγ stimulated cells were reduced by 50% to 70% when cells were treated with TTL3, LT-1-45, LT-1-85 and formula (IIB-A1). In agreement with these observations, the synthesis of NO induced by LPS/IFNγ (FIG. 43B) was also reduced. When COX-2 levels (FIG. 43C) were measured, a decrease of ~30-40%, depending on the compound tested was observed.

According FIG. 43D, TTL3, TTL1, LT-1-45, LT-1-85 and formula (IIB-A1) when tested at 10 µM did not affect RAW264.7 cell viability.

Example 33

Effect of TTL3, TTL1, LT-1-45, LT-1-85 and Formula (IIB-A1) on the NIK/NF-κB Pathway The ($κB_3$)ConA.LUC plasmid contains three copies of the κB motifs from the human immunodeficiency virus long terminal repeat enhancer linked to the minimal conalbumin A promoter and it was used to measure NF-κB activity. The ConA.LUC vector, lacking the κB tandem, was used as a control in the assays. A pRK5-myc-NIK and a kinase-deficient (K429A/K430A, NIK-KD) NIK expression vectors were used to transiently transfect the RAW264.7 cells. Plasmids were purified using EndoFree Qiagen columns. When co-transfection assays were performed the ratio between the NIK and κB-LUC plasmids was 3 to 1 in molecular terms. Subconfluent cell cultures (RAW264.7 cells) were washed twice with a phosphate-buffered saline and maintained with 2 ml of RPMI 1640 medium and 2% FCS in 6-cm-diameter dishes. Cells were transfected for 24 h with JetPEI following the instructions of the supplier. Treatment with tested compounds was carried out 30 min before stimulation with LPS/IFNγ. Reporter assays were performed measuring the luciferase activity of firefly/renilla dual transfection system, following the recommendations of the supplier.

Figure 44:
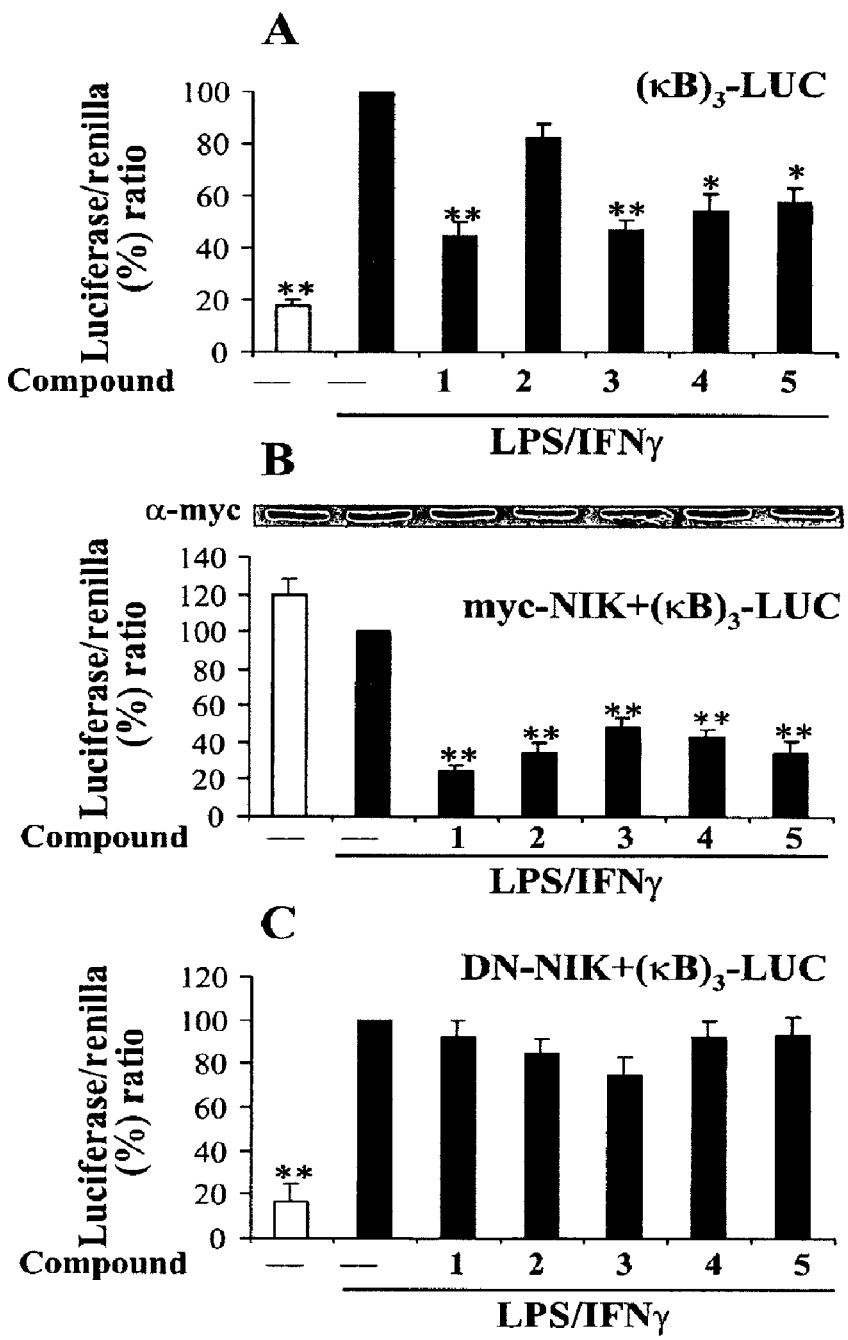
FIG. 44 depicts the effect of TTL3, TTL1, LT-1-45, LT-1-85 and Formula (IIB-A1) on the NIK/NF-κB pathway.

As shown in FIG. 44A, all tested compounds, except TTL1, inhibit the NF-κB mediated luciferase reporter gene activity in the $(κB)_3$-LUC transfected RAW 264.7 cells significantly. When the cells were co-transfected with a myc-NIK plasmid and the $(κB)_3$-LUC reporter construct. The INF-κB-mediated luciferase activity was almost abolished when cells were treated with tested compounds (FIG. 44B). These data suggest that NIK is a relevant target in the action of these compounds. These observations were further supported when cells were co-transfected with a kinase-dead NIK plasmid (DN-NIK) and the $(κB)_3$-LUC reporter construct. As shown in FIG. 44C, the inhibitory effects of tested compounds on NF-κB-mediated luciferase activity were diminished.

Example 34

Effect of TTL3 and Formula (IIB-A1) on the NIK Activity

After transfecting the RAW264.7 cells with pRK5-myc-NIK construct, $1 \times 10^7$ transfected cells were homogenized in buffer A (10 mM Hepes; pH 7.9, 1 mM EDTA, 1 mM EGTA, 100 mM KCl, 1 mM dithiothreitol, 0.5 mM phenylmethylsulfonyl fluoride, 2 µg/ml aprotinin, 10 µg/ml leupeptin, 2 µg/ml Nα-p-tosyl-L-lysine chloromethyl ketone, 5 mM NaF, 1 mM $Na_3VO_4$, 10 mM $Na_2MoO_4$). The tubes were gently vortexed for 15 s and centrifuged at 8000×g for 15 min. The supernatant (1 ml) was pre-cleared, and NIK was immunoprecipitated with 1 µg of anti-myc Ab. After extensive washing of the immunoprecipitate with buffer A, the pellet was resuspended in kinase buffer (modified buffer A containing 0.1 mM EDTA, 5 mM $MgCl_2$ and 10 nM okadaic acid). Kinase activity was assayed in 100 µl of kinase buffer containing 100 ng of immunoprecipitate, 50 µM [γ-$^{32}$P]ATP (0.5 µCi) and 100 ng of MBP as substrate.

Figure 45:
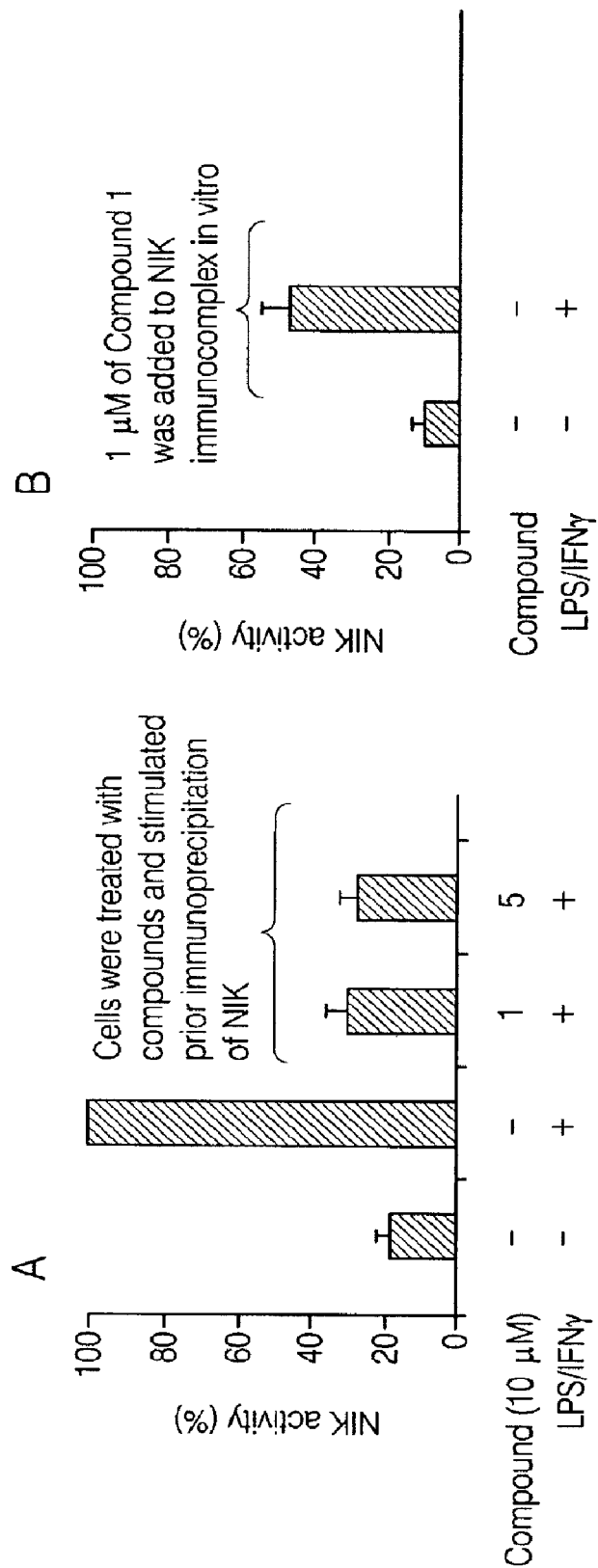
FIG. 45 depicts the effect of TTL3 and Formula (IIB-A1) on NIK activity. Compound 1 and 5 represent TTL3 and Formula (IIB-A1).

When cells transfected with a pRK5-myc-NIK plasmid and were stimulated with LPS/IFNγ in the presence of TTL3 and formula (IIB-A1), a 70% inhibition of the NIK kinase activity was observed (FIG. 45A). To further support this observation, TTL3 at 1 µM was directly added to the in vitro NIK kinase assay from LPS/IFNγ stimulated cells. As shown in FIG. 45B, the kinase activity of NIK was inhibited by 48%.

Example 35

TTL3 and Formula (IIB-A1) Inhibit the Myeloperoxidase Activity in the Mouse Ear Edema Model 2.5 µg of TPA dissolved in 20 µl of DMSO, was applied to both surfaces of the right ear of each mouse. The left ear (control) received the vehicle (DMSO). Tested compounds were administered topically (500 ng per ear in 20 µl of DMSO) simultaneously with TPA application. The reference drug, indomethacin, was administered at the same doses. After 4 h, the animals were killed by cervical dislocation and a 6 mm diameter disc from each ear was removed with a metal punch and weighed. Ear edema was calculated by subtracting the weight of the left ear (vehicle) from the right ear (treatment). Ear sections were homogenized in 750 μl of saline. After centrifugation at 10000×g for 15 min at 4° C., myeloperoxidase (MPO) activity was measured in supernatants.

Figure 46:
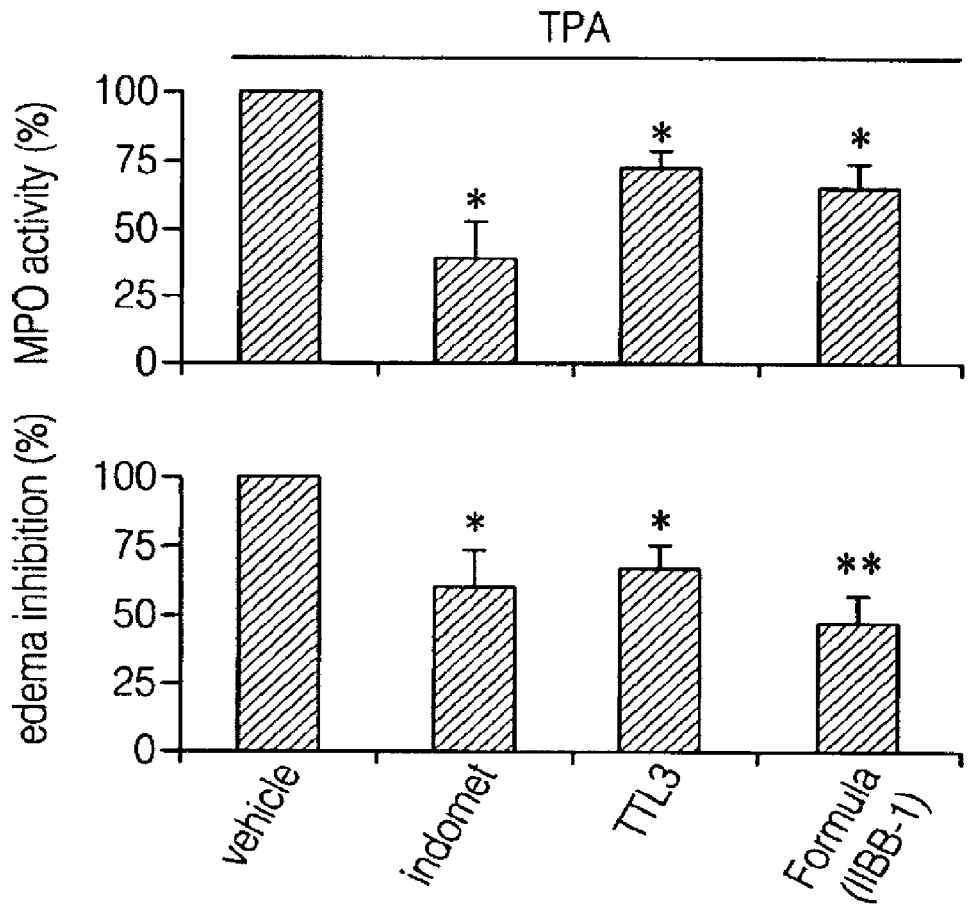
FIG. 46 shows that TTL3 and Formula (IIB-A1) inhibit TPA-induced ear edema.

As shown in the upper panel of FIG. 46, the myeloperoxidase activity due to infiltrated neutrophils, and induced by topic application of TPA to the ear, was significantly attenuated when animals received TTL3 or formula (IIB-A1). The edema was determined by weighing identical ear sections and this parameter was significantly reduced in animals treated with TTL3 or formula (IIB-A1).

Example 36

TTL3 and Formula (IIB-A1) Protect Against the Lethalit Induced by D-GalN/LPS in Mice Male BALB/c mice, 8 to 10 weeks old were induced an endotoxic shock. The lethal injury was produced by an intraperitoneal (i.p.) injection of LPS (2 μg/kg) in combination with D-GalN (800 mg/kg). 5 μmol/kg of TTL3 or formula (IIB-A1) were administered by i.p. injection (0.5 ml) 1 hour prior to the challenge of D-GalN/LPS. Saline was given to the control animals. The lethality was monitored until 24 h after the administration of D-GalN/LPS.

Figure 47:
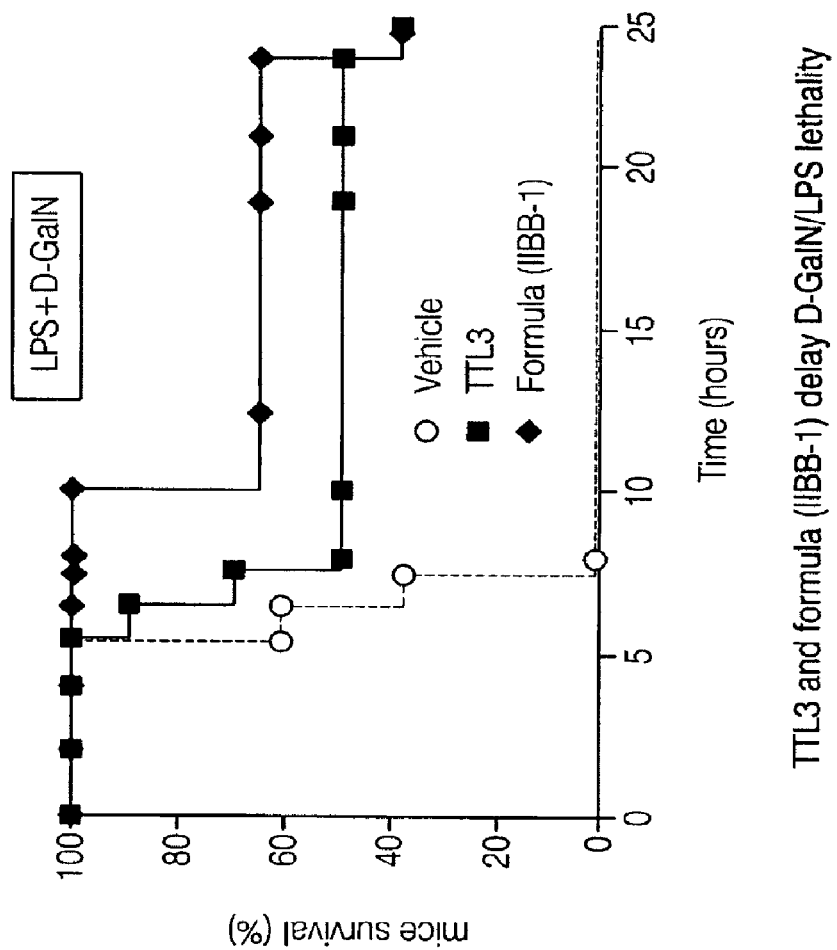
FIG. 47 shows that TTL3 and Formula (IIB-A1) delay D-GalN/LPS lethality.
Figure 48:
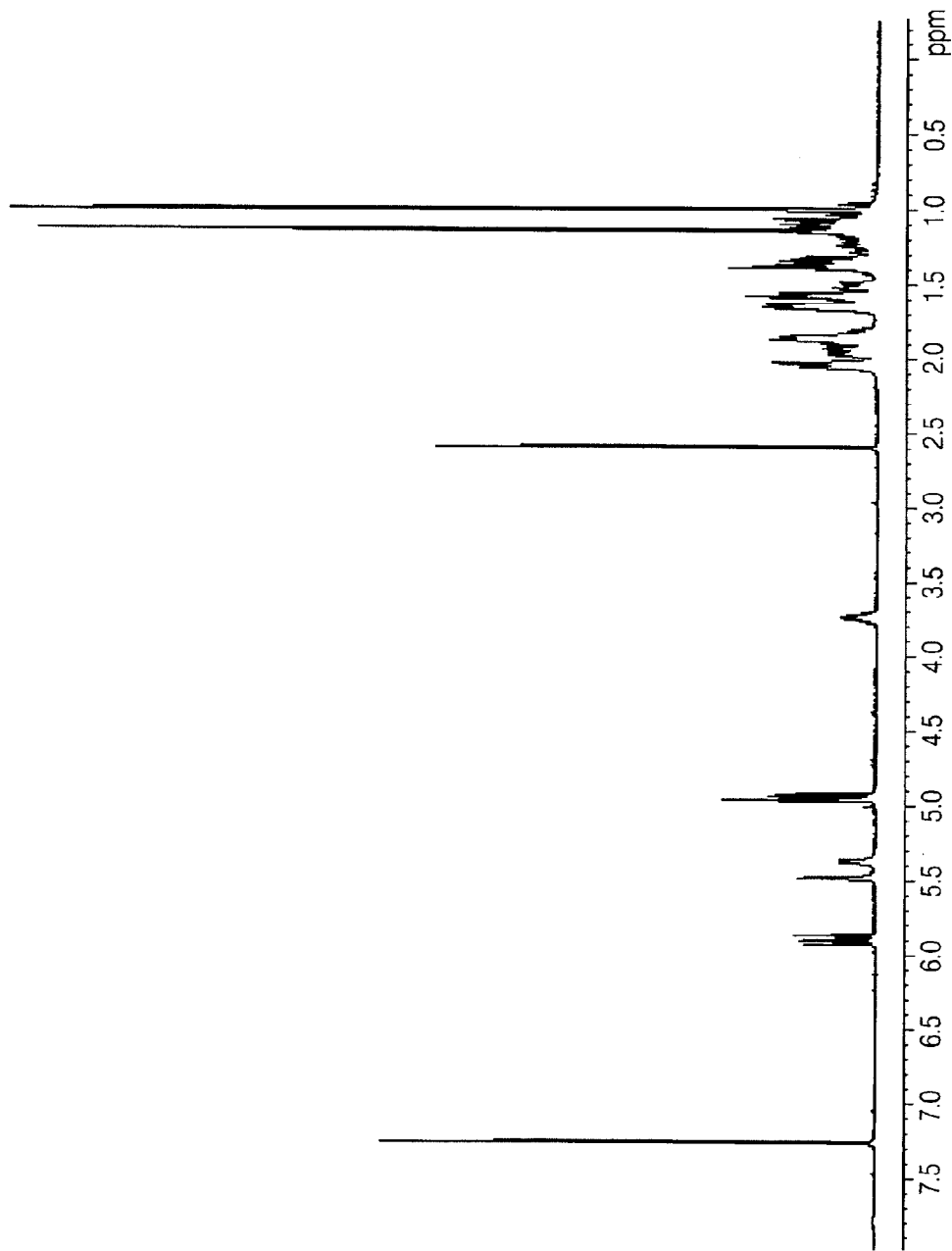
FIG. 48 depicts the $^1$H NMR spectrum in $CDCl_3$ of Formula (IIB-A1).
Figure 49:
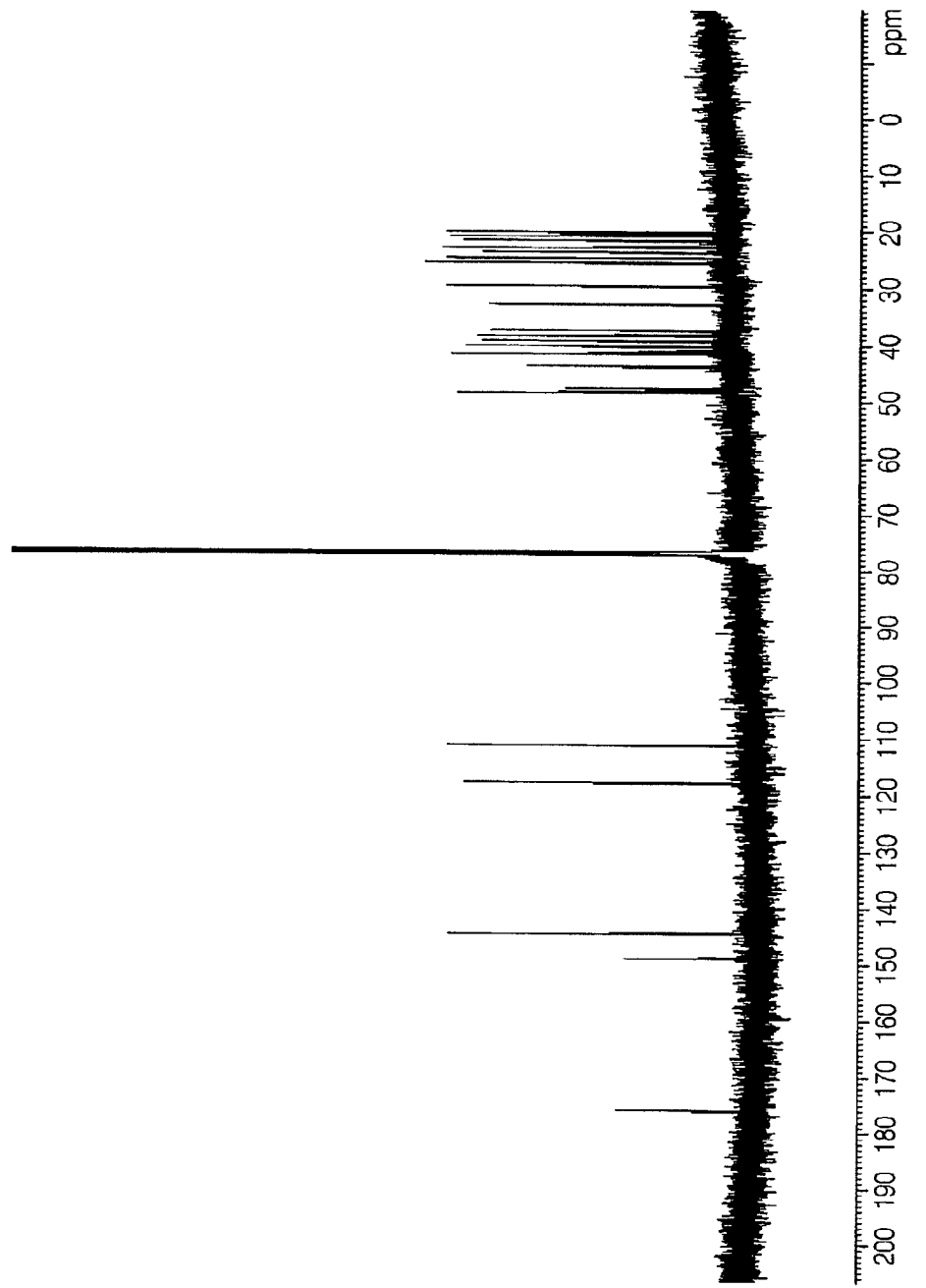
FIG. 49 depicts the $^{13}$C NMR spectrum in $CDCl_3$ of Formula (IIB-A1).
Figure 50:
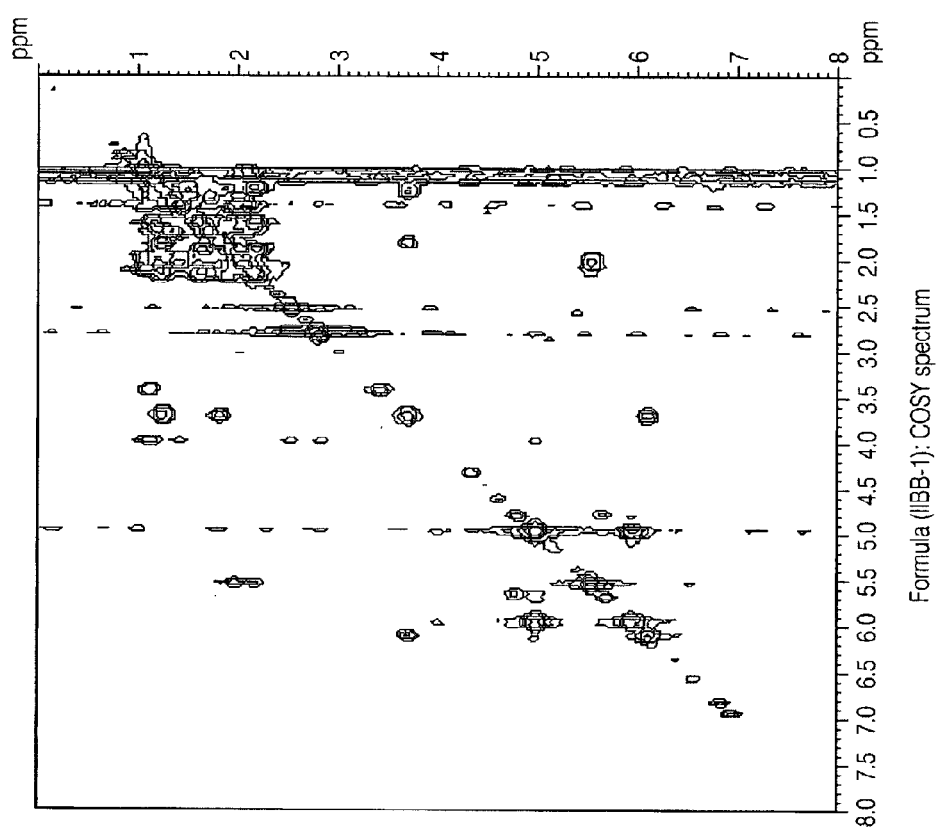
FIG. 50 depicts the COSY spectrum of Formula (IIB-A1).
Figure 51:
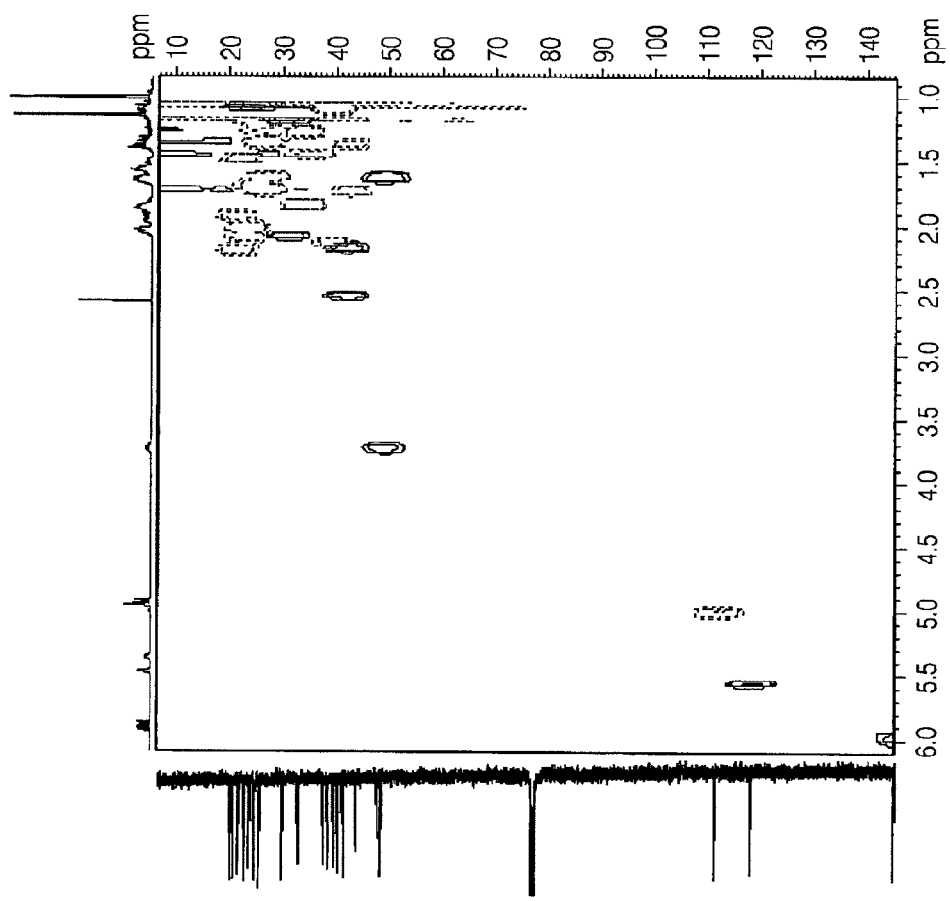
FIG. 51 depicts the $^1$H-$^{13}$C HSQC spectrum of Formula (IIB-A1).
Figure 52:
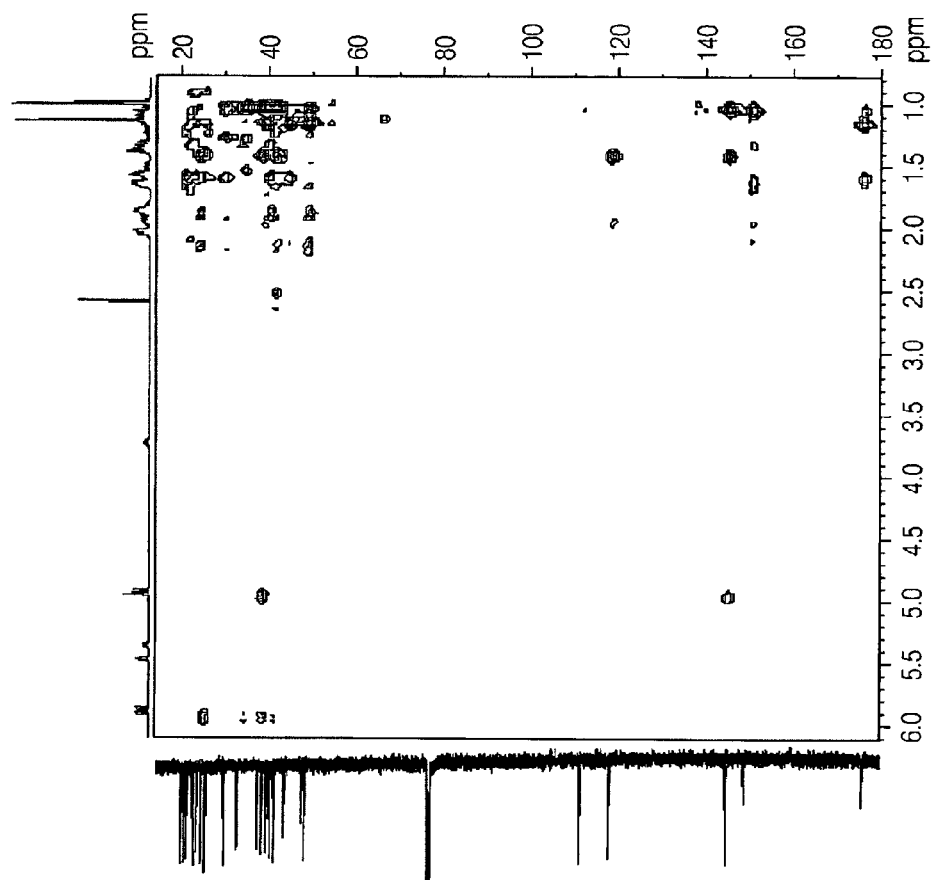
FIG. 52 depicts the $^1$H-$^{13}$C HMBC spectrum of Formula (IIB-A1).
Figure 53:
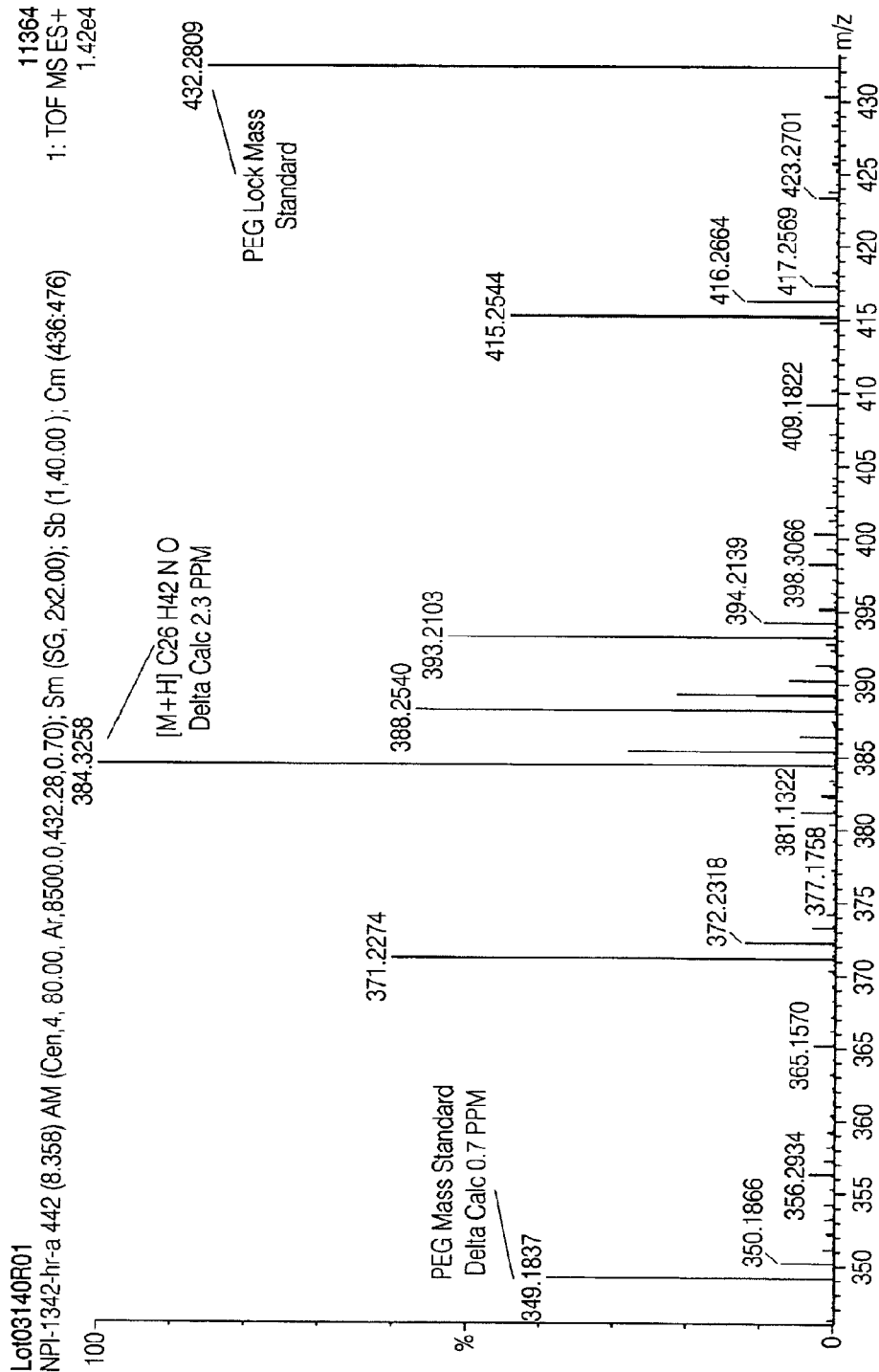
FIG. 53 depicts the HRMS spectrum of Formula (IIB-A1).
Figure 54:
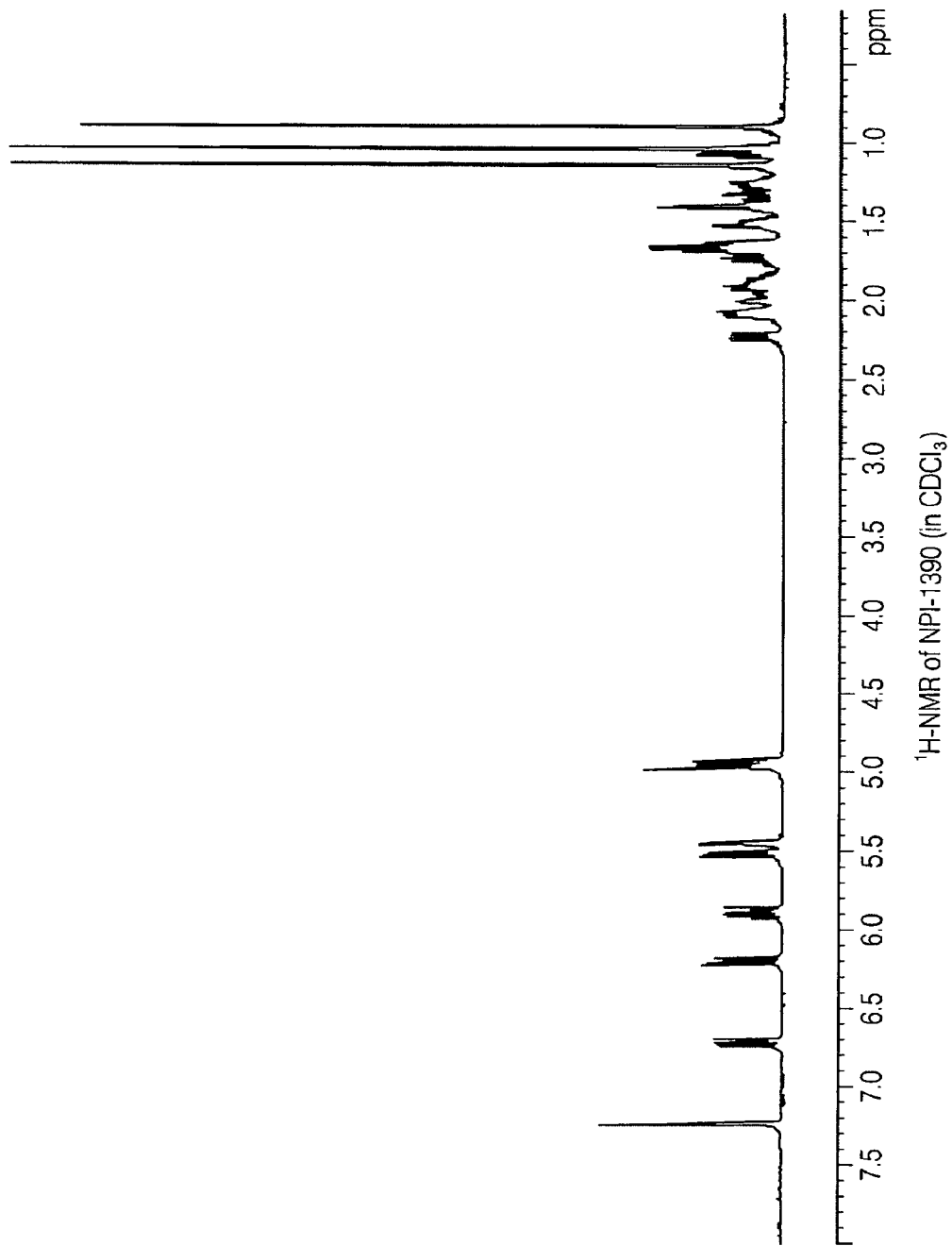
FIG. 54 depicts the $^1$H-NMR of NPI-1390 (in $CDCl_3$).
Figure 55:
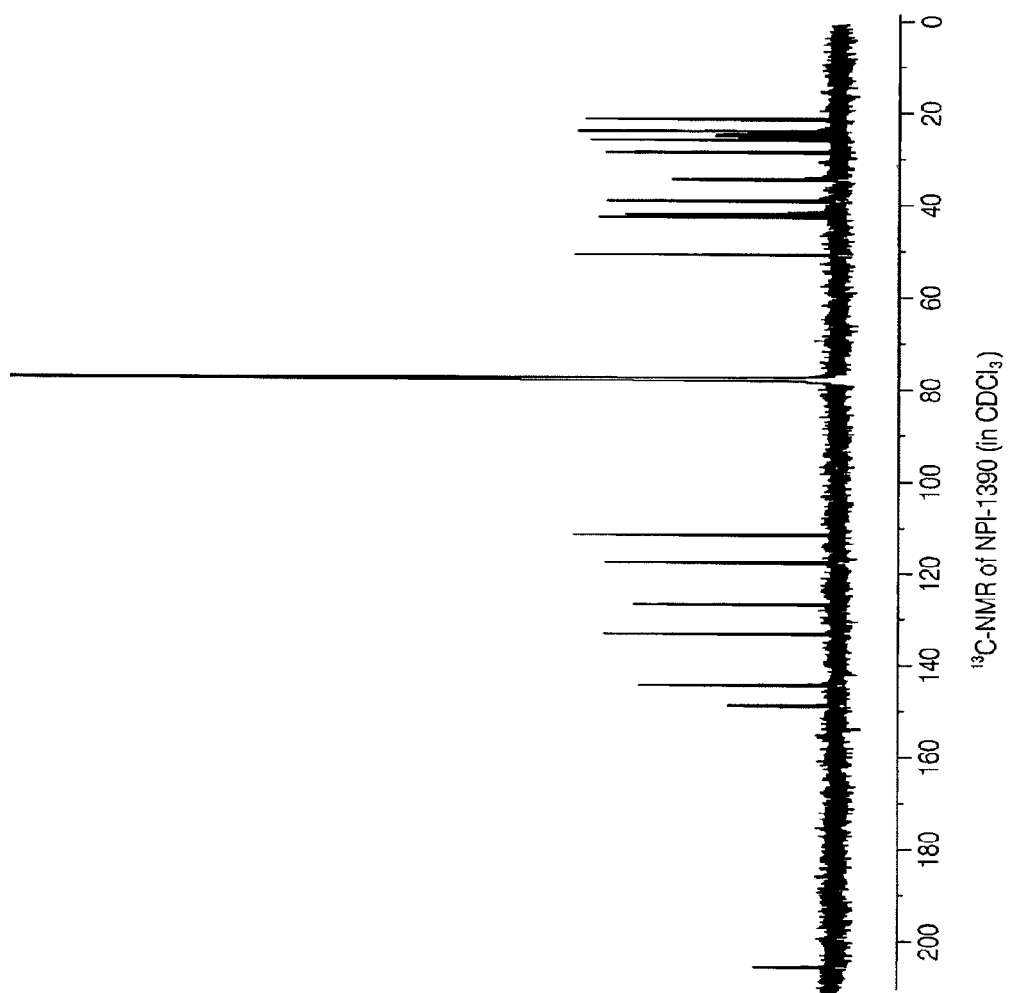
FIG. 55 depicts the $^{13}$C-NMR of NPI-1390 (in $CDCl_3$).
Figure 56:
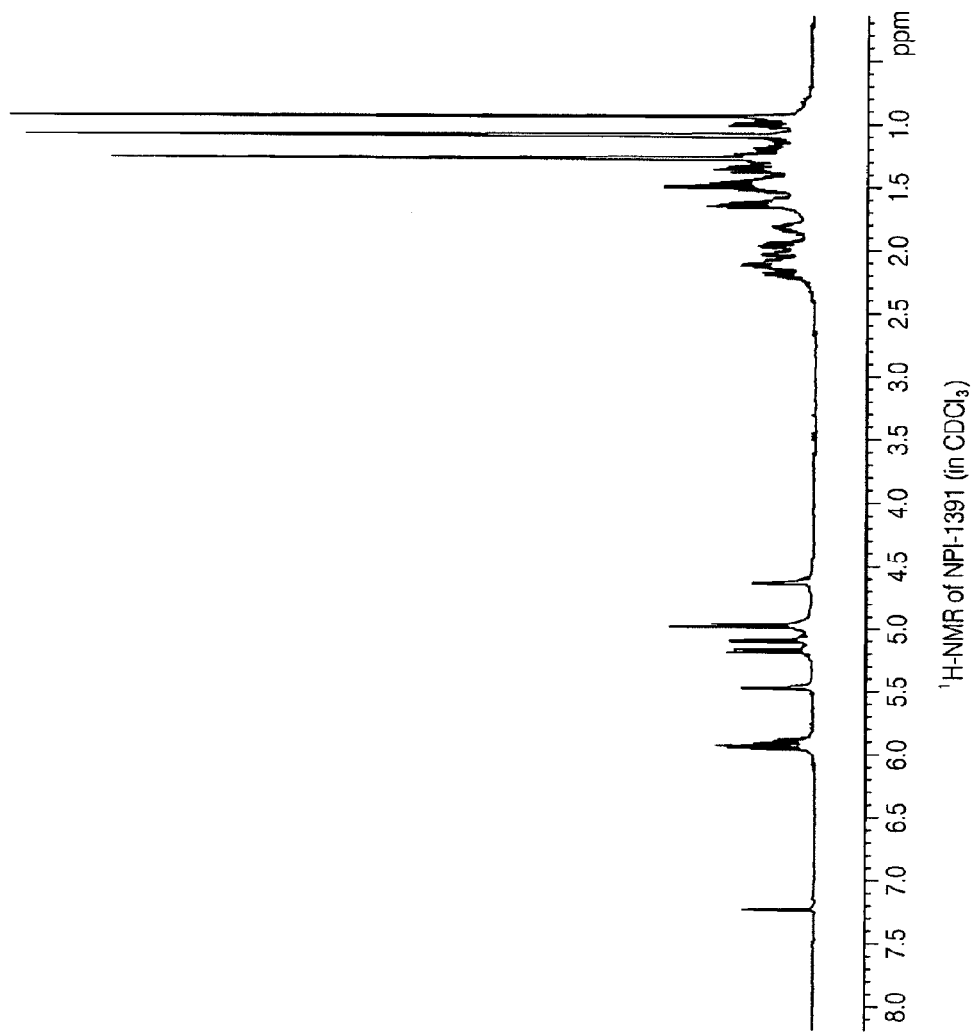
FIG. 56 depicts the $^1$H-NMR of NPI-1391 (in $CDCl_3$).
Figure 57:
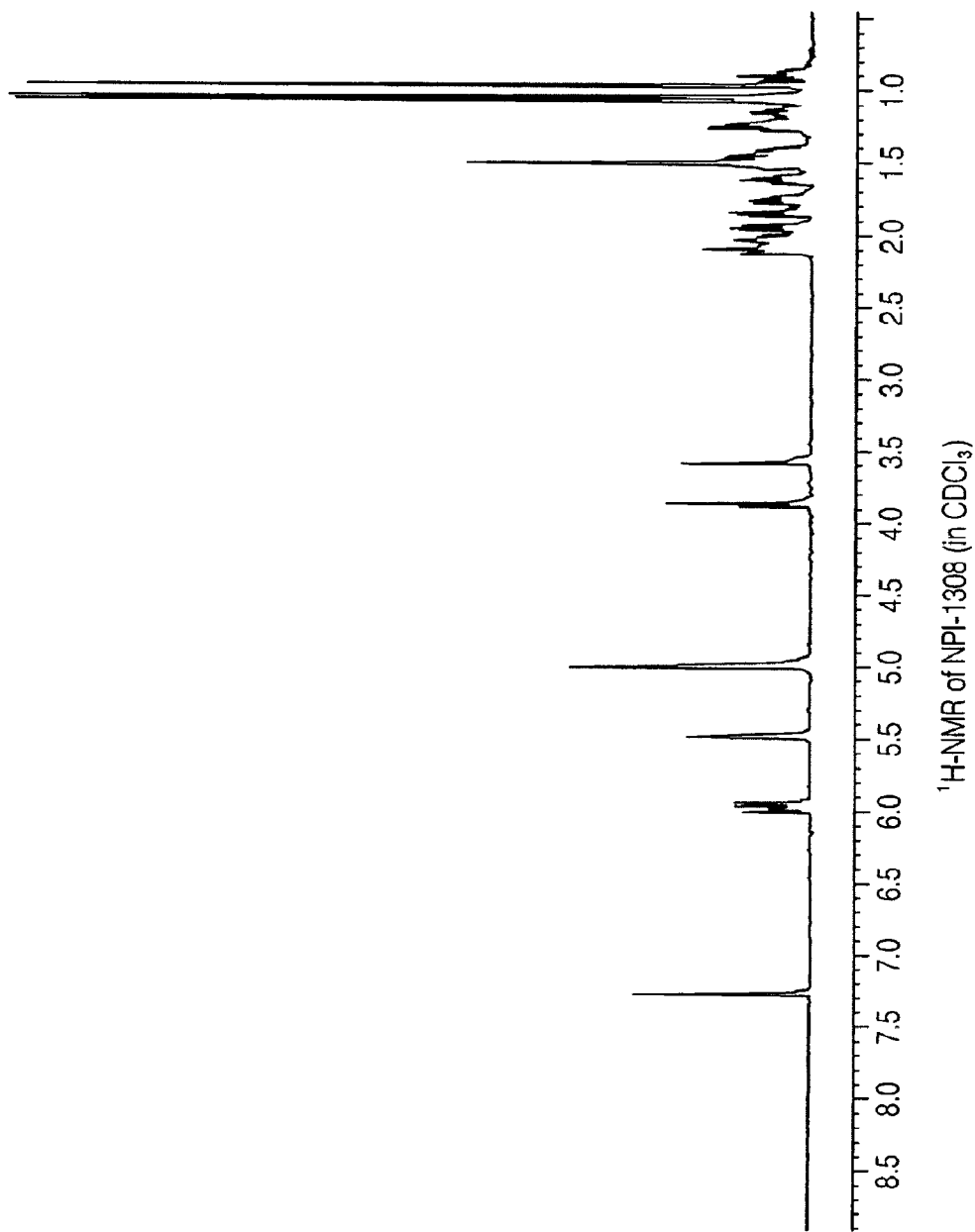
FIG. 57 depicts the $^1$H-NMR of NPI-1308 (in $CDCl_3$).
Figure 58:
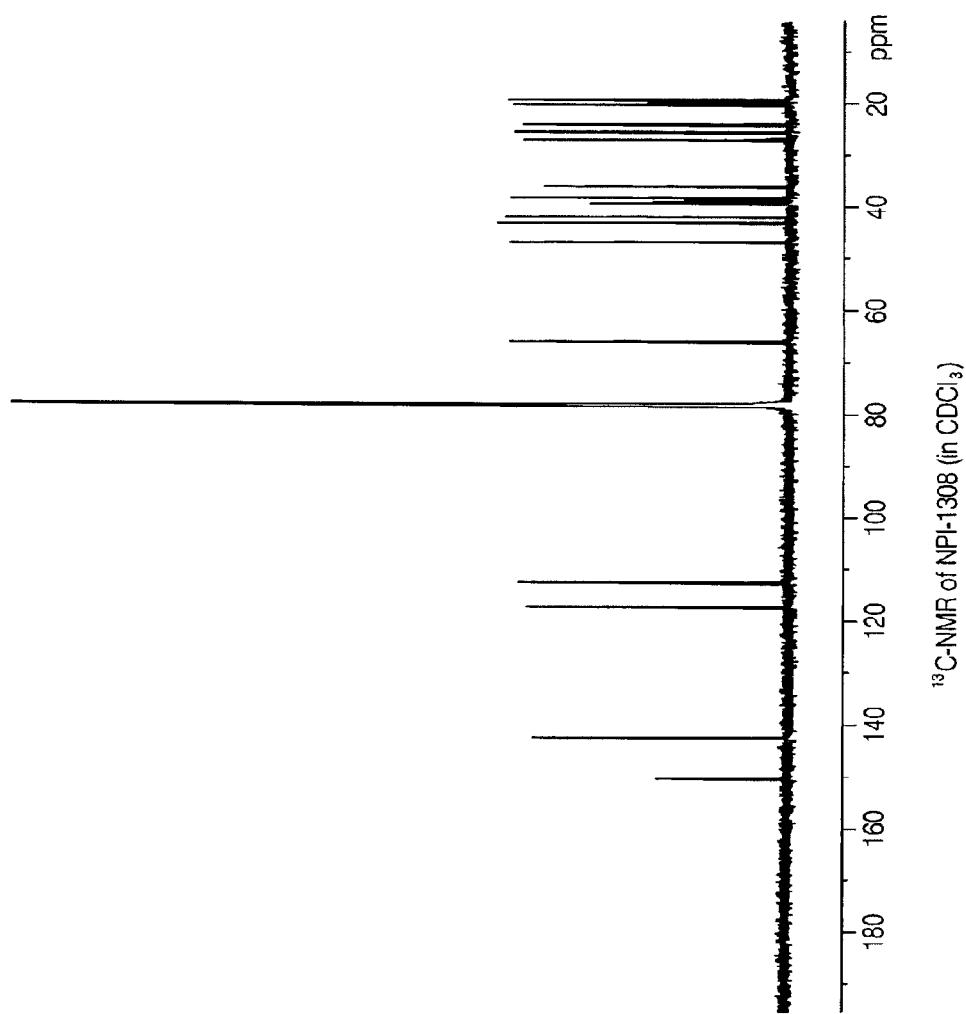
FIG. 58 depicts the $^{13}$C-NMR of NPI-1308 (in $CDCl_3$).
Figure 59:
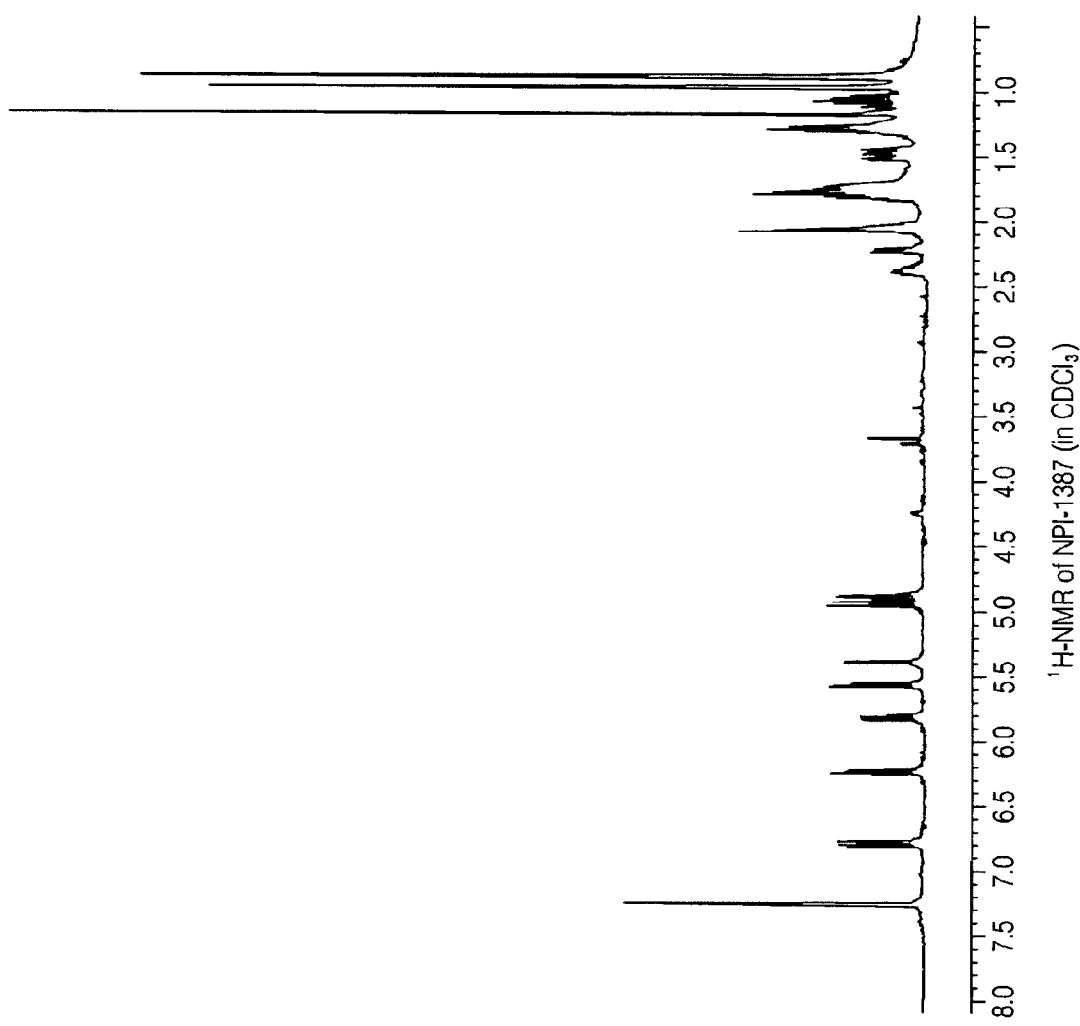
FIG. 59 depicts the $^1$H-NMR of NPI-1387 (in $CDCl_3$).
Figure 60:
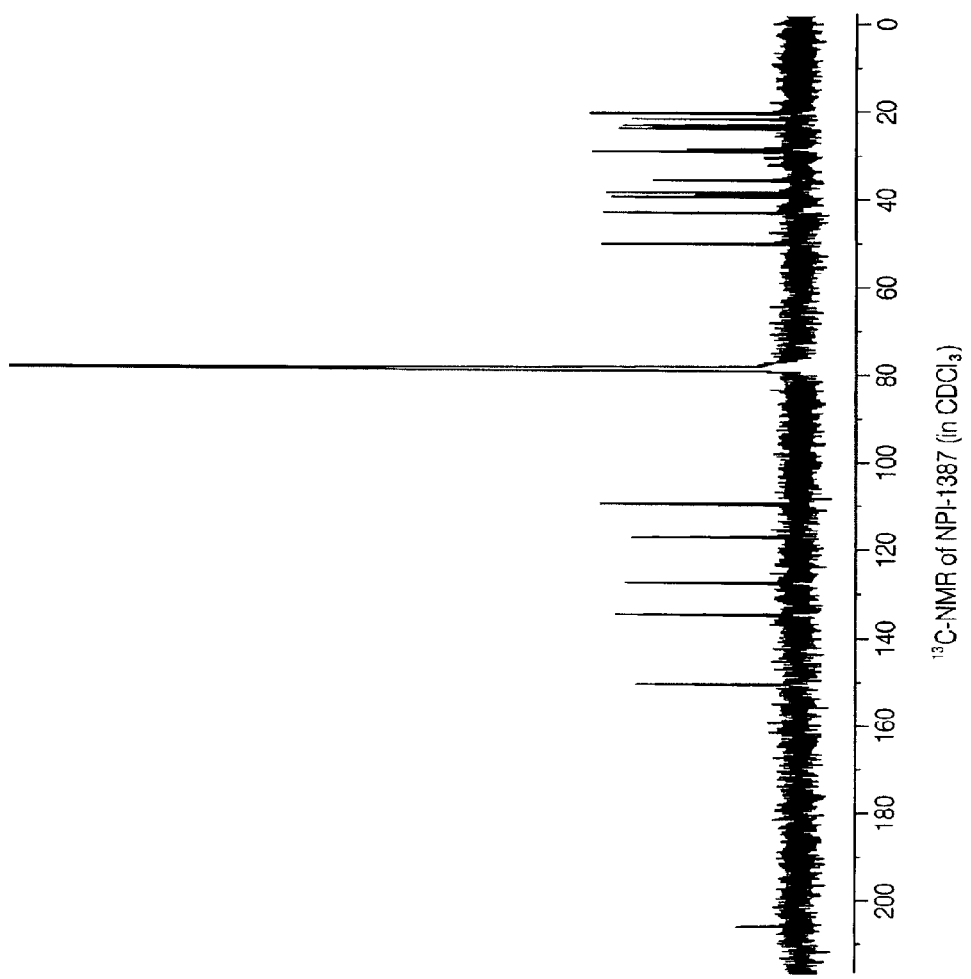
FIG. 60 depicts the $^{13}$C-NMR of NPI-1387 (in $CDCl_3$).
Figure 61:
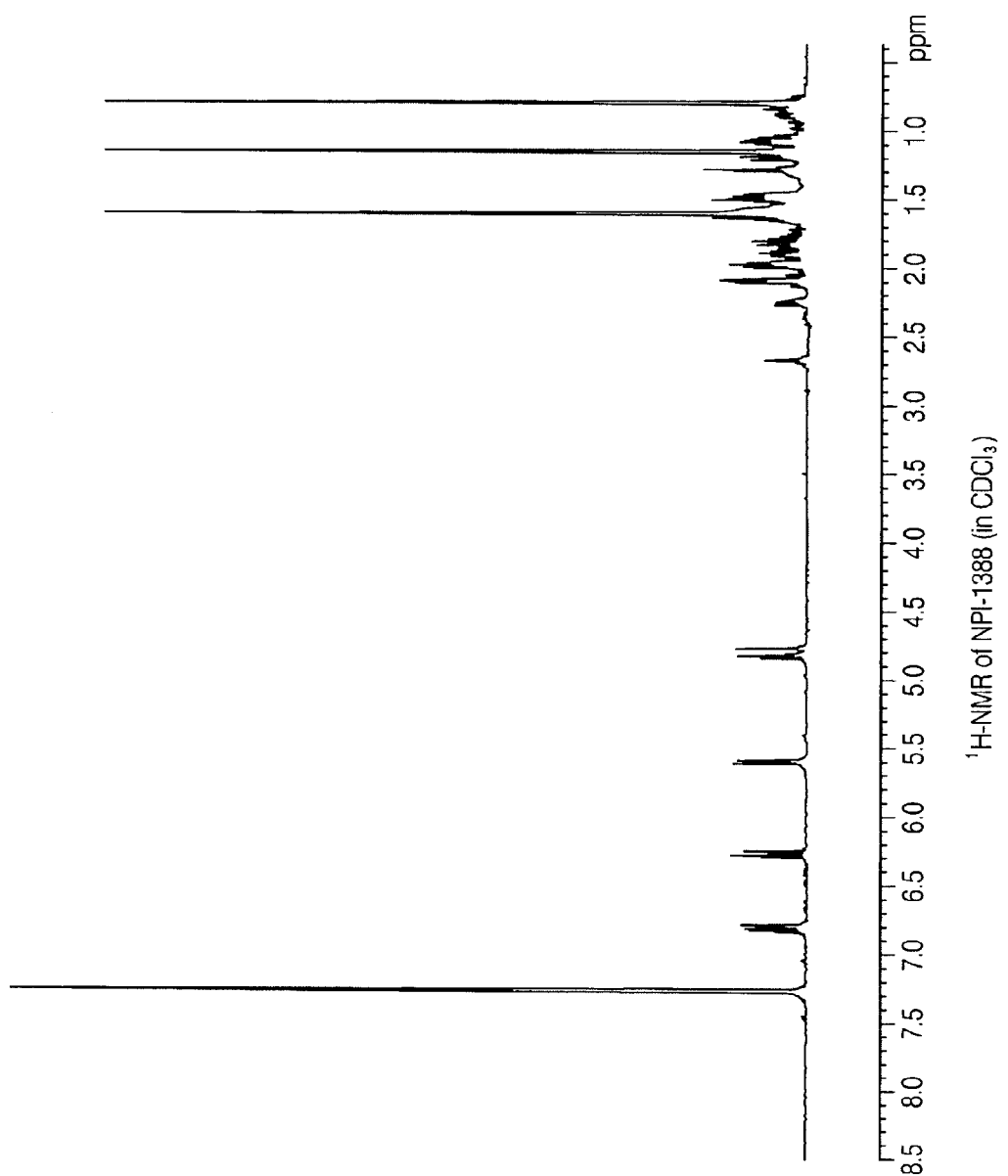
FIG. 61 depicts the $^1$H-NMR of NPI-1388 (in $CDCl_3$).

FIG. 47 shows that both TTL3 and formula (IIB-A1) exerted a significant protection against the lethality induced by an acute dose of D-GalN/LPS, extending three folds the survival time of the mice with respect to the controls treated with vehicle.

Example 37

TNF-α Inhibition Assay of the Acanthoic Acid Analogs RAW264.7 LPS/TNF Assay:

7.5×10³/well of RAW264.7 cells were seeded in 96 well plate overnight and the acanthoic acid analogs of an appropriate concentration were added 1 hr before LPS (10 ng/ml) stimulation. After 4 hr LPS stimulation, supernatants were harvested and analyzed for TNF production by ELISA.

DMSO was used as control. Identical sets of plates without LPS stimulation were used for the cytotoxicity assessment.

TABLE 24

TNF-α inhibitory activity of the acanthoic acid analogs possessing amide and peptide functionality

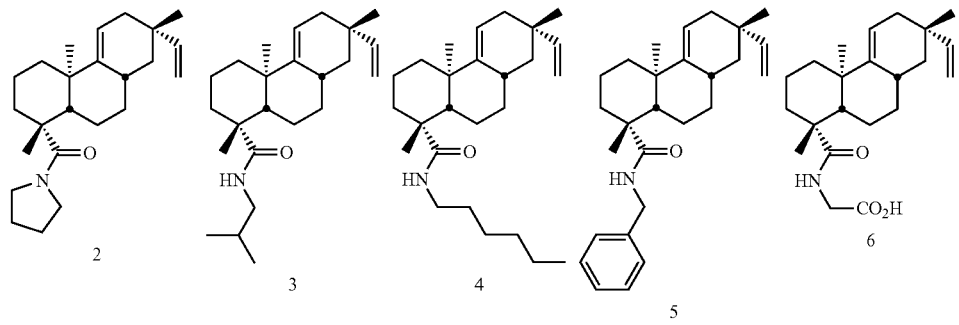

| | 2 | 3 | 4 | 5 | 6 |
|---|---|---|---|---|---|
| Inhibition (%) at 10 μM | 33.4 | 41.9 | 41.4 | 56.9 | 6.3 |

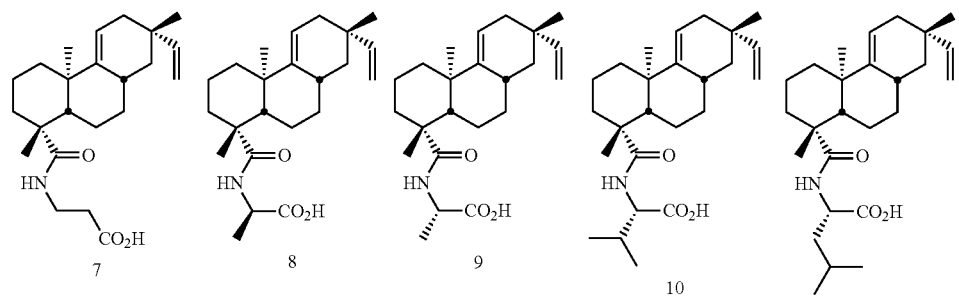

| | 7 | 8 | 9 | 10 | 11 |
|---|---|---|---|---|---|
| Inhibiton (%) at 10 μM | 10.3 | 41.6 | 96.7 | 88.0 | 81.0 |

TABLE 24-continued

TNF-α inhibitory activity of the acanthoic acid analogs possessing amide and peptide functionality

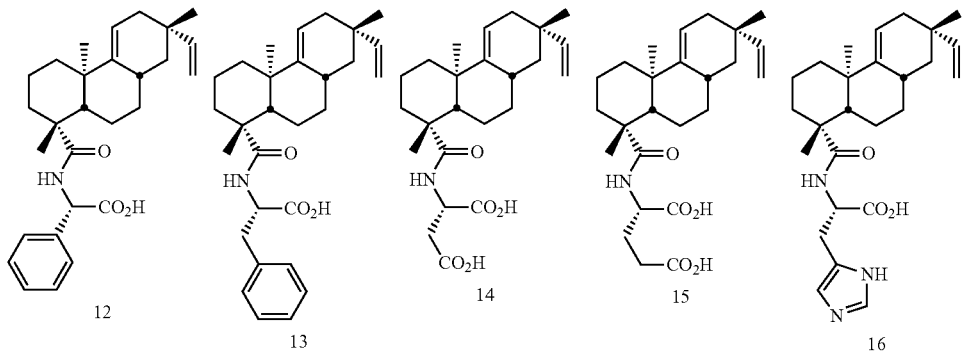

| | 12 | 13 | 14 | 15 | 16 |
|---|---|---|---|---|---|
| Inhibition (%) at 10 µM | 95.0 | 85.0 | — | — | — |

TABLE 25

TNF-α inhibitory activity of the acanthoic acid analogs possessing alcohol functionality

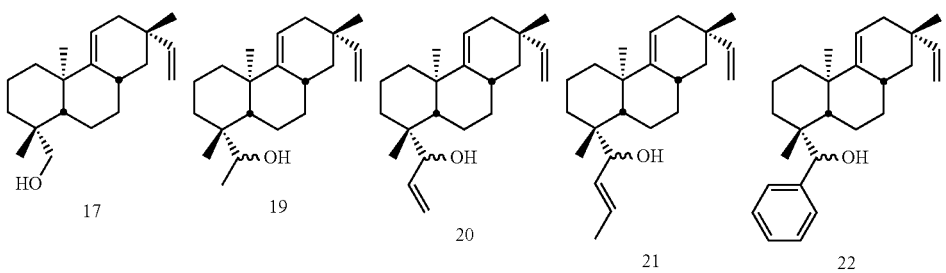

| | 17 | 19 | 20 | 21 | 22 |
|---|---|---|---|---|---|
| Inhibition (%) at 10 µM | 28.5 | 41.9 | 27.6 | 48.0 | 23.1 |

TABLE 26

TNF-α inhibitory activity of the acanthoic acid analogs possessing ketone functionality

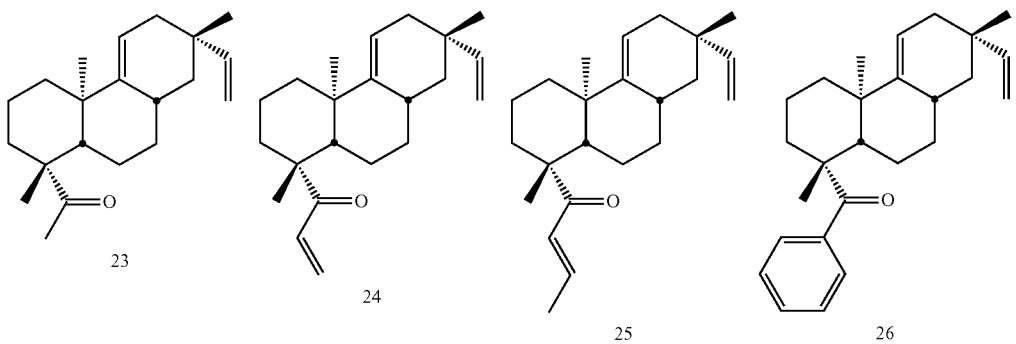

| | 23 | 24 | 25 | 26 |
|---|---|---|---|---|
| Inhibition (%) at 10 µM | 7.0 | 96.0 | 29.0 | 6.9 |

TABLE 27
TNF-α inhibitory activity of the acanthoic acid analogs possessing oxime functionality
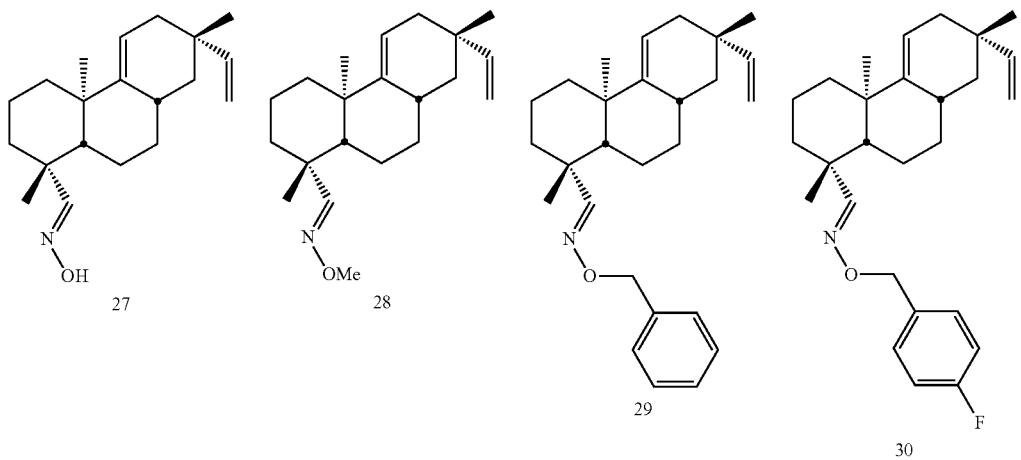
| | 27 | 28 | 29 | 30 |
|---|---|---|---|---|
| Inhibition (%) at 10 μM | 75.9 | No Activity | 13.0 | 6.0 |
TABLE 28
TNF-α inhibitory activity of the acanthoic acid analogs possessing sulfonate functionality
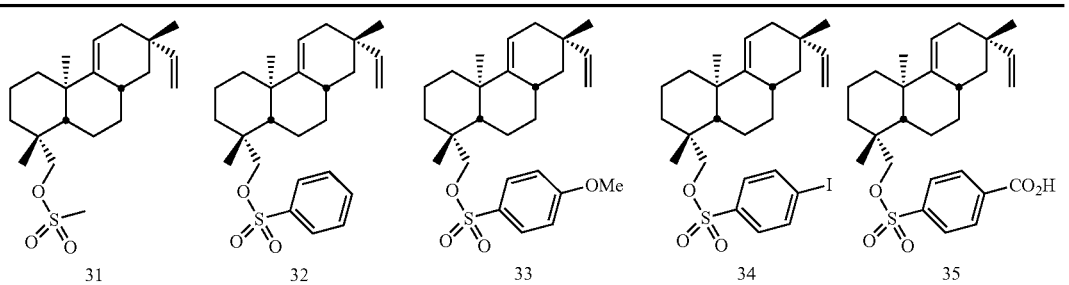
| | 31 | 32 | 33 | 34 | 35 |
|---|---|---|---|---|---|
| Inhibition (%) at 10 μM | 74.0 | 32.0 | 32.0 | 28.0 | 41.0 |
TABLE 29
TNF-α inhibitory activity of the acanthoic acid analogs possessing ester functionality
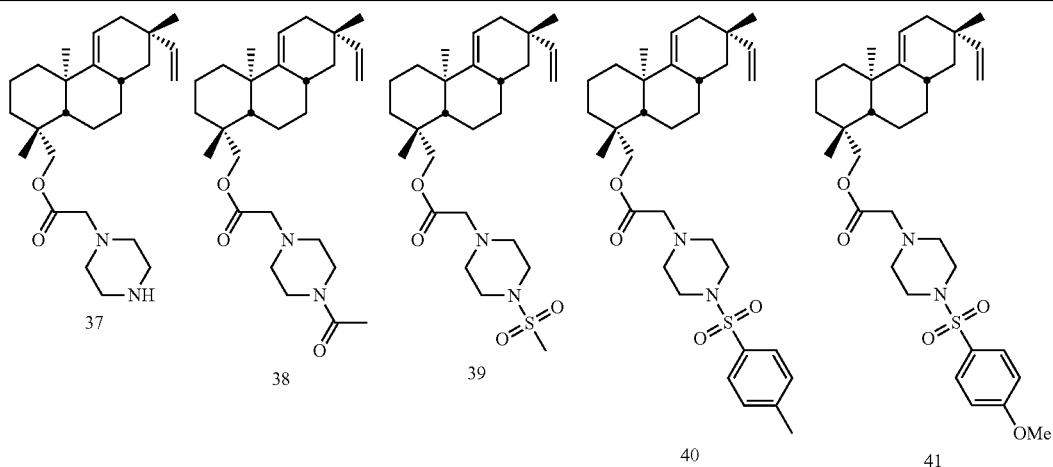

TABLE 29-continued

TNF-α inhibitory activity of the acanthoic acid analogs possessing ester functionality

| Inhibition (%) at 10 μM | 45.0 | 18.0 | 17.0 | 11.0 | 32.0 |
|---|---|---|---|---|---|
| Compound | 42 | 43 | 44 | 45 | 46 |
| Inhibition (%) at 10 μM | 68.5 | 86.0 | 30.0 | 81.9 | 11.5 |

Example 38

Anti-Cancer Assays

The compounds disclosed herein are tested against the National Cancer Institute (NCI) screening panel, which consists of 60 human tumor cell lines that represent leukemia, melanoma and cancers of the lung, colon, brain, ovary, breast, prostate and kidney. A detailed description of the screening procedure can be found at hypertext transfer protocol (http://) "dtp.nci.nih.gov/branches/btb/ivclsp.html." The following is a list of the cancers:

LUNG: NCI-H23, NCI-H522, A549-ATCC, EKVX, NCI-H226, NCI-H332M, H460, H0P62, HOP92; COLON: HT29, HCC-2998, HCT116, SW620, COL0205, HCT15, KM12; BREAST: MCF7, MCF7ADRr, MDAMB231, HS578T, MDAMB435, MDN, BT549, T47D; OVARIAN: OVCAR3, OVCAR4, OVCAR5, OVCAR8, IGROV1, SKOV3; LEUKEMIA: CCRFCEM, K562, MOLT4, HL60, RPMI8266, SR; RENAL: UO31, SN12C, A498, CAKI1, RXF393, 7860, ACHN, TK10; MELANOMA: LOXIMVI, MALME3M, SKMEL2, SKMEL5, SKMEL28, M14, UACC62, UACC257; PROSTATE: PC3, DU145; and CNS: SNB19, SNB75, U251, SF268, SF295, SM539.

In brief, each of the 60 human tumor cell lines are grown in RPMI 1640 medium, supplemented with 5% fetal bovine serum and 2 mM L-glutamine. Cells are plated at their appropriate density in 96-well microtiter plates and incubated at 37° C., 5% $CO_2$, 95% air and 100% relative humidity. After 24 hours, 100 μL of various 10-fold serial dilutions of a compound of Formula II, IIA, or IIB are added to the appropriate wells containing 100 μL of cells, resulting in a final compound concentration ranging from 10 nM to 100 μM. Cells are incubated for an additional 48 hours and a sulforhodamine B protein assay is used to estimate cell viability or growth.

Three dose response parameters are calculated as follows:
$GI_{50}$ indicates the concentration that inhibits growth by 50%.
TGI indicates the concentration that completely inhibits growth.
$LC_{50}$ indicates the concentration that is lethal to 50% of the cells.

Example 39

Growth Inhibition of Tumor Cell Lines

B16-F10 (ATCC; CRL-6475), DU 145 (ATCC; HTB-81), HEK293 (ATCC; CRL-1573), HT-29 (ATCC; HTB-38), LoVo (ATCC; CCL-229), MDA-MB-231 (ATCC; HTB-26), MIA PaCa-2 (ATCC; CRL-1420), NCI-H292 (ATCC; CRL-1848), OVCAR-3 (ATCC; HTB-161), PANC-1 (ATCC; CRL-1469), PC-3 (ATCC; CRL-1435), RPMI 8226 (ATCC; CCL-155) and U266 (ATCC; TIB-196) are maintained in appropriate culture media. The cells are cultured in an incubator at 37° C. in 5% CO2 and 95% humidified air.

For cell growth inhibition assays, B16-F10, DU 145, HEK293, HT-29, LoVo, MDA-MB-231, MIA PaCa-2, NCI-H292, OVCAR-3, PANC-1, PC-3, RPMI 8226 and U266 cells are seeded at $1.25 \times 10^3$, $5 \times 10^3$, $1.5 \times 10^4$, $5 \times 10^3$, $5 \times 10^3$, $1 \times 10^4$, $2 \times 10^3$, $4 \times 10^3$, $1 \times 10^4$, $7.5 \times 10^3$, $5 \times 10^3$, $2 \times 10^4$, $2.5 \times 10^4$ cells/well respectively in 90 μl complete media into Corning 3904 black-walled, clear-bottom tissue culture plates. 20 mM stock solutions of compounds of Formula II, IIA, and IIB are prepared in 100% DMSO, aliquoted and stored at −80° C. Compounds of Formula II, IIA, and IIB are serially diluted and added in triplicate to the test wells resulting in final concentrations ranging from of 20 μM to 0.2 pM. The plates are returned to the incubator for 48 hours. The final concentration of DMSO is 0.25% in all samples.

Following 48 hours of drug exposure, 10 μl of 0.2 mg/ml resazurin (obtained from Sigma-Aldrich Chemical Co.) in $Mg^{2+}$, $Ca^{2+}$ free phosphate buffered saline is added to each well and the plates are returned to the incubator for 3-6 hours. Since living cells metabolize Resazurin, the fluorescence of the reduction product of Resazurin is measured using a Fusion microplate fluorometer (Packard Bioscience) with $\lambda_{ex}=535$ nm and $\lambda_{em}=590$ nm filters. Resazurin dye in medium without cells was used to determine the background, which is subtracted from the data for all experimental wells. The data are normalized to the average fluorescence of the cells treated with media+0.25% DMSO (100% cell growth)

and $EC_{50}$ values (the drug concentration at which 50% of the maximal observed growth inhibition is established) are determined using a standard sigmoidal dose response curve fitting algorithm (generated by XLfit 3.0, ID Business Solutions Ltd or Prism 3.0, GraphPad Software Inc).

Example 40

Growth Inhibition of Tumor Cell Lines

Compounds 1387 and 1388 were tested as described in Example 39 against RPMI 8226, U266, PC-3, HT-29, MDA-MB-231, and B16-F10 melanoma. The results are shown below in Tables 30-31.

TABLE 30

In vitro cytotoxicity (48 hr) of NPI-1387 and NPI-1388 against various human tumor cell lines

| | Compound Tested (Ref# or Lot#) | | | |
|---|---|---|---|---|
| | NPI-1387 (05220R01, VRM.124.153.01, VRM.124.108.01) | | NPI-1388 (0522R02) | |
| Cell line | $IC_{50}$ (µM) | n | $IC_{50}$ (µM) | n |
| RPMI 8226 (MM) | 5.1 ± 1.0 | 5 | 4.1 ± 1.1 | 5 |
| U266 (MM) | 8.7 ± 6.4 | 5 | 8.6 ± 6.4 | 5 |
| PC3 (Prostate) | 11 ± 2 | 7 | 10 ± 3 | 5 |
| HT-29 (Colon) | 14 ± 6 | 8 | 17 ± 4 | 6 |
| MDA-MB-231 (Breast) | 18 ± 2 | 6 | 14 ± 5 | 6 |

TABLE 31

In vitro cytotoxicity (48 hr) against murine B16-F10 melanoma cells

| | | 10% FBS | |
|---|---|---|---|
| Compound | Lot/Ref # | IC50 (µM) | % cytotox |
| NPI-1387 | VRM.124.108.01 | 6.2 | 94 |
| | | 7.5 | 92 |

Individual values are shown

Example 40

Treatment/Inhibition of Resistant Multiple Myeloma

Transcription factor NF-KB is linked to growth and survival of multiple myeloma (MM) cells and blockade of NF-KB activity. NPI-1387 (Formula IIB-b1; compound 24 shown above under scheme 4), a potent small-molecule inhibitor of upstream activator of NF-KB, was administered to MM cells and its effect on the viability of MM cells, including those resistant to conventional agents dexamethasone or doxorubicin is shown. Treatment of MM cell lines (MM.1S, MM.1R, OCI-MyS, OPM-1, Dox-40) with NF-KB inhibitor for 48 h induces a dose-dependent significant (P<0.004; n=2) decrease in cell viability in all cell lines at pharmacological achievable concentrations ($IC_{50}$ range 25-40 µM). To determine whether NF-KB inhibitor-induced decrease in MM cell viability is due to apoptosis, various MM cell lines were treated at their respective $IC_{50}$ for 48 h; harvested; and analyzed for apoptosis.

Figure 62:
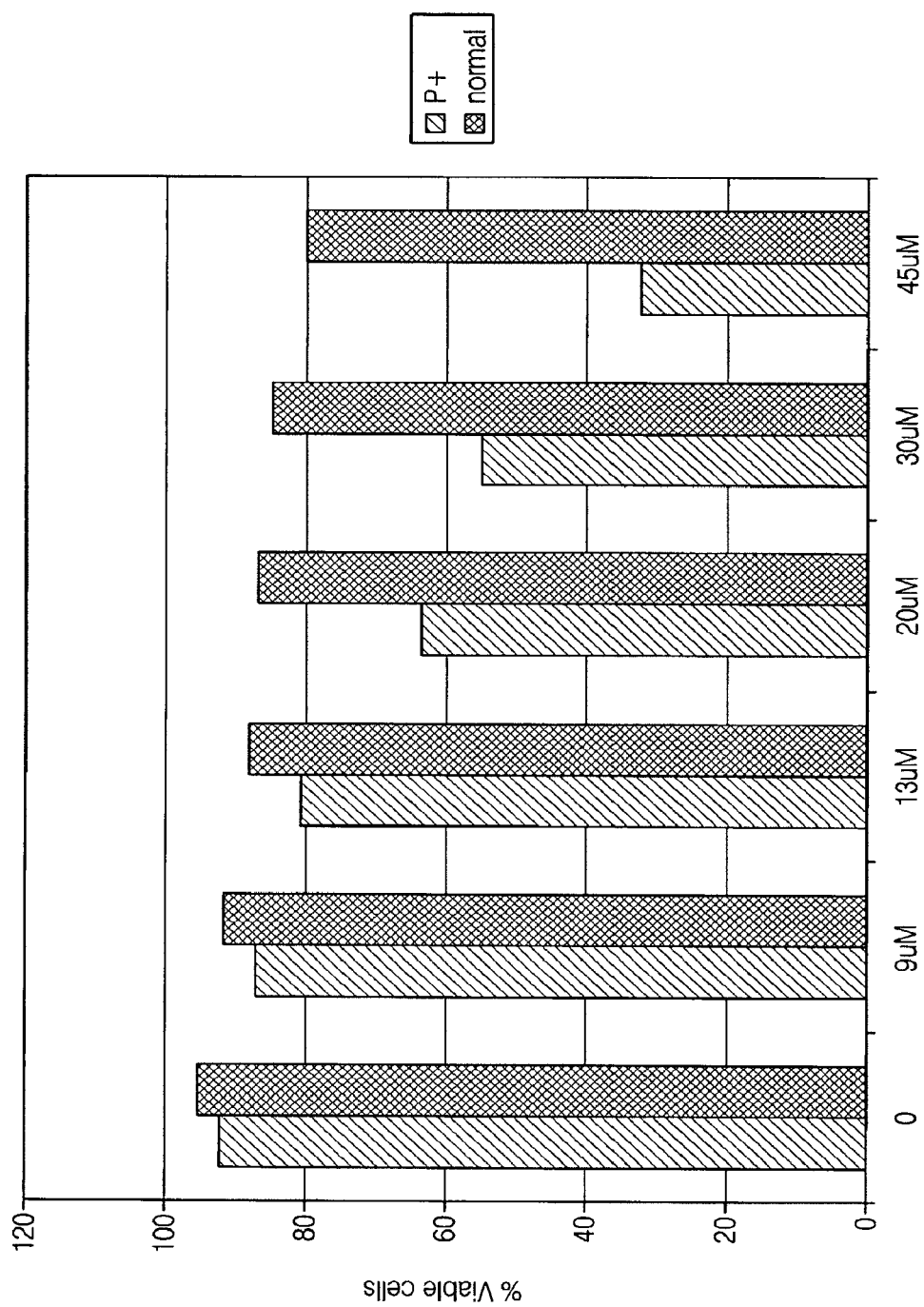
FIG. 62 shows the percentage of viable P+ and normal cells as a function of compound concentration.
Figure 63:
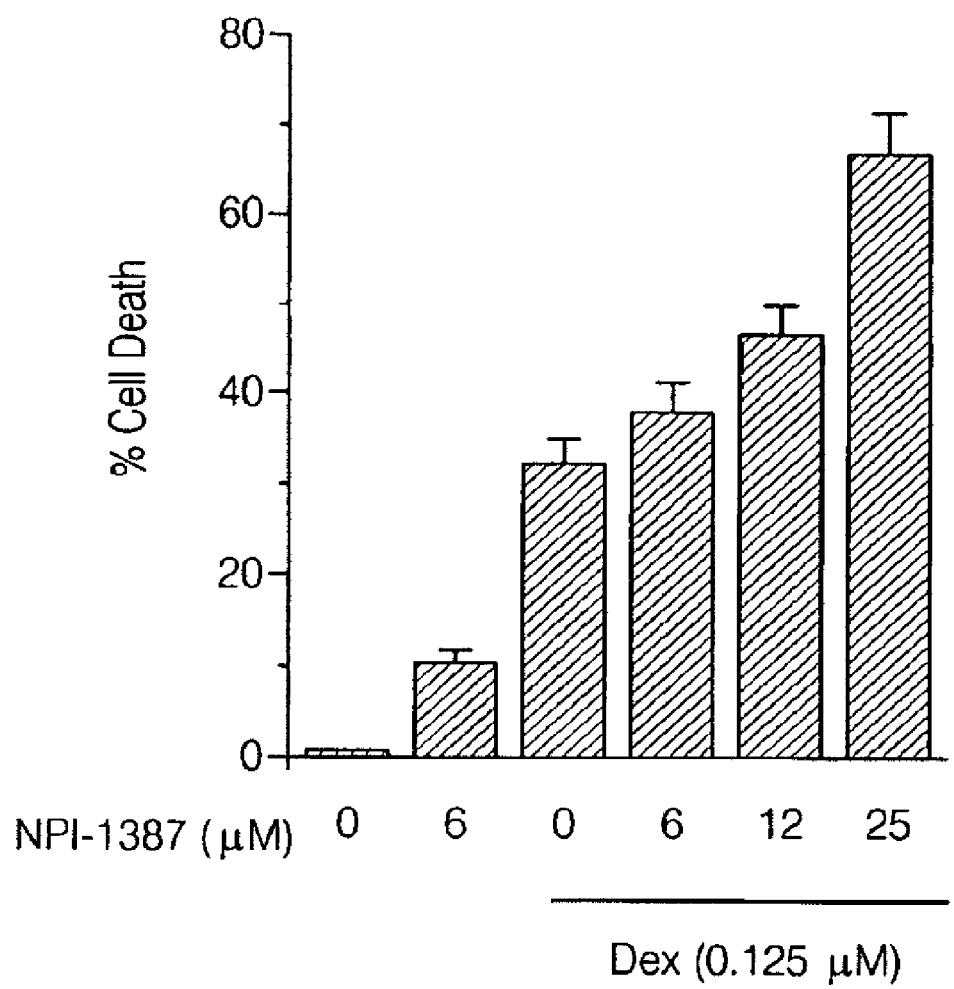
FIG. 63 shows the percentage of cell death as a function of NPI-1387 concentration.
Figure 64:
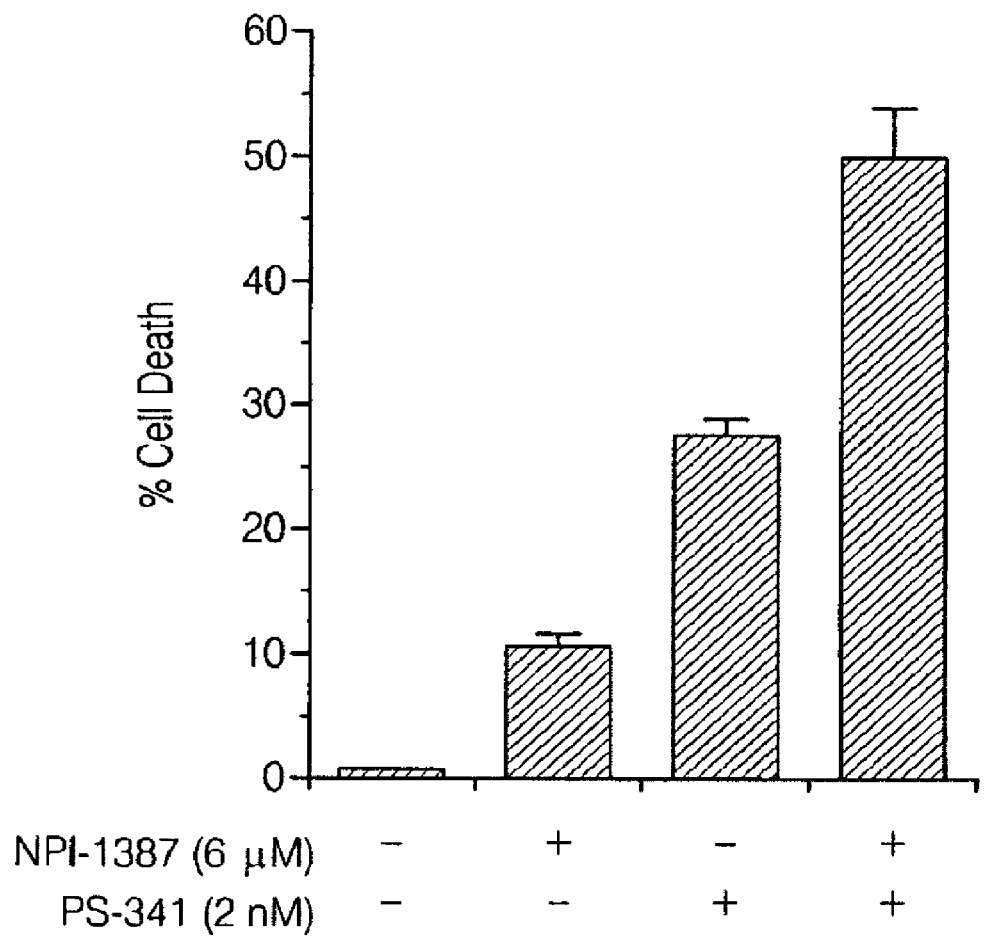
FIG. 64 shows the percentage of cell death as a function of NPI-1387 concentration as well as PS-341 concentration.
Figure 65:
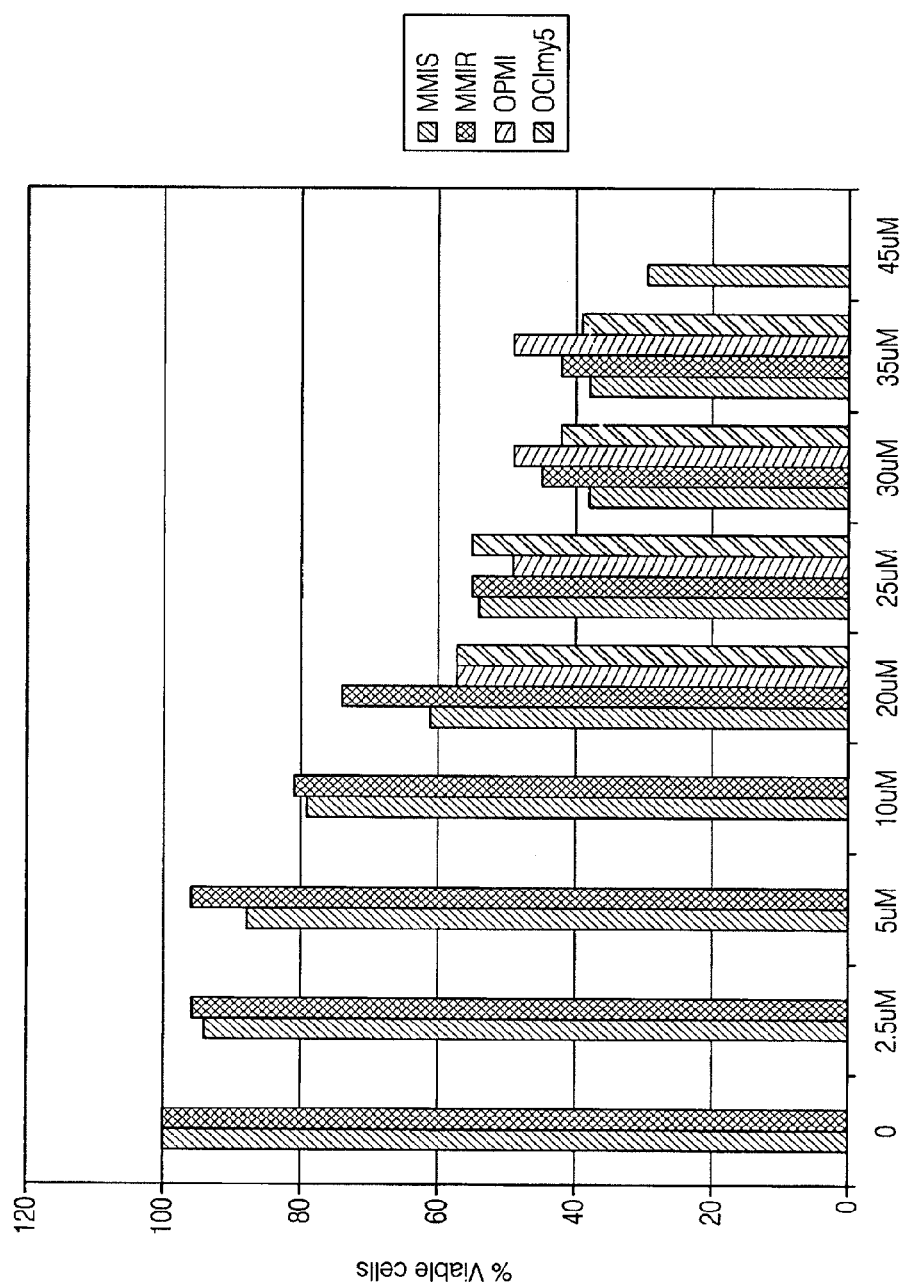
FIG. 65 shows percentage of cell viability for a variety of cell types as a function of compound concentration.

NF-KB inhibitor-triggered significant apoptosis in these cells as measured by a marked increase in nuclear condensation indicated by the dense staining pattern of DAPI observed under phase contrast microscopy. In contrast, untreated control cells exhibited homogeneous and intact nuclei. Besides nuclear condensation, NF-KB inhibitor triggered proteolytic cleavage of poly (ADP ribose) polymerase (PARP), a hallmark of apoptosis. Examination of purified patient MM cells demonstrated similar results. NF-KB inhibitor decreases the viability of cells obtained from Bortezomib-refractory MM patient under in vitro conditions. In contrast, no significant toxicity of NF-KB inhibitor was observed against peripheral blood mononuclear cells from normal healthy donors. Moreover, NF-KB inhibitor does not affect the viability of MM patient-derived bone marrow stromal cells (BMSCs). See FIG. 62.

Genetic and biochemical evidence indicates that apoptosis proceeds by two major cell death pathways: an intrinsic pathway that involves mitochondrial membrane permeabilization and release of several apoptogenic factors, followed by caspase-9 activation; and an extrinsic apoptotic signaling pathway that occurs via caspase-8 activation. Both caspase-8 and caspase-9 activate downstream caspase-3. NF-KB inhibitor (25 µM) induces activation of caspase-8, caspase-9, followed by caspase-3 cleavage. Together, these findings show that NF-KB inhibitor-triggered MM cell apoptosis predominantly proceeds via caspase-8/caspase-9>caspase-3 signaling pathway. Collectively, these findings show the efficacy of NF-KB inhibitor to enhance MM cell killing, overcome drug-resistance, and improve patient outcome in MM.

Example 41

Novel diterpene inhibitors of NFκB derived from acanthoic acid (NPI-1342 (Formula IIB-a1) and NPI-1387; compound 24 under scheme 4 above) show measurable effects in human pancreatic cancer cell lines in vitro. Seven of the nine cell lines were moderately sensitive to apoptosis induced by death receptor ligand Tumor Necrosis Factor (TNF) related apoptosis-inducing ligand (TRAIL). NPI-1342, and NPI-1387 reversed TRAIL resistance in the cell line Panc1 and HS766T, which were found to be resistant to TRAIL at baseline. Specific silencing of NFkB/p65 expression mimicked these effects. Furthermore, combination treatment of Salinosporamide A and either NPI-1342 or NPI-1387 led to induction of apoptosis as measured by PI FACS analysis. Specifically, levels of DNA fragmentation increased from 4% to 50% in HS766T cells and from 4% to 52% in Panc1 cells. The inhibitory effects of NPI-1342, NPI-1387 on NFκB were evaluated by Electromobility Shift Assays and confirmed by confocal microscopy.

Example 42

In vitro studies have demonstrated that acanthoic acid inhibits the production of proinflammatory cytokines such as TNF-α and IL-1. Two cell-based assays were used to screen a library of semi-synthetic acanthoic acid analogs. Among these analogs, NPI-1387 inhibited LPS-induced TNF-α synthesis in the murine macrophage-like RAW264.7 cell line most potently. In addition, NPI-1387 also reduced TNF-α induced nuclear factor-κB (NF-κB) activation in a HEK293 NF-κB/Luciferase reporter cell line, suggesting that NPI-1387 is an inhibitor in the NF-κB signaling pathway.

NF-κB is a key transcription factor that regulates survival in many cells and elevated levels of activated NF-κB have been shown to protect cancer cells (i.e. multiple myeloma and prostate) from apoptosis. The effects were tested of NPI-1387 on TNF-α or LPS-induced NF-κB DNA binding activity in the multiple myeloma cell line RPMI 8226 or the prostate carcinoma cell line PC-3 by using electrophoretic mobility shift assays (EMSA). The results show that NPI-1387 inhibited TNF-α or LPS-induced NF-κB DNA binding activity in both cell lines. In addition, NPI-1387 was most potent at inhibiting the proliferation of the multiple myeloma RPMI 8226 cell line ($IC_{50}$=5.1±1 μM), while in PC-3 clonogenicity assays, exposure of 6 hr to 20 μM of NPI-1387 was sufficient to completely abolish PC-3 colony formation. To elucidate the molecular target(s) of NPI-1387 in the NF-κB signaling pathway, RAW264.7 cells were treated with NPI-1387 before LPS stimulation and western blot and fluorescence microscopy analyses were performed. Results demonstrated that NPI-1387 not only inhibited the phosphorylation of endogenous IRAK1 and its downstream target IκBα in a dose-dependent manner, but also inhibited the nuclear translocation of activated IRAK1 and NF-κB suggesting that NPI-1387 functions as an upstream inhibitor in the NF-κB pathway.

Example 43

The CDDP resistant B-NHL Ramos cell line are treated with various concentrations of the compounds fo formula II, IIA, and IIB (including 1387) for one hour and then treated with predetermined nontoxic concentration of CDDP (15 ug/ml) for an additional 20 hours. The cells are then harvested and examined for apoptosis using the propidium iodide (PI) technique by flow cytometry examining DNA fragmentation. Combination treatment with one or more of the compounds and CDDP results in significant potentiation of cytotoxicity. In addition, treatment alone shows cytotoxicity and significant synergistic cytotoxicity is observed. Similar studies are performed with the Daudi B-NHL cell line. Significant cytotoxicty is observed.

Rituximab (chimeric anti-CD20 monoclonal antibody) has been used in the treatment of Non-Hodgkin's Lymphoma alone or in combination with chemotherapy. The clinical response has been very encouraging; however, some patients are initially unresponsive or develop resistance following treatment. The Daudi RR1 clone which is resistant to rituximab-induced signaling is studied. Unlike Daudi wild type, rituximab fails to sensitize Daudi RR1 to drug-induced apoptosis. In addition, Daudi RR1 also develops the highest degree of drug resistance compared to wild type. The compounds of formula II, IIA and IIB sensitize the cells to rituximab. The compounds are tested to determine their ability to sensitize the cells to rituximab. One or more of the compounds sensitize the cells to rituximab.

Example 44

NPI-1387 Inhibits NF-κB p65 Subunit Nuclear Translocation in a Dose-Dependent Manner upon LPS Stimulation in RAW264.7 Cells RAW 264.7 cells were seeded on coverslips at a density of $0.5 \times 10^5$ cells/well in 12-well plates, and left to attach overnight at 37° C., 5% $CO_2$ and 95% humidified air. Cells were pretreated with NPI-1387 (compound 24 under scheme 4 above) at 5, 10 and 20 μM for 1 hr, and then stimulated with 50 ng/ml LPS for 30 min. Coverslips were transferred to clean plates, washed twice in Dulbecco's phosphate buffered saline (DPBS), fixed in 10% formaldehyde for 10 min, and permeabilized with 0.2% Triton X-100 for additional 10 min. Blocking medium (DPBS, 2% BSA, 0.1% Triton X-100) was added for 2 h, and removed by aspiration. Polyclonal goat anti-p65 antibody (Santa Cruz Biotechnology) was added at a 1:1000 dilution for 1 hr. The wells were washed 3 times with DPBS containing 0.1% Triton X-100, and 100 ml of Alexa-488-conjugated anti-goat antibody (1:1000 dilution, Molecular Probes) were added for 30 min. Wells were washed again, and the coverslips were mounted face-down on microscope slides using Vectashield (Vector) mounting medium. Slides were observed under an Olympus fluorescent microscope, images acquired using a Magnafire digital camera, and processed using Adobe Photoshop.

Figure 66:
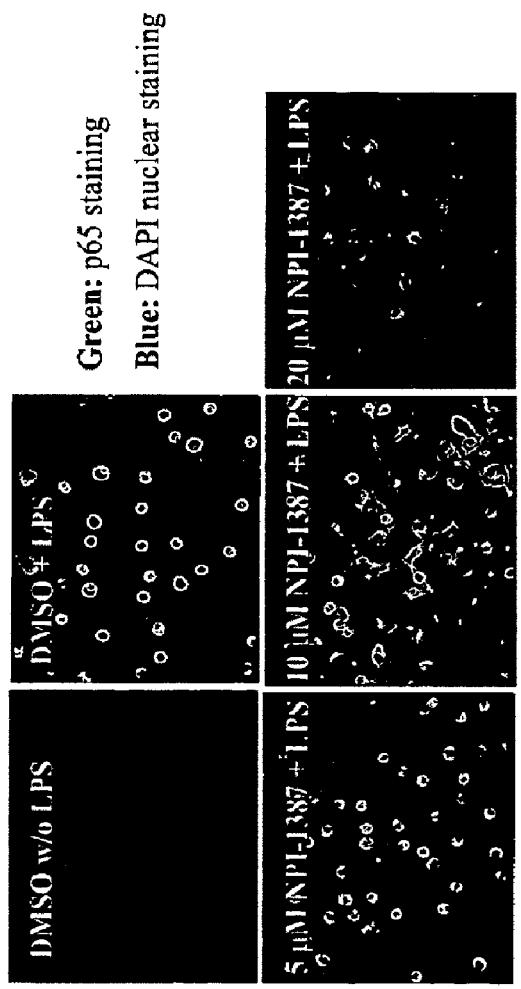
FIG. 66 shows an immunofluorescence stain depicting the effect of NPI-1387 on NF-κB p65 subunit nuclear translocation in RAW264.7 cells upon LPS stimulation.

The effect of NPI-1387 on NF-κB p65 subunit nuclear translocation in RAW264.7 cells is shown in FIG. 66. Without being bound to a particular theory, the results indicate that NPI-1387 inhibits the NF-κB p65 subunit nuclear translocation in a dose-dependent manner upon LPS stimulation in RAW264.7 cells.

Example 45

NPI-1387 Overcomes the Protective Effects of MM Bone Marrow Microenvironment

In vitro studies have shown that NPI-1387 does not affect the viability of bone marrow stem cells, but NPI-1387 does overcome the protective effects of IL-6 or IGF-1. These data suggest, without being bound to any particular theory, that NPI-1387 operates by blocking MM cell growth induced by both adhesion to bone marrow stem cells and related cytokine secretion.

Example 46

NPI-1387 Ovecomes Both Bortezomib-Resistance and Bcl-2-Mediated Resistance

Figure 67:
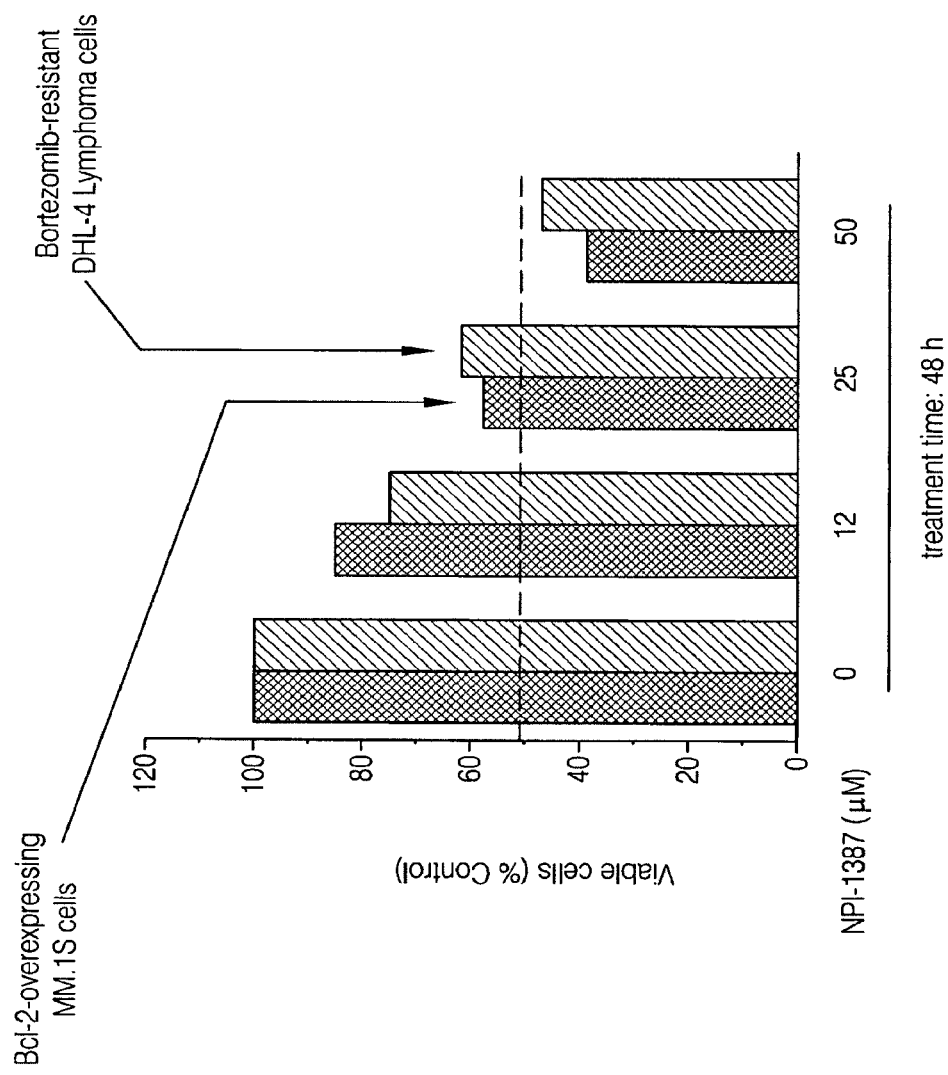
FIG. 67 shows the percentage of viable Bcl-2-overexpressing MM.1S cells and bortezomib-resistant DHL-4 lymphoma cells as a function of NPI-1387 concentration.

In vitro studies have demonstrated that NPI-1387 ovecomes both bortezomib-resistance and bcl-2-mediated resistance. Two cell-based assays were treated with NPI-1387 for 48 hours at concentrations of 0, 12, 25 and 50 uM. Both Bcl-2-overexpressing MM.1S cells and bortezomib-resistant DHL-4 lymphoma cells were used and the percentage of viable cells of each was recorded. The results showed a marked decrease in the percentage of viable cells of both Bcl-2-overexpressing MM.1S cells and bortezomib-resistant DHL-4 lymphoma cells corresponding to increased concentration of NPI-1387. (See FIG. 67).

Example 47

Figure 68:
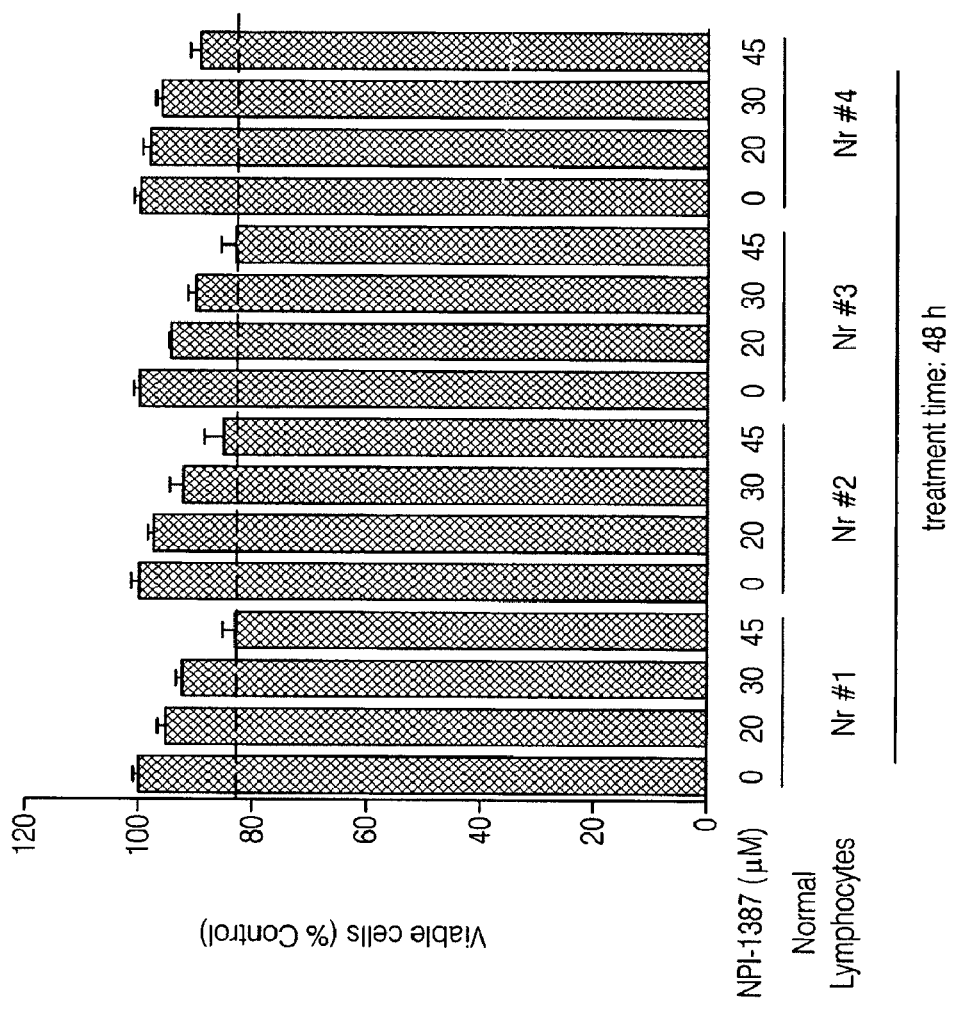
FIG. 68 shows the percentage of viable PMBNCs as a function of NPI-1387 concentration.

NPI-1387 Shows Minimal Effects on Peripheral Blood Mononuclear Cells (PBMNC) from Healthy Donors In vitro studies show that when viable PMBNCs are subjected to treatment with varying concentrations of NPI-1387, the change in the percentage of viable PMBNCs is relatively minimal. (See FIG. 68).

Example 48

Figure 69:
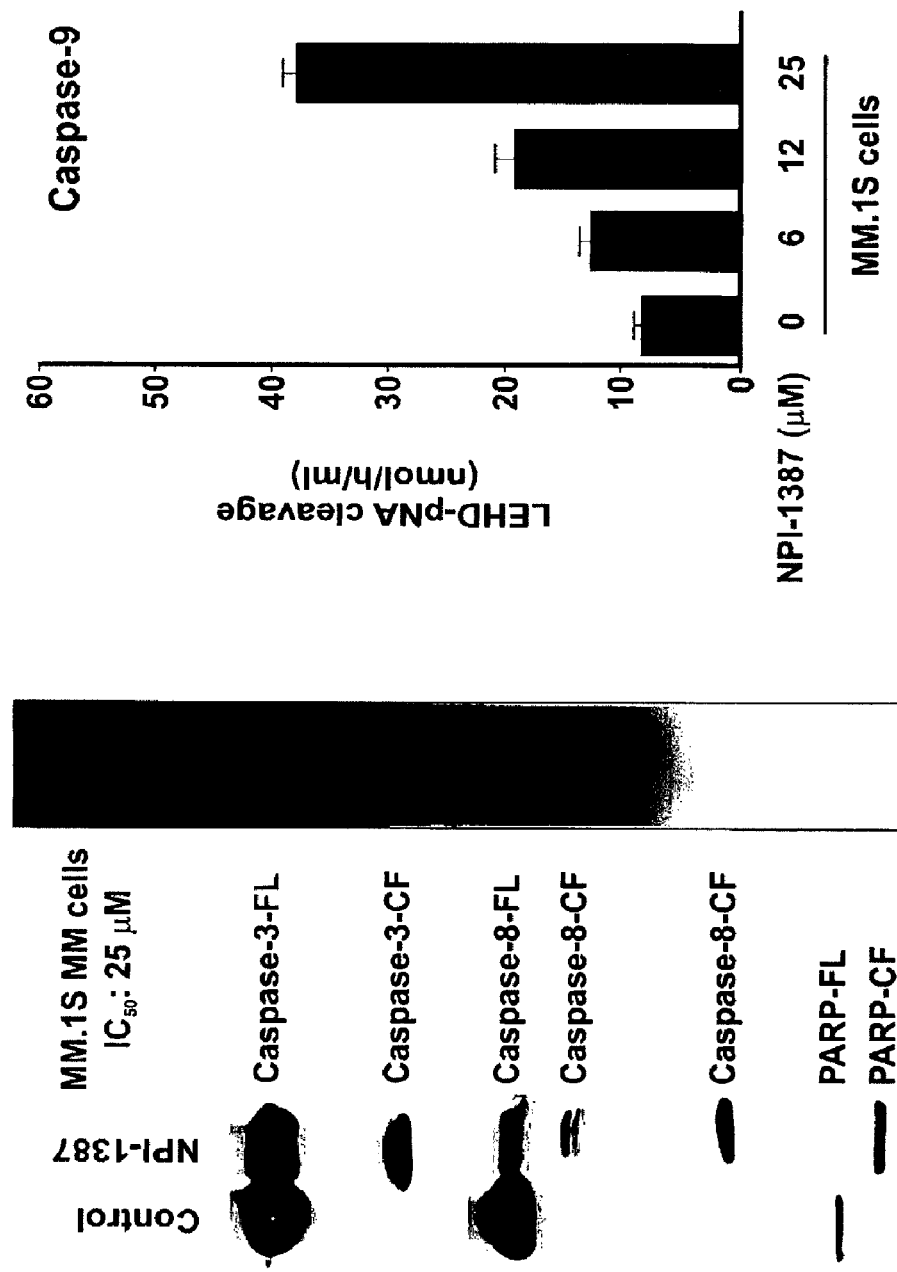
FIG. 69 shows the level of apoptic signaling in MM cells in the presence and absence of NPI-1387 and the level of apoptic signaling in MM cells as a function of NPI-1387 concentration.

Apoptic signaling has been shown to be triggered by NPI-1387 in MM cells, both in the intrinsic and extrinisic pathways. (See FIG. 69).

Example 49

Figure 70:
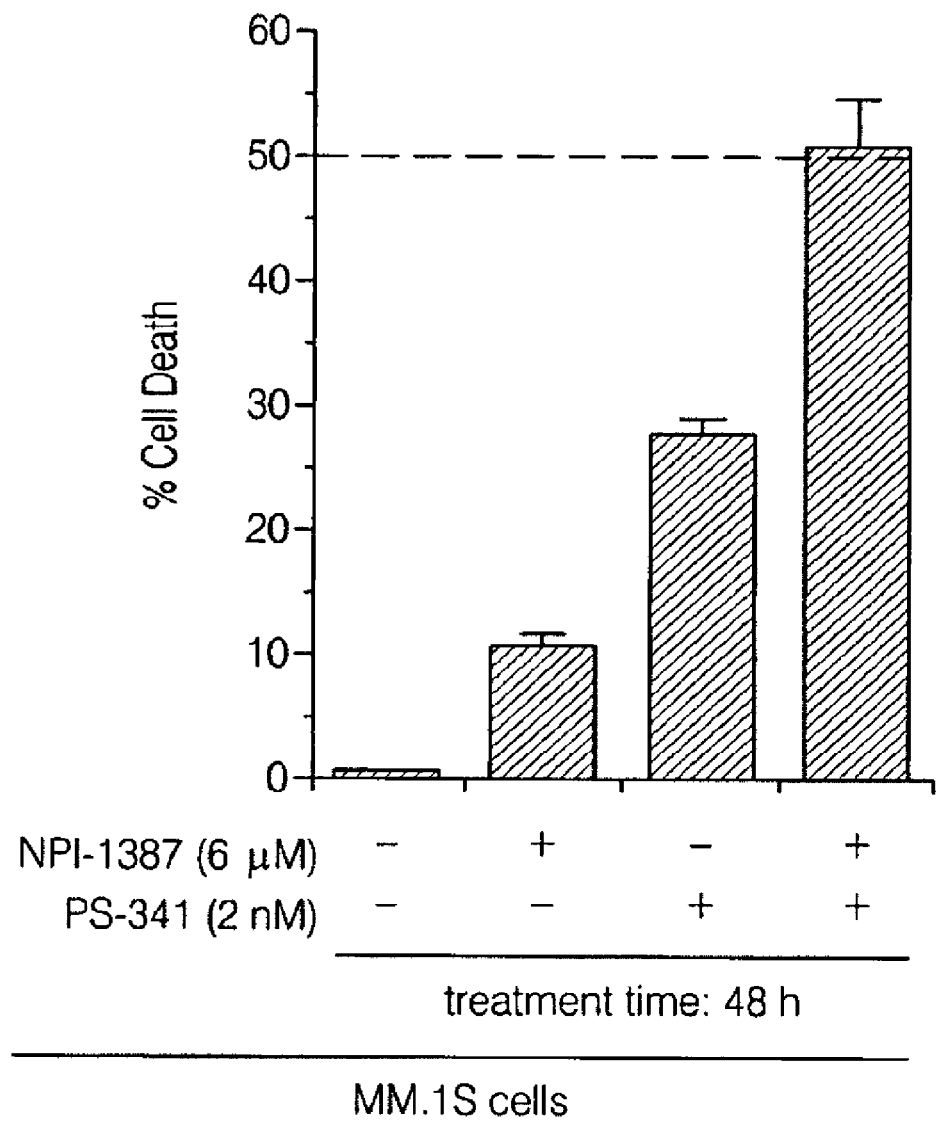
FIG. 70 shows an isobologram analysis of the percentage of MM.1S cell death as a function of NPI-1387 and PS-341 concentration.
Figure 71:
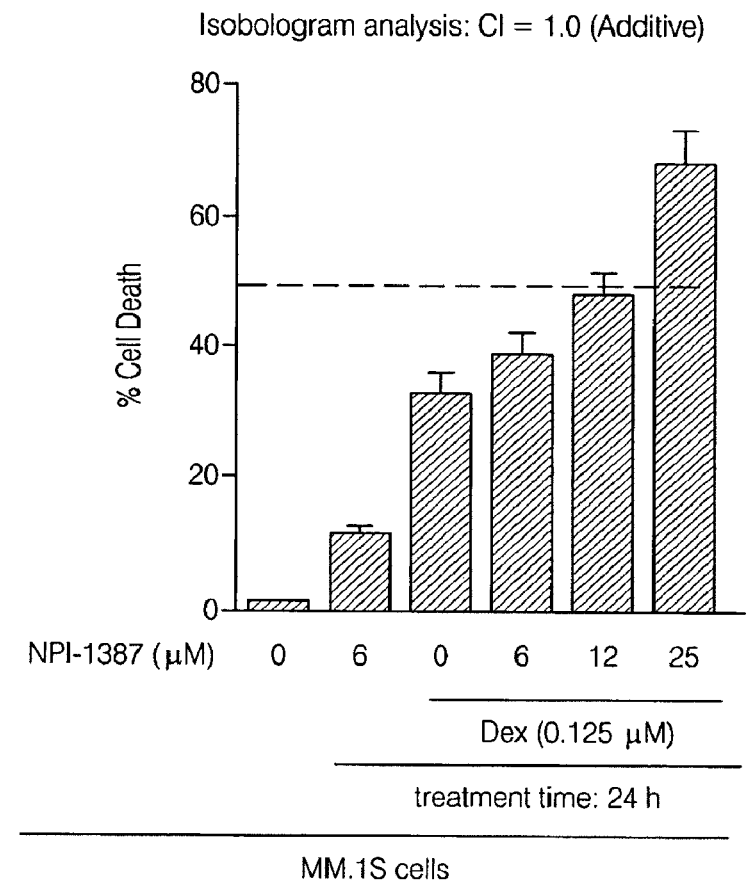
FIG. 71 shows an isobologram analysis of the percentage of MM.1S cell death as a function of NPI-1387 concentration.

Co-Administration of NPI-1387 with Other Drugs Triggers Additive Anti-MM Activity In Vitro assays measuring the percentage of MM cell death after 48 hours were carried out with bortezomib and dexamethasone, each in concert with NPI-1387. These assays suggest, without being bound to any particular theory, that co-administration of each drug with NPI-1387 results in additive effects in increasing the percentage of MM cell death. (See FIGS. 70 and 71).

Example 50

NPI-1387 Inhibits TNF-α Synthesis in LPS-Stimulated RAW264.7 Cells $7.5 \times 10^3$/well of RAW264.7 cells were seeded in 96 well plate and cultured overnight at 37° C., 5% $CO_2$ and 95% humidified air. Various concentrations of NPI-1387 prepared in DMSO were added to cells 1 hr before LPS (10 ng/ml) stimulation. DMSO was used as a control. After 4 hr of LPS stimulation, supernatants were harvested and the level of TNF-α from each sample was analyzed by using the human TNF-α cytoset ELISA kit (Biosource Internationals). $IC_{50}$ values (the drug concentration at which 50% of the maximal observed TNF-α production is inhibited) were determined using a standard sigmoidal dose response curve fitting algorithm (Prism 2.0, GraphPad Software Inc).

Figure 72:
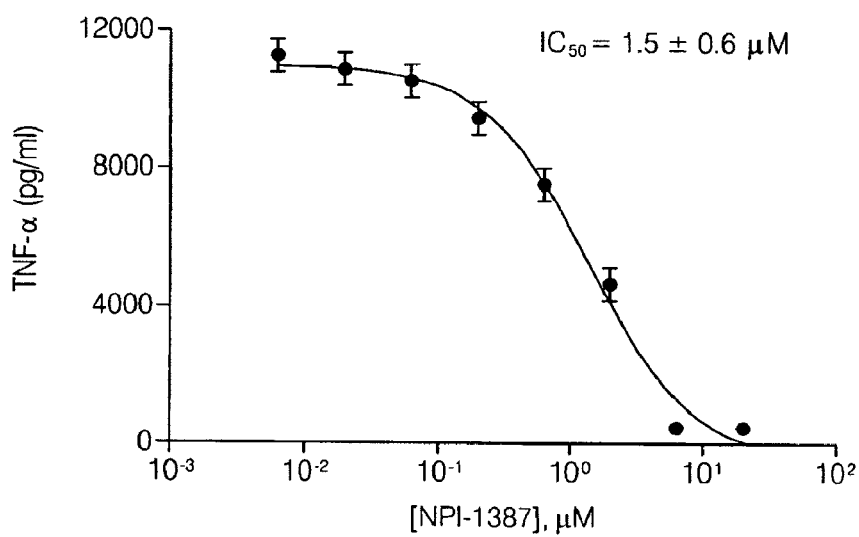
FIG. 72 shows the inhibition of TNF-α synthesis in LPS-stimulated RAW264.7 cells as a function of NPI-1387 concentration.

The effect on TNF-α production in RAW264.7 cells by NPI-1387 is shown in FIG. 72. Without being bound to a particular theory, the results indicate that NPI-1387 is effective in the inhibition of TNF-α production in LPS-stimulated RAW264.7 cells.

Example 51

NPI-1387 Inhibits the Phosphorylation of IRAK1 and Kinase Activity of IKKα in a Dose-Dependent Manner Upon LPS Stimulation in RAW264.7 Cells $5 \times 10^5$/well of RAW264.7 cells were seeded in a 6 well plate and cultured overnight at 37° C., 5% $CO_2$ and 95% humidified air. Cells were treated with 1, 5, 10 and 20 µM of NPI-1387 for 1 hour and then stimulated with 10 ng/ml LPS for 10 or 30 min. To determine the phosphorylation of IRAK1, whole cell extracts were prepared in RIPA buffer [0.9% NaCl, 50 mM Tris-HCl (pH7.4), 1% Triton X-100, 1 mM EDTA, 0.25% Na-deoxycholic acid, 0.1% SDS, 1 mM $Na_3VO_4$, 1 mM NaF and protease inhibitors]. The insoluble material was removed by centrifugation, the protein concentrations were determined using the BCA protein assay kit (Pierce Biotechnology) and 15 µg aliquots of the samples were resolved on 10% NuPAGE IVIES precast gels (Invitrogen). Following electro-transfer, the membranes were blocked in Blotto (5%, w/v) non-fat milk in 1×TBST [20 mM Tris, 0.8% (w/v) NaCl, pH 7.6, 0.1% (v/v) Tween 20]. Membranes were then incubated with primary antibodies against IRAK1 (Santa Cruz Biotechnology), total IκBα (Cell Signaling Technology), phospho-IκBα (Cell Signaling Technology) and Tubulin (Lab Vision) in Blotto for 2 hours. The membranes were washed in TBST and (where necessary) incubated with the HRP-conjugated secondary antibody in Blotto for 1 hour before washing extensively with TBST. HRP activity was visualized by utilizing either SuperSignal West Pico or Dura chemiluminescent detection systems (Pierce Biotechnology). To determine the in vitro kinase activity of immunoprecipitated IKKα, whole cell extracts were prepared in lysis buffer [150 mM NaCl, 20 mM Tris-HCl (pH7.5), 1% Triton X-100, 1 mM EDTA, 1 mM EGTA, 1 mM β-glycerophate, 1 mM NaF, 1 mM $Na_3VO_4$ and protease inhibitors]. The insoluble material was removed by centrifugation. Antibody against IKKα (Cell Signaling Technology) was added to the clarified supernatant and incubated at 4° C. for 2 hr. Immunopure immobilized protein G beads (Pierce Biotechnolgy) were added and the IKKα was immunoprecipitated at 4° C., overnight. After the beads were washed briefly in the lysis buffer, they were incubated with GST-IκBα substrate (Santa Cruz Biotechnology) in the kinase assay buffer supplemented with ATP at 30° C. for 1 hr. The protein samples were separated by 10% NuPAGE IVIES precast gels (Invitrogen) and the extent of GST-IκBα phosphorylation was evaluated by western blotting using the antibody against phospho-IκBα (Cell Signaling Technology).

Figure 73:
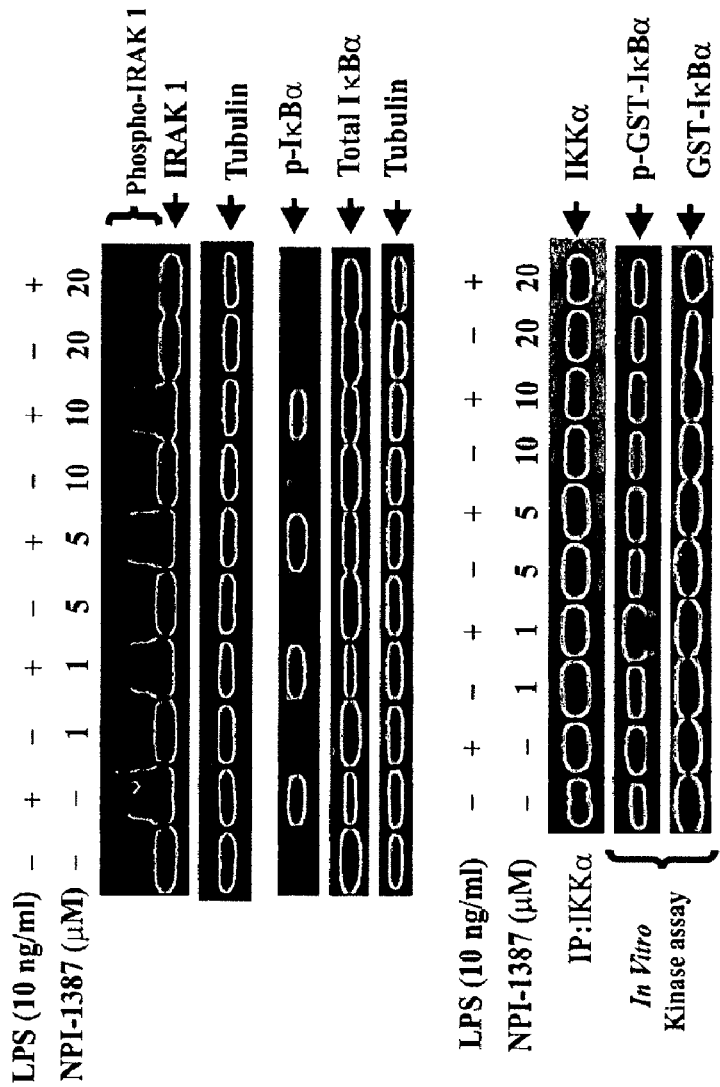
FIG. 73 shows the effect of varying concentrations of NPI-1387 on the phosphorylation of IRAK1 and the kinase activity of IKKα upon LPS stimulation in RAW264.7 cells.

The effects of NPI-1387 on phosphorylation of IRAK1 and IKKα kinase activity activated by LPS in RAW 264.7 cells are shown in FIG. 73. Without being bound to a particular theory, the results indicate that NPI-1387 inhibits the phosphorylation of IRAK1 and reduces kinase activity of IKKα in a dose-dependent manner upon LPS stimulation in RAW264.7 cells.

Example 52

NPI-1387 Inhibits TNF-α or LPS Induced NF-κB DNA Binding Activity in Cancer Cells RPMI 8226 or PC-3 cells seeded in 6 cm tissue culture dishes were pretreated with indicated concentrations of NPI-1387 for 1 hr. 0.25% (v/v) DMSO served as the vehicle control. For RPMI 8226 cells, 50 ng/ml of LPS was used to stimulate the cells for 2 hr. For PC-3 cells, 10 ng/ml of TNF-α was used to stimulate the cells for 0.5 hr. 0.2% (v/v) DPBS was used for the un-stimulated controls. Nuclear extracts were prepared using the NE-PER nuclear and cytoplasmic extraction reagent kit (Pierce Biotechnology) according to the manufacturer's instructions in the presence of protease inhibitors. The protein concentration of the nuclear extracts was determined using the BCA protein assay kit (Pierce Biotechnology) according to the manufacturer's protocol. The NF-κB DNA binding activity of the nuclear extracts was determined using the LightShift chemiluminescent EMSA kit (Pierce Biotechnology) as detailed by the vendor. The biotin NF-κB probe was prepared by annealing 5'-Biotin-AGT TGA GGG GAC TTT CCC AGG C and 5'-GCC TGG GAA AGT CCC CTC AAC T in 10 mM Tris-HCl, 1 mM EDTA and 50 mM NaCl, pH 8.0 using a Thermal Cycler PCR machine. Briefly, the binding reactions consisted of a normalized mass of nuclear extract in 1× binding buffer, 2.5% (v/v) glycerol, 5 mM $MgCl_2$, 50 ng/µl poly (dI.dC), 0.05% (v/v) NP-40 and 100 fmol biotin NF-κB probe in a total volume of 20 µl. The binding reactions were incubated for 60 minutes at room temperature. Where indicated, 2 µg of anti-p65 (Santa Cruz Biotechnology) or anti-c-Jun (Santa Cruz Biotechnolgy) antibodies was added to the binding reaction after 30 minutes. The binding reactions were resolved on a pre-run 6% polyacrylamide DNA retardation gel (Invitrogen) in 0.5×TBE (Invitrogen) before transferring onto a Biodyne B nylon membrane (Pierce Biotechnology). Following cross linking on a UV transilluminator, the blots were probed with a streptavidin-HRP conjugate and visualized with the chemiluminescent substrate.

Figure 74:
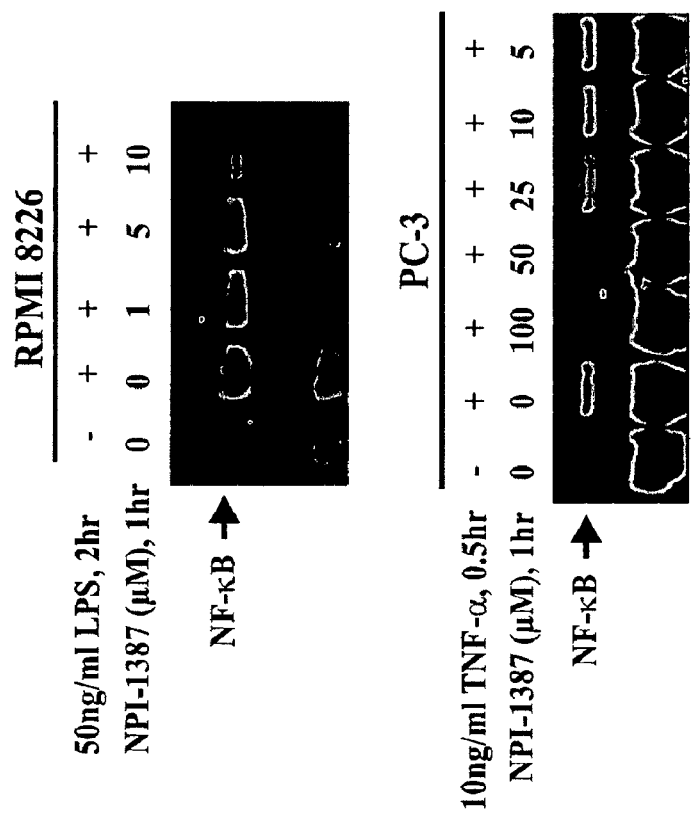
FIG. 74 shows the effect of varying concentrations of NPI-1387 on the NF-κB DNA binding activity in cancer cells.

The effects of NPI-1387 on DNA binding activity in RPMI 8226 and PC-3 cancer cells are shown in FIG. 74. Without being bound to a particular theory, the results indicate that NPI-1387 inhibits the DNA binding activity of NF-κB in a dose-dependent manner in both cancer cell lines upon LPS or TNF-α stimulation.

Example 53

NPI-1387 Inhibits PC-3 Colony Formation

PC-3 cells in 10 cm tissue culture dishes (200 cells/dish) were treated with 5 µM, 10 µM and 20 µM NPI-1387 for 0.5-24 hours in triplicates. DMSO was used as vehicle control. After each time point of drug treatment, the medium was removed, the dishes were washed two times with Dulbecco's phosphate buffered saline (DPBS), and supplied with fresh medium. Cells were cultured for 10 days with the medium replenished every 3 days. On the 10th day, dishes were washed with cold DPBS, fixed for 10 minutes in ice-cold 100% methanol at 4° C., and the colonies were stained with 0.5% (w/v) crystal violet. Colonies were counted manually, and the results expressed as % of colonies in relation to their respective vehicle control.

Figure 75:
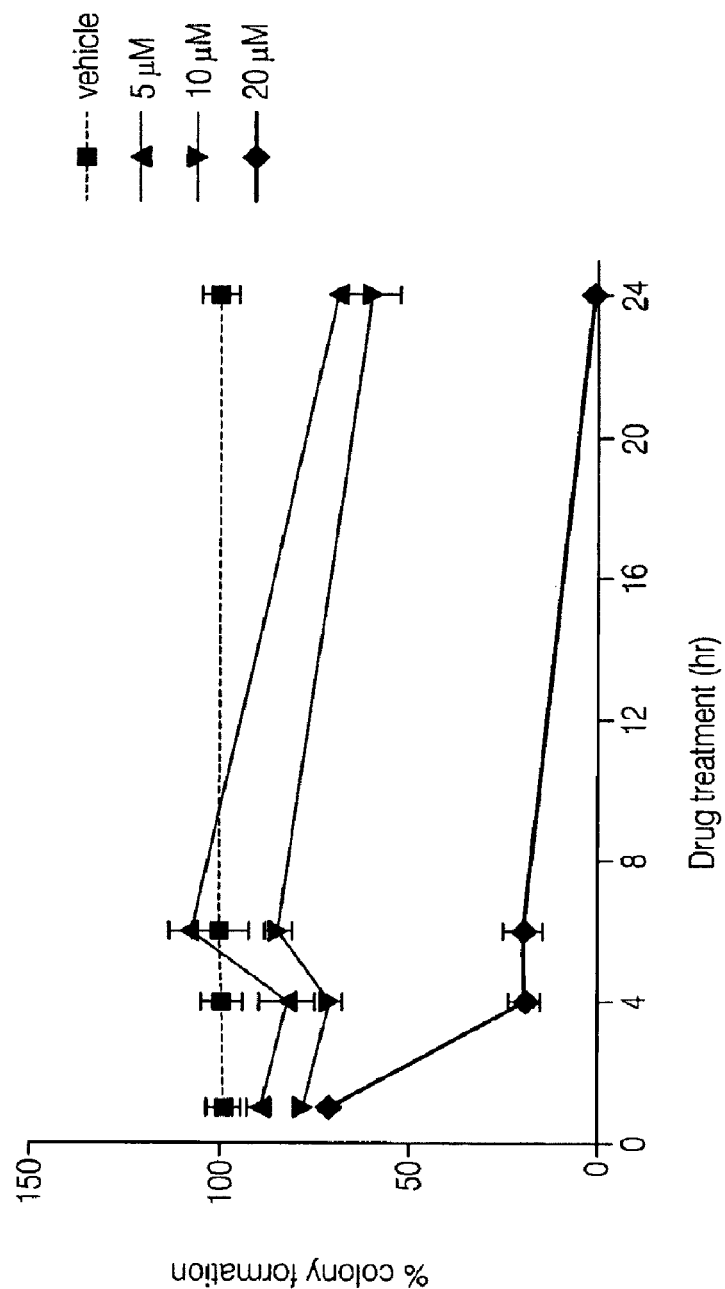
FIG. 75 shows the time-dependent and dose-dependent effect of NPI-1387 on PC-3 colony formation.

The inhibition of PC-3 cell colony formation by various concentrations of NPI-1387 is shown in FIG. 75. Without being bound to a particular theory, the results indicate that NPI-1387 inhibits the colony formation of PC-3 cancer cells in a time-dependent and dose-dependent fashion.

Example 54

48 hr Cytotoxicity: $IC_{50}$ Values of NPI-1387 in Human Cancer Cell Lines

Human colon adenocarcinoma HT-29 (ATCC# HTB-38), prostate adenocarcinoma PC-3 (ATCC# CRL-1435), breast adenocarcinoma MDA-MB231 (ATCC# HTB-26), Multiple Myeloma RPMI 8226 (ATCC# CCL-155) and U266 (ATCC #TIB-196) cell lines and human normal fibroblast CCD-27sk (ATCC# CRL-1475) were all purchased from ATCC (Manassas, Va.). The cells were maintained in their respective ATCC recommended culture media at 37° C., 5% $CO_2$ and 95% humidified air.

The cytotoxicity assays were performed by seeding individual cell lines at appropriate density in the 96 well flat-bottomed plates and allowed to attach for 24 hours at 37° C., 5% CO2 and 95% humidified air (RPMI 8226 and U266 cells were plated in 96 well plates on the day of compound addition). Serially diluted NPI-1387 was added in triplicate to cells at concentrations ranging from 160 nM to 20 µM. Final concentration of 0.25% (v/v) DMSO was used as the vehicle control. Cell viability was assessed 48 hours later by measuring the fluorescence of the reduction product of Resazurin by a Fusion microplate fluorometer (PerkinElmer) with $\lambda_{ex}$=535 nm and $\lambda_{em}$=590 nm filters. The $IC_{50}$ values (the drug concentration at which 50% of the maximal observed cytotoxicity is established) were calculated in XLFit 3.0 or XLFit 4.0 (ID Business Solutions Ltd) using a sigmoidal dose response model.

The $IC_{50}$ values of 48 hr cytotoxicity of NPI-1387 against various human cancer cell lines and normal skin fibroblast are shown in Table 32. Without being bound to a particular theory, the results indicate that NPI-1387 is less toxic to normal cells and demonstrates anti-cancer activity in vitro.

TABLE 32

Cytotoxicity profile of NPI-1387 in human cancer cell lines

| Tumor cell line | NPI-1387 $IC_{50}$ (µM) | n |
|---|---|---|
| RPMI 8226 | 5.5 ± 0.8 | 10 |
| U266 | 7.0 ± 1.9 | 10 |
| PC-3 | 10 ± 2 | 10 |
| HT-29 | 13 ± 6 | 11 |
| MDA-MB-231 | 15 ± 4 | 6 |
| CCD-27sk (human normal skin fibroblast) | ≧20 | 11 |

*48 hr drug exposure

TABLE 1

Inhibition of LPS-Induced TNF-α Synthesis by the Compound of Formula (I) and TTL1

| | LPS | Formula (I) (0.1 µg/ml) | Formula (I) (1 µg/ml) | Formula (I) (10 µg/ml) | TTL1 (0.1 µg/ml) | TTL1 (1 µg/ml) | TTL1 (5.4 µg/ml) |
|---|---|---|---|---|---|---|---|
| TNF-α (ng/ml) | 120 | 108 | 67 | 50 | 57 | 60 | 38 |

TABLE 2

Inhibition of SAC-Induced TNF-α Synthesis by the Compound of Formula (I) and TTL1

| | SAC | Formula (I) (0.1 µg/ml) | Formula (I) (1 µg/ml) | Formula (I) (10 µg/ml) | TTL1 (0.1 µg/ml) | TTL1 (1 µg/ml) | TTL1 (5.4 µg/ml) |
|---|---|---|---|---|---|---|---|
| TNF-α (ng/ml) | 385 | 410 | 275 | 165 | 250 | 285 | 150 |

TABLE 3

Inhibition of SAC-Induced IL-1 Synthesis by the Compound of Formula (I) and TTL1

| | SAC | Formula (I) (0.1 µg/ml) | Formula (I) (1 µg/ml) | Formula (I) (10 µg/ml) | TTL1 (0.1 µg/ml) | TTL1 (1 µg/ml) | TTL1 (5.4 µg/ml) |
|---|---|---|---|---|---|---|---|
| IL-1α (pg/ml) | 700 | 1350 | 1050 | 350 | 950 | 400 | 300 |

TABLE 4

The Compound of Formula (I) and TTL1 Do Not Inhibit SAC-Induced IL-6 Synthesis

|  | SAC | Formula (I) (0.1 μg/ml) | Formula (I) (1 μg/ml) | Formula (I) (10 μg/ml) | TTL1 (0.1 μg/ml) | TTL1 (1 μg/ml) | TTL1 (5.4 μg/ml) |
|---|---|---|---|---|---|---|---|
| IL-6 (ng/ml) | 75 | 65 | 90 | 80 | 83 | 86 | 65 |

TABLE 5

TTL3 Inhibits SAC-Induced TNF-α Synthesis

|  | Unstimulated | SAC | 0.001 μg/ml | 0.01 μg/ml | 0.1 μg/ml | 1 μg/ml | 10 μg/ml |
|---|---|---|---|---|---|---|---|
| TNF-α (ng/ml) | 5 | 375 | 80 | 75 | 85 | 60 | 80 |

TABLE 6

TTL3 Inhibits SAC-Induced IL-1 Synthesis

|  | Unstimulated | SAC | 0.001 μg/ml | 0.01 μg/ml | 0.1 μg/ml | 1 μg/ml | 10 μg/ml |
|---|---|---|---|---|---|---|---|
| IL-1α (pg/ml) | 0 | 650 | 200 | 220 | 190 | 180 | 170 |

TABLE 7

Inhibition of LPS-Induced TNF-α Synthesis by TTL3 (TNF-α (ng/ml))
LPS (1 μg/ml) + TTL3 (μg/ml)

| LPS alone | $(1 \times 10^{-7})$ | $(1 \times 10^{-6})$ | $(1 \times 10^{-5})$ | $(1 \times 10^{-4})$ | $(1.0)$ | $(1 \times 10^{2})$ |
|---|---|---|---|---|---|---|
| 88 | 41 | 18 | 10 | 15 | 13 | 4 |

TABLE 8

TTL3 Inhibits Mortality After LPS/D-Gal Administration

| Treatment* | Mortality 24 hours | Mortality 48 hours |
|---|---|---|
| LPS/D-Gal | 10/10 | 10/10 |
| LPS/D-Gal + DMSO | 8/10 | 9/10 |
| LPS/D-Gal + TTL3 | 2/10 | 2/10 |

*All treatments were i.p., TTL3 administration 45 minutes prior to LPS

TABLE 9

Assays Reflecting Examples 19-21

|  | Murine | | Human | |
|---|---|---|---|---|
|  | Dynamic Range (pg/ml) | Sensitivity (pg/ml) | Dynamic Range (pg/ml) | Sensitivity (pg/ml) |
| TNF-α | 15.63-1,000 | ≈15 | 8.19-800 | ≈10-15 |
| IL-1β | 15.63-1,000 | ≈20-30 | 3.28-800 | ≈4-5 |
| IL-1Ra | NT | NT | 8.19-800 | ≈10 |
| IL-6 | 15.63-1,000 | ≈15 | 8.19-800 | ≈10 |
| IL-8 | Not Producted | Not Producted | 3.28-800 | ≈4-5 |
| IL-10 | 31.25-2,000 | ≈31 | 3.28-800 | ≈5-8 |
| IL-12 | 7.81-500 | ≈15 | 10-1,000 | ≈10 |

TABLE 10

The Effect of Series 1 Analogs on Cell Viability.

| Compound | 10 ug/ml | 1 ug/ml | 100 ng/ml |
|---|---|---|---|
| TTL-1 | 85* | 100 | 100 |
| TTL-3 | 100 | 100 | 100 |
| TTL-4 | 100 | 100 | 100 |
| TTL-7 | 100 | 100 | 100 |
| TTL-14 | NA | 100 | 100 |
| TTL-15 | 100 | 100 | 100 |
| LT-1-33 | 75** | 80* | 100 |
| LT-1-37 | 55** | 50** | NA |
| LT-1-39 | 80* | 100 | 100 |
| LT-1-45 | 90* | 100 | 100 |
| LT-4-32 | 100 | 100 | 100 |

*Mild reduction in viability
**Marked reduction in viability
NA: Data are not available

TABLE 11

Percent TNF-α Inhibition by Series 1 Analogs

| Compound | 10 ug/ml | 1 ug/ml | 100 ng/ml |
|---|---|---|---|
| TTL-1 | 50 | 30 | 10 |
| TTL-3 | 70 | 55 | 30 |
| TTL-4 | 0 | 0 | 0 |
| TTL-7 | 0 | 0 | 0 |
| TTL-14 | 45 | 30 | 25 |
| TTL-15 | 0 | 0 | 0 |
| LT-1-33 | 40 | 20 | 0 |
| LT-1-37 | 50 | 45 | 0 |
| LT-1-39 | 50 | 30 | 15 |
| LT-1-45 | 50 | 30 | 0 |
| LT-4-32 | 0 | 0 | 0 |

TABLE 12

The Effect of Series 2 Analogs on Cell Viability.

| Compound | 10 ug/ml | 1 ug/ml | 100 ng/ml |
|---|---|---|---|
| TTL-1 | 70** | 100 | 100 |
| TTL-1Na | 80* | 90* | NA |
| TTL-1K | NA | NA | NA |
| LT-1-43 | 90* | 100 | NA |
| LT-1-44 | 90* | 100 | NA |

TABLE 13

Percent TNF-α Inhibition by Series 2 Analogs

| Compound | 10 ug/ml | 1 ug/ml | 100 ng/ml |
|---|---|---|---|
| TTL-1 | 50 | 30 | 10 |
| TTL-1Na | 50 | 40 | NA |
| TTL-1K | NA | 50 | 10 |
| LT-1-43 | 20 | 10 | NA |
| LT-1-44 | 0 | 0 | 0 |

TABLE 14

The Effect of Series 3 Analogs on Cell Viability.

| Compound | 10 ug/ml | 1 ug/ml | 100 ng/ml |
| --- | --- | --- | --- |
| LT-1-73 | NA | 100 | 100 |
| LT-1-74 | NA | 100 | 100 |
| LT-1-78 | 100 | 100 | 100 |
| LT-1-83 | 70** | 100 | 100 |
| LT-1-85 | 80* | 100 | 100 |
| LT-1-89 | 100 | 100 | 100 |

TABLE 15

Percent TNF-α Inhibition by Series 3 Analogs.

| Compound | 10 ug/ml | 1 ug/ml | 100 ng/ml |
| --- | --- | --- | --- |
| LT-1-73 | 25 | 25 | 0 |
| LT-1-74 | NA | 30 | 25 |
| LT-1-78 | 20 | 0 | 0 |
| LT-1-83 | 50 | 0 | 0 |
| LT-1-85 | 55 | 45 | 10 |
| LT-1-89 | 20 | 10 | 10 |

TABLE 16

The Effect of Series 4 Analogs on Cell Viability.

| Compound | 10 ug/ml | 1 ug/ml | 100 ng/ml |
| --- | --- | --- | --- |
| LT-1-90 ra | 45** | 90* | 100 |
| CC-3-13 ra | 20** | 75** | 95* |
| CC-3-15 ra | 100 | 100 | NA |
| CC-3-19 P | 70** | 100 | 100 |
| CC-3-22 | 100 | 100 | 100 |
| CC-3-23 | 100 | 100 | 100 |

TABLE 17

Percent TNF-α Inhibition by Series 4 Analogs

| Compound | 10 ug/ml | 1 ug/ml | 100 ng/ml |
| --- | --- | --- | --- |
| LT-1-90 ra | NA | 50 | 0 |
| CC-3-13 ra | 95 | 50 | 10 |
| CC-3-15 ra | 65 | 25 | NA |
| CC-3-19 P | 50 | 0 | 0 |
| CC-3-22 | 20 | 0 | 0 |
| CC-3-23 | 0 | 0 | 0 |

TABLE 18

The Effect of Series 5 Analogs on Cell Viability.

| Compound | 10 ug/ml | 1 ug/ml | 100 ng/ml |
| --- | --- | --- | --- |
| LT-1-98 | 100 | 100 | 100 |
| LT-1-97 | 100 | 100 | 100 |
| LT-1-104 | 100 | 100 | 100 |
| CC-3-17 | 75** | 85* | 90* |
| CC-3-20 | 100 | 100 | 100 |
| CC-3-25 | 90* | 100 | 100 |
| CC-3-27 | 100 | 100 | 100 |

TABLE 19

Percent TNF-α Inhibition by Series 5 Analogs

| Compound | 10 ug/ml | 1 ug/ml | 100 ng/ml |
| --- | --- | --- | --- |
| LT-1-98 | 55 | 0 | 0 |
| LT-1-97 | 50 | 20 | 0 |
| LT-1-104 | 25 | 0 | 0 |
| CC-3-17 | 25 | 20 | 10 |
| CC-3-20 | 50 | 20 | 0 |
| CC-3-25 | 30 | 10 | 0 |
| CC-3-27 | 15 | 0 | 0 |

TABLE 20

The Effect of Series 6 Analogs on Cell Viability

| Compound | 10 ug/ml | 1 ug/ml | 100 ng/ml |
| --- | --- | --- | --- |
| CC-3-09 | 100 | 100 | 100 |
| CC-3-14 | NA | 100 | 100 |

TABLE 21

Percent TNF-α Inhibition by Series 6 Analogs

| Compound | 10 ug/ml | 1 ug/ml | 100 ng/ml |
| --- | --- | --- | --- |
| CC-3-09 | 10 | 0 | 0 |
| CC-3-14 | NA | 30 | 25 |

TABLE 22

The Effect of Series 7 Analogs on Cell Viability

| Compound | 10 ug/ml | 1 ug/ml | 100 ng/ml |
| --- | --- | --- | --- |
| LT-1-99 | 100 | 100 | 100 |
| LT-1-96 (trans) | 100 | 100 | 100 |
| LT-1-96 (cis) | 100 | 100 | 100 |
| LT-1-102 | 100 | 100 | 100 |
| CC-3-24 | 100 | 100 | 100 |
| CC-3-26 | 100 | 100 | 100 |
| CC-3-45 | 100 | 100 | 100 |
| LT-1-46 | 90* | 90* | 100 |
| CC-3-69 | NA | 100 | 100 |
| CC-3-21 | NA | 100 | 100 |

TABLE 23

Percent TNF-α inhibition by Series 7 Analogs 1

| Compound | 10 ug/ml | 1 ug/ml | 100 ng/ml |
| --- | --- | --- | --- |
| LT-1-99 | 50 | 50 | 20 |
| LT-1-96 (trans) | 50 | 0 | 0 |
| LT-1-96 (cis) | 50 | 0 | 0 |
| LT-1-102 | 0 | 0 | 0 |
| CC-3-24 | 55 | 25 | 0 |
| CC-3-26 | 20 | 0 | 0 |
| CC-3-45 | 0 | 0 | 0 |
| LT-1-46 | 20 | 0 | 0 |
| CC-3-69 | NA | 20 | 0 |
| CC-3-21 | NA | 0 | 0 |

While specific embodiments of the broadly disclosed invention have been shown and described in detail, and exemplified to illustrate the application of and the underlying principles of the invention, it will be understood by those of skill in the art that the invention may be embodied otherwise without departing from such principles.

What is claimed is:

1. A method of treating cancer in an animal wherein the cancer is selected from the group consisting of: multiple myeloma and human prostate adenocarcinoma comprising:
contacting to living tissue of said animal the following compound:

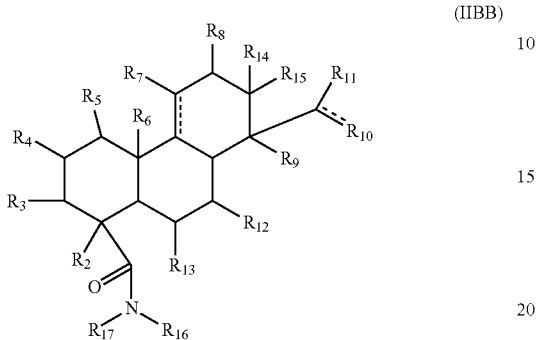

(IIBB)

wherein:

$R_2$ is selected from the group consisting of hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, and $C_5$-$C_{12}$ aryls;

$R_{17}$ is selected from $C_5$-$C_{12}$ cyclic alkyls; $C_5$-$C_{12}$ cyclic alkenyls; $C_5$-$C_{12}$ substituted cyclic alkyls; $C_5$-$C_{12}$ substituted cyclic alkenyls; phenyl and $C_5$-$C_{12}$ aryls;

$R_9$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, $C_1$-$C_{12}$ alcohol, $C_1$-$C_{12}$ acyl, and $C_5$-$C_{12}$ aryl;

$R_3$-$R_5$, $R_7$, $R_8$, and $R_{11}$-$R_{13}$ are each separately selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, $C_2$-$C_{12}$ alkynyl, and $C_5$-$C_{12}$ aryl;

$R_6$ is selected from hydrogen, a halogen, $C_1$-$C_{12}$ alkyl, $C_1$-$C_{12}$ substituted alkyls, $C_2$-$C_{12}$ alkenyl, $C_2$-$C_{12}$ substituted alkenyl, and $C_2$-$C_{12}$ alkynyl;

$R_{10}$ is selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_{12}$ alcohol, and $C_5$-$C_{12}$ aryl;

$R_{14}$ and $R_{15}$ are separately selected from hydrogen, a halogen, $CH_2$, $C_1$-$C_6$ alkyl, $C_1$-$C_6$ substituted alkyl, $C_2$-$C_6$ alkenyl, $C_2$-$C_6$ substituted alkenyl, $C_1$-$C_6$ alcohol, and $C_5$-$C_6$ aryl; and $R_{16}$ is selected from the group consisting of hydrogen, a halogen, COOH, $C_1$-$C_{12}$ carboxylic acids, $C_1$-$C_{12}$ acyl halides, $C_1$-$C_{12}$ acyl residues, $C_1$-$C_{12}$ esters, $C_1$-$C_{12}$ secondary amides, ($C_1$-$C_{12}$)($C_1$-$C_{12}$) tertiary amides, ($C_1$-$C_{12}$) cyclic amides, ($C_1$-$C_{12}$) amines, $C_1$-$C_{12}$ alcohols, ($C_1$-$C_{12}$)($C_1$-$C_{12}$) ethers, $C_1$-$C_{12}$ alkyls, $C_1$-$C_{12}$ substituted alkyls, $C_2$-$C_{12}$ alkenyls, $C_2$-$C_{12}$ substituted alkenyls, and $C_5$-$C_{12}$ aryls;

and the acid addition salts thereof.

2. The method of claim 1 wherein the compound has the following structure:

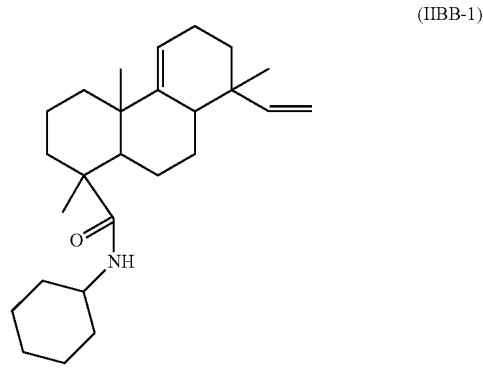

(IIBB-1)

and the acid addition salts thereof.

* * * * *